United States Patent [19]
Cooperman et al.

[11] Patent Number: 6,030,942
[45] Date of Patent: Feb. 29, 2000

[54] PEPTIDES PEPTIDE ANALOGS PEPTIDOMIMETICS AND OTHER SMALL MOLECULES USEFUL FOR INHIBITING THE ACTIVITY OF RIBONUCLEOTIDE REDUCTASE

[75] Inventors: Barry S. Cooperman, Penn Valley; Ralph F. Hirschmann, Blue Bell; Amos B. Smith, III, Merion, all of Pa.; Paul Laub, San José, Calif.; Setsuya Sasho, Shizuoka-Ken, Japan; Paul A. Sprengeler, Merion, Pa.; Bari A. Barwis, Philadelphia, Pa.; Alison Fisher, Blue Bell, Pa.; Shrikumar Nair, Upper Darby, Pa.

[73] Assignee: The Trustees of the University of Pennsylvania, Philadelphia, Pa.

[21] Appl. No.: 09/040,216

[22] Filed: Mar. 17, 1998

Related U.S. Application Data

[63] Continuation-in-part of application No. 08/919,748, Aug. 28, 1997, abandoned.
[60] Provisional application No. 60/025,146, Aug. 30, 1996.
[51] Int. Cl.[7] .......................... A61K 38/00; A61K 38/12; A61K 38/16
[52] U.S. Cl. .............................. 514/9; 530/317; 530/318; 530/322; 530/323; 514/2; 514/11; 514/12
[58] Field of Search .................................... 530/317, 318, 530/322, 323; 514/9

[56] References Cited

PUBLICATIONS

Yang et al. FEBS Letters, 272, 61–64, Oct. 1990.
Albain et al., 1990, Cancer Chemother. Pharmacol. 27:33–40.
Allard et al., 1994, J. Magn. Reson. 103:242–246.
Alley et al., 1988, Cancer Research 48:589–601.
Archimbaud et al., 1989, Cancer Chemother. Pharmacol. 25:223–225.
Bach et al., 1994, J. Amer. Chem. Soc. 116:3207–3219.
Ball et al., 1990, J. Molec. Recog. 3:55–64.
Bax et al., 1985, J. Magn. Reson. 63:207–213.
Bax et al., 1985, J. Magn. Reson. 65:355–360.
Bayer et al., 1970, J. Amer. Chem. Soc. 92:1735–1738.
Bergmann et al., 1989, Eur. J. Cancer Clin. Oncol. 25 Suppl 3, S31–S36.
Berman et al., 1989, Leukemia 3:115–121.
Bianchi et al., 1994, Proc. Natl. Acad. Sci. USA 91:8403–8407.
Björklund et al., 1990, Biochemistry 29:5452–5458.
Blanco et al., 1993, J. Am. Chem. Soc. 115:5887–5888.
Blumenkopf et al., 1992, J. Med. Chem. 35:2306–2314.
Bollinger et al., 1994, J. Am. Chem. Soc. 116:8024–8032.
Bollinger et al., 1991, Science 253:292–298.
Bonneau et al., 1996, J. Virol. 70:787–793.
Bowen et al.,1987, J. Org. Chem. 52:5162–5166.
Bradford, 1976, Anal. Biochem. 72:248–254.
Bushweller et al., 1991, Biochemistry. 30:8144–8151.
Campbell et al., 1993, Annu. Rev. Biophys. Biomol. Struc.22:99–122.
Campbell et al., 1991, J. Magn. Reson. 93:77–92.
Cannistra et al., 1989, Leukemia 3:328–334.
Cantwell et al., 1989, Cancer Chemother. Pharmacol.23:252–254.
Caras et al., 1985, J. Biol. Chem. 260:7015–7022.
Carmichael et al., 1990, Br. J Cancer 61:447–450.
Chamberlain et al., 1990, Arch. Neruol. 47:1113–1116.
Chandrasekaran et al., 1973, Biochim. Biophys. Acta 303:14.
Chang et al., 1978, Int. J. Peptide and Protein Res. 2:246–249.
Climent et al., 1992, Biochemistry 31:4801–4807.
Climent et al., 1991, Biochemistry. 30:5164–5171.
Clore et al., 1993, J. Mol. Biol. 231:82–102.
Clore et al., 1982, J. Magn. Res. 48:402–417.
Clore et al., 1989, CRC Crit. Rev. Biochem. Mol. Biol. 24:479–564.
Cory et al., 1993, Adv. Enzyme Regul. 33:129–140.
Cory et al., 1994, Biochem. Pharm. 47(2):365–371.
Cory, 1988, Adv. Enzyme Regul. 27:437–455.
Cosentino et al, 1991, Cell Biol., 69:79–83.
Cuatrecasas et al., 1972, Biochemistry 11:2291–2297.
Dastugue et al., 1990, Cancer Genet Cytogenet. 44:275–276.
Davis et al., 1994, J. Biol. Chem. 269:23171–23176.
Di Costanzo et al., 1991, J. Surg. Oncol. Suppl. 2:137–140.
Dratz et al., 1993, Nature 363:276–281.
Diaz et al., 1993, Tetrahedron 49, 17:3533–3545.
Eichler et al., 1993, Biochemistry 32:11035–11041.
Ekberg et al., 1996, J. Biol. Chem. 34: 20655–20659.
Engström et al., 1979, Biochemistry 18:2941–2948.
Erikson et al., Ribonucleotide Reductase. Allosteric Enzymes. 1989, 189–215.
Evans et al., 1982, J. Am. Chem. Soc. 104:1737–1739.
Farmer et al., Bridging the Gap between Bioactive Peptides and Nonpeptides: Some perspectives in Design. In *Drug Design*; Ari'ns, E. J., Ed.; Academic:New York, 1980; vol. X, p. 119.
Fenaux et al., 1990, Cancer 66:549–556.
Filatov et al., 1992, J. Biol. Chem. 267:15816–15822.
Fisher et al., 1993, J. Med. Chem. 36:3859–3862.
Fisher et al., 1995, Nature Structural Biology 2:11:951–955.
Fontecave, 1992, Adv. Enzymol Relat. Areas Mol. Biol. 147–183.

(List continued on next page.)

*Primary Examiner*—Cecilia Tsang
*Assistant Examiner*—Michael Borin
*Attorney, Agent, or Firm*—Akin, Gump, Strauss, Hauer & Feld, L.L.P.

[57] ABSTRACT

The invention relates to compositions which are useful for inhibiting ribonucleotide reductase enzymes, including the mammalian ribonucleotide reductase enzyme. The compositions include, but are not limited to, linear peptides, cyclic peptides, peptide analogs, and peptidomimetics. Methods of using the compositions of the invention to treat cancer and viral and bacterial infections are disclosed.

7 Claims, 39 Drawing Sheets

OTHER PUBLICATIONS

Fountzilas et al., 1990, Cancer 66:1453–1460.
Fraser–Reid et al., 1979, Can. J. Chem. 57:1746–1749.
Gaudreau et al., 1992, J. Med. Chem. 35:346–350.
Genin et al., 1993, J. Org. Chem. 58:860–866.
Genin et al., 1993, J. Org. Chem. 58:2334–2337.
Hansen et al., 1989, J. Immunol. Methods 119:203–210.
Heinemann et al., 1990, Mol. Pharmacol. 38:567–572.
Hirschmann 1992, J. Am. Chem. Soc. 114:9217.
Houghten et al., 1992, BioTechniques 13:412–421.
Jeener et al., 1981, J. Chem. Phys. 71:4546–4553.
Jensen et al. 1994, Proc. Natl. Acad. Sci. U.S.A., 91:9257–9261.
Kerr et al., 1993, BioMed.Chem.Lett. 3:463–468.
Kirkpatrick et al., 1983, Science, 220:671–680.
Krogsrud et al., 1993, Anal. Biochem. 213:386–394.
Kuhbock et al., 1988, Semin. Surg. Oncol..4:87–90.
Kushner et al., 1991, Cancer 68:242–247.
Larsson et al.,1986, EMBO J. 5:2037–2040.
Laub, 1995, J. Appl. Cryst. 28:632–634.
Laub et al., 1995, Prot. Sci. 4:973–982.
Leamon et al., 1991, Proc. Natl. Acad. Sci. USA 88:5572–5576.
Leamon et al., 1993, J. Biol. Chem. 268 (33):24847–24854.
Leamon et al., 1993, Biochem. J. 291:855–860.
Lee et al., 1994, J. Biol. Chem. 269:3198–3204.
Lee et al., 1995, Biochim. Biophys. Acta 1233: 134–144.
Liu et al., 1992, J. Magn. Reson. 98:163–175.
Liuzzi et al., 1994, Nature. 372:695–698.
Lofvenberg et al., 1990, Cancer Genet. Cytogenet. 49 :57–67.
Lokich et al., 1991, Cancer 68:744–746.
London et al., 1992, J. Magn. Reson. 97:79–98.
Lori et al., 1994, Science 266:801–805.
Lowenberg et al., 1989, J. Clin. Oncol. 7:1268–1274.
Lycksell et al., 1994, Biochemistry. 33:2838–2842.
Magnus et al., 1979, Carbohydr. Res. 76:261–264.
Mann et al., 1991, Biochemistry 30:1939–1947.
Marcello et al.,1994, Proc. Natl. Acad. Sci. USA 91:8994–8998.
Matsumoto et al., 1990, Cancer Chemother. Pharmacol. 26:323–329.
Mattano et al., 1990, Cancer Res. 50:4566–4571.
McDowell et al., 1992, J. Am. Chem. Soc. 114:9245–9253.
Meyer et al., 1988, Biochemistry 27:725–730.
Mohamadi et al., 1990, J. Comp. Chem. 11:440–467.
Moore et al., 1974, Biochemistry 13:2904–2907.
Moss et al., 1993, J. Med. Chem. 36:3005–3009.
Moss et al., 1996, J. Med. Chem. 39:2178–2187.
Moss et al. 1995, J. Med. Chem. 38:3617–3623.
Ni et al., 1990, Biochemistry 29:4479–4489.
Ni et al., 1992, Biochemistry 31:2545–2554.
Ni et al., 1994, Accts. of Chem. Res. 27, 257–264.
Ni, 1992, J. Magn. Reson. 96:651–656.
Nicholls et al., 1991, Proteins. 11:281–296.
Nocentini et al., 1993, Cancer Research 53:19–26.
Nordlund et al., 1993, J. Mol. Biol. 232:123–164.
Nyholm et al., 1993, J. Biol. Chem. 268 (35):26200–26205.
Nyholm et al., 1993, Biochemistry 32:11569–11574.
Ostresh et al., 1994, Proc. Natl. Acad. Sci. USA 91:11138–11142.
Parker et al., 1991, Cancer Res. 51:2386–2394.
Pinilla et al., 1994, Drug Devel. Res. 33:133–145.
Piver et al., 1989, J. Surg. Oncol. 42:120–125.
Piver, 1990, Semin. Surg. Oncol. 6:359–363.
Pötsch et al., 1994, Mol. Pharm. 45:792–796.
Powers et al., 1993, Biochemistry 32:6744–6762.
Ripka et al., 1993, Tetrahedron 49:17, 3609–3628.
Ripka et al., 1993, Tetrahedron 49:17:3593–3608.
Rose et al., 1985, Adv. Prot. Chem. 37:1–109.
Rova et al., 1995, Biochemistry. 34:4267–4275.
Rozental et al., 1989, Cancer 63:2475–2481.
Rubin et al., 1993, Proc. Natl. Acad. Sci. U.S.A. 90:9280–9284.
Sahlin et al., 1989, Biochemistry 28:2618–2625.
Sahlin et al., 1994, J. Biol. Chem. 269:11699–11702.
Salem et al., 1993, FEBS Lett. 323:93–95.
Salowe et al., 1986, J. Bacteriol.165;363–366.
Sander et al., 1991, Proteins: Struct. Funct. Genet. 9:56–68.
Sandkvist et al., 1987, J. Bacteriol. 169:4570–4576.
Sato et al., 1983, Anal. Biochem. 135:431–435.
Saunders et al., 1990, J. Am. Chem. Soc.112:1419–1427.
Sayle et al., 1995, TIBS 20: 374–376.
Shapiro et al., 1989, J. Neurosurg. 71:1–9.
Sjöberg, 1995, Nucleic Acids and Molecular Biology. 9:192–220.
Smit et al., 1991, Cancer 67:2826–2827.
Smith et al., 1994, J. Med. Chem. 37:215–218.
Smith et al., 1992, Ann. Rev. Biophys. Biomol. Struct. 21:25–47.
Srinivasan et al., 1994, Biochemistry 33:13553–13560.
Steeper et al.., 1970, Anal. Biochem. 34:123–130.
Stewart et al., Solid Phase Peptide Synthesis, 2nd ed., Pierce Chemical Co., Rockford, IL. 1984, 84–92.
Stubbe et al., 1990, Adv. Enzymol. Relat. Areas Mol. Biol. 63:349–419.
Su et al., 1993, Biorganic & Medicinal Chemistry Letters 3, 5:835–840.
Tay et al., 1991, J. Clin. Invest. 87:519–527.
Thelander et al., 1980, J. Biol. Chem. 255:7426–7432.
Tihan et al., 1991, Adv. Enzyme Regul. 31:71–78.
Tsang et al.,1994, J. Am. Chem. Soc. 116:3988–4005.
Uhlin et al. 1994, Nature 370:533–539.
Vokes et al., 1989, J. Clin. Oncol. 7:761–768.
Vokes et al., 1990, Cancer 66:437–442.
von Roedern and Kessler 1994, Angew. Chem., Int. Ed. Engl.33:687–689.
Wagner et al., 1993, Tetrahedron 49:10831–10842.
Wang et al., 1995, Proc. Natl. Acad. Sci. USA 92:3318–3322.
Wang et al., 1996, Bioconjugate Chem. 7:56–62.
Weitman et al., 1992, Cancer Res. 52:3396–3401.
Wilmot et al., 1990, Protein Eng. 3:479–493.
Wright et al., 1990, Proc. Natl. Acad. Sci. U S A. 87:1791–1795.
Yang et al., 1990, FEBS Lett. 272:61–64.

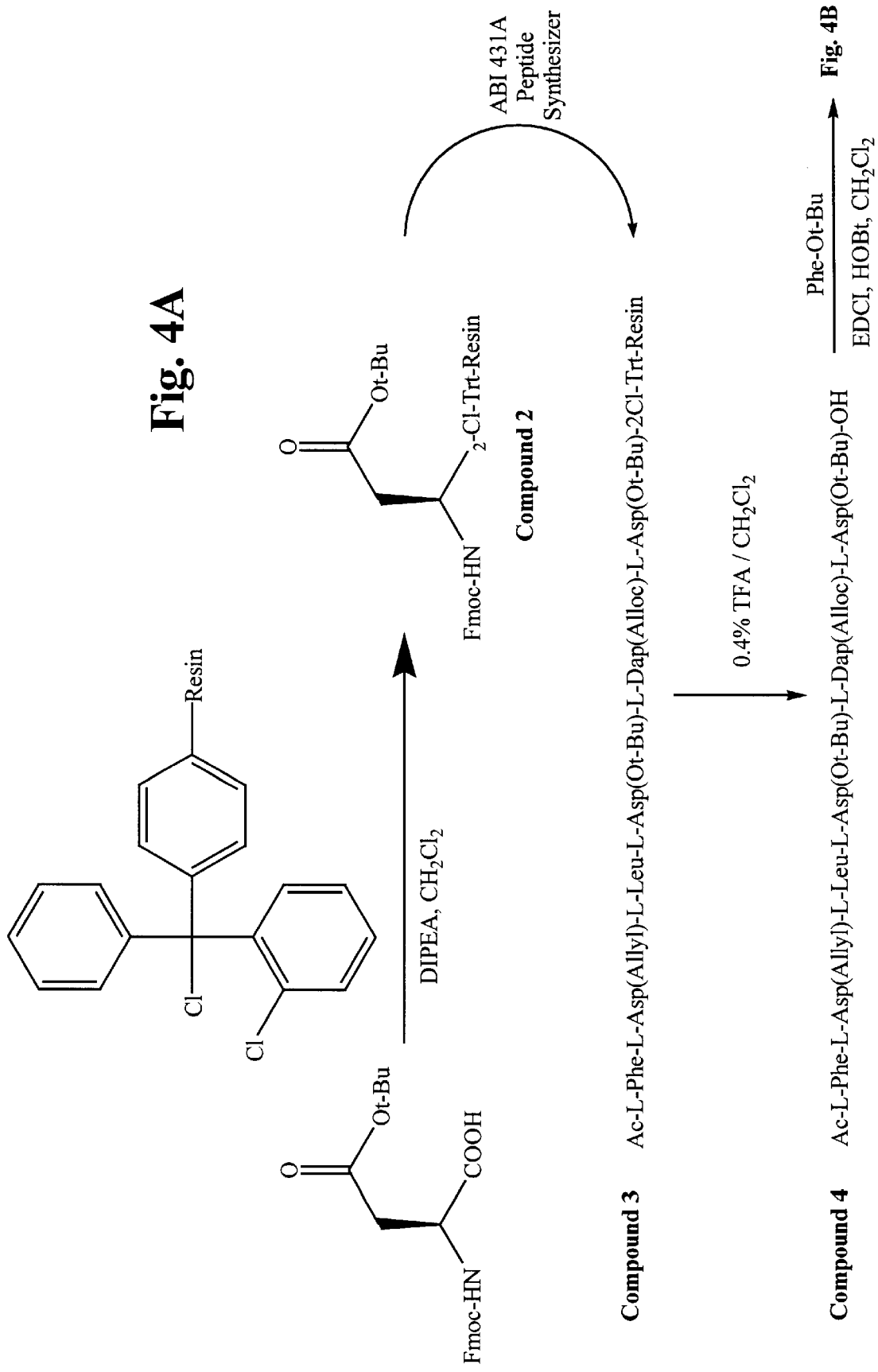

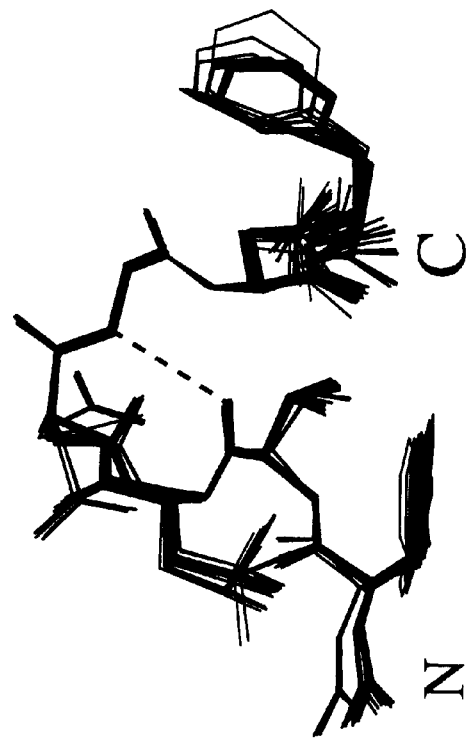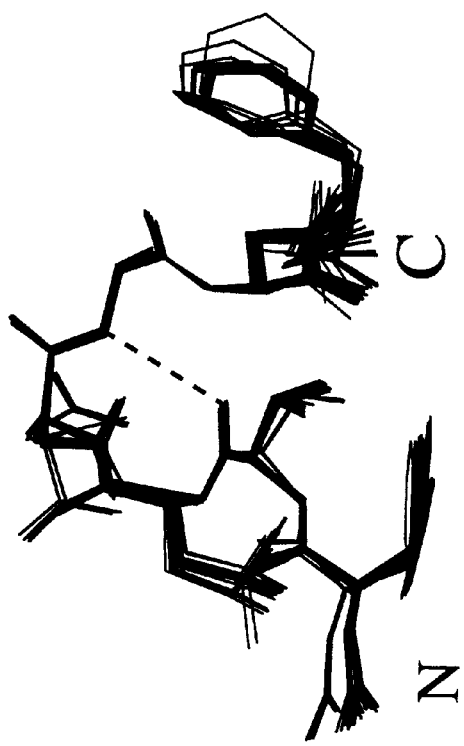
Fig. 13

X and Y = -CH$_2$-, -(CH$_2$)$_2$-
4a-d

X and Y = -CH$_2$-, -(CH$_2$)$_2$-, -CMe$_2$-
n=1, 5a-i
n=2, 6a-i

Ac-Phe-Xaa-Leu-Asp(t-Bu)-Yaa-Asp(t-Bu)-Phe-RESIN
   10a-d Xaa=(Ser,HSer)Bzl, Yaa=(Cys,HCys)Mob
   11a-d Xaa=(Cys,HCys)Mob, Yaa=(Ser,HSer)Bzl
     RESIN = 2-Chlorotrityl Resin 1) 0.75% TFA
            2) iso-Butylene Ac-Phe-Xaa-Leu-Asp(t-Bu)-Yaa-Asp(t-Bu)-Phe-t-Bu
   12a-d Xaa=(Ser,HSer)Bzl, Yaa=(Cys,HCys)Mob
   13a-d Xaa=(Cys,HCys)Mob, Yaa=(Ser,HSer)Bzl 1) $H_2$, Pd/C
            2) $CBr_4/PPh_3$
            3) $Hg(OCOCF_3)_2$/AcOH
            4) DIEA, reflux
            5) 50% $TFA/CH_2Cl_2$
            6) HPLC Ac-Phe-Xaa-Leu-Asp-Yaa-Asp-Phe-OH

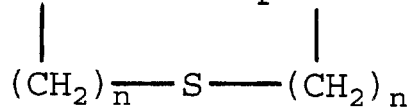

4a-d Xaa = Yaa = Gly
         n= 1,2

Fig. 23

Ac-Phe-Xaa-Leu-Asp(t-Bu)-Yaa-Asp(t-Bu)-Phe-RESIN
  15a-i Xaa,Yaa= (Cys,HCys,Pen)Acm
    RESIN = 2-Chlorotrityl Resin

| 1) 0.75% TFA
  | 2) iso-Butylene, H⁺
  ↓

Ac-Phe-Xaa-Leu-Asp(t-Bu)-Yaa-Asp(t-Bu)-Phe-t-Bu
  16a-i Xaa,Yaa= (Cys,HCys,Pen)Acm

| 1) I$_2$
  | 2) CH2Br$_2$ or Br-(CH$_2$)$_2$-Br, TEA
  | 3) 50% TFA
  | 4) RP-HPLC
  ↓

Ac-Phe-Xaa-Leu-Asp-Yaa-Asp-Phe-OH
         |            |
         P——(CH$_2$)$_{\overline{n}}$——Q Xaa,Yaa= (Cys,HCys,Pen),  P = Q = S
       n=1, 5a-i
       n=2, 6a-i

PEPTIDES PEPTIDE ANALOGS PEPTIDOMIMETICS AND OTHER SMALL MOLECULES USEFUL FOR INHIBITING THE ACTIVITY OF RIBONUCLEOTIDE REDUCTASE

CROSS REFERENCE TO RELATED APPLICATIONS

This application is a continuation-in-part of U.S. application Ser. No. 8/919,748, filed Aug. 28, 1997 (now abandoned), which application is entitled to priority under 35 U.S.C. § 119(e) to U.S. Provisional Application Ser. No. 60/025,146, filed on Aug. 30, 1996.

GOVERNMENT SUPPORT

Portions of this invention were made with U.S. Government support (NIH Grants CA 09035-20, GM 07229-21 and NIH Core Grant CA 06927) and the U.S. Government may therefore have certain rights in the invention.

BACKGROUND OF THE INVENTION

Ribonucleotide reductase (RR, EC 1.17.4.1), which reduces ribonucleotides to 2'-deoxyribonucleotides, is essential to de novo DNA synthesis and plays a direct role in regulating DNA replication (Cory, 1988, Adv. Enzyme Regul. 27:437–455). Class I, the most common form of RR, comprises two different subunits, a larger subunit denoted R1 and a smaller subunit, denoted R2. The active enzyme is a dimer of dimers, denoted $R1_2R2_2$. Mouse R1 (mR1) and mouse R2 (mR2) have molecular masses 90 kDa and 45 kDa, respectively. Class I RRs catalyze the reduction of nucleoside diphosphates. The NDP substrate binding site, as well as two kinds of allosteric sites, are located on the R1 subunit. R2 contains two high spin Fe (III), as well as 0.5–1.0 stable tyrosine radical per subunit. The catalytic reaction is believed to involve long-range electron transfer between the tyrosine radical and the substrate site. More complete descriptions of this enzyme may be found in three recent reviews (Stubbe, 1990, Adv Enzymol. Relat. Areas Mol. Biol. 63:349–419; Fontecave et al., 1992, Adv. Enzymol Relat. Areas Mol. Biol. 147–183; Sjöberg, 1995, Nucleic Acids and Molecular Biology. 9:192–224).

Necessary for RR activity, the association of the R1 and R2 subunits is completely governed by the binding of the C-terminal residues of R2 to R1, as demonstrated for *E. coli* RR (eRR, Climent et al., 1991, Biochemistry. 30:5164–5171; Climent et al., 1992, Biochemistry 31:4801–4807), HSV-RR (Filatov et al., 1992, J. Biol. Chem. 267:15816–15822) and mouse RR (mRR, Hamann, 1994, Purification, Characterization and Activity of Chimeric *E. coli*/Mouse and *Plasmodium faciparum* Small Subunits of Type I Ribonucleotide Reductase. Ph.D. Thesis in Chemistry, University of Pennsylvania). In addition, NMR studies of mR2 establish that the highly flexible C-terminal residues become rigid in the presence of added R1 protein (Lyckskell et al., 1994, Biochemistry. 33:2838–2842). The association constant of $R1_2$ to $R2_2$ is modest ($\sim 0.4$–$1 \times 10^7 M^{-1}$) (Climent et al., 1991, Biochemistry. 30:5164–5171; Hamann, 1994, Characterization and Activity of Chimeric *E. coli*/Mouse and *Plasmodium faciparum* Small Subunits of Type I Ribonucleotide Reductase. Ph.D. Thesis in Chemistry, University of Pennsylvania; Rova et al., 1995, Biochemistry. 34:4267–4275), and the C-terminal peptide of R2 is able to inhibit enzymatic activity by competing with R2 for association with R1 (Climent et al., 1991, Biochemistry. 30:5164–5171; Gaudreau et al., 1992, J. Med. Chem. 35:346–350; Fisher et al., 1993, J. Med. Chem. 36:3859–3862). The substantial difference between the HSV R2 C-terminal sequence (YAGAVVNDL; SEQ ID NO: 1) and the corresponding mammalian sequence (NSFTLDADF; SEQ ID NO: 2) has been exploited in the development of selective peptide inhibitors of viral RR (Liuzzi et al., 1994, Nature. 372:695–698; Moss et al., 1996, J. Med. Chem. 39:2178–2187). The feasibility of developing specific inhibitors for yeast RR (Fisher et al., 1993, J. Med. Chem. 36:3859–3862), *P. falciparum* RR (Rubin et al., 1993, Proc. Natl. Acad. Sci. U.S.A. 90:9280–9284) and eRR (Cosentino et al., 1990, Biochem. Cell Biol. 69:79–83) has also been demonstrated.

Refined crystal structures of both the R1 and R2 subunits from *E. coli* have been reported, at 2.7 Å and 2.2 Å resolution, respectively (Uhlin et al., 1993, Nature 370:533–539; Nordlund et al., 1993, J. Mol. Biol. 232:123–164). The structure of the R2 subunit reveals that the tyrosine radical, Y122, is buried inside the protein, 5 Å from the nearest Fe atom. The ligands directly coordinated to the two Fe (III) atoms, namely, two histidine residues, two glutamic acid residues, and an aspartic acid residue, are highly conserved evolutionarily.

The thirty carboxy-terminal residues of the R2 subunit cannot be located in the crystal structure of *E. coli* R2. The structure of the R1 subunit was determined in the presence of a synthetic twenty residue peptide homologous to the twenty carboxy terminal amino acid residues of *E. coli* R2, although only the eight carboxy-terminal residues of R2 have been located within the structure of R1. This octamer is bound between two α-helices of R1 corresponding to residues 340–350 and 710–726 of R1.

This result is consistent with evidence that a region near the carboxy-terminus of R1 forms at least part of the conserved site for binding by R1 of the carboxy-terminal portion of R2. An azidophenyl derivative of FTLDADF (SEQ ID NO: 3) was found to photoincorporate into a peptide of mouse R1 (Davis et al., 1994, J. Biol. Chem. 269:23171–23176) corresponding to residues 724–735 of mouse R1, the sequence of which corresponds to residues 718–728 of *E. coli* R1. These data suggest that this region of R1 is involved in binding the carboxy-terminal portion of R2.

R1 variants, denoted A1091S and P1090L, have been isolated from strains of HSV-1 which exhibit weak resistance to an R2 carboxy-terminal peptidomimetic inhibitor (Liuzzi et al., 1994, Nature 372:695–698; Bonneau et al., 1996, J. Virol. 70:787–793). The affinities of the A1091S R1 variant for R2 and for the inhibitory peptidomimetic are decreased by factors of 10 and 25, respectively, relative to wild type HSV-1 strains. Residues 1090 and 1091 of HSV-1 R1 correspond to residues 710 and 711 of *E coli* R1. These results are summarized in the alignment presented below. It is noteworthy that the region of R1 implicated in binding of R2 peptide is adjacent to the most conserved sequence (presented in bold type) within R1.

| | | |
|---|---|---|
| mouse R1[a] (SEQ ID NO: 4) | PNYGKLTSMHFYGWKOGLKTGMYY | residues 715–738 |
| HSV1- R1[b] (SEQ ID NO: 5) | IPASTLVRLLVHAYKRGLKTGMYY | 1089–1112 |

-continued

E. coli-R1 VPMQQLLKDLLTAYKFGVKT.LYY  709–731
(SEQ ID NO: 6)

[a] underlined residues correspond to affinity labeled peptide.
[b] underlined residues, when mutated, confer weak resistance to nonpeptide peptidomimetic inhibitors There is a need for the development of effective and selective ribonucleotide reductase inhibitors. Given the fact that ribonucleotide reductase enzymes are ubiquitous throughout nature, in certain instances, the use of a general inhibitor of these enzymes may have a deleterious effect in an organism to which the inhibitor is administered. It is also necessary therefore, to have the capability of generating inhibitors of specific ribonucleotide reductase enzymes, wherein inhibition of any one ribonucleotide reductase may be accomplished without significantly inhibiting other ribonucleotide reductases. Thus, there is a long felt need for the development of effective and selective inhibitors of ribonucleotide reductase activity and, in particular, for inhibitors which are designed to selectively inhibit particular ribonucleotide reductase enzymes while having a lesser or no effect on other ribonucleotide reductase enzymes. The present invention satisfies these needs.

SUMMARY OF THE INVENTION

The invention relates to an composition of matter comprising an inhibitor of ribonucleotide reductase, wherein the inhibitor comprises a peptide having the structure $$Y_1\text{-}AA_1\text{-}AA_2\text{-}AA_3\text{-}AA_4\text{-}AA_5\text{-}AA_6\text{-}AA_7$$

wherein:
$Y_1$ is selected from the group consisting of an acetyl group, a benzoyl group, nd a dibenzyl acetyl group;
$AA_1$ is selected from the group consisting of Phe, Trp, N-methyl-Phe, and D-he;
$AA_2$ is selected from the group consisting of Thr, N-methyl-Thr, Leu, Val, and D-Thr;
$AA_3$ is selected from the group consisting of Leu, γ-methyl-Leu, N-methyl-Leu, Ile, and D-Leu;
$AA_4$ is selected from the group consisting of Asp, D-Asp, Asp having a spirocyclopentane replacing the β-$CH_2$ of Asp, Asn having a pyrrolidine replacing the γ-$NH_2$ of Asn, N-methyl-Asp, and Glu;
$AA_5$ is selected from the group consisting of Phe, Val, Ile, N-methyl-Ala, and D-Ala;
$AA_6$ is selected from the group consisting of Asp, D-Asp, Asp having a spirocyclopentane replacing the β-$CH_2$ of Asp, Asn having a pyrrolidine replacing the γ-$NH_2$ of Asn, and N-methyl Asp; and
$AA_7$ is selected from the group consisting of Phe, Tyr, Trp, N-methyl-Phe, D-Phe, o-methyl Phe, m-methyl Phe, o,o-dimethyl Phe, o,m-dimethyl Phe, o-hydroxyl Phe, m-hydroxyl Phe, p-hydroxyl Phe, m-chloro Phe, o-pyridyl Phe, and p-pyridyl Phe.

In one aspect of this composition, the inhibitor is conjugated with a cell surface ligand-binding molecule, such as one selected from the group consisting of folic acid, the nontoxic B subunit of E. coli heat labile enterotoxin, and a fusion protein of the nontoxic B subunit of E. coli heat labile enterotoxin.

In another aspect of this composition, the composition further comprises a pharmaceutically acceptable carrier.

The invention also relates to a composition comprising an inhibitor of ribonucleotide reductase, wherein the inhibitor comprises a peptide having the structure $$W_1\text{-}AA_8\text{-}AA_9\text{-}AA_{10}\text{-}AA_{11}\text{-}AA_{12}\text{-}AA_{13}\text{-}Phe\text{ -}W_2$$

wherein:
$W_1$ is selected from the group consisting of acetyl, one amino acid residue, two amino acid residues, one N-acetyl-amino acid residue, and an N-acetyl-amino acid residue linked to a second amino acid residue by a peptide bond;
$AA_8$ is selected from the group consisting of Phe, p-amino-Phe, and p-azido-Phe;
$AA_9$ is selected from the group consisting of Thr, Ser, and Ala;
$AA_{10}$ is selected from the group consisting of Leu, Val, Phe, and Ala;
$AA_{11}$ is selected from the group consisting of Asp, Asn, and Ala;
$AA_{12}$ is selected from the group consisting of Ala, Leu, and Gly;
$AA_{13}$ is selected from the group consisting of Asp, Asn, Leu, Ala, and Glu; and
$W_2$ is selected from the group consisting of one amino acid residue and two amino acid residues. Preferably:
$AA_{10}$ is selected from the group consisting of Leu, Val, and Phe;
$AA_{11}$ is selected from the group consisting of Asp, and Asn;
$AA_{12}$ is selected from the group consisting of Ala, and Leu; and
$AA_{13}$ is selected from the group consisting of Asp, Asn, Leu, and Ala.

In another aspect of this composition, the inhibitor is selected from the group consisting of Phe-Thr-Leu-Asp-Ala-Asp-Phe (SEQ ID NO: 3), Phe-Thr-Phe-Asn-Glu-Asp-Phe (SEQ ID NO: 7), Phe-Thr-Ile-Asp-Glu-Asp-Phe (SEQ ID NO: 9), Phe-Cys-Leu-Asn-Thr-Glu-Phe (SEQ ID NO: 11), Phe-Ser-Leu-Asp-Val-Asp-Phe (SEQ ID NO: 12), Acetyl-Asn-Ser-Phe-Thr-Leu-Asp-Ala-Asp-Phe (SEQ ID NO: 13), Acetyl-Ser-Phe-Thr-Leu-Asp-Ala-Asp-Phe (SEQ ID NO: 14), Ser-Phe-Thr-Leu-Asp-Ala-Asp-Phe (SEQ ID NO: 15), Acetyl-Phe-Thr-Leu-Asp-Ala-Asp-Phe (SEQ ID NO: 16), Phe-Thr-Leu-Asp-Ala-Asp-Phe (SEQ ID NO: 17), Acetyl-Phe-Thr-Leu-Asp-Ala-Asp-Leu (SEQ ID NO: 18), Acetyl-Tyr-Thr-Leu-Asp-Ala-Asp-Phe (SEQ ID NO: 19), Acetyl-(p-amino-Phe)-Thr-Leu-Asp-Ala-Asp-Phe, Acetyl-(p-azido-Phe)-Thr-Leu-Asp-Ala-Asp-Phe, Acetyl-Phe-Ser-Leu-Asp-Ala-Asp-Phe (SEQ ID NO: 20), Acetyl-Phe-Ala-Leu-Asp-Ala-Asp-Phe (SEQ ID NO: 21), Acetyl-Phe-Thr-Val-Asp-Ala-Asp-Phe SEQ ID NO: 22), Acetyl-Phe-Thr-Phe-Asp-Ala-Asp-Phe (SEQ ID NO: 23), Acetyl-Phe-Thr-Ala-Asp-Ala-Asp-Phe (SEQ ID NO: 24), Acetyl-Phe-Thr-Leu-Asn-Ala-Asp-Phe (SEQ ID NO: 25), Acetyl-Phe-Thr-Leu-Ala-Ala-Asp-Phe (SEQ ID NO: 26), Acetyl-Phe-Thr-Leu-Asp-Gly-Asp-Phe (SEQ ID NO: 27), Acetyl-Phe-Thr-Leu-Asp-Leu-Asp-Phe (SEQ ID NO: 28), Acetyl-Phe-Thr-Leu-Asp-Ala-Glu-Phe (SEQ ID NO: 29), Acetyl-Phe-Thr-Leu-Asp-Ala-Asn-Phe (SEQ ID NO: 30), Acetyl-Phe-Thr-Leu-Asp-Ala-Leu-Phe (SEQ ID NO: 31), Acetyl-Phe-Thr-Leu-Asp-Ala-Ala-Phe (SEQ ID NO: 32), Acetyl-Phe-Thr-Leu-Asp-Ala-Asp-Leu (SEQ ID NO: 33), and Acetyl-Phe-Thr-Leu-Asp-Ala-Asp-Phe-Ala-Ala ((SEQ ID NO: 34); which formulae may be represented as follows by single-letter amino acid codes: FTLDADF (SEQ ID NO: 3), FTFNEDF (SEQ ID NO: 7), FTIDEDF (SEQ ID NO: 9), FCLNTEF (SEQ ID NO: 11), FSLDVDF (SEQ ID NO: 12), Ac-NSFTLDADF (SEQ ID NO: 13), Ac-SFTLDADF (SEQ ID NO: 14), SFTLDADF (SEQ ID NO: 15), Ac-FTLDADF (SEQ ID NO: 16), FTLDADF (SEQ ID NO: 17), Ac-FTLDADL (SEQ ID NO: 18), Ac-YTLDADF (SEQ ID NO: 19), Ac-F(4'-NH$_2$)TLDADF, Ac-F(4'-N$_3$)TLDADF, Ac-FSLDADF (SEQ ID NO: 20), Ac-FALDADF (SEQ ID NO: 21), Ac-FTVDADF (SEQ ID NO: 22), Ac-FTFDADF (SEQ ID NO: 23), Ac-FTADADF (SEQ ID NO: 24), Ac-FTLNADF (SEQ ID NO: 25), Ac-FTLAADF (SEQ ID NO: 26), Ac-FTLDGDF (SEQ ID NO: 27), Ac-FTLDLDF (SEQ ID NO: 28), Ac-FTLDAEF (SEQ ID NO: 29), Ac-FTLDANF (SEQ ID NO: 30), Ac-FTLDALF (SEQ ID NO: 31), Ac-FTLDAAF (SEQ ID NO: 32), Ac-FTLDADL (SEQ ID NO: 33), and Ac-FTLDADFAA (SEQ ID NO: 34)).

The invention also relates to a composition comprising an inhibitor of ribonucleotide reductase, wherein the inhibitor has a structure selected from the group consisting of the structure depicted in formula VII of FIG. 5 and the structure depicted in formula VIII of FIG. 5, wherein $X_1$ is from zero to twenty amino acids;

$X_2$ is from zero to five amino acids;

$X_3$ has a structure selected from the group consisting of the structure depicted in formula II of FIG. 5, wherein $R_1$ and $R_2$ are independently selected from the group consisting of amino acid side chain moieties and Z is selected from the group consisting of amide and disulfide bonds, and the structure depicted in formula III of FIG. 5; and $R_3$ is selected from the group consisting of oligomethylene chains of length $C_2$ to $C_6$.

The invention also relates to a composition comprising an inhibitor of ribonucleotide reductase, wherein the inhibitor has the structure $Y_2$-$Y_3$-Phe-$Y_5$-Asp-$Y_6$-$Y_4$-OH, wherein $Y_2$ is H or a blocking group;

$Y_3$ is from zero to twenty amino acids;

$Y_4$ is from zero to five amino acids;

$Y_5$ has a structure selected from the group consisting of the structure depicted in formula II of FIG. 5, wherein $R_1$ and $R_2$ are independently selected from the group consisting of amino acid side chain moieties and Z is selected from the group consisting of amide and disulfide bonds, and the structure depicted in formula III of FIG. 5; and $Y_6$ is selected from the group consisting of Phe, Tyr, Trp, N-methyl-Phe, D-Phe, o-methyl Phe, m-methyl Phe, o,o-dimethyl Phe, o,m-dimethyl Phe, o-hydroxyl Phe, m-hydroxyl Phe, p-hydroxyl Phe, m-chloro Phe, o-pyridyl Phe, and p-pyridyl Phe. Preferably, $Y_3$ is from zero to ten amino acids and $Y_4$ is from zero to five amino acids. More preferably, $Y_3$ is from zero to five amino acids and $Y_4$ is from zero or one amino acid. Most preferably, $Y_3$ and $Y_4$ are each zero amino acids. In another preferred embodiment, $Y_2$ is acyl, $Y_3$ is Asn-Ser, $Y_4$ is zero amino acids, and $Y_5$ has the structure depicted in formula II of FIG. 5, wherein the structures of $R_1$, $R_2$, and Z are selected from the group consisting of formulas IV, V, and VI of FIG. 5, wherein in formula IV, the structure of $R_1$ is —CH$_2$—CO—, the structure of $R_2$ is —NHCH$_2$—, and Z is an amide bond;

in formula V, the structure of $R_1$ is —CH$_2$S—, the structure of $R_2$ is —CH$_2$S—, and Z is a disulfide bond; and in formula VI, the structure of $R_1$ is —C(CH$_3$)$_2$S—, the structure of $R_2$ is —C(CH$_3$)$_2$S—, and Z is a disulfide bond.

In yet another preferred embodiment, the composition comprises an inhibitor having a structure selected from the group consisting of the structure depicted in formula 1a–h of FIG. 5, the structure depicted in formula 2a–h of FIG. 5, the structure depicted in formula 3a–i of FIG. 5, the structure depicted in formula 4a–d of FIG. 22, the structure depicted in formula 5a–i of FIG. 22, and the structure depicted in formula 6a–i of FIG. 22. Preferably, the inhibitor has a structure selected from the group consisting of the structure depicted in formula CVIII of FIG. 4 and the structure of Peptide 8 depicted in FIG. 27.

The invention further relates to a composition comprising an inhibitor of ribonucleotide reductase, wherein the inhibitor has the structure $Y_7$-$Y_8$-$Y_9$, wherein $Y_7$ is selected from the group consisting of an amino acid residue and an N-acetyl-amino acid residue;

$Y_8$ is selected from the group consisting of a nonstandard β-type 1 turn and a β-turn mimetic scaffold; and $Y_9$ is selected from the group consisting of one amino acid residue and two amino acid residues.

In one aspect, the inhibitor is selected from the group consisting of peptidomimetic 10, peptidomimetic P19, and Compound 23. In another aspect, the inhibitor is made by a synthetic method selected from the group consisting of the method depicted in FIG. 6, the method depicted in FIG. 7, and the method depicted in FIG. 26.

The invention also relates to a method of treating cancer in a patient comprising administering to the patient a pharmaceutical composition comprising a ribonucleotide reductase inhibitor of the invention.

The invention further relates to a method of treating an infection in a patient, the method comprising administering to the patient a pharmaceutical composition comprising a ribonucleotide reductase inhibitor of the invention.

BRIEF DESCRIPTION OF THE DRAWINGS

FIG. 9 is a representation of data obtained by 500 mHz, $^1$H NOESY (nuclear Overhauser effect spectroscopy) of 3 mM AcFTLDADF (SEQ ID NO: 16) plus 60 $\mu$M mR1 collected at 14° C. with mix time of 100-ms.

FIG. 11 is a representation of data obtained by 500 mHz $^1$H NOESY of 3 mM AcFTLDADL (SEQ ID NO: 18) plus 80 $\mu$M mR1 collected at 14° C.

FIG. 13 is stereoscopic representation of a superposition of the 26 lowest energy annealed structures of AcFTLDADF (SEQ ID NO: 16) which constitute Group I (from a total of the 299 structures). Alignment of backbone atoms from residues 1–7. N=N-terminus, C=C-terminus; dotted line is H-bond between Thr carbonyl oxygen and Ala N. Heavy atoms only are shown.

FIG. 23 depicts a chemical synthetic scheme described herein for making compounds 4a–d.

FIG. 24 depicts a chemical synthetic scheme described herein for making compounds 5a–i and 6a–i.

DETAILED DESCRIPTION OF THE INVENTION

Figure 1A:
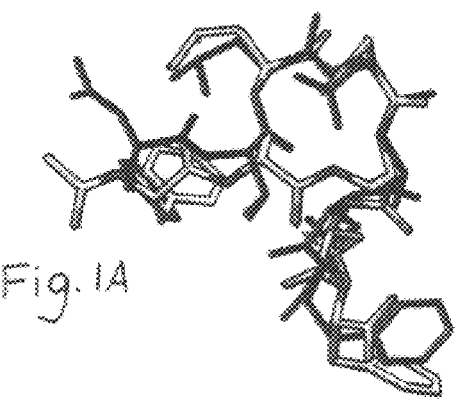
FIG. 1, comprising Panels A, B, and C, is a series of images which depict computer-generated models of peptides described herein. In Panel A, a series of connected gray lines which represents the structure of peptide 1a is overlaid atop a series of connected black lines which represents the structure of peptide AcFTLDADF (SEQ ID NO: 16). In Panel B, a series of connected gray lines which represents the structure of peptide 1a having protonated Asp residues is overlaid atop a series of connected black lines which represents the structure of the eight carboxy-terminal amino acid residues of the E. coli R2 subunit. In Panel B, a series of connected gray lines which represents the structure of peptide 1a having protonated Asp residues is overlaid atop a series of connected black lines which represents the structure of peptide AcFTLDADF (SEQ ID NO: 16).

Inhibitors of ribonucleotide reductase have been discovered according to the present invention which are useful for inhibition of this enzyme for the purpose of treating disorders associated with DNA replication, including, but not limited to tumor growth and metastasis, infectious disease, and the like.

The invention relates to an composition of matter comprising a peptide inhibitor of ribonucleotide reductase having the structure $Y_1$-$AA_1$-$AA_2$-$AA_3$-$AA_4$-$AA_5$-$AA_6$-$AA_7$. $Y_1$ may be any chemical substituent capable of blocking the amino terminus of a protein or a peptide. For example, $Y_1$ may be selected from the group consisting of an acetyl group, a benzoyl group, a dibenzyl acetyl group, and the like. $AA_1$ may be selected from the group consisting of Phe, Trp, N-methyl-Phe, and D-Phe. $AA_2$ may be selected from the group consisting of Thr, N-methyl-Thr, Leu, Val, and D-Thr. $AA_3$ may selected from the group consisting of Leu, γ-methyl-Leu, N-methyl-Leu, Ile, and D-Leu. AA$_4$ may be selected from the group consisting of Asp, D-Asp, Asp having a spirocyclopentane replacing the β-CH$_2$ of Asp, Asn having a pyrrolidine replacing the γ-NH$_2$ of Asn, N-methyl-Asp, and Glu. AA$_5$ may be selected from the group consisting of Phe, Val, Ile, N-methyl-Ala, and D-Ala. AA6 may be selected from the group consisting of Asp, D-Asp, Asp having a spirocyclopentane replacing the β-CH$_2$ of Asp, Asn having a pyrrolidine replacing the γ-NH$_2$ of Asn, and N-methyl Asp. As described herein in the examples, AA$_7$ can be any substantially hydrophobic amino acid residue. It is furthermore known that AA$_7$ can be a derivatized hydrophobic amino acid residue. Thus, by way of example, AA$_7$ may be selected from the group consisting of Phe, Tyr, Trp, N-methyl-Phe, D-Phe, o-methyl Phe, m-methyl Phe, o,o-dimethyl Phe, o,m-dimethyl Phe, o-hydroxyl Phe, m-hydroxyl Phe, p-hydroxyl Phe, m-chloro Phe, o-pyridyl Phe, and p-pyridyl Phe.

The invention also relates to a composition comprising an inhibitor of ribonucleotide reductase, wherein the inhibitor comprises a peptide having the structure

wherein:
 W$_1$ is selected from the group consisting of acetyl, one amino acid residue, two amino acid residues, one N-acetyl-amino acid residue, and an N-acetyl-amino acid residue linked to a second amino acid residue by a peptide bond;
 AA$_8$ is selected from the group consisting of Phe, p-amino-Phe, and p-azido-Phe;
 AA$_9$ is selected from the group consisting of Thr, Ser, and Ala;
 AA$_{10}$ is selected from the group consisting of Leu, Val, Phe, and Ala;
 AA$_{11}$ is selected from the group consisting of Asp, Asn, and Ala;
 AA$_{12}$ is selected from the group consisting of Ala, Leu, and Gly;
 AA$_{13}$ is selected from the group consisting of Asp, Asn, Leu, Ala, and Glu; and
 W$_2$ is selected from the group consisting of one amino acid residue and two amino acid residues. Conservative amino acid substitutions and modifications may be made for each of AA$_1$–AA$_7$. The RR inhibitory activity of peptides having such modified residues may be tested using the methods described herein. Preferably:
 AA$_{10}$ is selected from the group consisting of Leu, Val, and Phe;
 AA$_{11}$ is selected from the group consisting of Asp, and Asn;
 AA$_{12}$ is selected from the group consisting of Ala, and Leu; and
 AA$_{13}$ is selected from the group consisting of Asp, Asn, Leu, and Ala.

In another aspect, the composition of the invention comprises an inhibitor selected from the group consisting of Phe-Thr-Leu-Asp-Ala-Asp-Phe (SEQ ID NO: 3), Phe-Thr-Phe-Asn-Glu-Asp-Phe (SEQ ID NO: 7), Phe-Thr-Ile-Asp-Glu-Asp-Phe (SEQ ID NO: 9), Phe-Cys-Leu-Asn-Thr-Glu-Phe (SEQ ID NO: 11), Phe-Ser-Leu-Asp-Val-Asp-Phe (SEQ ID NO: 12), Acetyl-Asn-Ser-Phe-Thr-Leu-Asp-Ala-Asp-Phe (SEQ ID NO: 13), Acetyl-Ser-Phe-Thr-Leu-Asp-Ala-Asp-Phe (SEQ ID NO: 14), Ser-Phe-Thr-Leu-Asp-Ala-Asp-Phe (SEQ ID NO: 15), Acetyl-Phe-Thr-Leu-Asp-Ala-Asp-Phe (SEQ ID NO: 16), Phe-Thr-Leu-Asp-Ala-Asp-Phe (SEQ ID NO: 17), Acetyl-Phe-Thr-Leu-Asp-Ala-Asp-Leu (SEQ ID NO: 18), Acetyl-Tyr-Thr-Leu-Asp-Ala-Asp-Phe (SEQ ID NO: 19), Acetyl-(p-amino-Phe)-Thr-Leu-Asp-Ala-Asp-Phe, Acetyl-(p-azido-Phe)-Thr-Leu-Asp-Ala-Asp-Phe, Acetyl-Phe-Ser-Leu-Asp-Ala-Asp-Phe (SEQ ID NO: 20), Acetyl-Phe-Ala-Leu-Asp-Ala-Asp-Phe (SEQ ID NO: 21), Acetyl-Phe-Thr-Val-Asp-Ala-Asp-Phe (SEQ ID NO: 22), Acetyl-Phe-Thr-Phe-Asp-Ala-Asp-Phe (SEQ ID NO: 23), Acetyl-Phe-Thr-Ala-Asp-Ala-Asp-Phe (SEQ ID NO: 24), Acetyl-Phe-Thr-Leu-Asn-Ala-Asp-Phe (SEQ ID NO: 25), Acetyl-Phe-Thr-Leu-Ala-Ala-Asp-Phe (SEQ ID NO: 26), Acetyl-Phe-Thr-Leu-Asp-Gly-Asp-Phe (SEQ ID NO: 27), Acetyl-Phe-Thr-Leu-Asp-Leu-Asp-Phe (SEQ ID NO: 28), Acetyl-Phe-Thr-Leu-Asp-Ala-Glu-Phe (SEQ ID NO: 29), Acetyl-Phe-Thr-Leu-Asp-Ala-Asn-Phe (SEQ ID NO: 30), Acetyl-Phe-Thr-Leu-Asp-Ala-Leu-Phe (SEQ ID NO: 31), Acetyl-Phe-Thr-Leu-Asp-Ala-Ala-Phe (SEQ ID NO: 32), Acetyl-Phe-Thr-Leu-Asp-Ala-Asp-Leu (SEQ ID NO: 33), and Acetyl-Phe-Thr-Leu-Asp-Ala-Asp-Phe-Ala-Ala (SEQ ID NO: 34).

The invention also includes a composition comprising an RR inhibitor as described herein, conjugated with a cell surface ligand-binding molecule. The cell surface ligand-binding molecule is preferably one selected from the group consisting of folic acid, the nontoxic B subunit of *E. coli* heat labile enterotoxin, and a fusion protein of the nontoxic B subunit of *E. coli* heat labile enterotoxin.

The invention further includes a composition comprising an inhibitor of ribonucleotide reductase, wherein the inhibitor has a structure selected from the group consisting of the structure depicted in formula VII of FIG. 5 and the structure depicted in formula VIII of FIG. 5, wherein
 X$_1$ is from zero to twenty amino acids;
 X$_2$ is from zero to five amino acids;
 X$_3$ has a structure selected from the group consisting of the structure depicted in formula II of FIG. 5, wherein R$_1$ and R$_2$ are independently selected from the group consisting of amino acid side chain moieties and Z is selected from the group consisting of amide and disulfide bonds, and the structure depicted in formula III of FIG. 5; and
 R$_3$ is selected from the group consisting of oligomethylene chains of length C$_2$ to C$_6$.

The invention further includes a composition comprising an inhibitor of ribonucleotide reductase, wherein the inhibitor has the structure Y$_2$-Y$_3$-Phe-Y$_5$-Asp-Y$_6$-Y$_4$—OH, wherein
 Y$_2$ is H or a blocking group;
 Y$_3$ is from zero to twenty amino acids;
 Y$_4$ is from zero to five amino acids;
 Y$_5$ has a structure selected from the group consisting of the structure depicted in formula II of FIG. 5, wherein R$_1$ and R$_2$ are independently selected from the group consisting of amino acid side chain moieties and Z is selected from the group consisting of amide and disulfide bonds, and the structure depicted in formula III of FIG. 5; and
 Y$_6$ is selected from the group consisting of Phe, Tyr, Trp, N-methyl-Phe, D-Phe, o-methyl Phe, m-methyl Phe, o,o-dimethyl Phe, o, m-dimethyl Phe, o-hydroxyl Phe, m-hydroxyl Phe, p-hydroxyl Phe, m-chloro Phe, o-pyridyl Phe, and p-pyridyl Phe. Preferably, Y$_3$ is from zero to ten amino acids and Y$_4$ is from zero to five amino acids. More preferably, Y$_3$ is from zero to five amino acids and Y$_4$ is from zero or one amino acid.

Most preferably, $Y_3$ and $Y_4$ are each zero amino acids. In another preferred embodiment, $Y_2$ is acyl, $Y_3$ is Asn-Ser, $Y_4$ is zero amino acids, and $Y_5$ has the structure depicted in formula II of FIG. 5, wherein the structures of $R_1$, $R_2$, and Z are selected from the group consisting of formulas IV, V, and VI of FIG. 5, wherein in formula IV, the structure of $R_1$ is —$CH_2$—CO—, the structure of $R_2$ is —$NHCH_2$—, and Z is an amide bond;

in formula V, the structure of $R_1$ is —$CH_2S$—, the structure of $R_2$ is —$CH_2S$—, and Z is a disulfide bond; and in formula VI, the structure of $R_1$ is —$C(CH_3)_2S$—, the structure of $R_2$ is —$C(CH_3)_2S$—, and Z is a disulfide bond.

Figure 22A:
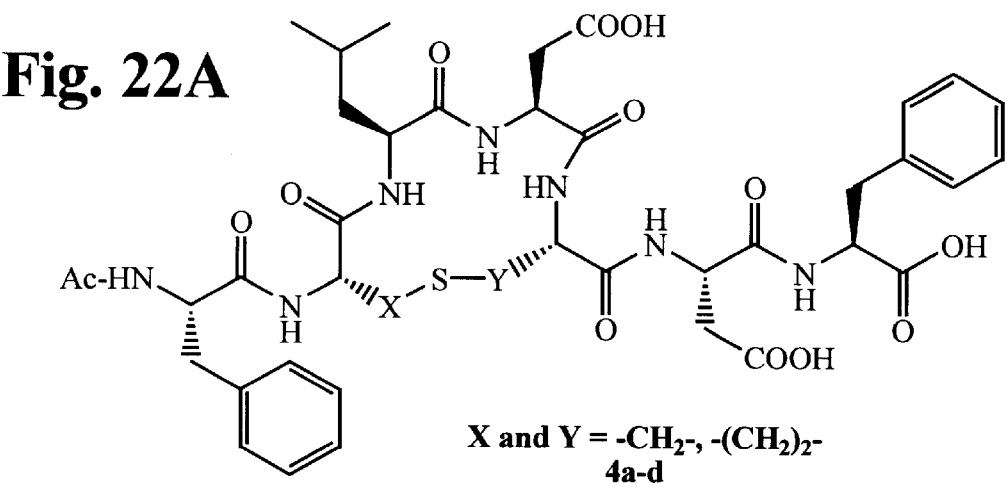
FIG. 22 is a pair of images depicting the chemical formulas of compounds 4a–d, 5a–i, and 6a–i, as described herein.
Figure 22B:
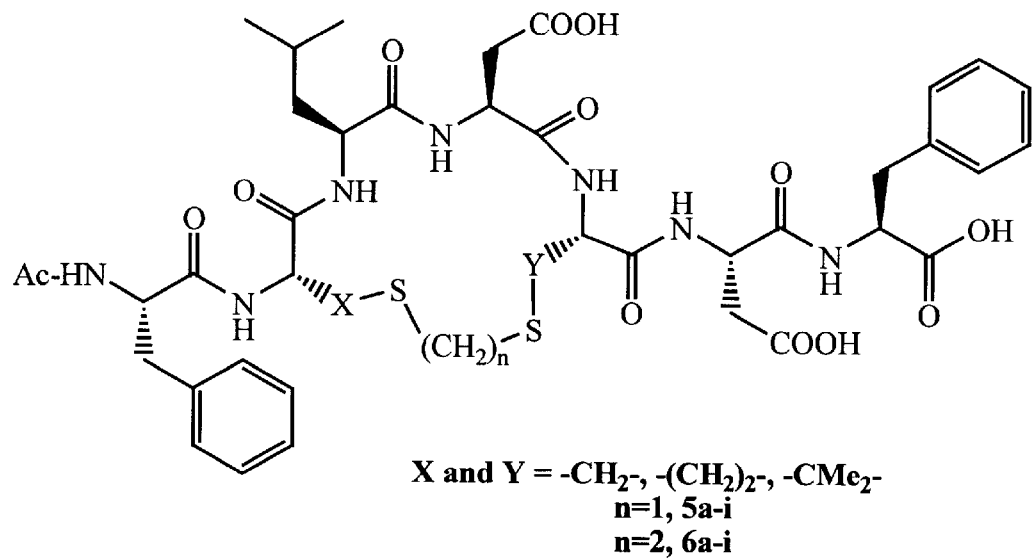

The RR inhibitor of the invention may have a chemical structure selected from the group consisting of the structure depicted in formula 1a–h of FIG. 5, the structure depicted in formula 2a–h of FIG. 5, the structure depicted in formula 3a–i of FIG. 5, the structure depicted in formula 4a–d of FIG. 22, the structure depicted in formula 5a–i of FIG. 22, and the structure depicted in formula 6a–i of FIG. 22. It is understood that the notation 1a–h refers to eight distinct compounds, corresponding to the eight combinations of n=1 or 2 and m=1–4 which are possible. Similarly, 2a–h refers to eight distinct compounds, 3a–i refers to nine distinct compounds, 4a–d refers to four distinct compounds, 5a–i refers to nine distinct compounds, and 6a–i refers to nine distinct compounds. Preferably, the inhibitor has a structure selected from the group consisting of the structure depicted in formula CVIII of FIG. 4 and the structure of Peptide 8 depicted in FIG. 27.

The leucine residue in each of chemical structures 1a–h, 2a–h, 3a–i, 4a–d, 5a–i, and 6a–i are depicted as L-leucine for the purpose of illustration. This residue may, in each structure, be either L-leucine or D-leucine. Substitution of an L-amino acid by the enantiomeric D-amino acid in position 2 of a β-turn is known to stabilize the secondary structure of the β-turn while retaining side chain relationships (Chandrasekaran et al., 1973, Biochim. Biophys. Acta 303:14).

The invention still further includes a composition comprising an inhibitor of ribonucleotide reductase, wherein the inhibitor has the structure $Y_7$-$Y_8$-$Y_9$, wherein $Y_7$ is selected from the group consisting of an amino acid residue and an N-acetyl-amino acid residue;

$Y_8$ is selected from the group consisting of a nonstandard β-type 1 turn and a β-turn mimetic scaffold; and $Y_9$ is selected from the group consisting of one amino acid residue and two amino acid residues.

A β-turn mimetic scaffold is a molecular structure which does not naturally occur in a protein and which comprises an arrangement of atoms which is structurally similar to a portion of a naturally occurring protein which comprises a β-turn. The inhibitor may, for example, be peptidomimetic 10, peptidomimetic P19, or Compound 23.

Figure 6A:
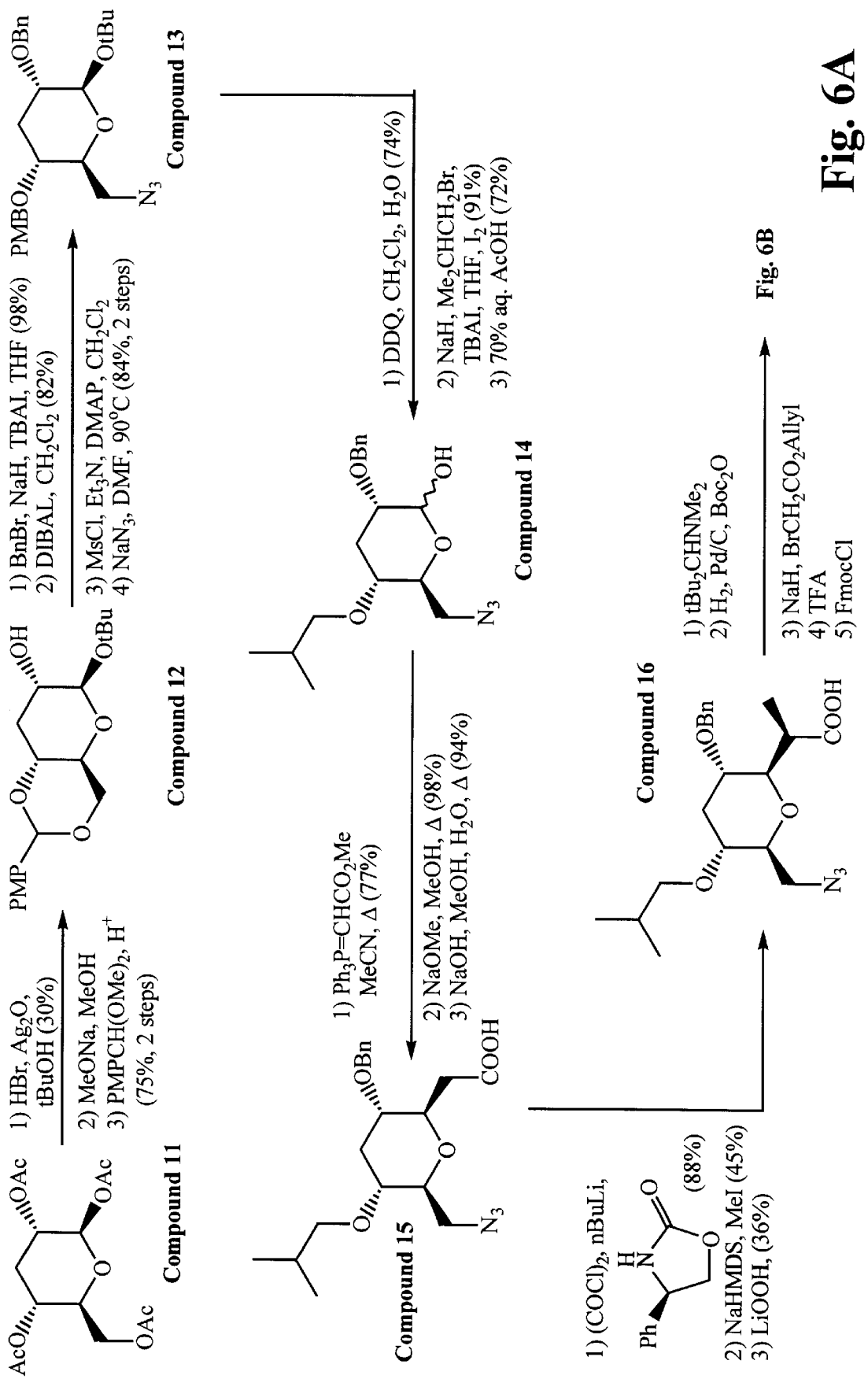
FIG. 6 depicts the chemical synthetic scheme described herein for making the peptidomimetic 10.
Figure 6B:
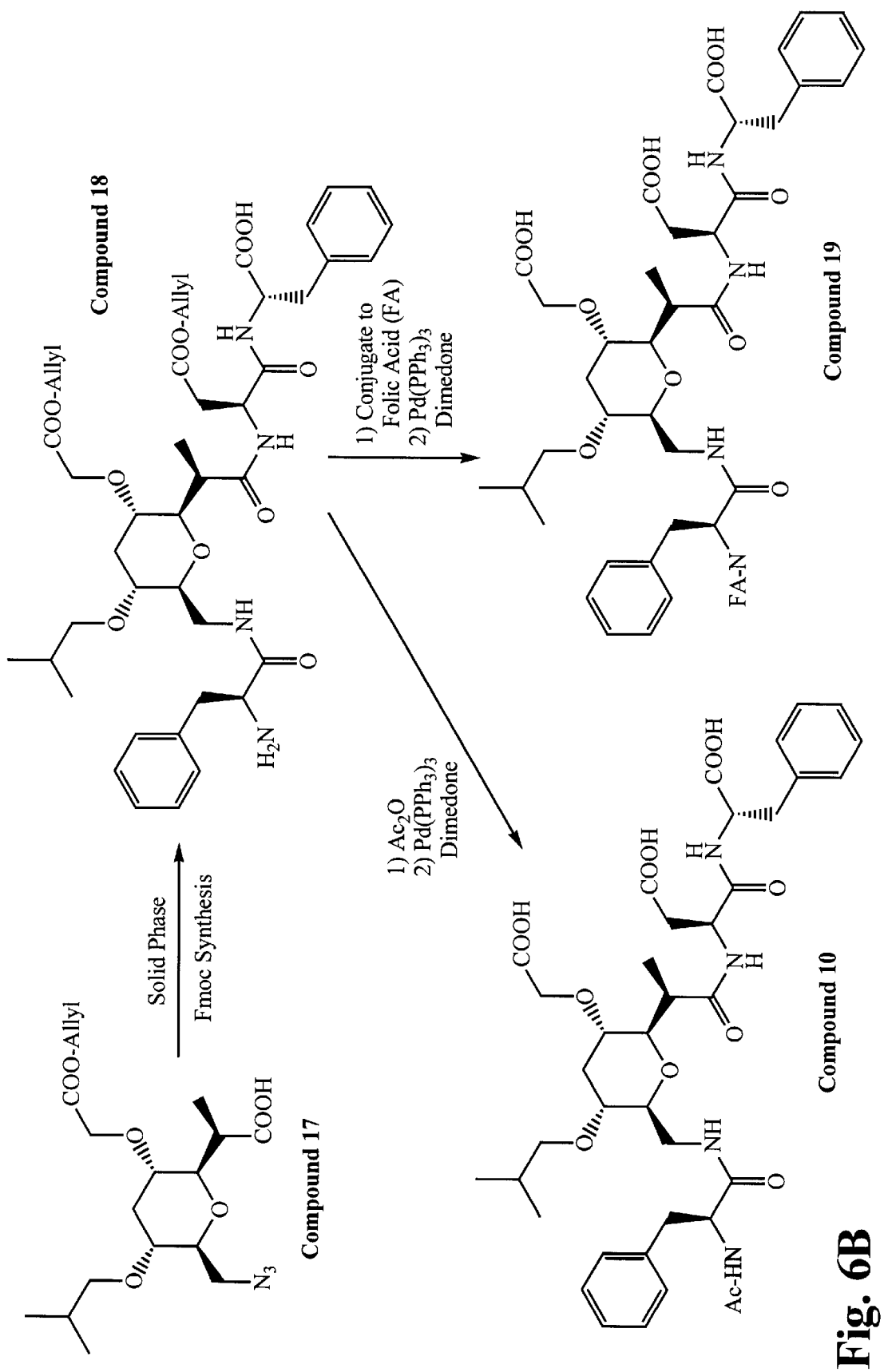
Figure 7A:
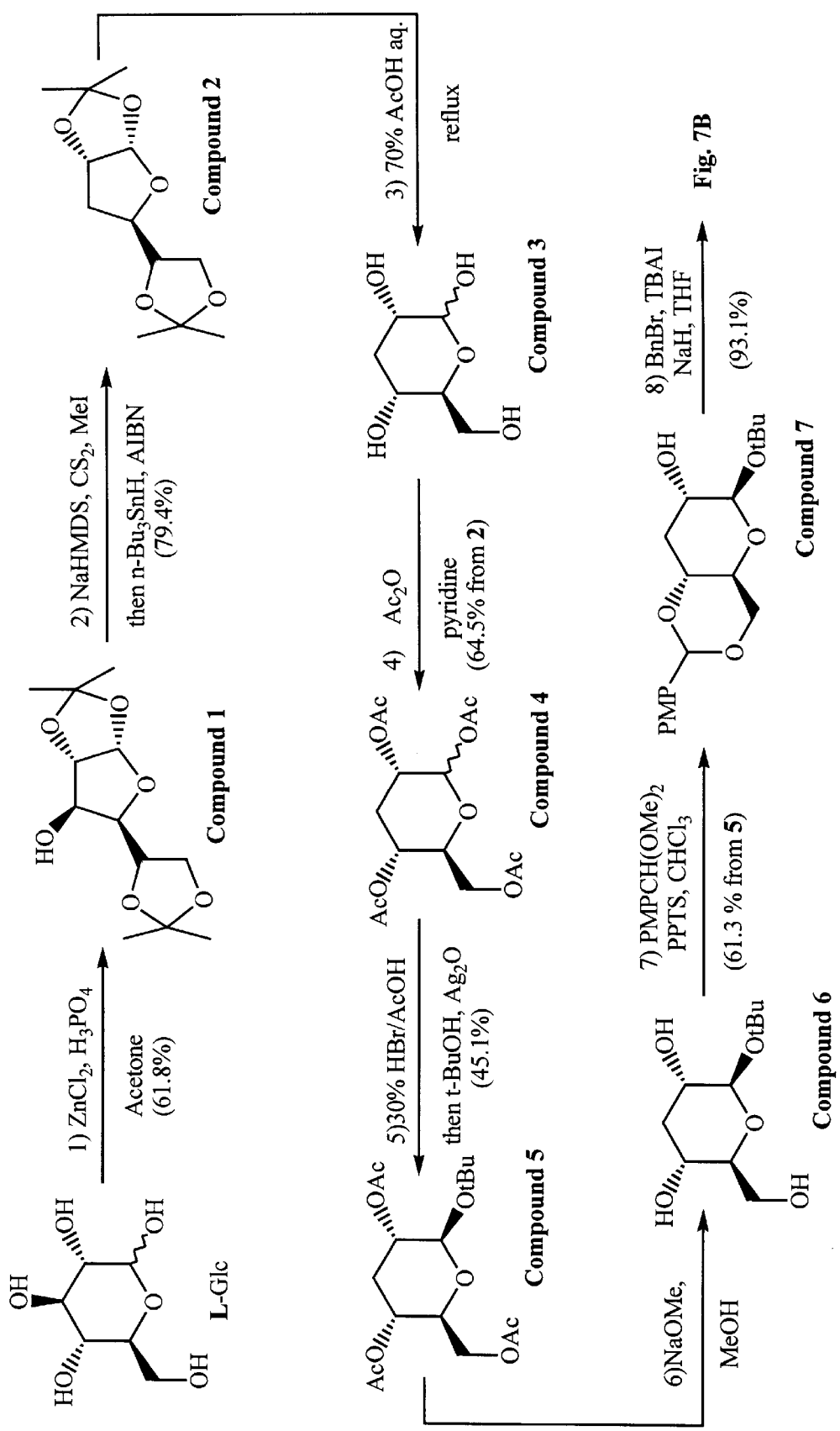
FIG. 7, depicts the chemical synthetic scheme described herein for making the peptidomimetic referred to herein as Compound 23.
Figure 7B:
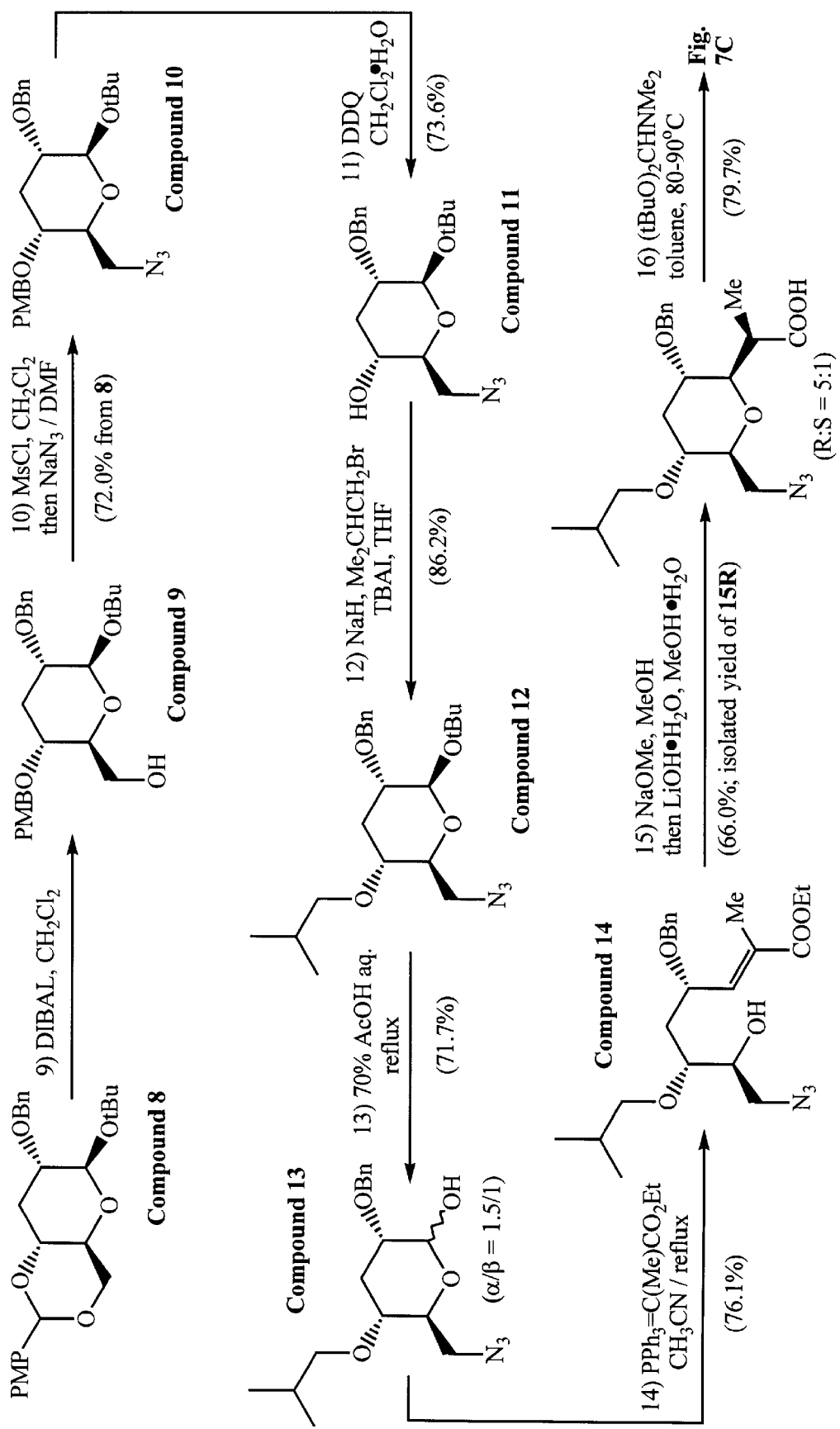
Figure 7C:
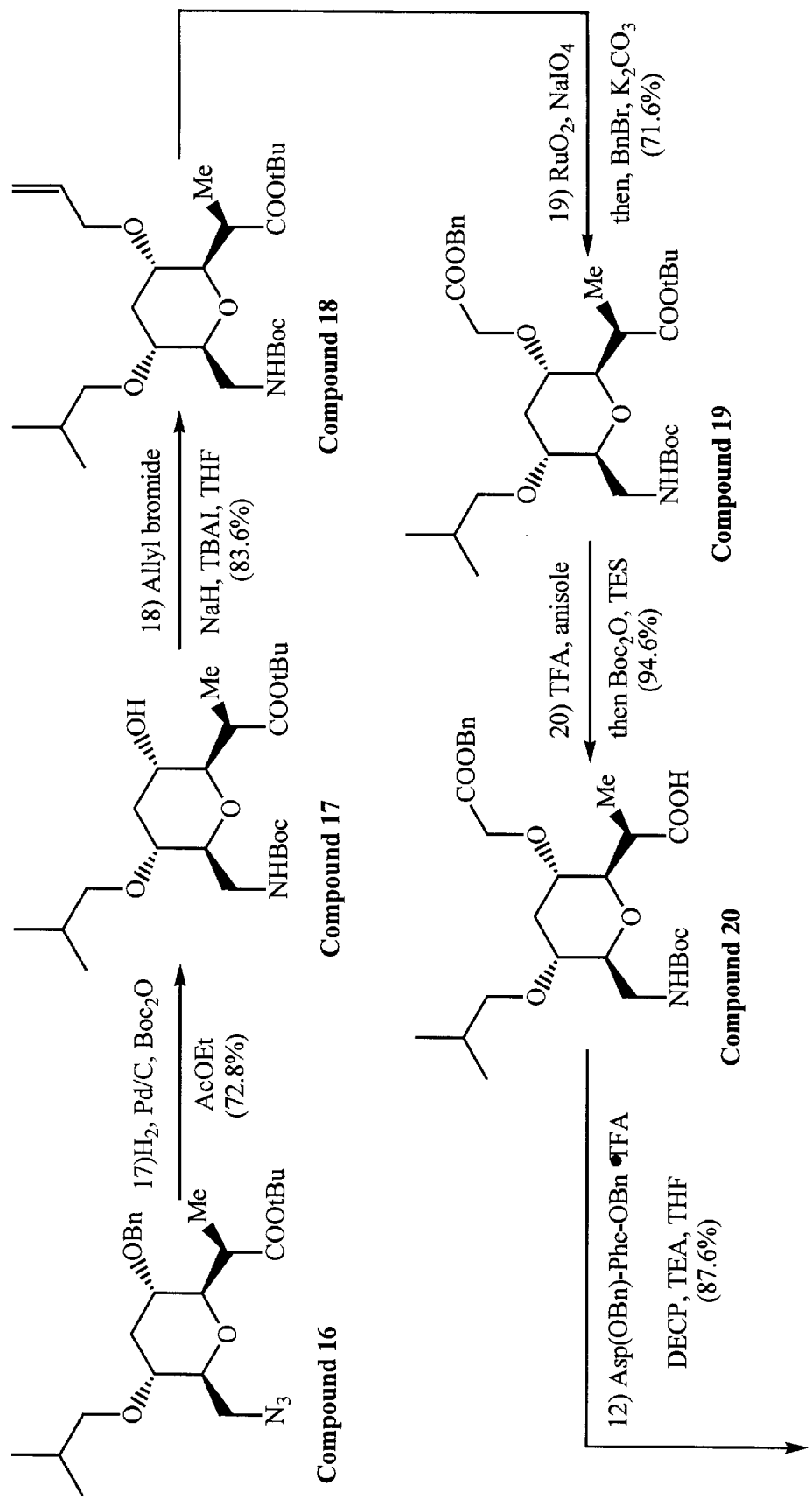
Figure 7D:
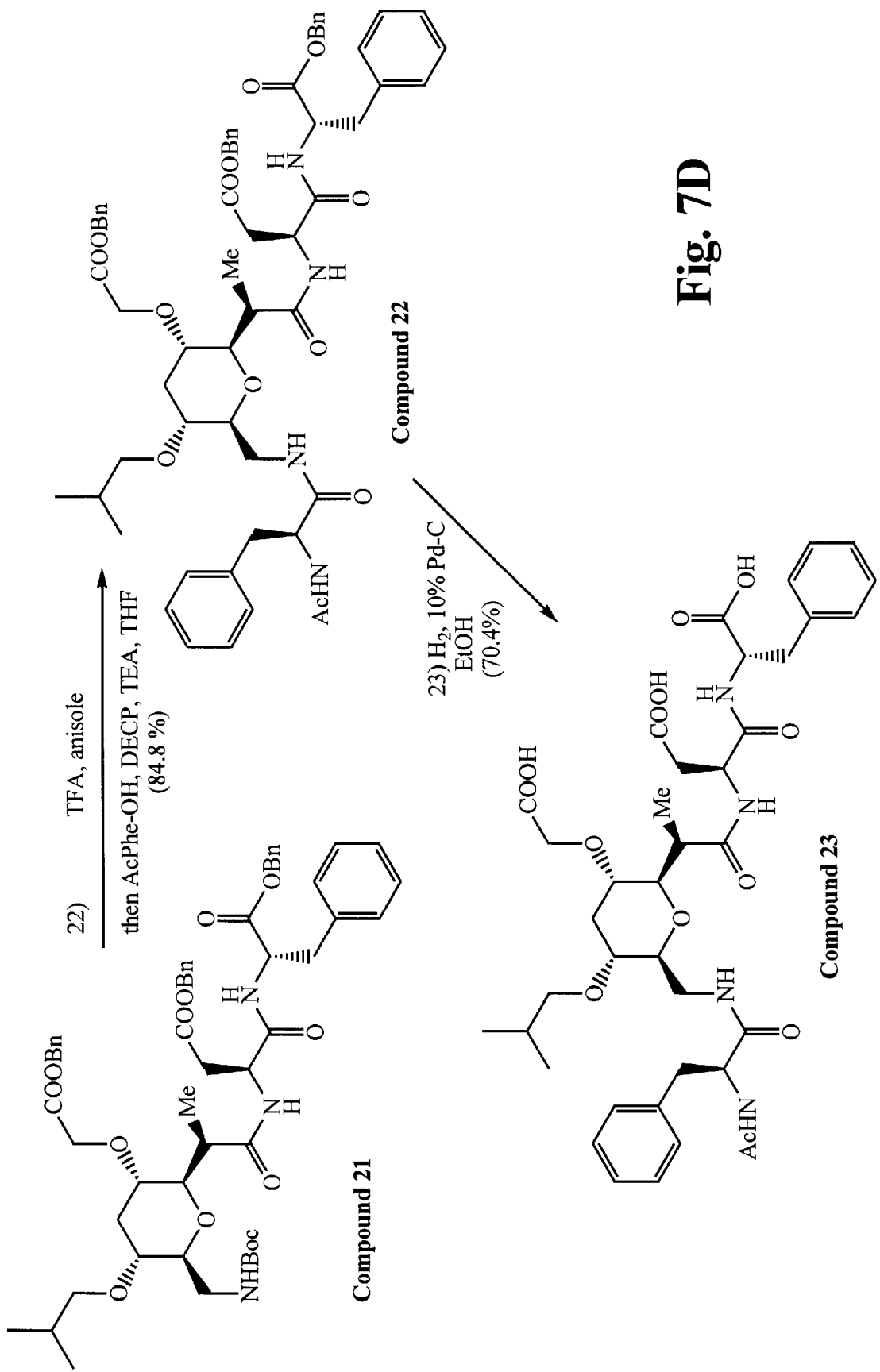
Figure 26A:
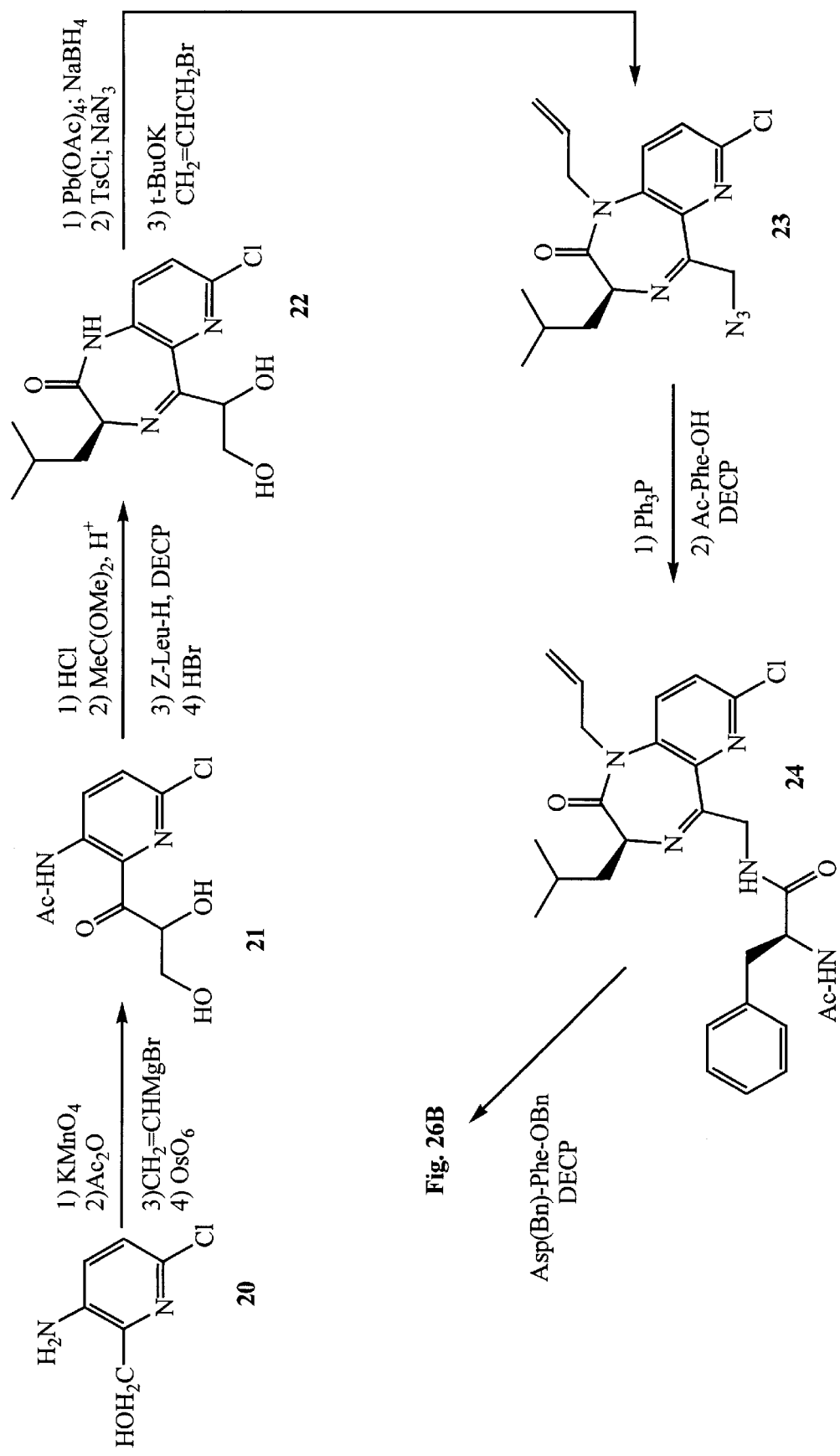
FIG. 26 depicts a chemical synthetic scheme described herein for making Peptidomimetic P19.
Figure 26B:
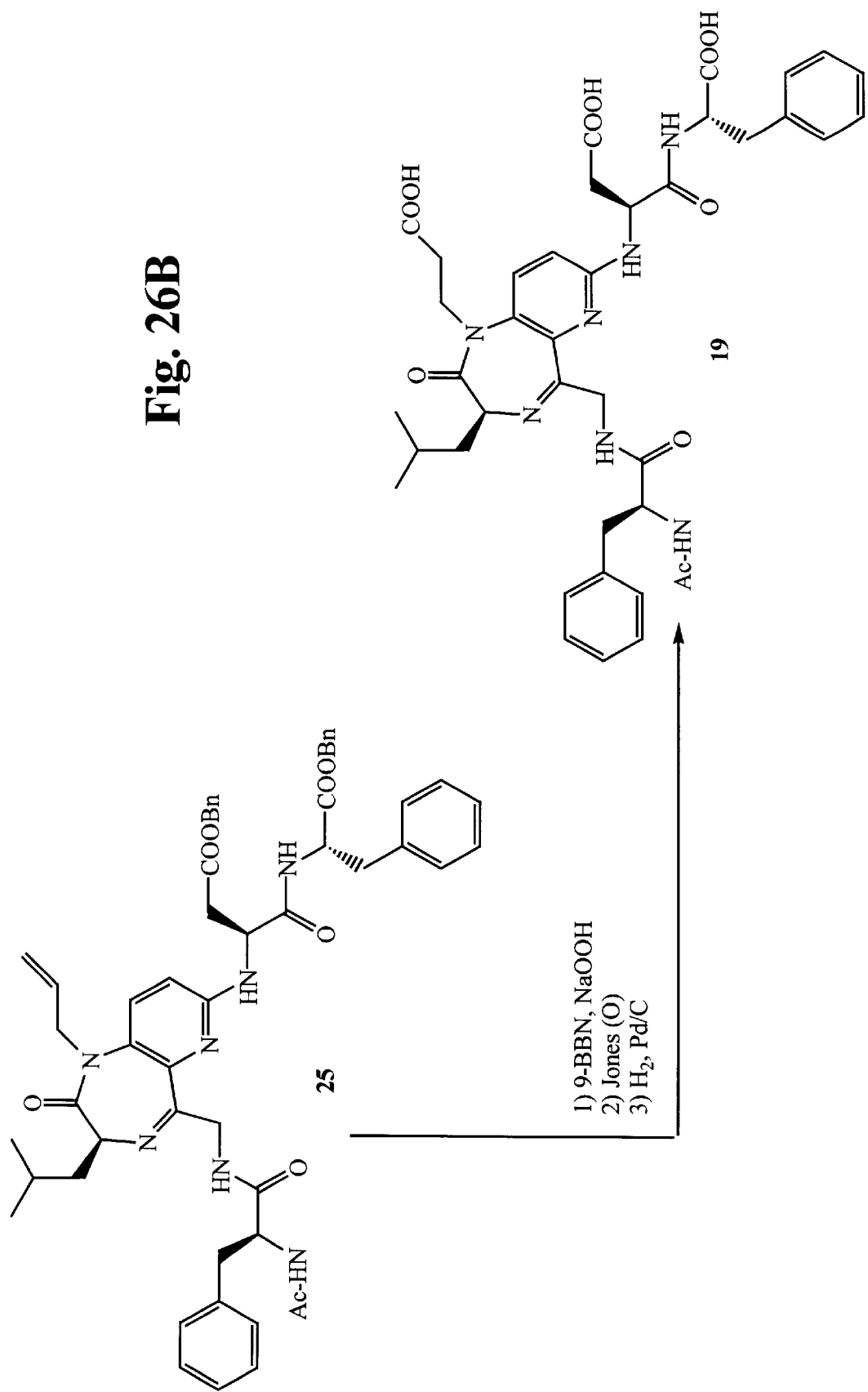

The inhibitor may be generated using a synthetic method selected from, for example, the group consisting of the method depicted in FIG. 6, the method depicted in FIG. 7, and the method depicted in FIG. 26. Details regarding the synthetic scheme depicted in FIG. 6 are described in Example 4 herein. Details regarding the synthetic scheme depicted in FIG. 7 are described in Example 5 herein. Details regarding the synthetic scheme depicted in FIG. 26 are described in Example 4 herein.

Data described herein in Example 9 indicate the Phe residue corresponding to the carboxyterminal amino acid residue of R2 significantly influences the ability of the carboxyterminal portion of R2 or of a peptide, peptide analog, or peptidomimetic derived from R2 to interact with R1. Thus, the ability of the inhibitors of the invention to inhibit RR activity may be improved by selecting carboxyterminal Phe residue derivatives which take advantage of potential interactions between the Phe derivative and sites in the binding region(s) of the R1. For example, it appears advantageous to substitute an o-methyl Phe residue, a m-methyl Phe residue, an o,o-dimethyl Phe residue, an o,m-dimethyl Phe residue, an o-hydroxyl Phe residue, a m-hydroxyl Phe residue, a p-hydroxyl Phe residue, a m-chloro Phe residue, an o-pyridyl Phe residue, or a p-pyridyl Phe residue in place of the Phe residue normally located at the carboxyl terminus of R2 in an inhibitor derived from the carboxyl terminus of R2 if inhibition of RR is desired.

Any of the embodiments of the composition of the invention described herein may further comprises a pharmaceutically acceptable carrier, preferably one selected from the group consisting of a liposome and phosphate buffered saline at physiological pH. Numerous other pharmaceutically acceptable carriers are known in the art and can be formulated with the composition of the invention using methods known in the art.

The composition of the invention may be used to inhibit the growth and replication of tumor cells and the growth and/or replication of infectious agents, such as viruses, bacteria, fungi and parasites. The composition of the invention may be used in vitro for inhibition of virus or cellular DNA replication, or they may be administered to an animal, preferably a human, in vivo for the same purpose.

When the composition of the invention is used in vitro, it may be suspended in any acceptable carrier, such as physiological saline or any other buffer which is compatible with the particular cell or viral system being targeted. In vitro formulations will thus be readily apparent to the artisan skilled in the art of inhibiting cell or virus DNA replication.

To test whether a ribonucleotide reductase inhibitor generated according to one of the protocols described herein is capable of inhibiting replication of a virus, the inhibitor is administered to cells either before, during or after infection of the cells with the desired virus. Following a period of incubation which will vary depending on the type of cells and virus used, virus replication is then assessed in any virus replication assay, including, but not limited to, a plaque assay, immunological assays for detection of replication products and DNA replication assays.

In a similar manner, the effects of the inhibitor on the replication of other infectious agents may be assessed by treating the infections agent or cells infected with the infectious agent with the inhibitor for a proscribed length of time and then assessing the replication of the infectious agent in any assay designed for that purpose.

To test the effects of an inhibitor of ribonucleotide reductase on tumor cell growth, the inhibitor is added to the cells and any subsequent growth of the cells is assessed in any cell growth assay available in the art.

Specific uses of the inhibitors of the invention are described in detail elsewhere herein.

When a ribonucleotide reductase inhibitor of the invention is administered in vivo in an animal, it may be formulated in any suitable formulation which will depend on any number of factors including the particular condition to be treated, the type and age of the animal, the degree of disease or disorder in the animal, and the like. The inhibitors of the invention may be administered to an animal in one of the traditional modes (e.g., orally, parenterally, transdermally or transmucosally), in a sustained release formulation using a biodegradable biocompatible polymer, or by on-site delivery using micelles, gels and liposomes, or rectally (e.g., by suppository or enema) or nasally (e.g., by nasal spray). The appropriate pharmaceutically acceptable carrier will be evident to those skilled in the art and will depend in large part upon the route of administration. Formulations may also include those which render the inhibitor capable of crossing the blood brain barrier when administered by any other route. In addition, the inhibitors of the invention may be formulated so as to target specific types of cells. For example, it is now known in the art to encapsulate or otherwise formulate compounds such that they a directed to specific receptors on cells. Such formulations include antibody-tagging formulations, receptor-ligand binding formulations and the like.

The inhibitors of the invention may also be administered by a peripheral route, or they may be administered systemically to the animal. "Peripheral administration" as used herein, denotes administration of a compound to an animal by any route other than direct administration to the brain. Thus, peripheral administration includes, but is not limited to, oral, nasopharyngeal, intraperitoneal, intramuscular and intravenous administration of any of the compounds of the invention.

Protocols for treatment of animals involving administration of a ribonucleotide reductase inhibitor will be apparent to those skilled in the art and will vary depending upon the type of disease and the type and age of the mammal. Treatment regimes which are contemplated include a single dose or dosage which is administered hourly, daily, weekly or monthly, or yearly. Dosages may vary from 1 $\mu$g to 1000 mg/kg of body weight of the inhibitor and will be in a form suitable for delivery of the compound to the animal. The route of administration may also vary depending upon the disorder to be treated.

In the present study, the binding of mammalian R2 C-terminal peptide to mammalian R1 as an important step in the development of potential cancer chemotherapeutic agents has been examined. In an earlier structure-function study of the inhibition of mammalian RR by R2 C-terminal peptides, it was demonstrated that the N-acetylated heptapeptide AcFTLDADF (SEQ ID NO: 16) was the minimal core peptide needed for effective inhibition of RR. Further, changes in the sequence and length of this peptide substantially affect inhibitory potency (Yang et al., 1990, FEBS Lett. 272:61–64; Fisher et al., 1993, J. Med. Chem. 36:3859–3862). In addition, the structure of AcYTLDADF (SEQ ID NO: 19) has been determined when this compound is bound to mR1 using restraints derived from two-dimensional transferred nuclear Overhauser effect spectroscopy (trNOESY) and restrained molecular dynamics (rMD) (Fisher et al., 1995, Nature Struct. Biol. 2:951–955). This structure is characterized by a nonstandard type 1 reverse $\beta$-turn, similar to the reverse turn seen in a trNOESY study of the N-acetylated *E. coli* R2 (eR2) C-terminal peptide, AcDDLSNFQL (SEQ ID NO: 35), bound to eR1 (Bushweller et al., 1991, Biochemistry. 30:8144–8151). The structure of bound AcYTLDADF (SEQ ID NO: 19) was determined first, even though it binds mR1 with 15-fold lower affinity than AcFTLDADF (SEQ ID NO: 16), because replacement of Phe 1 with Tyr made assigrunent of the NMR spectra more straightforward.

In the present study, the structure of mRI-bound AcFTLDADF (SEQ ID NO: 16) has been determined and the data establish that this structure arises from specific-site binding. Comparisons of this structure with those of mR1-bound AcYTLDADF (SEQ ID NO: 19) and eR1-bound DDLSNFQL (SEQ ID NO: 36), the latter determined by X-ray crystallography (Uhlin et al., 1994, Nature. 370, 533–539 Protein Data Bank Reference—1r1r) allow rationalization of structure-activity studies on mR2 C-terminal binding to mR1 and suggest a general strategy for the design of peptidomimetic RR inhibitors.

The selectivity of an RR inhibitor of the invention may be determined by comparing the activity of RR obtained from a first organism or cell type in the presence and absence of the RR inhibitor with the activity of RR obtained from a second organism or cell type in the presence and absence of the RR inhibitor. As is well understood in the art, it is desirable to selectively inhibit the activity of a RR of a pathological organism or cell type relative to the activity of a RR of a patient. Thus, it is desirable to selectively inhibit the RR of a human pathogen or of a pathological cell type of a human, such as a cancer cell, for example.

Uses of the Ribonucleotide Inhibitors of the Invention

The inhibitors of the invention are useful in cancer chemotherapy and as antiviral agents and anti-infectious agents in general. Inhibition of RR activity is a well recognized target for rational design of cancer chemotherapeutic and antiviral agents, given the direct role that this enzyme plays in regulating DNA replication (Cory et al., Adv Enzyme Regul.1988, 27, 437–455) as well as its indirect role in regulating other enzymes in the DNA synthesis pathway through its control of the nucleotide pool. With respect to cancer, Jensen et al. (1994, Proc. Natl. Acad. Sci. U.S.A., 91:9257–9261) have shown that human R2 is expressed at a level 4—30 times higher in premalignant breast lesions (noncomedo ductal carcinoma in situ—DCIS) than in normal breast epithelial cells, raising the question of whether R2 expression is correlated with progression to invasive cancer.

Thus, the inhibitors of ribonucleotide reductase described in the present invention may be used to treat cancer and infectious disease by following the protocols described and referenced herein.

A variety of small molecules, have been shown to inhibit tumor cell proliferation and viral replication in tissue culture through inhibition of RR activity (Tihan et al., 1991, Adv. Enzyme Regul. 31:71–78; Parker et al., 1991, Cancer Res. 51:2386–2394; Heinemann et al., 1990, Mol. Pharmacol. 38:567–572; Cory et al., 1993, Adv. Enzyme Regul. 33:129–140; Cory et al., 1994, Biochem. Pharm. 47(2):365–371; Matsumoto et al., 1990, Cancer Chemother. Pharmacol. 26:323–329; Blumenkopf et al., 1992, J. Med. Chem. 35:2306–2314; Nocentini et al., 1993, Cancer Research 53:19–26; Nyholm et al., 1993, J. Biol. Chem. 268 (35):26200–26205; Pötsch et al., 1994, Mol. Pharm. 45:792–796). One group of such molecules acts on the R2 subunit, via tyrosine radical quenching, Fe (III) reduction and/or sequestration, or some combination of these effects, although none of them appear to have any obvious specific binding site R2. This group contains functionalities such as hydroxamate, catechol, thiosemicarbazone, Fe-chelator, either alone, as in hydroxyurea or catechol itself, or in combination, as in trimidox (3,4,5-trihydroxybenzohydroxamic acid), 1-formylisoquinoline thiosemicarbazone, 2-acetylpyridinethiocarbanohydrazone, or 2,2'-bipyridyl-6-carbothioamide. A second group are 2'-deoxy-2'-substituted (azido, methylene, or difluoro) nucleoside derivatives capable of irreversibly inactivating the R1 subunit, through covalent modification of the substrate binding site.

The inhibitory effects of both groups of compounds have been shown to be synergistic when added together with antiviral nucleosides. Such synergy is thought to arise from the effects of RR inhibitors in decreasing levels of cellular dNTPs, leading to an increased uptake and metabolism of the nucleoside inhibitors of DNA synthesis. Some recent examples include the inhibition of colon tumor cell growth through combination of trimidox and araC (Szekeres et al., 1994, Wien Klin. Wochenschr. 106 (14):459–463) and of HIV-1 replication through combination of either hydroxyurea and ddl (Lori et al., 1994, Science 266:801–805), or 2'-deoxy-2'-difluorocytidine or 2'-deoxy-2'-azidocytidine and AZT (Bianchi et al., 1994, Proc. Natl. Acad. Sci. USA 91:8403–8407).

A large number of human trials have been carried out using a) inhibitors of RR alone, b) combinations of RR inhibitors with other cancer chemotherapeutic agents, and c) RR inhibitors in combination with radiotherapy. These studies include the following: phase 1 trials in patients with metastatic malignancies (Carmichael et al., 1990, Br. J Cancer 61:447–450; Lokich et al., 1991, Cancer 68:744–746), neuroblastoma (Kushner et al., 1991, Cancer 68:242–247), malignant melanoma (Bergmann et al., 1989, Eur. J. Cancer Clin. Oncol. 25 Suppl 3, S31–S36), non-small cell carcinoma of the lung (NSCLC) (Vokes et al., 1990, Cancer 66:437–442; Cantwell et al., 1989, Cancer Chemother. Pharmacol. 23:252–254), acute and chronic leukemias (Archimbaud et al., 1989, Cancer Chemother. Pharmacol. 25:223–225; Cannistra et al., 1989, Leukemia 3:328–334; Lowenberg et al., 1989, J. Clin. Oncol. 7:1268–1274; Berman et al., 1989, Leukemia 3:115–121), metastatic renal carcinoma (Kuhbock et al., 1988, J. Survey of Chemotherapy of Metastatic Renal Cancer. Semin. Surg. Oncol.4:87–90), malignant gliomas (Rozental et al., 1989, Cancer 63:2475–2481; Shapiro et al., 1989, J. Neurosurg. 71:1–9), cervical cancer (Piver et al., 1989, J. Surg. Oncol. 42:120–125; Piver, 1990, Semin. Surg. Oncol. 6:359–363), head and neck tumors (Fountzilas et al., 1990, Cancer 66:1453–1460; Vokes et al., 1989, J. Clin. Oncol. 7:761–768), hypereosinophilic syndrome (Smit et al., 1991, Cancer 67:2826–2827), breast, NSCLC, glioblastoma, ovarian, and mesothelioma (Albain et al., 1990, Cancer Chemother. Pharmacol. 27:33–40), primary lymphoma of the CNS (Chamberlain et al., 1990, Arch. Neurol. 47:1113–1116), and colon cancer (Di Costanzo et al., 1991, J. Surg. Oncol. Suppl. 2:137–140). Most of these studies indicate the utility of an RR inhibitor in one or more arms of a chemotherapeutic protocol. However, as expected, not all of these malignancies demonstrate a uniformly positive response to RR inhibitors. This lack of chemotherapeutic efficacy has, in part, been attributed to the observation that expression of RR is tightly coupled to S phase in the cell division cycle (Bjorklund et al., 1990, Biochemistry 29:5452–5458) whereas in the clinical situation, only a small fraction of the malignant cell population may be undergoing growth and division (Tay et al., 1991, J. Clin. Invest. 87(2):519–527; Thompson et al., 1989, Cancer Commun. 1(4):253–260). An interesting approach to overcome this problem has been to induce leukemic cells into S phase with cytokine stimulation and to then use an S phase active agent such as an inhibitor of RR to produce and maintain malignant cell death (Cannistra et al., 1989, Leukemia 3:328–334). Gene amplification and loss of feedback regulation (Carter et al., 1989, Cancer Commun. 1(1):13–20; Wright et al., 1990, Proc. Natl. Acad. Sci. U S A. 87(5):1791–1795) are two additional mechanisms of chemotherapeutic resistance that have been postulated. Although it is clear that resistance to RR inhibitors may emerge during therapy and it has been postulated that alterations in RR activity might induce mutations leading to secondary cancers (Tagger et al., 1989, J. Cancer Res. Clin. Oncol. 115:429–434; Dastugue et al., 1990, Cancer Genet Cytogenet. 44:275–276; Fenaux et al., 1990, Cancer 66:549–556; Lofvenberg et al., 1990, Cancer Genet. Cytogenet. 49:57–67; Mattano et al., 1990, Cancer Res. 50:4566–4571), the development of safer, more efficacious ribonucleotide reductase inhibitors remains a high priority for targeted cancer drug design.

A potential problem with the RR inhibitors used to date has been their relative lack of specificity as RR inhibitors, since each of the two groups mentioned above can interact with a variety of other enzymes. The C-terminal R2 oligopeptides that are included in the present study overcome this problem by their affinity for a specific site on the mR1 subunit, an affinity that may be enhanced as described herein. In this connection it is important to emphasize the results of Liuzzi et al., (1994, Nature 372:695–698) and Moss et al. (1995, J. Med. Chem. 38:3617–3623), who showed that peptide derivatives based on the HSV R2 C-terminus inhibit HSV replication in tissue culture, an effect that is synergized by the presence of acyclovir. Interestingly, cells infected with the HSV-Rl variants described herein, that exhibit weak resistance to an R2 C-terminal nonpeptide peptidomimetic also exhibit increased sensitivity to acyclovir, presumably because of reduced dNTP levels. The authors of these studies speculate that variants having more drastic effects on inhibitor binding are not seen because of the detrimental effects such variants would have for RR activity and viral growth (Bonneau et al., 1996, J. Virol. 70:787–793).

The invention should not be construed to be limited to cancer cells and virus replication as targets of RR inhibition. Rather, a similar approach may also be used to target infectious diseases in general, especially if the infectious species has an R2 C-terminal sequence different from that of human R2 (see, for example, Table 7, Example 11). This point is especially pertinent given the rapidly developing resistance of many infectious organisms to classical antibiotics.

Linear and cyclic peptides and peptidomimetics have been developed which are potent and selective inhibitors of mammalian ribonucleotide reductase (RR), a type 1 RR. Because mammalian RR is necessary for tumor cell proliferation and replication of certain viruses in mammalian cells, these peptides and peptidomimetics are effective inhibitors of tumor cell proliferation and viral replication. Furthermore, because certain infectious agents including, but not limited to, certain viruses and bacteria, and parasites of mammals, encode a viral RR enzyme which can be selectively inhibited by the peptides and peptidomimetics described herein, relative to inhibition of mammalian RR, the peptides and peptidomimetics described herein have broad utility as therapeutic compositions to alleviate infection by one or more of these certain infectious agents and the symptoms which accompany such infection.

The reaction catalyzed by RR, the reduction of nucleoside diphosphates (NDPs) to deoxynucleoside diphosphates (dNDPs), is the rate-limiting step in the de novo synthesis of dNTPs, and hence of DNA, and as such is a clear target for therapeutic agents directed against diseases and disorders associated with infectious agents. RR activity depends on association of a pair dimers of each of two different subunits, namely an $R1_2$ dimer and an $R2_2$ dimer. It has been discovered that a peptide homologous to the carboxyterminal portion of R2 inhibits RR activity. Thus, a lead molecule for inhibition of mammalian RR is the acetylated heptapeptide N-AcFTLDADF (SEQ ID NO: 16), derived from the carboxy-terminus of the R2 of mouse.

Peptide-based inhibitors have been developed based upon the carboxy-terminal sequence of the R2 subunit of mammalian RR, and particularly based upon the observed conformation of the carboxy-terminal sequence of the R2 subunit of mammalian RR during interaction thereof with the R1 subunit of mammalian RR, as determined by NMR spectroscopy. It has been discovered that the conformation of the acetylated heptapeptide N-AcFTLDADF (SEQ ID NO: 16), when associated with the R1 subunit of mouse RR exhibits common reverse turn conformation compared with the crystallographically-determined structure of the carboxy-terminal portion of the *E. coli* R2 subunit when associated with the *E. coli* R1 subunit.

The conformation exhibited by the carboxy-terminal portions of the mouse and *E. coli* R2 subunits of RR when each of these R2 subunits is bound to the R1 subunit of RR of the corresponding species has been determined and is described herein.

Peptides and peptidomimetics are described herein which exhibit the conformation exhibited by the carboxy-terminal portions of the mouse and *E. coli* R2 subunits of RR when each of these R2 subunits is bound to the R1 subunit of RR of the corresponding species. By tailoring the peptides and peptidomimetics to more closely resemble the conformation of the R1-bound R2 carboxy-terminal sequence of a first species than the conformation of the R1-bound R2 carboxy-terminal sequence of a second species, peptides and peptidomimetics have been made which inhibit the RR of the first species more effectively than they inhibit the RR of the second species.

The peptides and peptidomimetics which have been designed and made include linear peptides, cyclic peptides, and peptidomimetics. Conjugated high affinity peptides and peptidomimetics have also been designed to improve the delivery of the peptides and peptidomimetics of the invention to the interior of mammalian cells. Pharmaceutical compositions comprising a peptide or peptidomimetic of the invention are also contemplated.

The acetylated heptapeptide N-AcFTLDADF (SEQ ID NO: 16), corresponding to the C-terminus of mouse R2, was used as the lead molecule. Starting with this molecule, peptide- and nonpeptide-based RR inhibitors were developed, the RR inhibitors having
high affinity for mammalian R1.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |

-continued

| Full Name | Three-Letter Code | One-Letter Code |
|---|---|---|
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The present invention also provides for analogs of RR-inhibitory peptides. Analogs can differ from peptides described herein by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:

glycine, alanine;

valine, isoleucine, leucine;

aspartic acid, glutamic acid;

asparagine, glutamine;

serine, threonine;

lysine, arginine;

phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

Linear Peptide RR Inhibitors and Methods of Making the Same

A number of the peptides described herein are also described in Fisher et al. (1993, J. Med. Chem.

36:3859–3862). Peptides were prepared by standard stepwise solid-phase Merrifield techniques using a Milligen/Biosearch Model 9600 peptide synthesizer. Either N-tert-butoxy-carbonyl (tBoc) protected amino acids or N-9-fluorenylmethoxycarbonyl (Fmoc) protected amino acids were used. For the tBoc procedure, peptides were deprotected and cleaved from resin using HF (Stewart et al., Solid Phase Peptide Synthesis, 2nd ed., Pierce Chemical Co., Rockford, Ill. 1984, 84–92). For the Fmoc procedure, Fmoc groups were cleaved in piperidine/toluene/DMF and deprotection of amino acid side chains and cleavage of the peptide from the resin was performed in a mixture of dimethyl sulfide and TFA (Chang et al., 1978, Int. J. Peptide and Protein Res. 2:246–249). Peptides were purified by reverse-phase HPLC, using a $CH_3CN$ gradient in 0.1% trifluoroacetic acid. In general, the Fmoc procedure affords cleaner peptide preparations, so this is the preferred method. N$\alpha$-acetyl derivatives were obtained by acetylation of peptides with acetic anhydride in methylene chloride prior to release of the peptides from the solid support (Bayer et al., 1970, J. Amer. Chem. Soc. 92:1735–1738). All peptides were of high purity as determined by $^1$H NMR spectra (500 MHZ), high resolution mass spectra (using a VG ZAB E instrument under FAB conditions) and analytical HPLC.

Peptides having a sequence homologous to the R2 carboxy-terminal sequences listed in Table 6 or peptides having any of the sequences described in Table 8 may be used as linear peptide inhibitors of RR.

A synthetic peptide combinatorial library (SPCL) was made, the library comprising numerous linear peptides which are RR inhibitors. Some of the linear peptides have greater inhibitory potency toward RR than N-AcFTLDADF (SEQ ID NO: 16) and some have lesser potency. The dissociation constant for R2 dimer of the mammalian R1 dimer is rather high (0.1 $\mu$M) and the carboxy-terminal peptide appears to account for most if not all of the affinity of R2 for R1. It is possible that facile dissociation of R1 from R2 is important for cell function, and that an R2 carboxy-terminal sequence having only moderate affinity for R1 was evolutionarily preferred. This implies that other peptides, made up of natural amino acids, can have substantially higher affinity for mR1 than the native R2 carboxy-terminal sequence.

The Bioméga group (Liuzzi et al., 1994, Nature 372:695–698; Moss et al., 1995, J. Med. Chem. 38, 3617–3623; Moss et al., 1993, J. Med. Chem. 36:3005–3009; Krogsrud et al., 1993, Anal. Biochem. 213:386–394) have shown that derivatives of VVNDL (SEQ ID NO: 37), corresponding to the R2 carboxy-terminal sequence of HSV-RR, which increase its hydrophobicity and decrease its conformational flexibility, exhibit very strong inhibitory activity toward HSV-RR. The most potent of these derivatives yet published, BILD-1263, depicted in FIG. 5, has a dibenzyl acetyl group at the N-terminus (dibzAc), and, counting from the N-terminus, an N-methyl replacing the NH at Val1, a t-butyl group replacing the i-propyl group at Val2 ($\beta$-MeVal), a pyrrolidine replacing the —$NH_2$ at Asn3 (prlAsn), a spirocyclopentane replacing the $\beta$-$CH_2$ at Asp4 (spnAsp), a t-butyl group replacing the i-propyl group at Leu5 ($\gamma$-MeLeu), and an hydroxymethyl group replacing the C-terminal carboxyl (Leu-OH).

A combinatorial library has been designed, based on the structure of the lead compound, N-AcFTLDADF (SEQ ID NO: 16), wherein eight molecular sites are varied. The library may be represented by the following formula (CI).

　　　　　　　　　　　　　　　　　　(CI)

wherein:

$Y_1$ is an acetyl group, a benzoyl group, or a dibenzyl acetyl group;

$AA_1$ is Phe, Trp, N-methyl-Phe, or D-Phe;

$AA_2$ is Thr, N-methyl-Thr, Leu, Val, or D-Thr;

$AA_3$ is Leu, $\gamma$-methyl-Leu, N-methyl-Leu, Ile, or D-Leu;

$AA_4$ is Asp, D-Asp, Asp having a spirocyclopentane replacing the $\beta$-$CH_2$ of Asp, Asn having a pyrrolidine replacing the $\gamma$-$NH_2$ of Asn, N-methyl-Asp, or Glu;

$AA_5$ is Phe, Val, Ile, N-methyl-Ala, or D-Ala;

$AA_6$ is Asp, D-Asp, Asp having a spirocyclopentane replacing the $\beta$-$CH_2$ of Asp, Asn having a pyrrolidine replacing the $\gamma$-$NH_2$ of Asn, or N-methyl Asp; and $AA_7$ is Phe, Tyr, Trp, N-methyl-Phe, or D-Phe.

In the library, the molar ratios of Fmoc amino acids used in each coupling step are adjusted to compensate for reactivity differences, allowing the generation of each library member in equal amounts (Eichler et al., 1993, Biochemistry 32:11035–11041). A composition comprising a plurality of compounds of the library which exhibits the presence of a high affinity peptide are resolved by RP-HPLC in order to identify the high affinity peptide. A similar strategy has been used to identifying a peptide binding with very high affinity to the NK-1 receptor. Small increases in affinity (~5-fold) may be detected by directly testing the additivity of favorable substitutions with peptides incorporating several such substitutions simultaneously.

Another strategy is to generate an SPCL incorporating all of the above variation simultaneously, using the divide, couple, recombine (DCR) iterative strategy of Houghten (Pinilla et al., 1994, Drug Devel. Res. 33:133–145; Houghten et al., 1992, BioTechniques 13:412–421; Ostresh et al., 1994, Proc. Natl. Acad. Sci. USA 91:11138–11142). Such an SPCL comprises about 225,000 peptides. A potentially more attractive approach is to reduce the size of the library being scanned, so that the concentration of each peptide in a mixture is increased, as described by Kerr et al. (1993, BioMed.Chem.Lett. 3:463–468). For example, several sub-libraries can be constructed, each containing 20–100 peptides, in which two or three positions are allowed to vary simultaneously. Favorable variations may be identified and variations from several sub-libraries may be combined and assayed for synergistic effect.

EXAMPLE 2

Cyclic Peptide and Peptidomimetic RR Inhibitors and Methods of Making the Same

Small peptides are conformationally labile and it is likely that the conformation of N-AcFTLDADF (SEQ ID NO: 16) bound to mR1 as determined by TRNOE, as described herein, represents only a fraction of the conformations available to the peptide in solution. It may even represent a conformation having a higher enthalpy than the peptide in solution. Thus, on entropic and possibly enthalpic grounds, a peptide structurally constrained to resemble the conformation of the carboxy-terminal peptide of R2 when bound to mR1 is likely to have a much higher affinity for R1 than does the native R2 peptide sequence. In addition, constrained peptides and peptide mimetics have real potential for improved pharmacodynamic properties over their linear counterparts, as described (Farmer et al., Bridging the Gap between Bioactive Peptides and Nonpeptides: Some Perspectives in Design. In Drug Design; Ari'ns, E. J., Ed.; Academic: New York, 1980; Vol X, p 119; Smith et al., 1994, J. Med. Chem. 37:215–218).

Structure-activity studies indicated that Thr2 and Ala5 of the lead compound can be replaced by a variety of amino acids without a major loss of inhibitory potency, which may be an indication that the precise identities of these groups are not critical for binding. With this in mind, cyclic peptides were designed which use the positions occupied by these two residues as sites for incorporating amino acids capable of being cyclized via an amide or a disulfide bond. In order to optimize the conformation for binding to R1, six libraries of cyclic peptides embodying six structural types were designed. In two of these libraries, the peptides are cyclized via an amide linkage. For one of these two libraries, denoted 1a-h, Asp or Glu replaces Thr2 as the carboxyl component of the amide, and diaminopropionic acid (Dpa), diaminobutyric acid (Dba), Orn, or Lys replaces Ala5 as the amine component, resulting in an eight (2×4) component library. To produce a second eight component library, denoted 2a-h, the same residues are used, but their placement are inverted: i.e., Asp or Glu replaces Ala5, and Dpa, Dba, Orn, or Lys replaces Thr2. The third of the libraries, denoted 3a-i, comprises nine (3×3) cyclic peptides which are constructed using Cys, homo-Cys, or penacillamine (Pen; 3-mercapto-D-valine), in place of each of Thr2 and Ala5. Cyclization of the peptides of this third library is achieved via a disulfide bond. Cyclization of the peptides of a fourth library, designated 4a-d, is achieved by a sulfide bond. Cyclization of the peptides of a fifth library, designated 5a-i, and of the peptides of a sixth library, designated 6a-i is achieved by a pair of sulfide bonds. Libraries 1a-h, 2a-h, and 3a-i are depicted in FIG. 5. Libraries 4a-d, 5a-i, and 6a-i are depicted in FIG. 22.

Figure 1B:
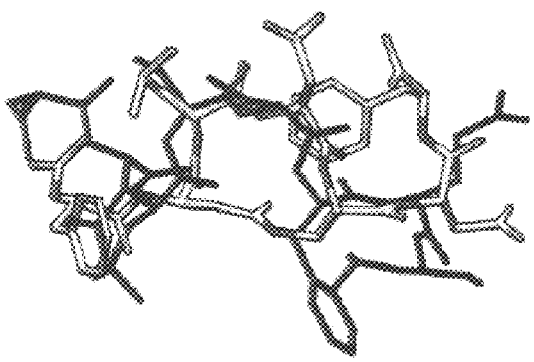
Figure 1C:
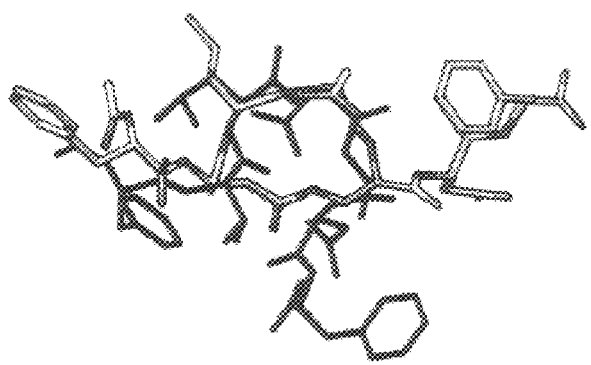

Modeling studies using the amber force field included with MacroModel (The Unix version of the MacroModel program (version 3.1x) was employed as described Mohamadi et al., 1990, J. Comp. Chem. 11:440–467) indicate that cyclic peptides 1a (n=m=1), 2a (n=m=1), and 3a (X=Y=—CH$_2$—) can adopt conformations similar to that required for binding of R2 to R1, as determined by NMR studies (FIG. 1a). Two Monte Carlo conformational searches (Saunders et al., 1990, J. Am. Chem. Soc. 112:1419–1427) were performed on 1a, one in which the aspartic acid residues were protonated and one in which they were the carboxylates. The lowest energy structures found in the first case have similar backbone conformations which closely match that determined in the X-ray structure of *E. coli* RR for the C-terminal DDLSNFQL (SEQ ID NO: 36) octapeptide (FIG. 1B). The second calculation produced a family of structures which closely match the NMR structure determined for AcFTLDADF (SEQ ID NO: 16), especially in the turn region, with some "fraying" at the N- and C-termini (FIG. 1C).

Figure 3:
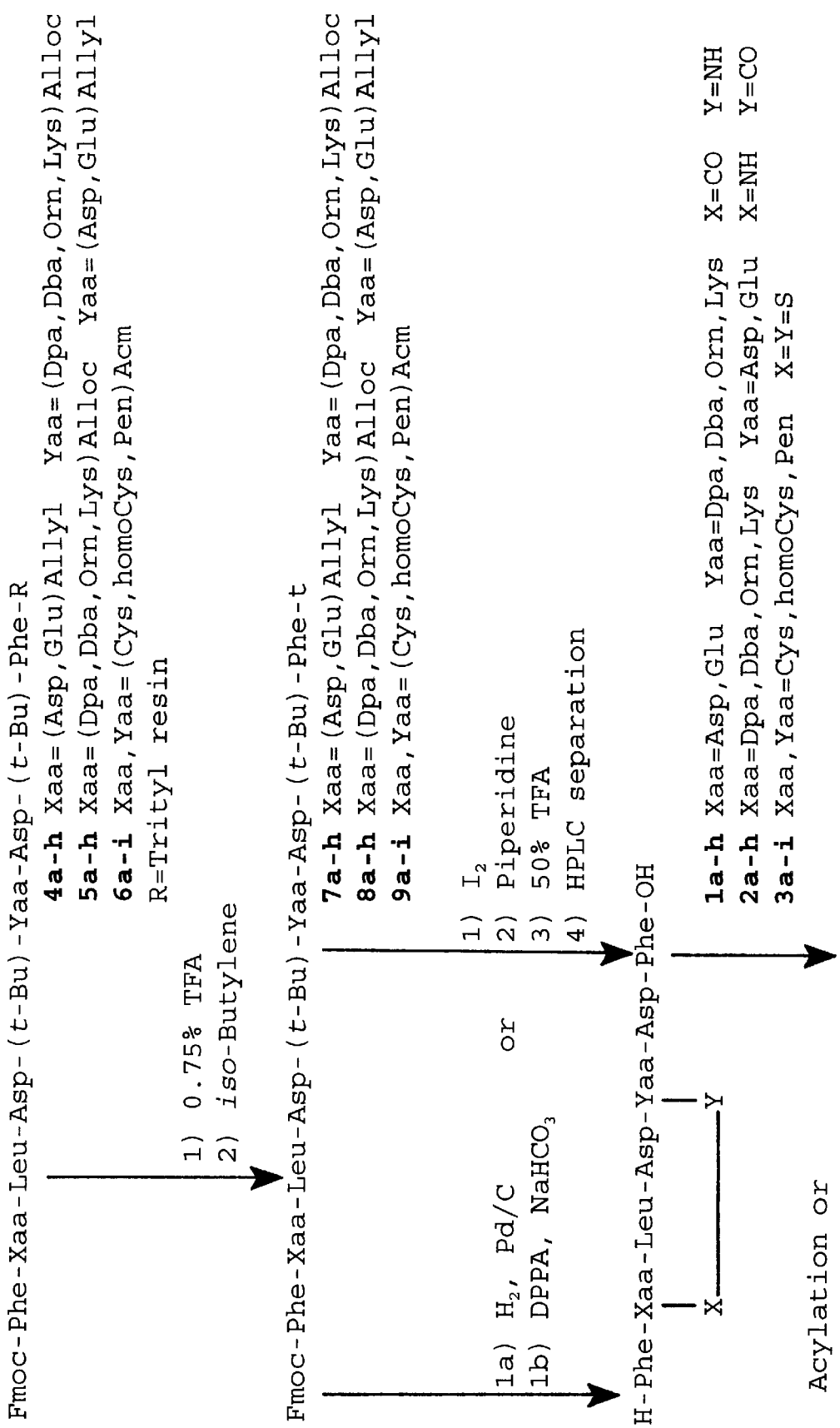
FIG. 3 depicts a chemical synthetic scheme described herein for making cyclic peptide inhibitors of RR.

Libraries 1a-h, 2a-h, and 3a-i are generated by solid phase synthesis of a mixture of linear precursors via Fmoc chemistry, using a trityl resin and tert-butyl ester protecting groups for the Asp residues of the final compounds, as depicted in FIG. 3. Cleavage of the mixture of peptides from the trityl resin will be accomplished by 0.75% TFA followed by protection of the C-terminus as a tert-butyl ester. Cyclization will then be performed in the case of libraries 1a-h and 2a-h by removal of the carboxyl Allyl and amine Alloc protecting groups by hydrogenolysis followed by cyclization of the mixture of peptides using the DPPA, NaHCO$_3$ conditions developed by the Hirschmann and Smith laboratories for cyclization of hexapeptide mixtures producing analogous libraries of between 4 and 12 components. In the case of library 3a-i, cyclization will be accomplished by oxidation with iodine. Cyclization of compounds of library 4a-d is accomplished by nucleophilic displacement of halide, as indicated in FIG. 23. Cyclization of compounds of library 5a-i and of compounds of library 6a-i is accomplished by treatment with 0.75% TFA and acidified isobutylene, followed by treatment with iodine, dibromomethane or 1,2-dibromoethane in the presence of TEA, and 50% TFA, as indicated in FIG. 24. Removal of the N-terminal Fmoc protecting group followed by acylation will then allow completion of the syntheses of the libraries following final deprotection of the esters.

Separation of the individual components by RP-HPLC is relatively straightforward and is well within the ordinary level of skill in the art of peptide purification. At this point, purified peptides can be acetylated or conjugated with folic acid and used for in vitro or in vivo testing, respectively. Cyclic peptide affinity for R1 may be optimized by substituting the side chains attached to the cyclic peptide, based on the results of the linear peptide studies described herein.

Libraries comprising cyclic peptides which have a non-standard β-type 1 turn resembling that found for N-AcFTLDADF (SEQ ID NO: 16) binding to R1 have been designed. In one embodiment, the cyclic peptides have the structure depicted in the following formula (I):

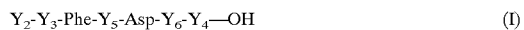

$$Y_2\text{-}Y_3\text{-Phe-}Y_5\text{-Asp-}Y_6\text{-}Y_4\text{—OH} \qquad (I)$$

wherein $Y_2$ is H or a blocking group;

$Y_3$ is from zero to twenty amino acids;

$Y_4$ is from zero to five amino acids;

$Y_5$ has a structure selected from the group consisting of the structure depicted in formula II of FIG. 5, wherein $R_1$ and $R_2$ are independently selected from the group consisting of amino acid side chain moieties and Z is selected from the group consisting of amide and disulfide bonds, and the structure depicted in formula III of FIG. 5; and $Y_6$ is selected from the group consisting of Phe, Tyr, Trp, N-methyl-Phe, D-Phe, o-methyl Phe, m-methyl Phe, o,o-dimethyl Phe, o,m-dimethyl Phe, o-hydroxyl Phe, m-hydroxyl Phe, p-hydroxyl Phe, m-chloro Phe, o-pyridyl Phe, and p-pyridyl Phe.

Preferred cyclic peptides according to formula I are those wherein $Y_3$ is from zero to ten amino acids and $Y_4$ is from zero to five amino acids and $Y_6$ is Phe. More preferred compounds are those compounds wherein $Y_3$ is from zero to five amino acids and $Y_4$ is from zero or one amino acid. Most preferred compounds are those compounds wherein $Y_3$ and $Y_4$ are zero amino acids.

Particularly preferred compounds according to formula I are those wherein $Y_2$ is acyl, $Y_3$ is Asn-Ser, $Y_4$ is zero amino acids, $Y_5$ has the structure depicted in formula II of FIG. 5, and $Y_6$ is Phe, wherein the structures $R_1$, $R_2$, and Z are selected from the group consisting of formulas IV, V, and VI, wherein in formula IV, the structure of $R_1$ is —CH$_2$—CO—, the structure of $R_2$ is —NHCH$_2$—, and Z is an amide bond;

in formula V, the structure of $R_1$ is —CH$_2$S—, the structure of $R_2$ is –CH$_2$S—, and Z is a disulfide bond; and in formula VI, the structure of $R_1$ is —C(CH$_3$)$_2$S—, the structure of $R_2$ is —C(CH$_3$)$_2$S—, and Z is a disulfide bond.

TABLE 1

Preferred compounds according to formula I wherein Y is acyl, $X_1$ is Asn-Ser, $X_2$ is zero amino acids, and $X_3$ has the structure depicted in formula II of Figure 5.

| Formula | $R_1$ | $R_2$ | Z |
|---------|-------|-------|---|
| IV | —$CH_2$—CO— | —$NHCH_2$— | amide |
| V | —$CH_2$S— | —$CH_2$S— | disulfide |
| VI | —$C(CH_3)_2$S—, | —$C(CH_3)_2$S— | disulfide |

EXAMPLE 3

Synthesis of Compound CVIII

Figure 4B:
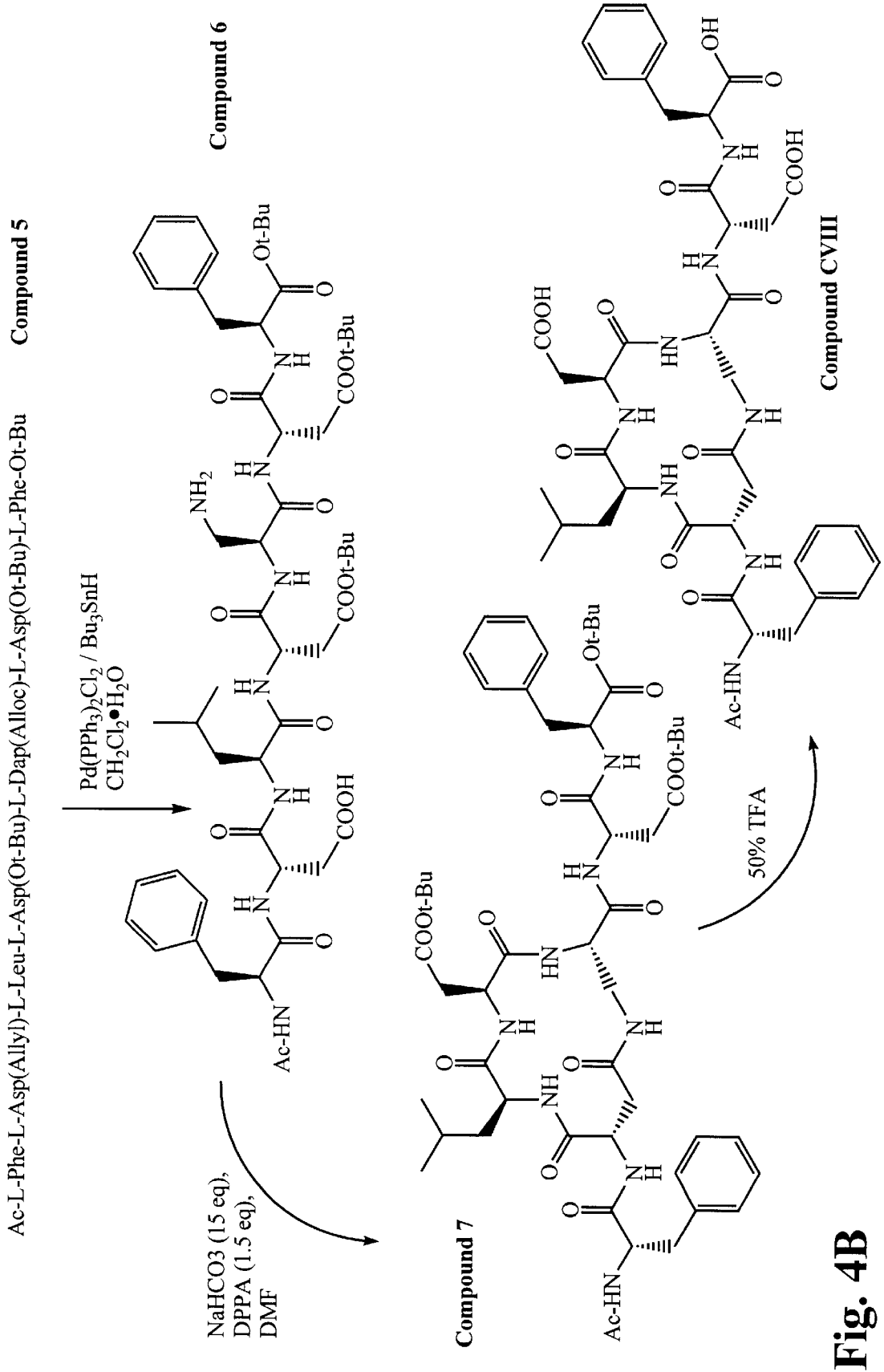
FIG. 4 depicts the chemical synthetic scheme described herein for making the cyclic peptide inhibitor of RR depicted in formula CVIII.
Figure 5A:
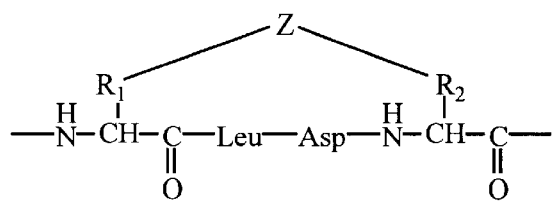
FIG. 5 is a series of chemical formulas referred to herein.
Figure 5B:
Figure 5C:
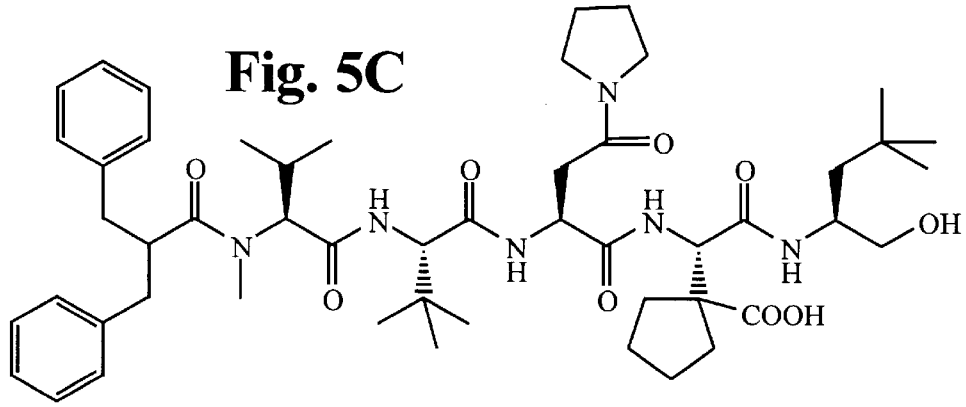
Figure 5D:
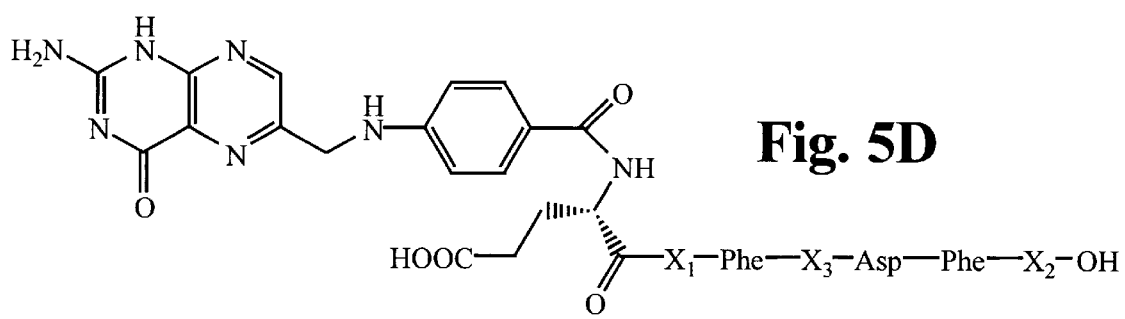
Figure 5E:
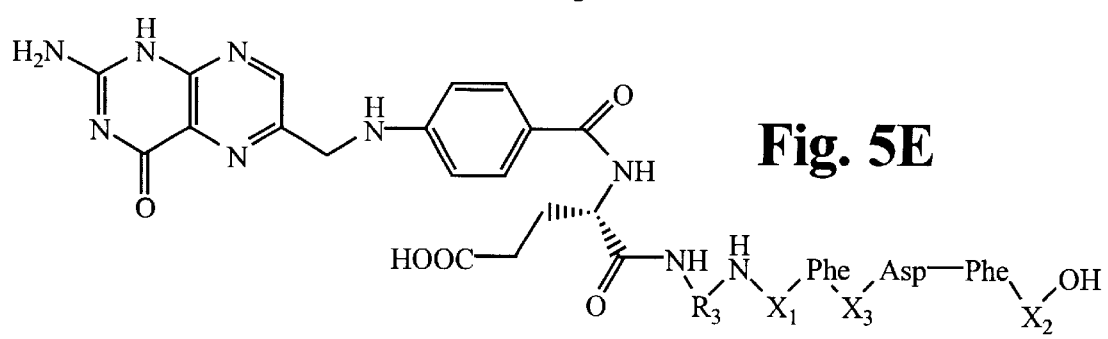
Figure 5G:
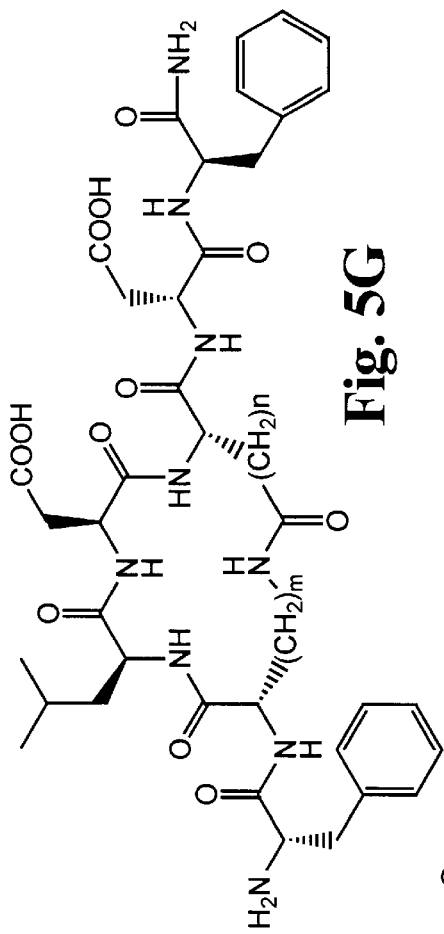
Figure 5F:
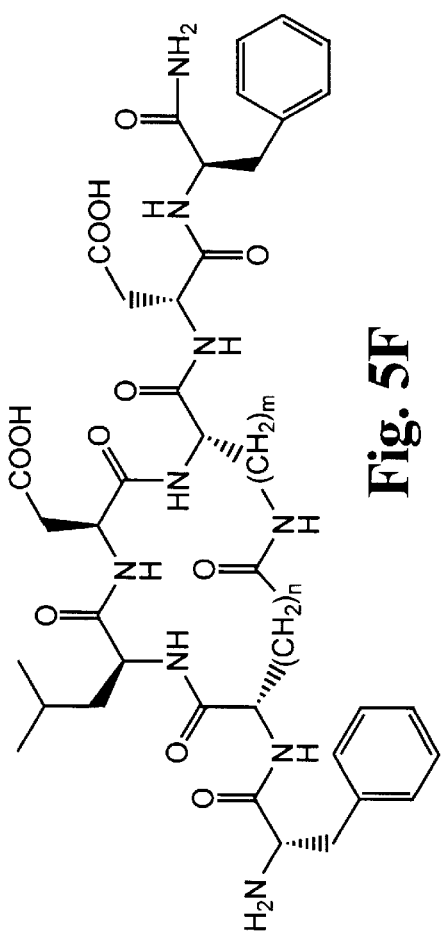
Figure 5H:
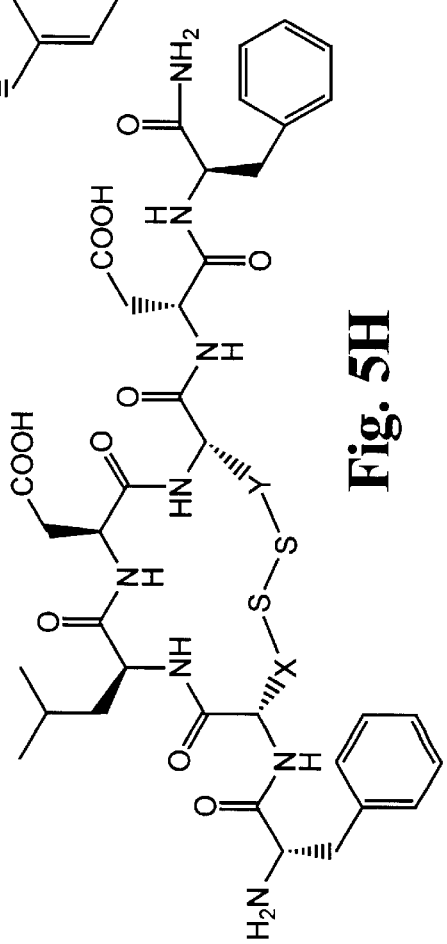
Figure 5J:
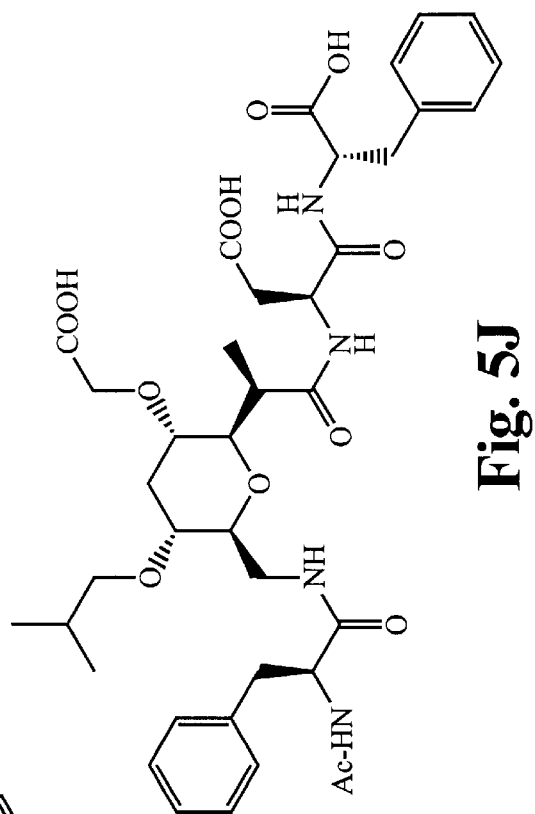
Figure 5I:
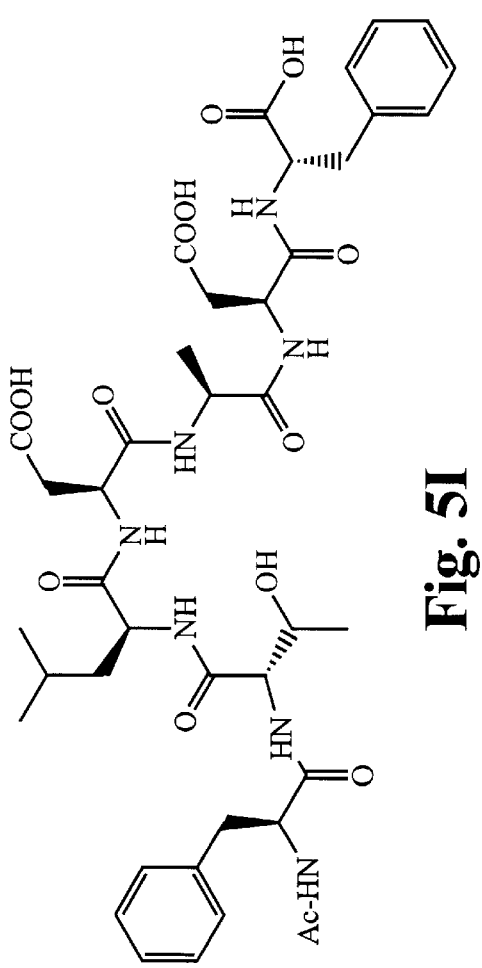

The synthesis of Compound CVIII is depicted in FIG. 4 and described herein. All reactions are carried out under inert atmosphere unless otherwise noted.

Anhydrous solvents may be purchased from Aldrich and used as such or dried over 4 Å molecular sieves. Unless otherwise indicated, all reagents may be obtained from commercial sources and used without further purification. All reactions may be monitored by Thin Layer Chromatography (TLC) on Anal tech plates (Silica gel GF, 250μ), for example. Flash column chromatography can be performed on silica gel (230–400 mesh, 60 Å), for example. Analytical reverse-phased HPLC can be performed on a Perkin-Elmer system fitted with a series 410 BIO LC pump and a LC-235 Diode Array detector, for example. The HPLC columns which are used may be, for example, either Synchropak RP-P or RP-8 (250×4.6 mm) for analytical runs and (250×10 mm) for semi-preparative runs. Mobile solvents which can be used include buffer A ($CH_3CN$, 0.1%TFA) and buffer B ($H_2O$, 0.1%TFA). $^1$H-NMR and $^{13}$C-NMR spectra may be obtained by standard methods, such as by recordation using a Bruker AMX-500 spectrophotometer. Chemical shifts are reported in (δ) ppm relative to TMS. FAB-mass spectra may be obtained using standard methods, such as using a VG-ZAB-E spectrometer.

Synthesis of Ac-Asp(O-t-Bu)-2-Cl-Trt-resin (Compound 2 in FIG. 4).

2-Chlorotrityl resin (1.3 mmol/g, Novabiochem) and Fmoc-Asp(O-t-Bu)-OH (Compound (1)) are dried under vacuum over KOH for 12 h. 2-Chlorotrityl resin (0.50 g, 0.65 mmol) is taken in a dry 100 mL rb flask along with DCM (4 mL) and gently stirred at room temperature to swell the resin. Fmoc-Asp(O-t-Bu)-OH (0.79 g, 1.91 mmol) is dissolved in DCM:DMF (8 mL, 1:1) and added to the flask with continuous stirring along with a total amount of DIPEA (1.33 mL, 7.65 mmol). The reaction is vigorously stirred for 1.5 h, after which time the reaction is quenched by addition of 20 mL MeOH:DIPEA (9:1) and stirring for another 10 min. The reaction mixture is filtered under vacuum and the resin is successively washed with DMF (e.g. 20 mL×3), iPr-OH (e.g. 20 mL×2), DMF (e.g. 20 mL×4), iPr-OH (e.g. 15 mL×2), MeOH e.g. (20 mL×1) and ethanol (EtOH; e.g. 20 mL×3). The resin is further dried in a vacuum desiccator over KOH until it appears as free flowing pale yellow beads (0.637 g).

The substitution level, by weight, of the resin may, for instance, be determined to be approximately 0.573 mmol/g of resin. The substitution level of the resin may be determined by measuring the absorbance of N-(9-fluorenylmethyl) piperidine at 301 nm (ε=7800). In a test tube, 5.1 mg of the Fmoc-Asp(O-t-Bu)-resin is weighed out. 0.5 mL of 20% piperidine in DMF is added. 0.5 mL 20% piperidine in DMF in an empty test tube is used as a blank. Over the next 1 h, the test tube containing the Fmoc-AA-resin is swirled several times to ensure that all the resin comes in contact with the piperidine solution. DMF is added to both tubes to bring the volume to 50 mL in a volumetric flask. The spectrophotometer is zeroed at 301 nm with the blank, and the absorbance of the Fmoc-Asp(O-t-Bu)-resin solution is read. The process may be repeated. An average absorbance at 301 nm of 0.466 corresponds to a substitution level of approximately 0.58 mmol/g.

Synthesis of Ac-L-Phe-L-Asp(OBn)-L-Leu-L-Asp(O-t-Bu)-L-Dpr(Alloc)-L-Asp(O-t-Bu)-2-Cl-Trt-resin (Compound 3 in FIG. 4).

Assembly of the peptide on the solid support is carried out using an Applied Biosystems, Inc. Model 431A automated peptide synthesizer. Fmoc amino acids from Bachem (Torrance, Calif.) and SNPE (Princeton, N.J.) with appropriately protected side-chains may be employed throughout. Starting with 0.25 mmol of Fmoc-L-Asp(O-t-Bu)-2-chlorotrityl resin (0.44 g, 0.57 mmol/g), Fmoc-L-Phe-L-Asp(OBn)-L-Leu-L-Asp(O-t-Bu)-L-Dpr(Alloc)-L-Asp(O-t-Bu)-2-Cl-Trt-resin is assembled according to the standard procedure, with some modification as described herein. Fmoc removal using 20% piperidine in DMF, 1.0 mmol individual amino acids, and HBTU as the coupling agent are used in each of the coupling steps. The coupling reaction is carried out at room temperature for 2 h. The following amino acids are incorporated in the order: Fmoc-L-Dpr(Alloc)-OH, Fmoc-L-Asp(O-t-Bu)-OH, Fmoc-L-Leu-OH, Fmoc-L-Asp(OBn)-OH, and Fmoc-L-Phe-OH. After each coupling, a Kaiser test is performed to monitor completion of the coupling reaction. If necessary, a second coupling reaction is performed. After the completion of the solid-phase synthesis, the resin is dried under vacuum to yield 0.676 g of the peptide resin (Compound (3) in FIG. 4).

Synthesis of Ac-L-Phe-L-Asp(OBn)-L-Leu-L-Asp(O-t-Bu)-L-Dpr(Alloc)-L-Asp(O-t-Bu)-OH (Compound 4 in FIG. 4).

Ac-L-Phe-L-Asp(OBn)-L-Leu-L-Asp(O-t-Bu)-L-Dpr(Alloc)-L-Asp(O-t-Bu)-2-Cl-Trt-resin (Compound 3 in FIG. 4) is treated with TFA/$CH_2Cl_2$ (0.40% v/v) at room temperature. After 45 min, an orange colored slurry is filtered and washed several times with a solution comprising 0.40% v/v TFA/$CH_2Cl_2$. The filtrate is concentrated to half its original volume, and flushed with benzene. The resulting solid is triturated using ice-cold dry ether to obtain a white crystalline solid (Compound 4 in FIG. 4). This material should be reasonably pure and may be used for the next step without any purification.

Synthesis of Ac-L-Phe-L-Asp(OBn)-L-Leu-L-Asp(O-t-Bu)-L-Dpr(Alloc)-L-Asp(O-t-Bu)-L-Phe-O-t-Bu (Compound 5 in FIG. 4).

Ac-L-Phe-L-Asp(OBn)-L-Leu-L-Asp(O-t-Bu)-L-Dpr(Alloc)-L-Asp(O-t-Bu)-OH (Compound 4 in FIG. 4) is dissolved in dry $CH_2Cl_2$ and stirred at 0° C. HOBt and EDC are added to this solution. Phe-O-t-Bu (HCl salt) is separately dissolved in $CH_2Cl_2$ along with 1 equivalent of TEA. The clear solution that is obtained is added to the original flask along with 1.2 equivalent of TEA. The reaction is stirred overnight and allowed to warm to room temperature. After completion of the reaction (TLC), the solvent is removed in vacuo and the residual oil is taken up in EtOAc. The organic layer is washed with 1 N HCl (e.g. 30 mL×2), saturated $NaHCO_3$ (e.g. 30 mL×2), brine (e.g. 30 mL), dried over $Na_2SO_4$ and filtered. The filtrate is evaporated in vacuo to yield Compound 5 in the form of a white solid which may be used without further purification.

Synthesis of Ac-L-Phe-L-Asp-L-Leu-L-Asp(O-t-Bu)-L-Dpr-L-Asp(O-t-Bu)-L-Phe-O-t-Bu (Compound 6 in FIG. 4).

Ac-L-Phe-L-Asp(OBn)-L-Leu-L-Asp(O-t-Bu)-L-Dpr (Alloc)-L-Asp(O-t-Bu)-L-Phe-O-t-Bu (Compound 5 in FIG. 4) is taken in EtOH and acetic acid (AcOH), along with 30 mg of Pd—C (10% w/w) in a Parr shaker (at a peptide concentration of about 7–8 mM). The mixture is shaken under an $H_2$ atmosphere (55 psi) for two days until complete removal of the benzyl on the Asp and the alloc on the Dpr is achieved, as evidenced by NMR. The catalyst is filtered over celite and washed several times with EtOH. The filtrate is evaporated in vacuo to yield a colorless oil. This oil is chromatographed on a silica gel flash column using $CH_2Cl_2$/MeOH (9/1 ratio) followed by preparative TLC (Silica gel plate 250×250 mm, 500 μm) using $CH_2Cl_2$/MeOH/AcOH (8/2/0.01 ratio) to yield Compound 6 in the form of a pure white solid.

Synthesis of Compound 7.

DPPA is added dropwise to a suspension of Ac-L-Phe-L-Asp-L-Leu-L-Asp(O-t-Bu)-L-Dpr-L-Asp(O-t-Bu)-Phe-O-t-Bu and $NaHCO_3$ in dry DMF at 0° C. The reaction mixture is stirred at 4° C. until the reaction proceeds to completion, as assessed by analytical RP-HPLC. After stirring at 4° C. for 36 h, the reaction mixture is filtered and washed with DMF. The combined filtrates are concentrated in vacuo. The resulting crude material is further purified by semi-preparative reverse phase HPLC (e.g using a Synchropak: RP-P, 250×10 mm, gradient 60% buffer A-1'; 60-5'-70% A; 70-20'-90% A at 2 mL/min; effluent monitored at 215 and 255 nm). The fraction eluting at about 18.6 min is collected and lyophilized to yield Compound 7 in the form of a white amorphous solid.

Synthesis of Compound CVIII.

Compound 7 is mixed with $CH_2Cl_2$ and $H_2O$. TFA is added dropwise to the mixture at room temperature. The resulting mixture is stirred for 1.5 h. After completion of the reaction, the reaction mixture is concentrated to half its original volume and flushed with dry ether. The resulting solid is further triturated with ice-cold ether and evaporated to dryness. The crude solid obtained is purified on a semi-preparative RP-HPLC (e.g. using a Synchropak: RP-P, 250× 10 mm, gradient 40% buffer A-10; 40-400-80% A; at 1.5 mL/min; effluent monitored at 215 and 255 nm). The fraction eluting at about 25.4 min is collected and lyophilized to yield Compound CVIII in the form of a white fluffy solid.

EXAMPLE 4

Peptidomimetic RR Inhibitors and Methods of Making the Same

The peptidomimetics described in this example are derived from the β-turn mimetic glucose scaffold developed by Hirschmann (1992, J. Am. Chem. Soc. 114:9217). A β-turn mimetic scaffold is a molecular structure which does not naturally occur in a protein and which comprises an arrangement of atoms which is structurally similar to a portion of a naturally occurring protein which comprises a β-turn. Other β-turn mimetics providing alternative scaffolds include spirolactams (Genin et al., 1993, J. Org. Chem. 58:860–866; Genin et al., 1993, J. Org. Chem. 58:2334–2337) benzodiazepins (Ripka et al., 1993, Tetrahedron 49:17:3593–3608; Ripka et al., 1993, Tetrahedron 49:17, 3609–3628), and an 11-membered ring bislactam (Su et al., 1993, Biorganic & Medicinal Chemistry Letters 3, 5, 835–840). While Hirschmann and Smith have not to date incorporated the glucose scaffold into a peptide as a turn mimetic, von Roedern and Kessler (1994, Angew. Chem., Int. Ed. Engl.33:687–689) have used amino acid sugars as turn templates in cyclic peptidomimetics, thereby demonstrating the applicability of the methods described herein.

In the compounds described in this Example, the i+1 and i+2 functionality, i.e., the leucine and aspartic acid side chains, were attached at the 2- and 4-positions of L-glucose. A methyl group corresponding to the β-methyl group of Ala5 was included β to the 5-position, because of the apparent importance of a hydrophobic interaction between this methyl group and Phe7 in the TRNOE structure, as described herein. Furthermore, the N-terminal acetyl phenylalanine was attached to the 6-position of the sugar. The C-terminal Asp and Phe residues were then connected by a two carbon linker at the anomeric carbon. This design process led to the nonpeptide peptidomimetic 10, which is depicted in FIG. 5. The similarity can be ascertained by comparing the structures of peptidomimetic 10 and AcFTLDADF-OH (SEQ ID NO: 16), which are depicted in FIG. 5.

Figure 2:
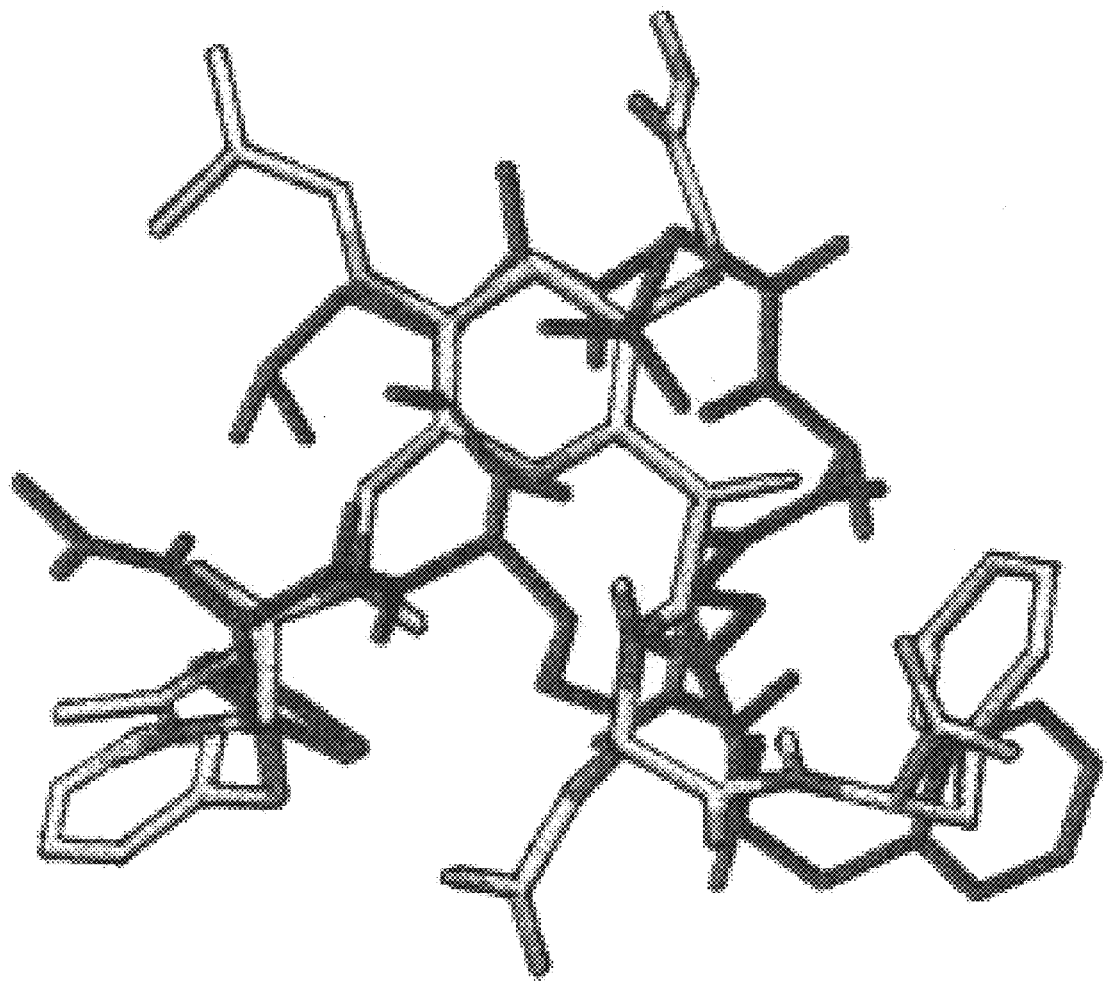
FIG. 2 is an image which depicts computer-generated models of peptides described herein. A series of connected gray lines which represents the structure of sugar based peptidomimetic 10 is overlaid atop a series of connected black lines which represents the structure of AcFTLDADF (SEQ ID NO: 16).

Modeling studies using the MM2 force field (The 1987 version of the MM2 force field was used: Bowen et al.,1987, J. Org. Chem. 52:5162–5166) included with MacroModel (v3.1) indicate that nonpeptide peptidomimetic 10 can adopt conformations similar to that required for binding to R1, as determined by NMR studies. FIG. 2 shows the overlap of 10 with the NMR-determined conformation of N-AcFTLDADF (SEQ ID NO: 16).

The synthesis of peptidomimetic 10 is depicted in FIG. 6 beginning from the L-isomer of the tetraacetate identified as Compound 4 in FIG. 7. Koenigs-Knorr coupling (Magus et al., 1979, Carbohydr. Res. 76:261–264) with tert-butyl alcohol (30% yield), followed by acetate hydrolysis and acetal formation, yielded Compound 12 in FIG. 6 in 75% yield for the two steps. Protection of the C(2) alcohol as the benzyl ether (98% yield) and reductive opening of the acetal (82% yield) was followed by activation of the primary hydroxyl and azide formation to yield Compound 13 in FIG. 6 in 82% yield for the two steps. Oxidative removal of the C(4) PMB group (74% yield) was followed by installation of the leucine mimicking side chain (91% yield). Cleavage of the tert-butyl ether (72% yield) preceded installation of the C-terminal carboxyl via a Wittig reaction, ester hydrolysis, and base induced ring closure to yield Compound 15 in FIG. 6 (Fraser-Reid et al., 1979, Can. J. Chem. 57:1746–1749) (71% yield overall). Stereoselective installation of the methyl group was accomplished using Evans methodology (Evans et al.,1982, J. Am. Chem. Soc. 104:1737–1739) yielding Compound 16. Installation of the aspartic acid mimicking side chain is achieved following protection of the acid as the sterically hindered quaternary ammonium salt and reductive removal of the benzyl protecting group. These reactions result in concomitant generation of the azide and in situ Boc protection of the amine. TFA treatment removes both the acid and amine protecting groups. Fmoc protection completes the synthesis of the amino acid identified as Compound 17 in FIG. 6, which is employed in the solid phase Fmoc peptide synthesis of Compound 18 in FIG. 6. Acetylation and removal of the Allyl protecting groups yields the target nonpeptide peptidomimetic 10. Alternatively, conjugation of Compound 18 in FIG. 6 to folic acid is performed. Subsequent removal of the allyl protecting groups yields Compound 19 in FIG. 6, which is suitable for in vivo testing, as described herein. Adaptations of the synthetic scheme depicted in FIG. 6 to incorporate substituents found to increase the affinity of cyclic peptides for R1 are within the level of ordinary skill in the art of peptidomimetic synthesis.

Figure 25:
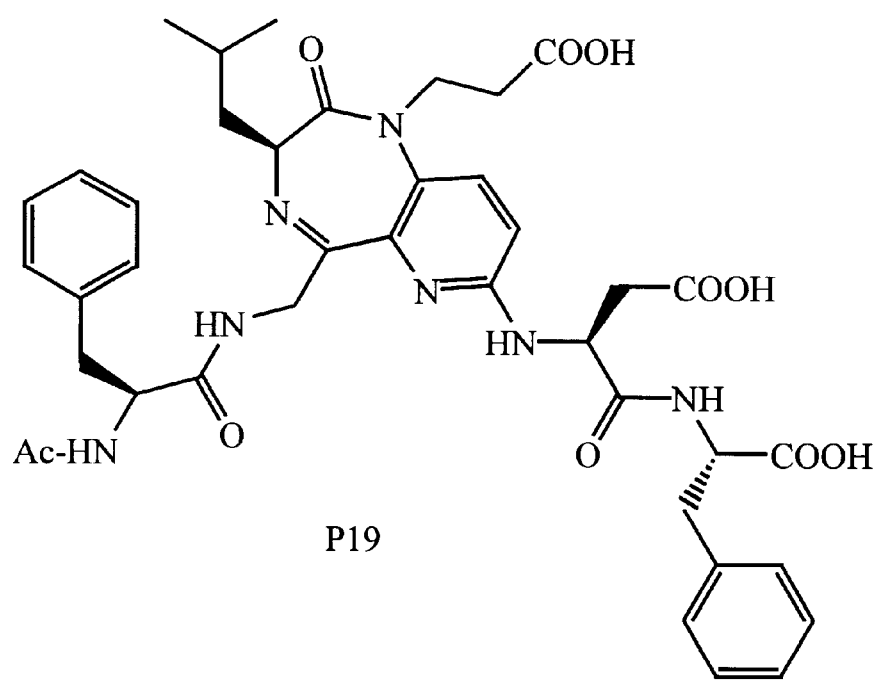
FIG. 25 is the chemical formula of Peptidomimetic P19, as described herein.

A peptidomimetic derived from a β-turn mimetic benzodiazepin scaffold and designated "peptidomimetic P19" is depicted in FIG. 25. The structure of peptidomimetic P19 is believed to mimic the structure of N-AcFTLDADF (SEQ ID NO: 16) bound to the R1 subunit of RR, as assessed by modeling studies similar to those performed for peptidomimetic 10. The synthesis of peptidomimetic P19 is depicted schematically in FIG. 26 and described herein.

This synthetic scheme used to generate peptidomimetic P19 employs pyridodiazapene synthetic chemistry which has been described for construction of a variety of psychotherapeutic agents that are analogs of diazepam. Thus, the synthetic steps are not described in detail herein. Briefly, (3-amino-6-chloro-pyridine-2-yl)-methanol (compound 20), is subjected to oxidation, followed by a Grignard reaction to yield compound 21. Compound 21 is reacted with benzyloxycarbonyl-Leu-OH and diethyl cyanophosphonate (DECP) in the presence of 2,2-dimethoxy propane ($Me_2C(OME)_2$) to generate the seven-membered ring structure of compound 22. Compound 22 is reacted with lead tetraacetate in the presence of sodium borohydride, with sodium azide in the presence of tosyl chloride, and then with allyl bromide in the presence of potassium tert-butoxide to yield compound 23. Compound 23 is reacted with Ac-Phe-OH-DECP in the presence of triphenylphosphine to yield compound 24. Compound 24 is reacted with Asp(Bn)-Phe-OBn-DECP to yield compound 25. Compound 25 is reacted as indicated in FIG. 26 to yield compound 19, which is peptidomimetic P19. The portion of the P19 molecule which does not include the N-acetyl-Phe residue or the C-terminal Phe residue appears to be a β-torn mimetic scaffold.

EXAMPLE 5

Synthesis of (R)-2-{(2S,3S,5R,6S)-2-[3-[[Carboxomethyl]oxy]-6-AcPhe-aminomethyl-5-isobutyloxy]-2,3,4,5-tetrahydropyranyl}propionyl-Asp-Phe The synthesis of (R)-2-{(2S,3S,5R,6S)-2-[3-[[Carboxomethyl]oxy]-6-AcPhe-aminomethyl-5-isobutyloxy]-2,3,4,5-tetrahydropyranyl}propionyl-Asp-Phe is depicted schematically in FIG. 7 and described herein. Compound numbers referred to in this Example refer to the numbers associated with compounds depicted in FIG. 7, unless otherwise noted. Reaction numbers referred to in this Example refer to the numbers associated with arrows depicting chemical reactions in FIG. 7.

Reaction 1) Production of Diacetone-L-glucose (Compound 1)

A solution comprising 35.0 grams (194.3 mmol) L-glucose (denoted "L-Glc in FIG. 7) and 30.0 grams (220.1 mmol) zinc chloride in 350 ml acetone was treated with 1.4 ml 86% phosphoric acid and stirred for 3 days at room temperature. Insoluble matter was removed by filtration, and the filtrate was cooled in an ice bath. The acetone solution was made slightly alkaline by addition of 25 N NaOH. The precipitate was removed by filtration and washed with acetone. The filtrate and washings were combined and concentrated in vacuo. The $CH_2Cl_2$ solution of the residue (200 mL) was washed with water (3×200 mL), dried over magnesium sulfate and concentrated in vacuo. The residual solid was triturated with n-hexane to yield 28.49 grams of compound 1 in the form of a white solid. The filtrate was concentrated and the residue was triturated with n-hexane to afford an additional 2.74 grams of compound 1 (total amount 31.23 g, 61.8% yield).

Compound 1 had the following properties: mp 109–110° C. (n-hexane); $[\alpha]^{20}_D$+9.4° (c 1.1, $CHCl_3$); IR ($CHCl_3$) 3580 (m), 3450 (m), 2990 (s), 2930 (s), 2880 (m), 1450 (m), 1360 (s), 1340 (s), 1200–1250 (s, br), 1160 (s), 1070 (s), 1010 (s), 940 (m), 870 (m), 830 (s), 700–800 (m, br), 615 (w), 330–400 (m, br), 230 (m) $cm^{-1}$; $^{13}C$-NMR (125 MHZ, $CDCl_3$) δ 111.71, 109.47, 105.16, 85.08, 81.19, 74.81, 73.08, 67.53, 26.74, 26.68, 26.09, 25.09; $^1H$-NMR (500 MHZ, $CDCl_3$) δ 5.94 (d, J=3.6 Hz, 1H), 4.53 (d, J=3.6 Hz, 1H), 4.32 (m, 2H), 4.17 (dd, J=6.3, 8.6 Hz, 1H), 4.07 (dd, J=2.8, 7.7 Hz, 1H), 3.98 (dd, J=5.4, 8.6 Hz, 1H), 2.55 (br s, 1H), 1.50 (s, 3H), 1.44 (s 3H), 1.36 (s, 3H), 1.32 (s, 3H).

Reaction 2) Production of Diacetone-3-deoxy-L-glucose (Compound 2)

To a solution of 27.0 grams (103.7 mmol) of compound 1 in tetrahydrofuran (THF) was added sodium bis(trimethylsilyl)amide (1.0 M in THF, 125 ml, 125 mmol) at –63° C. After 5 min at –63° C., carbon disulfide (8.8 mL, 146.3 mmol) was added to the solution. After 25 min at –63° C., iodomethane (19.4 mL, 311.6 mmol) was added to the solution. The mixture was allowed to warm to room temperature over 30 min. Ice water (400 mL) was added to the pale yellow solution, and the resulting biphasic solution was then extracted with ethyl acetate (300 mL). The organic layer was washed with brine (2×300 mL), dried and concentrated in vacuo. A solution of the residue dissolved in toluene (500 mL) was treated with tributyltin hydride (30 mL, 108.2 mmol) and 2,2'-azobisisobutyronitrile (AIBN, 10 mg, 0.06 mmol), and heated to reflux for 3 h. The reaction mixture was concentrated in vacuo and the residue was partitioned between acetonitrile and petroleum ether. The acetonitrile layer was separated, further washed with petroleum ether (2×100 mL) and concentrated in vacuo. The residue was chromatographed on silica gel (ethyl acetate/n-hexane=1/5) to yield compound 2 (20.1 g, 79.4% yield) as a pale yellow syrup.

Compound 2 had the following properties: $[\alpha]^{20}_D$+7.4° (c 2.25, $CHCl_3$); IR ($CHCl_3$) 3670 (w), 3510 (w), 2990 (s), 2940 (s), 2900 (m), 2450 (w), 1480 (w), 1450 (m), 1430 (m), 1385 (s), 1370 (s), 1320 (w), 1260 (s), 1220 (s), 1160 (s), 1135 (m), 1105 (s), 1055 (s), 1020 (s), 950 (m), 930 (m), 900 (m), 865 (m), 840 (s), 770 (w), 710 (m), 650 (w) $cm^{-1}$; $^{13}C$-NMR (125 MHZ, $CDCl_3$) δ 111.10, 109.41, 105.48, 80.28, 78.51, 76.76, 67.05, 35.21, 26.63, 26.32, 26.00, 25.03; $^1H$-NMR (500 MHZ, $CDCl_3$) δ 5.74 (d, J=3.7 Hz, 1H), 4.68 (t, J=4.2 Hz, 1H), 4.09 (m, 1H), 4.04 (m, 2H), 3.75 (m, 1H), 2.12 (dd, J=4.4, 13.5 Hz, 1H), 1.69 (ddd, J=4.9, 10.3, 13.5 Hz, 1H), 1.44 (s, 3H), 1.35 (s, 3H), 1.28 (s, 3H), 1.25 (s, 3H); high-resolution mass spectrum (CI, ammonia) m/z 262.1641 [$(M+NH_4)^+$; calcd for $C_{12}H_{24}NO_5$:262.1655].

Reactions 3) and 4) Production of 1,2,4,6-Tetra-O-acetyl-3-deoxy-L-glucopyranoside (Compound 4)

A solution of 3-deoxydiacetone-L-glucose (compound 2) (20.0 g, 81.2 mmol) in 60% aqueous acetic acid (150 mL) was heated at 90° C. for 7 h, cooled, and concentrated in vacuo. The residue was azeotroped with toluene (2×30 mL) to yield compound 3. A solution of crude compound 3 in pyridine (100 mL) was treated with acetic anhydride (78 mL, 0.83 mol) and DMAP (200 mg, 1.64 mmol), and stirred at room temperature for 13 h. After concentration in vacuo, the residue was dissolved in ether (150 mL). The ether solution was washed with brine, dried and concentrated in vacuo. The residue was chromatographed on silica gel (ethyl acetate/n-hexane=2/5) to yield a mixture of α- and β-anomers of compound 4 as a pale yellow syrup (18.9 g). The syrup was dissolved in ether/n-hexane (each 35 mL) and stored in refrigerator for 2 days to afford a pure β-anomer as a white fluffy solid (6.77 g). Concentration of the filtrate gave a mixture of α- and β-anomers of compound 4 as a pale yellow syrup (10.78 g, total 64.5% yield).

The β-anomer of compound 4 had the following properties: mp 123–126° C. (ether/n-hexane); $[\alpha]^{20}_D$+10.9° (c 1.06, CHCl$_3$); IR (CHCl$_3$) 3660 (w), 3460–3600 (w, br), 3005 (m), 2940 (w), 2860 (w), 1740 (s), 1450 (w), 1420 (w), 1365 (s), 1225 (s), 1140 (w), 1110 (m), 1060 (s), 1030 (s), 940 (w), 905 (w), 875 (w), 680–810 (w, br), 350 (w), 590 (w), 565 (w) cm$^{-1}$; $^{13}$C-NMR (125 MHZ, CDCl$_3$) δ 170.66, 169.43, 169.30, 169.18, 93.16, 75.79, 67.43, 65.15, 62.18, 32.74, 20.92, 20.80, 20.76, 20.71; $^1$H-NMR (500 MHZ, CDCl$_3$) δ 5.69 (d, J=7.9 Hz, 1H), 4.88 (m, 2H), 4.23 (dd, J=5.0, 12.3 Hz, 1H), 4.15 (dd, J=2.5, 12.3 Hz, 1H), 3.82 (ddd, J=2.5, 5.0, 9.1 Hz, 1H), 2.62 (dt, J=5.0, 12.3 Hz, 1H), 2.11 (s, 3H), 2.07 (s, 3H), 2.05 (s, 3H), 2.04 (s, 3H), 1.66 (dd, J=11.0, 23.0 Hz, 1H); high-resolution mass spectrum (CI, ammonia) m/z 350.1456 [(M+NH$_4$)$^+$; calcd for C$_{14}$H$_{24}$NO$_9$: 350.1450]. Anal. Calcd for C$_{14}$H$_{20}$O$_9$: C, 50.60; H, 6.07. Found: C,; H,.

Reaction 5) Production of 1-O-tert-Butyl-2,4,6-tri-O-acetyl-3-deoxy-β-L-glucopyranoside (Compound 5)

1,2,4,6-Tetra-O-acetyl-3-deoxy-β-L-glucopyranoside (compound 4) (3.70 g, 11.13 mmol) was dissolved in 30% HBr in AcOH (12 mL) and the solution was stirred at room temperature for 6.5 h. Ether (50 mL) was added to the reaction mixture and the resulting solution was gradually added to saturated aqueous sodium bicarbonate solution (50 mL) at 0° C. The organic layer was separated, washed with saturated aqueous sodium bicarbonate (3×50 mL) and brine (2×50 mL), and concentrated in vacuo. The residue was dissolved in t-BuOH (35 mL), and silver (I) oxide (3.2 g, 13.7 mmol) and powdered 4 Å molecular sieves (5 g) were added to the solution. The reaction vessel was covered with aluminum foil, and the mixture was stirred at room temperature for 5 days. Insoluble matter was filtered through Celite, the filtrate was concentrated in vacuo. The residue was chromatographed on silica gel (ethyl acetate/n-hexane= 1/1) to yield crude compound 5 (1.95 g) in the form of a pale colored solid. The crude compound 5 was recrystallized from isopropylether afforded a pure compound 5 in the form of a white solid (1.74 g, 45.1% yield).

Compound 5 had the following properties: mp 115–117° C. (isopropylether); $[\alpha]^{20}_D$+14.1° (c 1.06, CHCl$_3$); IR (CHCl$_3$) 3680 (w), 3005 (m), 2985 (m), 2865 (w), 1740 (s), 1515 (w), 1450 (w), 1400–1440 (w, br), 1365 (m), 1220 (s), 1160 (m), 1125 (w), 1070 (m), 1030 (s), 905 (w), 865 (w), 680–810 (m, br), 650 (m), 590 (w) cm$^{-1}$; $^{13}$C-NMR (125 MHZ, CDCl$_3$) δ 170.69, 169.46, 169.28, 96.84, 75.89, 74.87, 68.77, 66.35, 63.11, 33.34, 28.46, 20.87, 20.85, 20.71; $^1$H-NMR (500 MHZ, CDCl$_3$) δ 4.78 (ddd, J=5.0, 9.6, 10.7 Hz, 1H), 4.71 (ddd, J=5.2, 7.6, 11.2 Hz, 1H), 4.59 (d J=7.6 Hz, 1H), 4.16 (d, J=4.6 Hz, 2H), 3.68 (dt, J=4.6, 9.6 Hz, 1H), 2.57 (dt, J=5.1, 12.1 Hz, 1H), 2.05 (s, 3H), 2.03 (s, 3H), 2.02 (s, 3H), 1.59 (dd, J=11.1, 23.1 Hz, 1H), 1.24 (s, 9H); high-resolution mass spectrum (CI, ammonia) m/z 364.1970 [(M+NH$_4$)$^+$; calcd for C$_{16}$H$_{30}$NO$_8$: 364.1970]. Anal. Calcd for C$_{16}$H$_{26}$O$_8$: C, 55.48; H, 7.57. Found: C,; H,.

Reactions 6) and 7) Production of 1-O-tert-Butyl-4,6-O-p-methoxybenzylidene-3-deoxy-β-L-gluco-pyranoside (Compound 7)

A solution of compound 5 (11.13 g, 32.13 mmol) in methanol (200 mL) was treated with 4.37 M sodium methoxide in methanol (3 mL, 13.11 mmol). After the reaction mixture was stirred at room temperature for 50 min, Dowex-50W (H$^+$ form) was added. The resulting suspension was stirred at room temperature for 50 min, and then the resin was removed by filtration. The filtrate was concentrated in vacuo to yield crude 1-0-tert-butyl-3-deoxy-β-L-glucopyranoside (compound 6). Crude compound 6 was used in subsequent reactions without further purification.

Compound 6 had the following properties: IR (CHCl$_3$) 3570 (w), 3400 (w), 2960 (m), 2920 (m), 2870 (m), 1360 (m), 1140 (m), 1070 (s), 1020 (s), 860 (w) cm$^{-1}$; $^1$H-NMR (500 MHZ, CDCl$_3$) δ 4.43 (d, J=7.4 Hz, 1H), 3.85 (dd, J=4.1, 11.6 Hz, 1H), 3.76 (dd, J=5.2, 11.6 Hz, 1H), 3.72 (ddd, J=4.8, 9.0, 11.0 Hz, 1H), 3.42 (ddd, J=4.8, 7.4, 11.7 Hz, 1H), 3.35 (ddd, J=4.1, 5.2, 9.0 Hz, 1H), 2.42 (dt, J=4.8, 12.2 Hz, 1 H), 2.22 (br s, 3H), 1.58 (dd, J=11.3, 23.4 Hz, 1H), 1.29 (s, 9H).

A solution of compound 6 in chloroform (150 mL) was treated with p-methoxybenzaldehyde dimethylacetal (7.7 mL, 45.22 mmol) and then with pyridinium p-toluenesulfonate (150 mg, 0.6 mmol). After the reaction mixture was refluxed for 30 min, potassium carbonate (5.0 g, 36.17 mmol) was added to the solution. The resulting suspension was refluxed for 30 min, then insoluble matter was filtered off. The filtrate was washed with brine (2×100 mL), dried over magnesium sulfate and concentrated. The residue was purified by silica gel column chromatography (CH$_2$Cl$_2$/ether=10/1) to yield crude compound 7 in the form of a pale yellow solid. This was triturated with n-hexane to give pure compound 7 in the form of a white solid (6.66 g, 61.3% yield in 2 steps).

Compound 7 had the following properties: mp 107–108° C. (n-hexane); $[\alpha]^{20}_D$+38.2° (c 1.14, CHCl$_3$); IR (CHCl$_3$) 3570 (w), 2980 (m), 2860 (m), 1610 (m), 1510 (m), 1460 (m), 1365 (m), 1245 (s), 1150 (m), 1070 (s), 1060 (s), 1000 (s) cm$^{-1}$; $^{13}$C-NMR (125 MHz, CDCl$_3$) δ 160.16, 129.91, 127.47, 113.71, 101.70, 99.94, 76.29, 76.19, 70.66, 69.16, 69.10, 55.28, 35.12, 28.80; $^1$H-NMR (500 MHz, CDCl$_3$) δ 7.41 (d, J=8.7 Hz, 2H), 6.89 (d, J=8.7 Hz, 2H), 5.47 (s, 1H), 4.49 (d, J=7.5 Hz, 1H), 4.24 (dd, J=4.9, 10.5 Hz, 1H), 3.80 (s, 3H), 3.75 (t, J=10.3 Hz, 1H), 3.58 (m, 2H), 3.43 (ddd, J=4.9, 9.2, 9.9 Hz, 1H), 2.47 (dt, J=4.6, 11.9 Hz, 1H), 2.19 (d, J=2.2Hz, 1H), 1.75 (dd, J=11.9, 23.4 Hz, 1H), 1.31 (s, 9H); high-resolution mass spectrum (CI, ammonia) m/z 339.1804 [(M+H)$^+$; calcd for C$_{18}$H$_{27}$O$_6$: 339.1807]. Anal. Calcd for C$_{18}$H$_{26}$O$_6$: C, 63.89; H, 7.74. Found: C,; H,.

Reaction 8) Production of 1-O-tert-Butyl-2-O-benzyl-4,6-O-p-methoxybenzylidene-3-deoxy-β-L-glucopyranoside (Compound 8)

To an ice cooled solution of compound 7 (2.13 g, 6.29 mmol) in dry THF (30 mL) was added 60% NaH (300 mg, 7.5 mmol). After being stirred for 20 min, the mixture was treated with benzyl bromide (0.91 mL, 7.5 mmol) and tetra n-butylammonium iodide (700 mg, 1.9 mmol). The resulting solution was stirred at room temperature overnight. Ice water (30 mL) was added to the reaction mixture, and the resulting solution was concentrated in vacuo. The aqueous residue was extracted with ether/ethyl acetate (2×40 mL/4 mL), and the combined extracts were washed with brine (2×40 mL). The organic layer was separated, dried and concentrated in vacuo. Flash chromatography (ethyl acetate/ n-hexane=1/6) yielded compound 8 in the form of an amorphous solid (2.51 g, 93.1% yield). Compound 8 had the following properties: mp 87–90° C. (n-hexane); $[\alpha]^{20}_D$+ 32.5° (c 1.06, CHCl$_3$); IR (CHCl$_3$) 2970 (w), 2860 (w), 1610 (w), 1510 (w), 1450 (w), 1380 (w), 1360 (w), 1300 (w), 1240 (m), 1160 (m), 1075 (s), 1000 (m),820 (w) cm$^{-1}$; $^{13}$C-NMR(125 MHz, CDCl$_3$) δ 160.05, 138.48, 129.93, 128.24, 127.63, 127.59, 127.56, 127.48, 127.44, 127.39, 113.66, 113.61, 101.45, 99.72, 75.99, 75.94, 75.55, 72.80, 70.05, 69.18, 55.18, 35.21, 28.77; $^1$H-NMR (500 MHz, CDCl$_3$) δ 7.41 (d, J=8.7 Hz, 2H), 7.36 (m, 4H), 7.29 (m, 1H), 6.89 (d, J=8.7 Hz, 2H), 5.44 (s, lH), 4.83 (d, J=12.0 Hz, 1H), 4.68 (d, J=12.0 Hz, 1H), 4.66 (d, J=7.5 Hz, 1H), 4.24 (dd, J=4.9, 10.5 Hz, 1H), 3.80 (s, 3H), 3.73 (t, J=10.3 Hz, 1H), 3.50 (m, 1H), 3.39 (m, 2H), 2.41 (dt, J=4.6, 12.0 Hz, 1H), 1.77 (dd, J=11.8, 23.4 Hz, 1H), 1.34 (s, 9H); high-resolution mass spectrum (CI, ammonia) m/z 429.2276 [(M+H)$^+$; calcd for $C_{25}H_{33}O_6$: 429.2276].

Reactions 9) and 10) Production of 1-O-tert-Butyl-2-O-benzyl-4-O-p-methoxybenzyl-3,6-dideoxy-6-azido-β-L-glucopyranoside (Compound 10)

An ice-cooled solution of compound 8 (2.28 g, 5.34 mmol) in dry $CH_2Cl_2$ (50 mL) was treated with diisopropyl aluminum hydride (1.5 M solution in toluene, 10 mL, 15 mmol). The mixture was stirred at room temperature for 1.5 h, and then cooled in an ice bath again. Saturated aqueous Rochelle salt (potassium, sodium tartrateetetrahydrate, 50 mL) solution was added to the solution. The resulting biphasic solution was stirred at room temperature overnight. The organic layer was separated and washed with brine (2×40 mL), dried over magnesium sulfate and concentrated in vacuo. This alcohol (compound 9) was used for the next reaction without further purification.

Compound 9 had the following properties: IR (CHCl$_3$) 1960 (w), 1860 (w), 1610 (w), 1505 (w), 1450 (w), 1390 (w), 1360 (w), 1300 (w), 1240 (m), 1070 (s), 1040 (m) cm$^{-1}$; $^{13}$C-NMR (125 MHz, CDCl$_3$) δ 159.32, 138.62, 129.94, 129.31, 128.28, 127.60, 127.52, 127.47, 113.85, 99.53, 78.00, 75.86, 75.09, 72.80, 72.53, 70.76, 62.81, 55.21, 35.24, 28.83, 28.79, 28.76; $^1$H-NMR (500 MHz, CDCl$_3$) β 7.35 (m, 4H), 7.30 (m, 1H), 7.22 (d, J=8.6 Hz, 2H), 6.87 (d, J=8.6 Hz, 2H), 4.85 (d, J=11.9 Hz, 1H), 4.65 (d, J=11.9 Hz, 1H), 4.59 (d, J=7.6 Hz, 1H), 4.54 (d, J=11.1 Hz, 1H), 4.37 (d, J=11.1 Hz, 1H), 3.83 (dd, J=2.8, 11.8 Hz, 1H), 3.80 (s), 3.64 (dd, J=5.2, 11.8 Hz, 1H), 3.39 (m, 2H), 3.24 (m, 1H), 2.50 (m, 1H), 2.02 (br s, 1H), 1.56 (m, 1H), 1.33 (s, 9H).

To a solution of the alcohol (compound 9) in dry $CH_2Cl_2$ (50 mL) were added triethylamine (1.5 mL, 10.76 mmol) and a catalytic amount of DMAP. The solution was cooled in an ice bath, methanesulfonyl chloride (0.8 mL, 10.34 mmol) was added. After being stirred for 40 min, the reaction mixture was poured into ice-water (50 mL). The organic layer was separated, washed with 0.1 N hydrochloric acid (2×50 mL), saturated aqueous sodium bicarbonate (2×50 mL) and brine (2×50 mL). The organic layer was dried over magnesium sulfate and concentrated in vacuo. A solution of the residue dissolved in DMF (25 mL) was treated with sodium azide (1.74 g, 28.01 mmol), and the mixture was heated at 80° C. for 3.5 h. The resulting suspension was poured into water (150 mL), and then extracted with ether (1×100 mL). The organic layer was washed with brine (2×100 mL), dried and concentrated in vacuo. The residue was chromatographed on silica gel (ethyl acetate/n-hexane=1/5) to give pure compound 10 in the form of a pale yellow oil (1.75 g, 72.0% yield from compound 8). Compound 10 had the following properties: [α]$^{20}_D$ –19.4° (c 1.18, CHCl$_3$); IR (CHCl$_3$) 2970 (m), 2860 (m), 2090 (s), 1710 (w), 1610 (m), 1510 (m), 1450 (m), 1360 (m), 1240 (s), 1140 (m), 1070 (s), 1020 (s), 860 (w), 810 (w), 540 (w) cm$^{-1}$; $^{13}$C-NMR (125 MHz, CDCl$_3$) δ 159.36, 138.64, 129.71, 129.34, 128.24, 127.59, 127.56, 127.54, 127.51, 127.48, 127.44, 113.76, 99.50, 76.94, 75.91, 74.95, 72.86, 72.77, 70.53, 55.17, 51.92, 35.07, 28.77, 28.72, 28.67; $^1$H-NMR (500 MHz, CDCl$_3$) δ 7.36 (m, 4H), 7.30 (m, 1H), 7.20 (d, J=8.6 Hz, 2H), 6.88 (d, J=8.6 Hz, 2H), 4.88 (d, J=11.9 Hz, 1H), 4.66 (d, J=11.9 Hz, 1H), 4.59 (d, J=7.6 Hz, 1H), 4.54 (d, J=11.0 Hz, 1H), 4.32 (d, J=11.0 Hz, 1H), 3.81 (s, 3H), 3.47 (m, 2H), 3.28 (m, 3H), 2.53 (dt, J=4.8, 12.3 Hz, 1H), 1.54 (dd, J=11.8, 23.3 Hz, 1H), 1.36 (s, 9H); high-resolution mass spectrum (CI, ammonia) m/z 473.2775 [(M+NH$_4$)$^+$; calcd for $C_{25}H_{37}N_4O_5$: 473.2764].

Reaction 11) Production of 1-O-tert-Butyl-2-O-benzyl-3,6-dideoxy-6-azido-β-L-glucopyranoside (Compound 11)

A solution of compound 10 (1.75 g, 38.42 mmol) in $CH_2Cl_2$ (40 mL) and water (2 mL) was treated with DDQ (1.33 g, 57.42 mmol) and stirred at room temperature for 1 h. The insoluble matter was removed by filtration, the filtrate was washed with saturated aqueous sodium bicarbonate (3×40 mL) and brine (2×40 mL). The organic layer was separated, dried over magnesium sulfate and concentrated in vacuo. The residue was chromatographed on silica gel (ethyl acetate/n-hexane=1/4) to afford pure compound 11 as a pale yellow oil (948 mg, 73.6% yield).

Compound 11 had the following properties: [α]$^{20}_D$ +31.2° (c 1.0, CHCl$_3$); IR (CHCl$_3$) 3580 (w), 3380 (w), 2970 (m), 2860 (m), 2090 (s), 1450 (w), 1360 (m), 1270 (m), 1150 (m), 1050 (s), 860 (w) cm$^{-1}$; $^{13}$C-NMR (125 MHz, CDCl$_3$) δ 138.42, 128.34, 128.30, 128.26, 127.69, 127.64, 99.16, 78.03, 75.98, 74.82, 72.79, 66.58, 52.09, 38.33, 28.75, 28.73, 28.68; $^1$H-NMR (500 MHz, CDCl$_3$) δ 7.33 (m, 4H), 7.28 (m, 1H), 4.83 (d, J=11.9 Hz, 1H), 4.64 (d, J=11.9 Hz, 1H), 4.59 (d, J=7.3 Hz, 1H), 3.48 (m, 2H), 3.40 (m, 1H), 3.36 (m, 1H), 3.29 (m, 1H), 2.33 (dt, J=12.4 Hz, 1H), 1.83 (br s, 1H), 1.56 (dd, J=11.2, 23.5 Hz, 1H), 1.34 (s, 9H); high-resolution mass spectrum (CI, ammonia) m/z 353.2182 [(M+NH$_4$)$^+$; calcd for $C_{17}H_{29}N_4O_4$: 353.2189].

Reaction 12) Production of 1-O-tert-Butyl-2-O-benzyl-4-O-isobutyl-3,6-dideoxy-6-azido-β-L-glucopyranoside (Compound 12)

To an ice cooled solution of compound 11 (843 mg, 2.51 mmol) in dry THF (40 mL) was added 60% NaH (1.0 g, 25.0 mmol). After being stirred for 20 min, the mixture was treated with isobutyl bromide (2.7 mL, 24.58 mmol) and tetra n-butylammonium iodide (930 mg, 2.52 mmol). The resulting solution was refluxed for 6.5 h. Then, additional 60% NaH (2.0 g, 50.0 mmol) and isobutyl bromide (5.4 mL, 49.16 mmol) were added and the reaction mixture was refluxed for 24 h. Ice water (30 mL) was gradually added to the suspension and THF in the solution was concentrated in vacuo. The aqueous residue was extracted with ether (2×40 mL), and the combined extracts were washed with brine (2×40 mL). The ether layer was separated, dried and concentrated in vacuo. Flash chromatography (ethyl acetate/n-hexane=1/5) yielded compound 12 in the form of a pale yellow syrup (848 mg, 86.2% yield).

Compound 12 had the following properties: [α]$^{20}_D$ –2.5° (c 0.52, CHCl$_3$); IR (CHCl$_3$) 3040 (w), 2960 (m), 2860 (m), 2090 (s), 1450 (m), 1360 (m), 1280 (m), 1140 (m), 1090 (s), 1020 (m), 870 (w), 750 (w), 510 (m) cm$^{-1}$; $^{13}$C-NMR (125 MHz, CDCl$_3$) δ 138.71, 128.34, 127.69, 127.62, 127.49, 127.44, 99.59, 77.14, 75.94, 75.79, 74.96, 73.88, 72.87, 52.06, 35.16, 28.81, 28.76, 28.63, 19.25, 19.21; $^1$H-NMR (500 MHz, CDCl$_3$) δ 7.35 (m, 4H), 7.27 (m, 1H), 4.86 (d, J=11.9 Hz, 1H), 4.65 (d, J=11.9 Hz, 1H), 4.57 (d, J=7.6 Hz, 1H), 3.49 (dd, J=2.1, 12.6 Hz, 1H), 3.41 (ddd, J=2.0, 7.4, 9.4 Hz, 1H), 3.33 (d, J=7.4, 12.6 Hz, 1H), 3.31 (dd, J=6.4, 8.7 Hz, 1H), 3.27 (ddd, J=5.0, 7.6, 12.1 Hz, 1H), 3.12 (ddd, J=4.7, 9.2, 11.1 Hz, 1H), 3.02 (dd, J=6.7, 8.7 Hz, 1H), 2.49 (dt, J=4.8, 12.4 Hz, 1H), 1.76 (m, 1H), 1.44 (dd, J=11.8, 23.4 Hz, 1H), 1.35 (s, 9H), 0.87 (d, J=6.7 Hz, 3H), 0.86, (d, J=6.7 Hz, 3H); high-resolution mass spectrum (CI, ammonia) m/z 409.2831 [(M+NH$_4$)$^+$; calcd for $C_{21}H_{37}N_4O_4$: 409.2815].

Reaction 13) Production of 2-O-Benzyl-4-O-isobutyl-3,6-dideoxy-6-azido-L-glucopyranoside (Compound 13)

A solution of compound 12 (776 mg, 1.98 mmol) in 70% aqueous acetic acid (20 mL) was refluxed for 14 h, then cooled and concentrated in vacuo. The residue was dissolved in ethyl acetate (20 mL), and the resulting solution was washed with saturated aqueous sodium bicarbonate (3×20 mL) and brine (2×20 mL), dried and concentrated in vacuo. The residue was purified by flash chromatography (ethyl acetate/n-hexane=1/5) to afford a mixture of α- and β-anomers of compound 13 (α/β=1.5/1, 476 mg, 71.7% yield) in the form of a pale yellow syrup.

The mixture of α- and β-anomers of compound 13 had the following properties: $[\alpha]^{20}{}_D$–76.3° (c 0.52, CHCl$_3$); IR (CHCl$_3$) 3580 (m), 3400 (m), 3080 (w), 3030 (m), 2960 (s), 2880 (s), 2100 (s), 1710 (m), 1610 (w), 1500 (m), 1450 (m), 1370 (m), 1290 (s), 1090 (s), 1030 (s), 1010 (s), 900 (m), 840 (m), 550 (m) cm$^{-1}$; $^{13}$C-NMR (125 MHz, CDCl$_3$) δ 138.29 (β), 137.65 (α), 128.48, 128.45, 128.43, 128.41, 128.36, 127.92, 127.74, 127.72, 127.68, 127.64, 98.82 (β), 90.08 (α), 77.37 (β), 76.07 (β), 75.95 (β), 75.57 (α), 73.72 (α), 73.22 (β), 72.82 (α), 72.29 (β), 70.86 (α), 70.34, (α), 51.48, 34.15 (β), 29.05 (α), 28.62, 19.26, 19.24, 19.22, 19.20; $^{1}$H-NMR (500 MHz, CDCl$_3$) δ 7.35 (m, 5H), 5.25 (d, J=3.3 Hz, 0.6H), 4.80 (d, J=11.8 Hz, 0.4H), 4.72 (d, J=7.5 Hz, 0.4H), 4.69 (d, J=11.8 Hz, 0.4H), 4.61 (ABq, J=11.9 Hz, 2×0.6H), 3.93 (ddd, J=2.5, 5.0, 9.5 Hz, 0.6H), 3.54 (m, 2×0.6H+0.4H), 3.48 (m, 0.4H), 3.42 (dd, J=5.0, 13.0 Hz, 0.6H), 3.41 (dd, J=6.1, 12.7 Hz, 0.4H), 3.36 (dd, J=6.3, 8.8 Hz, 0.6H), 3.33 (dd, J=6.3, 8.7 Hz, 0.4H), 3.24 (m, 0.6H+ 0.4H), 3.07 (dd, J=6.9, 8.8 Hz, 0.6H), 3.06 (dd, J=7.3, 8.7 Hz, 0.4H), 2.53 (dt, J=4.8, 12.4 Hz, 0.4H), 2.35 (dt, J=4.6, 11.8 Hz, 0.6H), 1.79 (m, 0.6H+0.4H), 1.73 (dd, J=11.7, 23.3 Hz, 0.6H), 1.44 (dd, J=11.7, 23.5 Hz, 0.4H), 0.90 (d, J=6.7 Hz, 3×0.6H), 0.89 (d, J=6.7 Hz, 3×0.6H), 0.88 (d, J=6.6 Hz, 3×0.4H), 0.87 (d, J=6.6 Hz, 3×0.4H); high-resolution mass spectrum (CI, ammonia) m/z 353.2178 [(M+NH$_4$)$^+$; calcd for C$_{17}$H$_{29}$N$_4$O$_4$: 353.2189].

Reaction 14) Production of (4S,6R,7S)-Ethyl 8-azido-4-benzyloxy-7-hydroxy-6-isobutyloxy-2-methyl-2-octenoate (Compound 14)

A solution of the mixture of α- and β-anomers of compound 13 (2.65 g, 7.90 mmol) and (carboethoxyethylidene)triphenyl-phosphorane (94%, 5.0 g, 13.0 mmol) in acetonitrile (70 mL) was refluxed for 2 days. After 1 h, 4.14 g (10.7 mmol) of (carboethoxyethylidene)triphenylphosphorane was added, and after 40 h, and additional 3.05 g (8.0 mmol) of (carboethoxyethylidene)triphenylphosphorane was added. The reaction mixture was concentrated in vacuo, and ethyl acetate/n-hexane (10 mL and 50 mL, respectively) was added to the residue. Precipitated triphenylphosphine oxide was filtered off and the filtrate was concentrated in vacuo. The residue was chromatographed on silica gel (ethyl acetate/n-hexane=1/5) to yield compound 14 in the form of a pale yellow syrup (2.52 g, 76.1% yield).

Compound 14 had the following properties: $[\alpha]^{20}{}_D$–31.6° (c 1.6, CHCl$_3$); IR (CHCl$_3$) 3480 (w), 3000 (m), 2940 (m), 2920 (m), 2860 (m), 2090 (s), 1705 (s), 1645 (w), 1450 (w), 1360 (m), 1240 (s), 1090 (s), 750 (m), 685 (m), 650 (m) cm$^{-1}$; $^{13}$C-NMR (125 MHz, CDCl$_3$) δ 167.47, 141.15, 137.13, 130.14, 128.59, 128.19, 128.13, 77.48, 76.47, 71.77, 71.35, 60.91, 53.53, 34.03, 28.80, 19.41, 19.37, 14.22, 12.84; $^{1}$H-NMR (500 MHz, CDCl$_3$) δ 7.34 (m, 2H), 7.31 (m, 3H), 6.70 (dq, J=1.4, 9.1 Hz, 1H), 4.54 (d, J=11.2 Hz, 1H), 4.53 (m, 1H), 4.36 (d, J=11.2 Hz, 1H), 4.23 (q, J=7.1 Hz, 2H), 3.75 (ddd, J=2.9, 6.6, 8.0 Hz, 1H), 3.43 (dd, J=3.9, 12.6 Hz, 1H), 3.35 (m, 1H), 3.33 (dd, J=6.6, 12.6 Hz, 1H), 3.22 (dd, J=6.4, 8.7 Hz, 1H), 3.07 (dd, J=6.4, 8.7 Hz, 1H), 2.07 (ddd, J=3.6, 9.0 Hz, 15.4, 1H), 1.88 (d, J=1.4 Hz, 3H), 1.78 (m, 1H), 1.32 (t, J=7.1 Hz, 3H), 1.29 (m, 1H), 0.89 (d, J=6.7 Hz, 3H), 0.88 (d, J=6.7 Hz, 3H).

Reaction 15) Production of (R)-2-[(2S,3S,5R,6S)-2-(6-Azidomethyl-3-benzyloxy-5-isobutyloxy)-2,3,4,5-tetrahydropyranyl]propionic acid (Compound 15R)

Figure 8A:
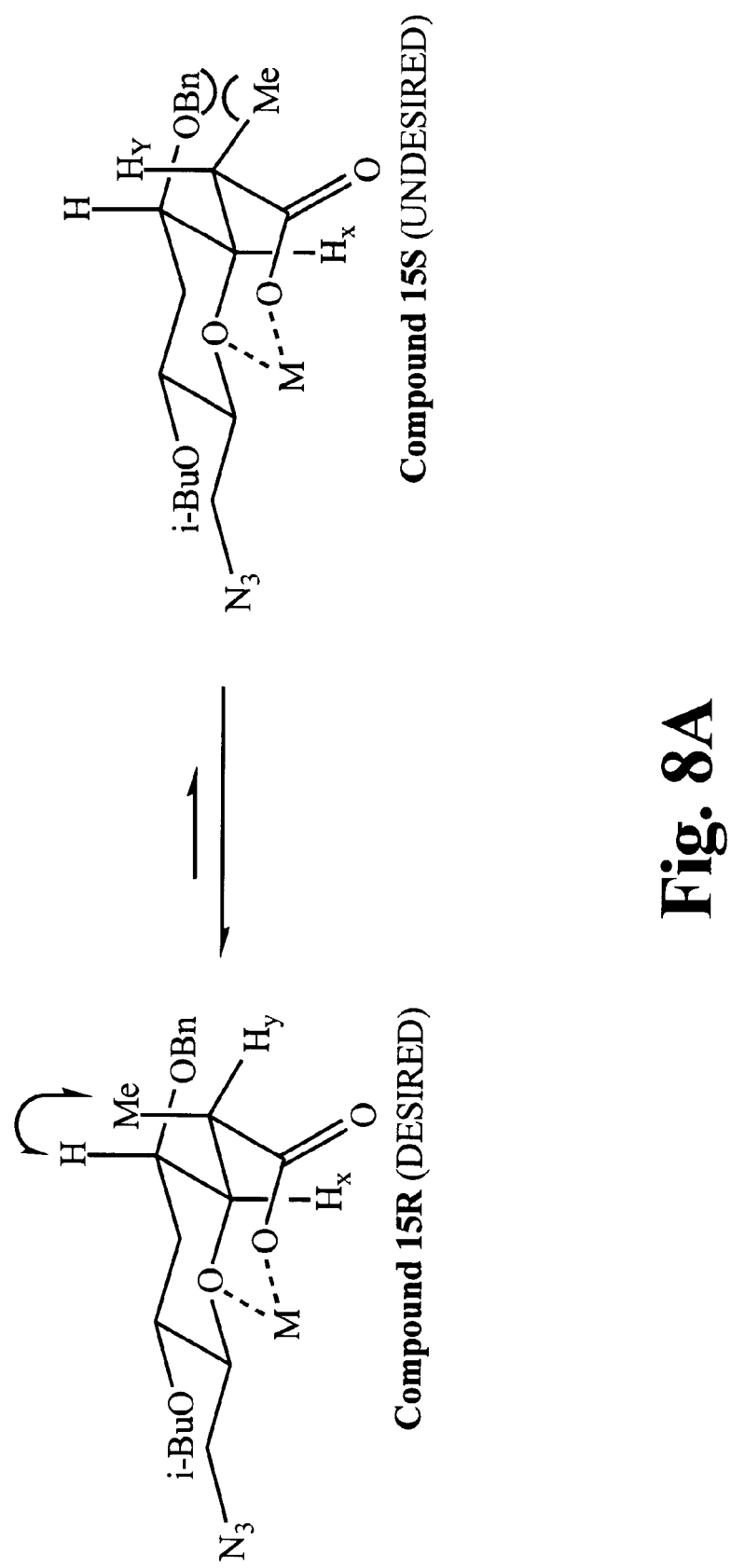
FIG. 8, comprising Panels A and B, depicts steric repulsion between groups of compound 15R of FIG. 7. In Panel A, a hypothesized cause of the stereoselectivity observed in reaction 15) of FIG. 7 is illustrated. In Panel B, an experiment performed to confirm this hypothesis is illustrated.
Figure 8B:
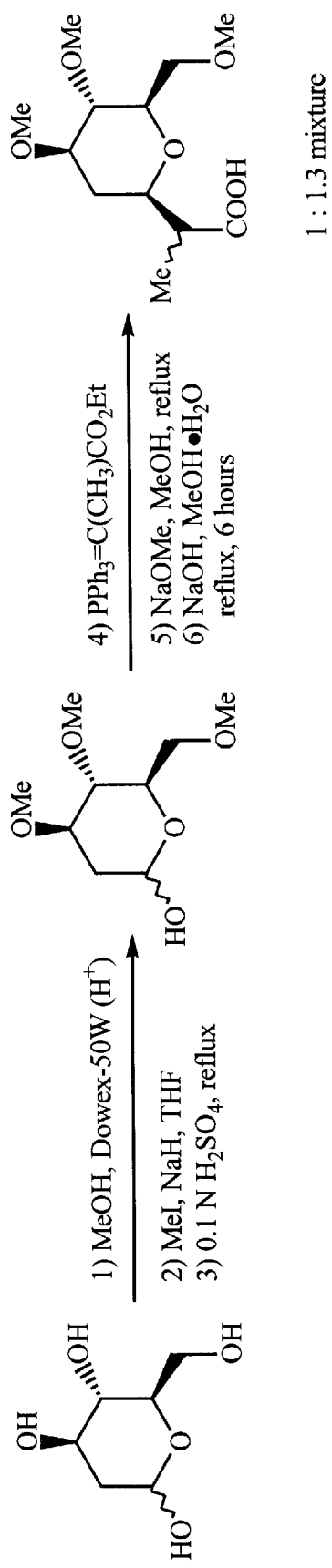

A solution of compound 14 (980 mg, 2.34 mmol) and 4.37 M sodium methoxide in methanol (2.7 mL, 11.8 mmol) in MeOH (60 mL) was refluxed for 2h. To the mixture was added Dowex-50W (H$^+$ form, 1.0 g) and the suspension was stirred for 1 h. The resin was removed by filtration and the filtrate was concentrated in vacuo. The residue was dissolved in ethyl acetate (60 mL) and washed with 0.1 N HCl (2×60 mL) and brine (2×60 mL). The organic layer was dried over magnesium sulfate and concentrated in vacuo. Methanol (45 mL) and an aqueous solution of lithium hydroxide monohydrate (980 mg, 23.36 mmol in 12 mL water) were added to the residue. The resulting mixture was refluxed for 2.5 h, cooled in an ice bath, and then acidified with concentrated HCl. The mixture was concentrated in vacuo and the residue was partitioned between CH$_2$Cl$_2$ and brine. The organic layer was separated, dried and concentrated in vacuo. Flash chromatography (chloroform/methanol=50/1) followed by a second flash chromatography procedure (chloroform/methanol=60/1) afforded compound 15R (600 mg, 66.0% yield) in the form of a pale yellow oil. At the same time, the epimer of compound 15R, (S)-2-[(2S, 3S,5R,6S)-2-(6-azidomethyl-3-benzyloxy-5-isobutyloxy)-2,3,4,5-tetrahydropyranyl]propionic acid ("compound 15S"; 177 mg, 19.5% yield), was also obtained. This epimer was recrystallized from isopropylether to yield pure compound 15S in the form of a white crystal. It was hypothesized that a steric repulstion between the methyl and the benzyloxy group may cause the stereoselectivity observed in this synthetic step (FIG. 8, Panel A). In order to confirm this hypothesis, the same reaction was performed using compounds which were unsubstituted at the 2-position of the glucose ring. As depicted in FIG. 8, Panel B, the stereoselectivity of the reaction was greatly reduced using these compounds.

Compound 15R had the following properties: $[\alpha]^{20}{}_D$+3.4° (c 1.12, CHCl$_3$); IR (CHCl$_3$) 3010 (s), 2960 (m), 2880 (m), 2100 (s), 1710 (m), 1460 (w), 1440 (w), 1230 (s), 1200 (s), 1100 (s), 920 (w), 790 (m), 670 (m) cm$^{-1}$; $^{13}$C-NMR (125 MHz, CDCl$_3$) δ 177.56, 137.76, 128.49, 127.90, 127.81, 80.26, 75.97, 73.32, 73.03, 70.54, 51.46, 40.21, 34.48, 29.70, 28.71, 19.32, 19.28, 9.86; $^{1}$H-NMR (500 MHz, CDCl$_3$) δ 7.32 (m, 5H), 4.67 (d, J=11.5 Hz, 1H), 4.44 (d, J=11.5 Hz, 1H), 3.78 (dd, J=4.0, 9.4 Hz, 1H), 3.47 (dd, J=2.3, 13.0 Hz, 1H), 3.42 (ddd, J=2.3, 5.3, 9.2 Hz, 1H), 3.36 (dd, J=6.3, 8.8 Hz, 1H), 3.33 (ddd, J=4.3, 9.5, 11.0 Hz, 1H), 3.28 (dd, J=5.3, 13.0 Hz, 1H), 3.20 (ddd, J=4.5, 9.4, 11.2 Hz, 1H), 3.07 (dd, J=6.8, 8.8 Hz, 1H), 2.90 (dq, J=4.0, 7.1 Hz, 1H), 2.75 (dt, J=4.4, 11.8 Hz, 1H), 1.79 (m, 1H), 1.40 (dd, J=11.2, 22.6 Hz, 1H), 1.11 (d, J=7.1 Hz, 3H), 0.89 (d, J=6.7 Hz, 3H), 0.88 (d, J=6.7 Hz, 3H); high-resolution mass spectrum (CI, ammonia) m/z 409.2467 [(M+NH$_4$)$^+$; calcd for C$_{20}$H$_{33}$N$_4$O$_5$: 409.2451].

Compound 15S had the following properties: mp 88–90° C. (isopropylether); $[\alpha]^{20}{}_D$–5.7° (c 1.0, CHCl$_3$); IR (CHCl$_3$) 3010 (m), 2960 (s), 2880 (s), 2100 (s), 1715 (s), 1460 (m), 1350 (m), 1290 (m), 1220 (m), 1110 (s), 990 (w), 910 (w), 690 (w), 660 (w) cm$^{-1}$; $^{13}$C-NMR (125 MHz, CDCl$_3$) δ 178.49, 137.92, 128.35, 127.89, 127.72, 82.08, 80.47, 75.92, 73.30, 73.26, 71.11, 51.46, 40.38, 34.78, 28.65, 19.28, 19.24, 12.81; $^{1}$H-NMR (500 MHz, CDCl$_3$) δ 7.33 (m, 4H), 7.28 (m, 1H), 4.63 (d, J=11.1 Hz, 1H), 4.52 (d, J=11.1 Hz, 1H), 3.64 (ddd, J=4.4, 9.6, 10.8 Hz, 1H), 3.50 (m, 2H), 3.40 (ddd, J=2.3, 5.6, 11.4 Hz, 1H), 3.35 (dd, J=6.3, 8.7 Hz, 1H), 3.31 (dd, J=5.6, 13.0 Hz, 1H), 3.21 (ddd, J=4.4, 9.4, 11.1 Hz, 1H), 3.07 (dd, J=6.8, 8.8 Hz, 1H), 3.03 (dq, J=2.7, 7.2 Hz, 1H), 2.71 (dt, J=4.4, 11.8 Hz, 1H), 1.79 (m, 1H), 1.35 (dd, J=11.3, 22.7 Hz, 1H), 1.27 (d, J=7.2 Hz, 3H), 0.89 (d, J=6.7 Hz, 3H), 0.88 (d, J=6.7 Hz, 3H).

Reaction 16) Production of (R)-tert-Butyl 2-[(2S,3S,5R,6S)-2-(6-azidomethyl-3-benzyloxy-5-isobutyloxy)-2,3,4,5-tetrahydropyranyl]propionate (Compound 16)

A solution of compound 15R (600 mg, 1.53 mmol) in toluene (7 mL) was heated at 85–87° C. in an oil bath. To the reaction mixture was dropwise added N,N-dimethylformamide di-tert-butylacetal (3.7 mL, 15.4 mmol). The resulting mixture was heated at 85° C. for 8 h, then washed with brine. The organic layer was dried over magnesium sulfate and concentrated in vacuo. The residue was chromatographed on silica gel (ethyl acetate/n-hexane=1/5) to yield pure compound 16 (547 mg, 79.7% yield) in the form of a pale yellow syrup.

Compound 16 had the following properties: $[\alpha]^{20}_D$+1.64° (c 0.55, CHCl$_3$); IR (CHCl$_3$) 3000 (m), 2950 (s), 2870 (s), 2100 (s), 1750 (s), 1450 (m), 1330 (s), 1270 (s), 1220 (m), 1160 (s), 1100 (s), 990 (m), 830 (w), 680 (w) cm$^{-1}$; $^{13}$C-NMR (125 MHz, CDCl$_3$) δ 173.36, 137.92, 128.45, 127.89, 127.87, 80.77, 80.17, 80.06, 75.92, 73.51, 72.88, 70.54, 51.75, 40.84, 34.61, 28.71, 28.00, 19.30, 19.26, 9.35; $^1$H-NMR (500 MHz, CDCl$_3$) δ 7.34 (m, 5H), 4.66 (d, J=11.6 Hz, 1H), 4.45 (d, J=11.6 Hz, 1H), 3.79 (dd, J=3.5, 9.5 Hz, 1H), 3.46 (dd, J=2.4, 12.9 Hz, 1H), 3.36 (m, 2H), 3.30 (ddd, J=4.3, 9.6, 10.9 Hz, 1H), 3.25 (dd, J=5.3, 12.9 Hz, 1H), 3.20 (ddd, J=4.7, 9.3, 11.1 Hz, 1H), 3.07 (dd, J=6.7, 8.8 Hz, 1H), 2.80 (dq, J=3.5, 7.2 Hz, 1H), 2.74 (dt, J=4.4, 11.7 Hz, 1H), 1.79 (m, 1H), 1.43 (s, 9H), 1.39 (dd, J=8.3, 22.6 Hz, 1H), 1.03 (d, J=7.2 Hz, 3H), 0.90 (d, J=6.7 Hz, 3H), 0.89 (d, J=6.7 Hz, 3H); high-resolution mass spectrum (CI, ammonia) m/z 465.3091 [(M+NH$_4$)$^+$; calcd for C$_{24}$H$_{41}$N$_4$O$_5$: 465.3077].

Reaction 17) Production of (R)-tert-Butyl 2-[(2S,3S,5R,6S-2-(6-tert-butoxycarbonylaminomethyl-3-hydroxy-5-isobutyloxy)-2,3,4,5-tetrahydropyranyl]propionate (Compound 17)

To a solution of compound 16 (498 mg, 1.11 mmol) in ethyl acetate (20 mL) were added di-tert-butyl dicarbonate (365 mg, 1.67 mmol) and 10% Pd—C (50% water, 100 mg). The suspension was stirred at room temperature for 24 h under a hydrogen atmosphere. The catalyst was filtered off and the filtrate was concentrated in vacuo. The residue was chromatographed on silica gel (ethyl acetate/n-hexane=1/5) to provide pure compound 17 (338 mg, 72.8% yield) in the form of a white foam.

Compound 17 had the following properties: mp 101–103° C.; $[\alpha]^{20}_D$ _41.6° (c 1.07, CHCl$_3$); IR (CHCl$_3$) 3460 (w), 3010 (m), 2980 (m), 1720 (s), 1510 (m), 1460 (w), 1390 (w), 1370 (m), 1240 (s), 1160 (s), 1105 (m), 1040 (m), 780 (m), 700 (m), 660 (m) cm$^{-1}$; $^{13}$C-NMR (125 MHz, CDCl$_3$) δ 174.04, 155.71, 81.96, 80.45, 79.55, 76.11, 74.91, 66.64, 42.08, 41.22, 38.62, 28.64, 28.32, 28.06, 19.28, 9.71; $^1$H-NMR (500 MHz, CDCl$_3$) δ 4.86 (br s, 1H), 3.62 (m, 1H), 3.49 (m, 2H), 3.27 (m, 1H), 3.15 (m, 1H), 3.07 (dd, J=6.6, 8.8 Hz, 1H), 3.02 (m, 2H), 3.28 (m, 1H), 2.51 (dt, J=4.4, 11.8 Hz, 1H), 2.29 (br s, 1H), 1.78 (m, 1H), 1.51 (s, 9H), 1.48 (s, 9H), 1.46 (m, 1H), 1.06 (d, J=7.1 Hz, 3H), 0.87 (d, J=6.7 Hz, 3H), 0.86 (d, J=6.7 Hz, 3H). Anal. Calcd for C$_{22}$H$_{41}$NO$_7$: C, 61.23; H, 9.58; N, 3.25. Found: C,; H,; N,.

Reaction 18) Production of (R)-tert-Butyl 2-{(2S,3S,5R,6S)-2-[6-tert-butoxycarbonylaminomethyl-5-isobutyloxy-3-(2-propenyloxy)]-2,3,4,5-tetrahydropyranyl}propionate (Compound 18)

Compound 17 (245 mg, 0.568 mmol) was dissolved in THF (9 mL) and cooled in an ice bath. To the solution was added 60% NaH (25 mg, 0.625 mmol) and the solution was stirred for 10 min. Tetra n-butylammmonium iodide (63 mg, 0.171 mmol) and allyl bromide (0.14 mL, 1.602 mmol) were added to the suspension. After being stirred for 23 h, the resulting solution was treated with a few drops of acetic acid. The mixture was concentrated in vacuo, and the residue was partitioned between ether and saturated aqueous sodium bicarbonate (2×10 mL). The organic layer was separated, washed with brine (2×10 mL), dried and concentrated. The residue was chromatographed on silica gel (ethyl acetate/n-hexane=1/7→1/4) to yield compound 18 (224 mg, 83.6% yield) in the form of a pale colored oil.

Compound 18 had the following properties: $[\alpha]^{20}_D$-7.7° (c 1.0, CHCl$_3$); IR (CHCl$_3$) 3460 (m), 2980 (s), 2860 (s), 1710 (s), 1500 (s), 1450 (m), 1390 (m), 1370(s), 1280(m), 1240(s), 1170(s), 1110(s), 990(m), 920(w), 870(w) cm$^{-1}$; $^{13}$C-NMR (125 MHz, CDCl$_3$) δ 173.59, 155.67, 134.72, 117.34, 80.41, 80.19, 79.70, 78.87, 76.21, 74.95, 72.76, 69.59, 42.12, 40.66, 34.75, 28.74, 28.35, 28.14, 19.35, 19.34,9.17; $^1$H-NMR (500 MHz, CDCl$_3$) δ 5.88 (m, 1H), 5.27 (dq, J=1.6, 17.2 Hz, 1H), 5.18 (dq, J=1.3, 10.4 Hz, 1H), 4.81 (br s, 1H), 4.10 (ddt, J=1.3, 5.5, 12.5 Hz, 1H), 3.91 (ddt, J=1.3, 6.0, 12.5 Hz, 1H), 3.68 (dd, J=3.3, 9.5, 1H), 3.66 (br m, 1H), 3.31 (br m, 1H), 3.20 (m, 2H), 3.07 (dd, J=6.7, 8.6 Hz, 1H), 2.99 (br m, 2H), 2.79 (br m, 1H), 2.64 (dt, J=4.5, 11.7 Hz, 1H), 1.79 (m, 1H), 1.44 (s, 9H), 1.40 (s, 9H), 1.32 (dd, J=11.2, 22.6 Hz, 1H), 1.06 (d, J=7.1 Hz, 3H), 0.90 (d, J=7.0 Hz, 3H), 0.88 (d, J=7.0 Hz, 3H); high-resolution mass spectrum (CI, ammonia) m/z 489.3526 [(M+NH$_4$)$^+$; calcd for C$_{25}$H$_{45}$NO$_7$: 489.3540].

Reaction 19) Production of (R)-tert-Butyl 2-{(2S,3S,5R,6S)-2-[3-[[(benzyloxycarbonyl)methyl]oxy]-6-tert-butoxycarbonylaminomethyl-5-isobutyloxy]-2,3,4,5-tetrahydropyranyl}propionate (Compound 19)

A solution of compound 18 (224 mg, 0.475 rnmol) in CCl$_4$ (1.5 mL), acetonitrile (1.5 mL) and water (2.3 mL) was treated with sodium periodate (508 mg, 2.38 mmol) and ruthenium dioxide.exhydrate (2 mg). After being stirred at room temperature overnight, the mixture was diluted with CHCl$_3$ (10 mL) and washed with water (1×10 mL) and brine (1×10 mL). The organic layer was separated, dried and concentrated in vacuo. To a solution of the oily residue in DMF (2 mL) were added potassium carbonate (330 mg, 2.39 mmol) and benzyl bromide (0.17 mL, 1.4 mmol). After being stirred at room temperature for 1 h, the reaction mixture was diluted with ether (15 mL). The ether solution was washed with water (1×15 mL) and brine (2×15 mL), dried over magnesium sulfate and concentrated in vacuo. Flash chromatography of the residue (ethyl acetate/n-hexane=1/7) yielded compound 19 (196.8 mg, 71.6%) in the form of a pale yellow oil.

Compound 19 had the following properties: $[\alpha]^{20}_D$-0.68° (c 1.48, CHCl$_3$); IR (CHCl$_3$) 3000 (s), 2960 (m), 2390 (w), 1720 (s), 1500 (m), 1360 (m), 1190 (s), 1150 (s), 1100 (s), 920 (w), 700 (s), 650 (s) cm$^{-1}$; $^{13}$C-NMR (125 MHz, CDCl$_3$) δ 173.48, 169.92, 155.64, 135.26, 128.62, 128.53, 128.46, 80.19, 79.63, 78.88, 76.23, 74.77, 73.90, 66.69, 65.63, 42.01, 40.51, 34.32, 28.71, 28.34, 28.11, 29.31, 9.01; $^1$H-NMR (500 MHz, CDCl$_3$) δ 7.36 (m, 5H), 5.19 (s, 2H), 4.81 (br s, 1H), 4.16 (ABq, J=16.3 Hz, 2H), 3.73 (dd, J=3.0, 9.4 Hz, 1H), 3.67 (m, 1H), 3.33 (m, 1H), 3.28 (m, 1H), 3.21 (m, 1H), 3.06 (dd, J=6.7, 8.5 Hz, 1H), 2.99 (m, 2H), 2.90 (m, 1H), 2.64 (dt, J=4.5, 11.7 Hz, 1H), 1.78 (m, 1H), 1.45 (s, 9H), 1.42 (s, 9H), 1.36 (dd, J=11.3, 22.6 Hz, 1 H), 1.08 (d, J=7.1 Hz, 3H), 0.90 (d, J=7.0 Hz, 3H), 0.88 (d, J=7.0 Hz, 3H); high-resolution mass spectrum (CI, ammonia) m/z 597.3765 [(M+NH$_4$)$^+$; calcd for C$_{31}$H$_{53}$N$_2$O$_9$: 597.3751].

Reaction 20) Production of (R)-2-{(2S,3S,5R,6S)-2-[3-[[(Benzyloxycarbonyl)methyl]oxy]-6-tert-butoxycarbonylaminomethyl-5-isobutyloxy]-2,3,4,5-tetrahydropyranyl}propionic acid (Compound 20)

A solution of compound 19 (131.7 mg, 0.227 mmol) in $CH_2Cl_2$ (5 mL) was treated with anisole (1 mL, 9.2 mmol) and trifluoroacetic acid (TFA, 5 mL) at 0° C. After being stirred for 3 h, the reaction mixture was concentrated in vacuo to yield the TFA salt of (R)-2-{(2S,3S,5R,6S)-2-[3-[[(benzyloxycarbonyl)methyl]oxy]-6-aminomethyl-5-isobutyloxy]-2,3,4,5-tetrahydropyranyl}propionic acid in the form of a pale brown syrup which was used for the next reaction without further purification.

This compound had the following properties: $^1$H-NMR (500 MHz, $CDCl_3$) δ 7.87 (br s, 3H), 7.36 (m, 5H), 5.19 (s, 2H), 4.17 (ABq, J=16.4 Hz, 2H), 3.81 (m, 1H), 3.50 (m, 1H), 3.41 (m, 2H), 3.31 (dd, J=6.4, 8.6 Hz, 1H), 3.08 (m, 1H), 3.04 (m, 1H), 3.02 (dd, J=6.7, 8.6 Hz, 1H), 2.91 (br m, 1H), 2.69 (dt, J=4.4, 11.8 Hz, 1H), 1.78 (m, 1H), 1.39 (dd, J=11.3, 23.5 Hz, 1H), 1.13 (d, J=7.1 Hz, 3H), 0.87 (d, J=6.7 Hz, 3H), 0.86 (d, J=6.7 Hz, 3H).

To a solution of this compound in $CH_2Cl_2$ (3 mL) were added triethylamine (0.16 mL, 1.15 mmol) and di-tert-butyl dicarbonate (65 mg, 0.298 mmol). After being stirred for 1 h at room temperature, the mixture was washed with cold 0.1 N hydrochloric acid (2×5 mL) and brine (2×5 mL). The organic layer was dried over magnesium sulfate and concentrated in vacuo. The residue was purified by flash chromatography (chloroform/methanol=30/1) and by a second flash chromatography step (chloroform/methanol=50/1) to yield compound 20 (112.5 mg, 94.6% yield in 2 steps) in the form of a pale yellow oil.

Compound 20 had the following properties: $[α]^{20}_D$+5.7° (c 3.4, $CHCl_3$); IR ($CHCl_3$) 3440 (w), 3000 (m), 2950 (m), 2860 (m), 1750 (m), 1705 (s), 1500 (m), 1440 (w), 1380 (w), 1360 (m), 1300 (m), 1150 (s), 1100 (s), 1020 (w), 920 (w), 690 (w), 650 (w) $cm^{-1}$; $^{13}$C-NMR (125 MHz, $CDCl_3$) δ 179.41, 169.87, 155.84, 135.23, 128.58, 128.48, 128.42, 79.52, 79.24, 79.03, 77.20, 76.17, 74.24, 66.65, 65.49, 41.74, 40.24, 34.13, 28.64, 28.31, 19.27, 9.96; $^1$H-NMR (500 MHz, $CDCl_3$) δ 7.36 (m, 5H), 5.18 (s, 2H), 4.15 (ABq, J=16.3 Hz, 2H), 3.69 (br m, 1H), 3.52 (br m, 1H), 3.34 (ddd, J=4.4, 9.4, 11.0 Hz, 1H), 3.24 (m, 3H), 3.03 (m, 2H), 2.98 (dd, J=3.9, 7.1 Hz, 1H), 2.64 (dt, J=4.5, 11.8 Hz, 1H), 1.79 ((m, 1H), 1.43 (s, 9H), 1.37 (dd, J=11.3, 22.7 Hz, 1H), 1.19 (d, J=7.0 Hz, 3H), 0.90 (d, J=6.8 Hz, 3H), 0.89 (d, J=6.8Hz, 3H); high-resolution mass spectrum (CI, ammonia) m/z 524.2863 [(M+H)$^+$; calcd for $C_{27}H_{42}NO_9$: 524.2859].

Reaction 21) Production of (R)-2-{(2S,3S,5R,6S)-2-[3-[[(Benzyloxycarbonyl)methyl]oxy]-6-tert-butoxycarbonylaminomethyl-5-isobutyloxy]-2,3,4,5-tetrahydropyranyl}propionyl-Asp(OBn)-Phe-OBn (Compound 21)

A solution of compound 20 (74.8 mg, 0.143 mmol) and Asp(OBn)-Phe-OBn.TFA (110 mg, 0.191 mmol) in THF (2 mL) was cooled to 0° C. in an ice bath. To the solution were added dropwise diethyl cyanophosphonate (DECP; 0.035 mL, 0.215 mmol) in THF (0.5 mL) followed by triethylamine (0.03 mL, 0.215 mmol) in THF (0.5 mL). After being stirred for 1.5 h, the mixture was diluted with toluene (5 mL) and ethyl acetate (10 mL). The resulting solution was washed with ice-cooled 0.1 N hydrochloric acid (2×15 mL), ice water (1×15 mL), ice-cooled brine (1×15 mL), ice-cooled saturated aqueous sodium bicarbonate (2×15 mL), ice water (1×15 mL) and ice-cooled brine (1×15 mL). The organic layer was dried over magnesium sulfate and concentrated in vacuo. The residue was chromatographed on silica gel (ethyl acetate/n-hexane=1/2) to yield compound 21 (120.8 mg, 87.6% yield) in the form of an amorphous solid.

Compound 21 had the following properties: mp 107–108° C. (n-hexane); $[α]^{20}_D$+3.7° (c 1.0, $CHCl_3$); IR ($CHCl_3$) 3665 (w), 3605 (w), 3350 (w), 3005 (s), 2970 (m), 2880 (w), 2400 (w), 1720 (s), 1660 (s), 1600 (w), 1505 (s), 1360 (m), 1200 (s), 1100 (s), 1020 (w), 920 (w), 690 (s), 655 (s) $cm^{-1}$; $^{13}$C-NMR (125 MHz, $CDCl_3$) δ 175.08, 171.69, 170.79, 170.30, 170.05, 155.94, 135.61, 135.36, 135.15, 135.09, 129.23, 128.58, 128.49, 128.47, 128.42, 128.38, 128.33, 128.23, 128.14, 128.08, 127.01, 79.32, 79.20, 79.03, 76.02, 74.15, 74.03, 67.04, 66.70, 66.68, 65.33, 53.53, 49.20, 41.81, 41.62, 37.64, 35.51, 34.03, 28.65, 28.31, 19.27, 11.56; $^1$H-NMR (500 MHz, $CDCl_3$) δ 7.33 (m, 12H), 7.27 (m, 2H), 7.25 (m, 3H), 7.05 (m, 3H), 5.17 (s, 2H), 5.16 (br s, 1H), 5.13 (d, J=12.2 Hz, 1H), 5.09 (s, 2H), 5.08 (d, J=12.2 Hz, 1H), 4.81 (m, 2H), 4.16 (s, 2H), 3.51 (m, 1H), 3.37 (br dd, J=2.6, 9.1 Hz, 1H), 3.29 (m, 2H), 3.19 (m, 2H), 3.12 (dd, J=5.9, 14.0 Hz, 1H), 3.06 (m, 2H), 2.99 (m, 1H), 2.98 (dd, J=5.7, 16.9 Hz, 1H), 2.83 (dq, J=3.2, 7.2 Hz, 1H), 2.73 (br dd, J=6.1, 16.8 Hz, 1H), 2.63 (dt, J=4.4, 11.8 Hz, 1H), 1.80 (m, 1H), 1.41 (s, 9H), 1.31 (dd, J=11.3, 22.6 Hz, 1H), 1.09 (d, J=7.2 Hz, 3H), 0.91 (d, J=6.7 Hz, 3H), 0.89 (d, J=6.7 Hz, 3H); high-resolution mass spectrum (FAB) m/z 985.4565 [(M+Na)$^+$; calcd for $C_{54}H_{67}N_3O_{13}$: 985.4571].

Reaction 22) Production of (R)-2-{(2S,3S,5R,6S)-2-[3-[[(Benzyloxycarbonyl)methyl]oxy]-6-AcPhe-aminomethyl-5-isobutyloxy]-2,3,4,5-tetrahydropyranyl}propionyl-Asp(OBn)-Phe-OBn (Compound 22)

A solution of compound 21 (61.5 mg, 0.064 mmol) and anisole (0.35 mL, 3.22 mmol) in $CH_2Cl_2$ (3 mL) was treated with TFA (3 mL) at 0° C. After being stirred for 2.5 h, the reaction mixture was concentrated in vacuo and azeotroped with toluene (2×10 mL) to furnish the corresponding amine TFA salt. This amine was used without purification in the next step.

This amine had the following properties: $^1$H-NMR (500 MHz, $CDCl_3$) δ 7.79 (br s, 3H), 7.42 (br s, 1H), 7.33 (m, 18H), 7.10 (br d, J=5.6 Hz, 1H), 7.07 (m, 2H), 5.18 (ABq, J=12.4 Hz, 2H), 5.09 (ABq, J=12.1 Hz, 2H), 5.06 (s, 2H), 4.76 br s, 1H), 4.70 (br d, J=4.9 Hz, 1H), 4.15 (s, 2H), 3.36 (br m, 5H), 3.11 (dd, J=4.8, 13.9 Hz, 1H), 3.04 (dd, J=6.1, 13.9 Hz, 1 H), 3.01 (m, 4H), 2.70 (m, 2H), 2.69 (m, 1H), 1.77 (m, 1H), 1.30 (m, 1H), 1.09 (d, J=6.6 Hz, 3H), 0.87 (d, J=6.6 Hz, 6H).

A solution of this amine and AcPhe-OH (26 mg, 0.125 mmol) in THF (3 mL) was cooled in an ice water bath and treated with DECP (0.016 mL, 0.098 mmol) in THF (0.4 mL), followed by triethylamine (0.027 mL, 0.194 mmol) in THF (0.4 mL). After being stirred for 1.5 h, the mixture was diluted with toluene (5 mL) and ethyl acetate (10 mL). The resulting solution was washed with ice-cooled 0.1 N hydrochloric acid (2×15 mL), ice water (1×15 mL), ice-cooled brine (1×15 mL), ice-cooled saturated aqueous sodium bicarbonate (2×15 mL), ice water (1×15 mL) and ice-cooled brine (1×15 mL). The organic layer was separated, dried and concentrated in vacuo. The residue was chromatographed on silica gel (chloroform/methanol=50/1) to yield compound 22 (56.9 mg, 84.8% yield in 2 steps) in the form of a pale yellow foam.

Compound 22 had the following properties: $[α]^{20}_D$+5.5° (c 1.59, $CHCl_3$); IR ($CHCl_3$) 3660 (w), 3340 (w), 3000 (m), 2950 (m), 1730 (s), 1650 (s), 1490 (s), 1450 (m), 1375 (w), 1220 (s), 1140 (m), 1095 (m), 1020 (w), 940 (w), 750 (s), 655 (s), 610 (w) $cm^{-1}$; $^{13}$C-NMR (125 MHz, $CDCl_3$) δ 174.58, 171.96, 171.10, 170.94, 170.75, 170.04, 169.52, 136.72, 135.74, 135.41, 135.20, 129.40, 129.31, 129.26, 128.65, 128.60, 128.54, 128.53, 128.49, 128.44, 128.38, 128.30, 128.19, 128.17, 127.12, 126.87, 79.34, 79.23, 75.90, 74.05, 73.85, 67.14, 66.87, 66.75, 65.45, 54.44, 53.84, 49.05, 41.79, 40.58, 39.01, 37.66, 36.14, 34.08, 28.71, 23.08, 19.32, 19.29, 11.62; $^1$H-NMR (500 MHz, CDCl$_3$) δ 7.31 (m, 14H), 7.18 (m, 7H), 7.06 (m, 4H), 5.14 (s, 2H), 5.09 (d, J=12.2 Hz, 1H), 5.04 (d, J=12.2 Hz, 1H), 5.02 (s, 2H), 4.79 (dd, J=7.0, 13.4 Hz, 1H), 4.72 (dd, J=6.4, 14.2 Hz, 1H), 4.58 (dd, J=7.1, 15.0 Hz, 1H), 4.10 (ABq, J=16.5 Hz, 2H), 3.56 (ddd, J=2.6, 5.9, 13.9 Hz, 1H), 3.22 (m, 3H), 3.10 (m, 1H), 3.09 (dd, J=5.7, 14.0 Hz, 1H), 2.96 (m, 4H), 2.90 (dd, J=6.9, 13.7 Hz, 1H), 2.84 (ddd, J=4.5, 9.5, 10.9 Hz, 1H), 2.78 (dd, J=6.2, 17.0 Hz, 1H), 2.75 (m, 1H), 2.71 (dd, J=6.5, 17.0 Hz, 1H), 2.56 (m, 1H), 1.86 (s, 3H), 1.74 (m, 1H), 1.22 (m, 1H), 1.01 (d, J=7.3 Hz, 3H), 0.86 (d, J=7.0 Hz, 3H), 0.84 (d, J=7.0 Hz, 3H); high-resolution mass spectrum (FAB) m/z 1077.4858 [(M+Na)$^+$; calcd for C$_{60}$H$_{70}$N$_4$O$_{13}$: 1077.4836].
Reaction 23) Production of (R)-2-{(2S,3S,5R,6S)-2-[3-[[(Carboxomethyl)oxy]-6-AcPhe-aminomethyl-5-isobutyloxy]-2,3,4,5-tetrahydropyranyl}propionyl-Asp-Phe (Compound 23)

To a solution of compound 22 (31.0 mg, 0.029 mmol) in ethanol (4 mL) was added 10% Pd—C (50% water, 10 mg). The suspension was stirred at room temperature for 0.5 h under hydrogen atmosphere. The catalyst was filtered off and the filtrate was concentrated in vacuo. The residue was purified by RP-HPLC [C-18 MICROSORB (10×200 mm) column; gradient, 0'-40%-30'-85%-32'-95% of 0.1% TFA in acetonitrile/0.1% TFA in water; flow rate, 3 mL/min] to give pure compound 23 (16.2 mg, 70.4% yield) as a white fluffy solid.

Compound 23 had the following properties: mp 120–123° C.; [α]$^{20}_D$ –1.90° (c 0.16, EtOH); $^{13}$C-NMR (125 MHz, CD$_3$OD) δ 177.59, 174.06, 173.98, 173.93, 173.65, 173.02, 172.85, 138.59, 138.04, 130.50, 130.33, 129.58, 127.95, 127.74, 81.47, 80.31, 76.88, 75.41, 75.26, 66.27, 56.16, 55.00, 51.01, 42.55, 41.61, 39.12, 38.34, 35.43, 34.35, 30.00, 22.51, 19.73, 11.19; $^1$H-NMR (500 MHz, CD$_3$OD) δ 7.14 (m, 4H), 7.08 (m, 6H), 4.62 (dd, J=5.3, 8.0 Hz, 1H), 4.56 (dd, J=5.2, 7.6 Hz, 1H), 4.51 (dd, J=6.2, 8.8 Hz, 1H), 4.04 (ABq, J=16.5 Hz, 2H), 3.47 (dd, J=2.4, 13.8 Hz, 1H), 3.23 (m, 3H), 3.08 (m, 2H), 3.00 (dd, J=6.6, 8.5 Hz, 1H), 2.96 (m, 2H), 2.91 (dd, J=7.6, 13.9 Hz, 1H), 2.89 (m, 1H), 2.76 (dd, J=7.8, 13.9 Hz, 1H), 2.75 (m, 1H), 2.66 (dd, J=5.3, 16.9 Hz, 1H), 2.62 (m, 1H), 2.60 (dd, J=8.1, 16.9 Hz, 1H), 1.78 (s, 3H), 1.68 (m, 1H), 1.10 (dd, J=11.3, 22.1 Hz, 1H), 1.00 (d, J=7.2 Hz, 3H), 0.81 (d, J=6.7 Hz, 3H), 0.80 (d, J=6.7 Hz, 3H); high-resolution mass spectrum (FAB) m/z 807.3442 [(M+Na)$^+$; calcd for C$_{39}$H$_{52}$N$_4$O$_{13}$: 807.3429].

As described in Table 2, compound 23 is a RR inhibitor.

TABLE 2

Inhibition of RR by Compound 23. RR activity is reported in units of residual relative activity, which represents the percentage of RR activity in the absence of Compound 23 which is observed in the presence of the indicated concentration of Compound 23.

| [Compound 23] μM | Residual Relative Activity |
|---|---|
| 0 | 100 |
| 30 | 86 ± 8 |
| 100 | 73 ± 6 |
| 300 | 64 ± 6 |
| 500 | 48 ± 4 |
| 1000 | 32 ± 6 |

EXAMPLE 6

Compositions Comprising a Peptide or Peptidomimetic RR Inhibitor and Methods of Making the Same Peptides and peptidomimetics of the invention may be used to form conjugates with a cell surface ligand-binding molecule. Preferably, the cell surface ligand-binding molecule is a molecule capable of internalization into a cell by the process of receptor-mediated endocytosis. Most preferably, the ligand-binding molecule is folic acid. Alternatively, the fusion protein of the nontoxic B subunit of E. coli heat labile enterotoxin is chemically coupled to a free amino group of the peptide or peptidomimetic of the invention to form a conjugate. Particularly preferred conjugates are conjugates selected from the group consisting of conjugates having the structure depicted in formula VII of FIG. 5 and conjugates having the structure depicted in formula VIII of FIG. 5, wherein $X_1$ is from zero to twenty amino acids;

$X_2$ is from zero to five amino acids;

$X_3$ has a structure selected from the group consisting of the structure depicted in formula II of FIG. 5, wherein $R_1$ and $R_2$ are independently selected from the group consisting of amino acid side chain moieties and Z is selected from the group consisting of amide and disulfide bonds, and the structure depicted in formula III of FIG. 5; and $R_3$ is selected from the group consisting of oligomethylene chains of length $C_2$ to $C_6$.

In one embodiment of the invention, the peptide or peptidomimetic of the invention is combined with a pharmaceutically acceptable carrier suitable for administration to a subject, preferably an animal subject, more preferably a mammalian subject, most preferably a human subject.

As used herein, the term "pharmaceutically-acceptable carrier" means a chemical composition with which a peptide or peptidomimetic of the invention may be combined and which, following the combination, can be used to administer a peptide or peptidomimetic of the invention to a subject.

The pharmaceutical compositions useful for practicing the invention may be administered to deliver a dose of a peptide or peptidomimetic of the invention of between 1 ng/kg/day and 100 mg/kg/day.

Pharmaceutical compositions that are useful in the methods of the invention may be administered systemically in oral solid dosage forms, ophthalmic, suppository, aerosol, topical or other similar dosage forms. In addition to a peptide or peptidomimetic of the invention, such pharmaceutical compositions may contain pharmaceutically-acceptable carriers and other ingredients known to enhance and facilitate drug administration. Other possible dosage forms, such as nanoparticles, liposomes, resealed erythrocytes, and immunologically based systems may also be used to administer a peptide or peptidomimetic of the invention according to the methods of the invention.

Alternatively, a suitable carrier comprises a vesicle that incorporates folate and a peptide or peptidomimetic of the invention. For example, liposomes conjugated to folate via a polyethylene glycol spacer may be used to deliver materials contained within the liposome, such as the peptide or peptidomimetic of the invention. As another alternative, one may employ the enterotoxin as a recombinant carrier for receptor mediated delivery into the cell.

The intravenous carrier most advantageously comprises a pharmaceutically acceptable buffer solution such as phosphate buffered saline at physiological pH, preferably in combination with a pharmaceutically acceptable compound for adjusting isotonic pressure, such as mannitol or sorbitol, and similar substances.

EXAMPLE 7

Peptide Binding to mR1
Screening of Peptides Generated by SPCL

SPCLs prepared as described herein can be screened in many ways, of which three methods are described herein.

In a first method, R1 subunit is coupled to CNBr-activated Sepharose, and peptide mixtures are applied to the R1-Sepharose column. Using this method, peptides having a high binding affinity for R1 protein are selectively retained by the R1-Sepharose column.

In a second method, the ability of peptides or peptide mixtures to block photoaffinity labeling of R1 is measured using a radioactive, photolabile derivative of the R2 carboxy-terminal peptide. The feasibility of this approach is clear from its successful application to measuring the binding to HSV-R1 of analogues of the HSV-R2 carboxy-terminal nonapeptide YAGAVVNDL (SEQ ID NO: 38) and the demonstration by Davis et al. (Davis et al.,1994, J. Biol. Chem. 269(37):23171–23176) that 3(3-azido-4-hydroxyphenyl)propionyl derivatives of FTLDADF (SEQ ID NO: 3) photoincorporate in a site-specific fashion into mR1.

In a third method, R1 subunit is bound to a plastic well that has been coated with a monoclonal antibody which specifically binds R1 protein. Such an antibody is commercially available from In Ro BioMedTek (Umea, Sweden). The ability of a test peptide or peptide mixture to displace a radioactively labeled peptide of high affinity bound to immobilized R1 is determined. Such an approach has been used with peptide inhibitors of HSV-RR (Liuzzi et al., 1994, Nature, 372:695–698; Moss et al., 1995, J. Med. Chem. 38:3617–3623). This third method requires a high affinity peptide to survive the requisite washing procedures.

Effects on RR Activity

Peptides having affinity for R1 greater than or equal to that of N-AcFTLDADF (SEQ ID NO: 16) and nonpeptide peptidomimetics are tested for their ability to inhibit RR. Inhibitory effects are used to determine dissociation constants for peptide or nonpeptide peptidomimetic binding to R1 that are $\geq 0.2$ $\mu$M. In order to determine dissociation constants lower than this value another assay is needed. This is because accurate determination of the peptide dissociation constant can only be carried out at protein concentrations $\leq K_d$, and at protein concentrations much below 0.1 $\mu$M, the $R1_2R2_2$ complex, necessary for activity, dissociates, as described herein. For very tight binding peptides or nonpeptide peptidomimetics, $K_d$s is determined using either the photoaffinity labeling approach or the displacement approach described herein.

EXAMPLE 8

Determination of Peptide Conformation and Structure

The ability to correlate measures of binding affinity to mR1 with the elucidation of the inhibitor structure is essential for a feedback process, whereby data obtained using a peptide or peptidomimetic of the invention enables the selection of peptide or peptidomimetic structures having greater affinity for mR1.

Elucidation of the Structure of N-AcFTLDADF Bound to mR1.

Figure 17:
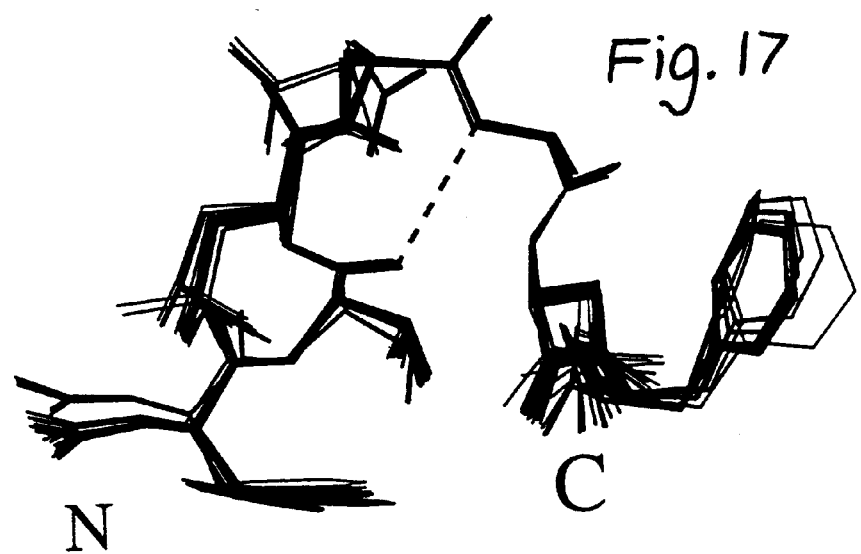
FIG. 17 is a diagram of superposition of 26 of the 299 lowest energy annealed structures of AcFTLDADF (SEQ ID NO: 16) constituting group I. Alignment of backbone atoms from residues 1–7. Dotted line is H-bond between Thr carbonyl oxygen and Ala nitrogen.

In the TRNOE-based structure of mR1-bound N-AcFTLDADF (SEQ ID NO: 16), the conformations of both the amino- and carboxy-termini are incompletely defined (FIG. 17). Rotational resonance NMR (RR-NMR) may be used to more closely define the structure of N-AcFTLDADF (SEQ ID NO: 16) bound to mR1. RR-NMR is a solid-state, magic angle spinning technique that permits estimation of distances between homonuclear spins separated by about 2–7 Å with an approximate precision of ±0.5 Å (Smith et al., 1992, Ann. Rev. Biophys. Biomol. Struct. 21:25–47). RR-NMR is typically applied to analysis of biomolecular structure by placing $^{13}$C labels at two discrete positions and using homonuclear dipolar coupling (protons are decoupled), having an $r^{-3}$ dependence, to obtain a measure of the distance between the spins. RR-NMR will provide an effective way to resolve the structure of mR1-bound N-AcFTLDADF (SEQ ID NO: 16) by enabling measurement of distances between the well-defined core portion of the bound peptide and the Phe1, Asp6, and Phe7 residues, thereby permitting a choice to be made among the family of structures described by the TRNOE data. Sample $^{13}$C: $^{13}$C interactions that can be measured using RR-NMR and for which rather wide distance ranges are now permitted include: Asp6 carbonyl:Phe7ζ, Asp6γ:Phe7ζ, Thr2γ:Phe7α, and Thr2γ:Phe7ζ.

RR-NMR experiments are performed using frozen solutions of peptide bound to mR1. In contrast to the TRNOE experiments described herein, a stoichiometric amount of R1 is present, such that substantially all of the peptide is present in the R1-bound form. Approximately 50 mg of mR1 is required per experiment. Most of the protein utilized in RR-NMR experiments can subsequently be used for other purposes.

Solution Structures of Cyclic Peptides and Nonpeptide Peptidomimetics

It has been a working hypothesis that when a constrained molecule is found to have high affinity for mR1, it will reflect agreement between the structure of the molecule in aqueous solution, as predicted by molecular modeling, and the structure of N-AcFTLDADF (SEQ ID NO: 16) bound to mR1, whereby such agreement reflects lack of agreement between the structure of the molecule in aqueous solution and the structure of N-AcFTLDADF (SEQ ID NO: 16) bound to mR1 for constrained molecules having low affinity for mR1. To test this hypothesis, solution structures of both high- and low-affinity constrained RR inhibitors are determined using standard NMR approaches, and are compared with the structure of mR1-bound N-AcFTLDADF (SEQ ID NO: 16). Assignments are made by a combination of TOCSY and ROESY. Conformational information is obtained by two-dimensional NOESY and ROESY, the latter sometimes providing a greater number of cross peaks for fast tumbling molecules. Examples of the applications of these two approaches may be found in the following references: Bach et al., 1994, J. Amer. Chem. Soc. 116:3207–3219; Blanco et al., 1993, J. Am. Chem. Soc. 115:5887–5888; McDowell et al., 1992, J. Am. Chem. Soc. 114:9245–9253; Wagner et al., 1993, Tetrahedron 49:10831.

High resolution 1-D NMR and phase sensitive COSY are used to determine coupling constants, allowing calculation of torsion angles through the Karplus equation for structure refinement (McDowell et al., 1992, J.Am. Chem. Soc. 114:9245–9253). Structural models are generated from the NMR data through application of restrained molecular dynamics implementing simulated annealing, as described herein. Amide shift temperature coefficients are used to confirm the presence of hydrogen bonding observed in the models (Bach et al., 1994, J. Amer. Chem. Soc. 116:3207–3219; Blanco etal., 1993, J. Am. Chem. Soc. 115:5887–5888; McDowell et al., 1992, J.Am. Chem. Soc.

114:9245–9253; Tsang et al.,1994, J. Am. Chem. Soc. 116:3988–4005; D'az et al., 1993, Tetrahedron 49 (17):3533–3545).

If suitable crystals can be prepared, then structure determination by X-ray diffraction provides an important alternative measure of structure for comparison with NMR structures. The results of these experiments defines the extent to which deviations from the structure of bound N-AcFTLDADF (SEQ ID NO: 16) are tolerated with retention of high affinity, a matter of obvious importance in the design of RR inhibitors.

Structures of Linear Peptides of High Affinity Bound to mR1

The R1-bound conformation of linear peptides having substantially higher affinity for mR1 than N-AcFTLDADF (SEQ ID NO: 16) is determined to indicate whether inhibitor design can be improved by incorporation of conformations other than that observed for N-AcFTLDADF (SEQ ID NO: 16) bound to R1. For a peptide exhibiting only a modest (<10-fold) increase in affinity for R1, relative N-AcFTLDADF (SEQ ID NO: 16), conformation of the peptide can be determined by TRNOE if it binds within the fast exchange limits. A very high affinity peptide is unlikely to bind in the fast exchange limit. In the case of such very high affinity peptides, selected RR-NMR experiments can be used to determine whether interactions analogous to those important for the conformation of bound N-AcFTLDADF (SEQ ID NO: 16) are present in the very high affinity peptide when it is bound to R1.

EXAMPLE 9

An Energy-Minimization Model for Devising the Structure of an Efficient RR Inhibitor A model of the peptide binding site on the mouse enzyme has been developed, based on the crystal structure of the *E. coli* R1 subunit/bound R2 carboxy-terminal peptide complex. Homology modeling of the mouse R1 peptide binding site is performed using the program, QUANTA. The model begins at the C-terminal position of the peptide, which has a deep binding pocket in the *E. coli* crystal structure and a conserved covariance of two residues in R1 that vary depending on the identity of the carboxy-terminal residue of the peptide. The residues of *E. coli* R1 that directly interact with this position of the peptide were changed to the corresponding aligned residues in the mouse sequence, and modeled so as to give the lowest energy structure at this site. To test this preliminary model, the 19 other amino acids were substituted into this newly generated site, and each amino acid was permitted to achieve a minimum energy state in the model pocket.

As indicated in Table 4A, the native carboxy-terminal residue of the mouse peptide, Phe, had one of the lowest energies in the pocket, and the native carboxy-terminal residue of *E. coli*, Leu, had an energy in the mouse model that was significantly higher. Interestingly, we found that a Gln residue used in place of the carboxy-terminal Phe in the model had an even lower energy in the model than the Phe residue. The low energy state of bound Gln seemed to arise from a hydrogen-bond interaction with a Trp residue in the pocket.

The same substitution of the 19 other amino acids into the *E. coli* C-terminal binding pocket, as assessed by the crystal structure thereof, was performed. Again it was noted that the native carboxy-terminal residue of *E. coli* had a lower energy in its pocket than the carboxy-terminal mouse residue. It was further observed that although a Glu residue at this position had a lower energy that the native Leu residue, the energy corresponding to substitution of the Leu residue with a Gln residue was much higher than the energy corresponding to the Leu residue. It was concluded that the peptide Ac-FTLDADQ (SEQ ID NO: 39), that is, the mouse peptide having a Gln residue at the end thereof, may prove to be a better and specific inhibitor of mammalian RR than the lead compound.

TABLE 4A

Energy of each amino acid when minimized in the carboxy-terminal residue binding pocket of R1

| RESIDUE | *E. COLI* | MOUSE |
|---|---|---|
| residues of low polarity | | |
| Phe (F) | −25 | −62* |
| Leu (L) | −40* | −48 |
| Tyr (Y) | −20 | −38 |
| Trp (W) | 63 | −40 |
| Ile (I) | −31 | −46 |
| Val (V) | −19 | −44 |
| Ala (A) | −28 | −43 |
| Gly (G) | −28 | −42 |
| Met (M) | −27 | −47 |
| Pro (P) | −10 | −25 |
| Ser (S) | −23 | −36 |
| Thr (T) | −25 | −40 |
| Cys (C) | −25 | −41 |
| His (H) | −25 | −52 |
| polar residues | | |
| Asn (N) | −42 | −61 |
| Gln (Q) | −38 | −63 |
| Lys (K) | −36 | −62 |
| Arg (R) | −18 | −67 |
| Asp (D) | −42 | −54 |
| Glu (E) | −66 | −60 |

*Note: Highlighted in the table are the native c-terminal residues for *E. Coli* and mouse respectively. Energies were calculated using quanta and are expressed in relative units.

Inspection of the modeled position of the carboxyterminal Phe residue of murine RR suggests why this residue is preferred in the naturally-occurring form of the enzyme. This Phe residue makes several edge-to-face aromatic interactions with amino acid residues of the carboxyterminal R1 binding pocket, notably Phe 725 and Trp 728. Thus, it is believed that it is important to preserve the aromatic character of the carboxyterminal residue of a peptide or peptidomimetic designed to mimic the carboxyterminal end of R2.

The interaction of numerous phenylalanine derivatives with amino acid residues of the carboxyterminal R1 binding pocket of murine RR was modeled to determine whether derivatization of this residue could affect the ability of a peptide to inhibit RR. Using a relative energy framework, various derivatives were modeled at the carboxyl terminus of the peptide, and then minimized within the pocket. The relative energies obtained by modeling the various derivatives are presented in Table 4B.

TABLE 4B

Energy of peptides comprising derivatized phenylalanine residues when minimized in the carboxyterminal residue binding pocket of murine R1

| Ring Position and Group | Calculated Energy |
|---|---|
| non-derivatized | −56 |
| o-CH$_3$ | −57 |

TABLE 4B-continued

Energy of peptides comprising derivatized phenylalanine residues when minimized in the carboxyterminal residue binding pocket of murine R1

| Ring Position and Group | Calculated Energy |
|---|---|
| m-CH$_3$ | −58 |
| p-CH$_3$ | −46 |
| o,o-CH$_3$ | −60 |
| m,m-CH$_3$ | −53 |
| o,m-CH$_3$ | −59 |
| o,p-CH$_3$ | −47 |
| m,p-CH$_3$ | −36 |
| o-OCH$_3$ | −53 |
| o-OH | −66 |
| m-OCH$_3$ | −50 |
| m-OH | −61 |
| p-OCH$_3$ | −27 |
| p-OH | −59 |
| o-Cl | −55 |
| m-Cl | −60 |
| p-Cl | −46 |
| o-pyridine | −59 |
| m-pyridine | −56 |
| p-pyridine | −59 |

Note: o- means ortho-; m- means meta-; p- means para-; Energies were calculated in relative units.

It was observed that ortho-hydroxyl-substituted phenylalanine residue at the carboxyl terminus exhibited the lowest energy of the derivatives examined. Inspection of the model indicates that the ortho-hydroxyl group forms a hydrogen bond with Glu 343 in the murine R1 binding pocket. This observation, along with the observation that several other Phe derivatives described in Table 4B had lower energy than non-derivatized Phe, indicates that the ability of peptides to inhibit RR may be improved by selecting carboxyterminal Phe residue derivatives take advantage of potential interaction sites in the R1. For example, it appears advantageous to substitute an o-methyl Phe residue, a m-methyl Phe residue, an o,o-dimethyl Phe residue, an o,m-dimethyl Phe residue, an o-hydroxyl Phe residue, a m-hydroxyl Phe residue, a p-hydroxyl Phe residue, a m-chloro Phe residue, an o-pyridyl Phe residue, or a p-pyridyl Phe residue in place of the Phe residue normally located at the carboxyl terminus of R2 in a peptide derived from the carboxyl terminus of R2 if inhibition of RR is desired.

EXAMPLE 10

Mouse Ribonucleotide Reductase: NMR Structure of the Small Subunit C-Terminal Peptide When Bound to the Large Subunit The materials and methods used in this Example are now described.

Peptides, Proteins, and NMR Sample Preparation

All peptides were synthesized using Fmoc chemistry on a Milligen 9600 peptide synthesizer and were purified as described previously (Fisher et al., 1993, J. Med. Chem. 36:3859–3862.). Peptide characterization utilized FAB mass spectroscopy, NMR, and analytical HPLC. Recombinant proteins mR1 (Salem et al., 1993, FEBS Lett. 323:93–95) and mR2 (Mann et al., 1991, Biochemistry 30:1939–1947) were prepared as described. Protein eR1 was a gift of Professor Jo Anne Stubbe (MIT). Other proteins were purchased from Sigma and were used without further purification. The buffer used for NMR experiments, 25 mM NaH$_2$PO$_4$ (pH 7.0), 1 mM EDTA, 1.5 mM DTT, 15 mM MgSO$_4$, and 10% D$_2$O, was similar to those used in earlier trNOE experiments with eR1 by Bushweller et al. (1991, Biochemistry 30:8144–8151) and Allard et al. (1994, J. Magn. Reson. 103:242–246). Prior to use, the buffer was treated with Chelex and sparged with argon. Loss of amide intensity due to solvent exchange was negligible over 24 hours at 14° C. Minor protein precipitation (<20%) was observed over the course of an overnight NMR experiment in some samples, but the precipitated material could be redissolved and was enzymatically active (Fisher et al., 1993, J. Med. Chem. 36:3859–3862).

NMR Studies NMR spectra were acquired at 500 and 600 MHZ on Bruker AMX-500, Bruker DMX-500, and Bruker AMX-600 spectrometers. Two-dimensional spectra were obtained at 14° C. in the phase sensitive mode. The water resonance was suppressed by 1.5 sec presaturation For NOESY spectra (Jeener et al., 1981, J. Chem. Phys. 71:4546–4553; Macura et al., 1980, Molec. Phys. 41: 95–117) of free peptides, mixing times ranged from 200 to 700 ms. NOESY mixing times ranged from 75 to 140 ms for peptide plus R1. Mixing times of 65 ms and 250 ms were used for TOCSY (Bax et al., 1985, J. Magn. Reson. 65:355–360) and ROESY (Bax et al., 1985, J. Magn. Reson. 63:207–213) experiments, respectively. trNOESY spectra used for structure refinement were collected from a pH 7.0 solution of 60 μM mR1 protein and 3 mM peptide using mix times of 75–100 ms. eR1, mR1 and mR2 concentrations, reported as protein monomers, were determined by Bradford (1976, Anal. Biochem. 72:248–254) assay using bovine serum albumin as a standard. A total of 512 FIDs of 2048 complex points were collected with 80–124 scans per FID. All two-dimensional data were premultiplied by a 45° or 90°-shifted sine bell in both dimensions. The programs UXNMR (Bruker Instruments) and NMR Compass 2.5 (Molecular Simulations, Inc.) were run on a Silicon Graphics workstation and used for processing spectra and maintaining the data base of spectral cross peaks.

Minimizing spin diffusion effects on trNOESY performed with high molecular mass proteins such as R1 dimer (180 kDa) dictates the use of a high ligand:protein molar ratio and short mix times (Campbell et al., 1991, J. Magn. Reson. 93:77–92; Campbell et al., 1993, Annu. Rev. Biophys. Biomol. Struc. 22:99–122). Ligand:protein molar ratios were examined in the range 25–200. A value of 50 was found optimal for generating the maximal number of trNOEs at an acceptable signal:noise ratio. Inspection of trNOE spectra run at mixing times of 25 ms to 400 ms for AcFTLDADF (SEQ ID NO: 16) in the presence of mR1 exhibited a linear buildup of intensities up to at least 100 ms, the longest mix time used in structure refinement. These findings agree with those of other investigators who performed similar trNOESY studies of ligand binding to eR1. Bushweller et al. (1991, Biochemistry. 30:8144–8151) noted the absence of spin diffusion at 125 ms mixing time, while Allard et al. (1994, J. Magn. Reson. 103:242–246) found that spin diffusion had a minor effect at 200 ms mixing time.

Assignment of Peptide Spectra

TOCSY, ROESY, and NOESY experiments were used to assign the spectrum of AcFTLDADF (SEQ ID NO: 16). Assignment of the Phe side chains was aided by experiments utilizing the deuterated Ac-F(D6)TLDADF peptide. Methylene, δ and ε aromatic protons, and δ geminal methyls were not stereospecifically assigned. In comparing the 2D spectra of all three peptides, patterns of connectivity were nearly identical for α-C through side chain regions of TLDAD (SEQ ID NO: 40). Based on the assignments made for AcFTLDADF (SEQ ID NO: 16), assignments were made on the basis of TOCSY alone (for AcYTLDADF; SEQ ID NO: 19) or of TOCSY and NOESY (for AcFTLDADL; SEQ ID NO: 18).

Structure Refinement

Structures consistent with observed NOE cross peaks were refined by restrained molecular dynamics (Clore et al., 1989, CRC Crit. Rev. Biochem. Mol. Biol. 24:479–564) using XPLOR 3.0 (Brünger, 1992, X-PLOR Version 3.1. A system for X-ray crystallography and NMR. New Haven: Yale University Press). MD used the topallh6x.pro and parmallh3x.pro topology and parameter sets, respectively, with hydrogens added with the Hbuild facility of XPLOR. At all stages of refinement, MD was done in vacuo, using a 0.001 ps step size, a dielectric constant of 4.0, a shifted electrostatic potential, and a switched van der Waals potential. Truncation of nonbonded interactions was begun at a distance of 6.5 Å and was completed by 7.5 Å. NOE distance restraints were incorporated through a PE function which is zero between the lower and upper bounds and quadratically increasing beyond. The NOE force constant was 20 kcal/(mol Å$^2$).

Random conformations of AcFTLDADF (SEQ ID NO: 16) were saved at 4 ps intervals from unrestrained MD at 1000 K. Visual assessment of animated sequences of these structures as well as the time series plot of the Cα distance between Phe 1 and Phe 7 demonstrate the sampling of extensive regions of conformation space. Refinement of these conformations utilized simulated annealing with reduction of temperature from 1000° K. to 200° K. in 5 ps, from 200° K. to 100° K. in 2 ps, and from 100° K. to near 0° K. in 1 ps. The composition and parameterization of the PE function remained unchanged during annealing. Following annealing, 1000 steps of restrained Powell minimization were applied to conclude refinement.

At the beginning and end of refinement, covalent bond angle and length strain were checked with the overall RMS deviation from equilibrium reported as well as the identities of individual angles and bonds deviating more than 0.1 Å and 10°, respectively. In like manner, the RMS violation of the NOE restraints as well as the identities of individual restraints violated by more than 0.15 Å were reported. Careful monitoring of the balance between strain and restraint violation over the course of annealing was essential during the initial iterations of refinement, particularly for the evaluation and incorporation of restraints.

Distance restraints were initially generated by classifying NOE cross peak intensities as strong, medium, and weak, with single proton upper bounds set to 2.7 Å, 3.3 Å, and 5.0 Å, respectively (Clore et al., 1993, J. Mol. Biol. 231:82–102; Wüthrich, 1986, NMR of Proteins and Nucleic Acids. New York: John Wiley & Sons). Lower bounds were uniformly set to 1.8 Å. The upper bounds to restraints to methyl and δ and ε aromatic protons were extended by 20% and 12%, respectively, when NOE violations appeared systematically in the majority of refined structures of low energy. Such extensions take into account spin populations >1 (Liu et al., 1992, J. Magn. Reson. 98:163–175). For the geminal methylene protons, none of which were stereospecifically assigned, center of mass distance averaging was used with the extension of the upper bound by 0.9 Å.

Structure refinement of AcFTLDADF (SEQ ID NO: 16) bound to mR1 proceeded iteratively, beginning with the subset of the 97 total distance restraints derived from only the most unambiguous NOE cross peaks. With each iteration, a set of 3×50 structures were annealed and assessed, both visually and by statistics generated by XPLOR, for restraint violations, evidence of strain, and steric clashes. Assignment and intensity classification of cross peaks used for restraints were continually reassessed. In early iterations, distortion of intensity by noise or overlap with other cross peaks were found to be the cause of all violations >0.15 Å above the upper bound of the restraint. Significant violations present in later iterations were systematic, affecting >90% of structures, and derived from cross peaks having intensities on the strong/medium or medium/weak borderline. Consequently, these restraints were reclassified to the next weaker intensity class. Classification and subsequent reclassification of NOE intensities into qualitative strong, medium, and weak intensity groups has been shown to produce both accurate and precise structures (Powers et al., 1993, Biochemistry 32:6744–6762; Clore et al., 1993, J. Mol. Biol. 231:82–102; Laub et al., 1995, Prot. Sci. 4:973–982). Remaining violations were small in magnitude and nonsystematic. Lower bound violations were rare and small in magnitude. No systematic violations were experienced involving weak intensity cross peaks, a spin diffusion phenomenon anticipated from the long correlation time of R1 dimer [100 ns at 25° C. (Allard et al., 1994, J. Magn. Reson. 103:242–246)].

Selected structures were aligned to their mean structure by XPLOR using the backbone C, Cα, O, and N atoms of residues 1 to 7, inclusively. For each structure, atomic coordinate RMSDs were then computed with respect to the mean structure. Quanta (MSI), the Rasmol 2.5 molecular visualization program (Sayle et al., 1995, TIBS 20: 333–379) and GRASP (Nicholls et al., 1991, Proteins. 11:281–296; Nicholls et al., 1993, GRASP: Graphical representation and analysis of surface properties. New York: Columbia University) were used for molecular graphics. XPLOR input files performing the refinement are based on those used previously (Fisher et al., 1995, Nature Struct. Biol. 2:951–955) and were developed with the use of the program XPLCHK (Laub, 1995, J. Appl. Cryst. 28:632–634). Two-sided statistical tests employed Minitab release 8 (State College, Pa.).

The Results of the experiments presented in Example 10 are now described.

NOESY and ROESY of AcFTLDADF, AcYTLDADF, and AcFTLDADL, in Solution

The $^3J_{HN\alpha}$ coupling constants for all three peptides in 10% D$_{2O}$ were between 6 and 8 Hz, indicating the absence of helical structure (Wüthrich, 1986, NMR of Proteins and Nucleic Acids. New York: John Wiley & Sons). Nearly all NOEs seen in ROESY spectra of AcFTLDADF (SEQ ID NO: 16) were intraresidue. However, a medium intensity NOE between 6NH–7NH and a very low intensity NOE between overlapped amide peaks were also observed (2NH/3NH to 4NH/5NH) indicating that this peptide might have some minor structure in solution, such as a kink or bend in this region of the backbone. NOESY experiments revealed a few weak intraresidue and sequential NOEs at a mix time of 700 ms as would be expected for a small peptide with a short correlation time. No sequential NOEs, including NH to NH (i, i+1), were observed.

TRNOESY of AcFTLDADF in the Presence of mR1 and eR1

Figure 9A:
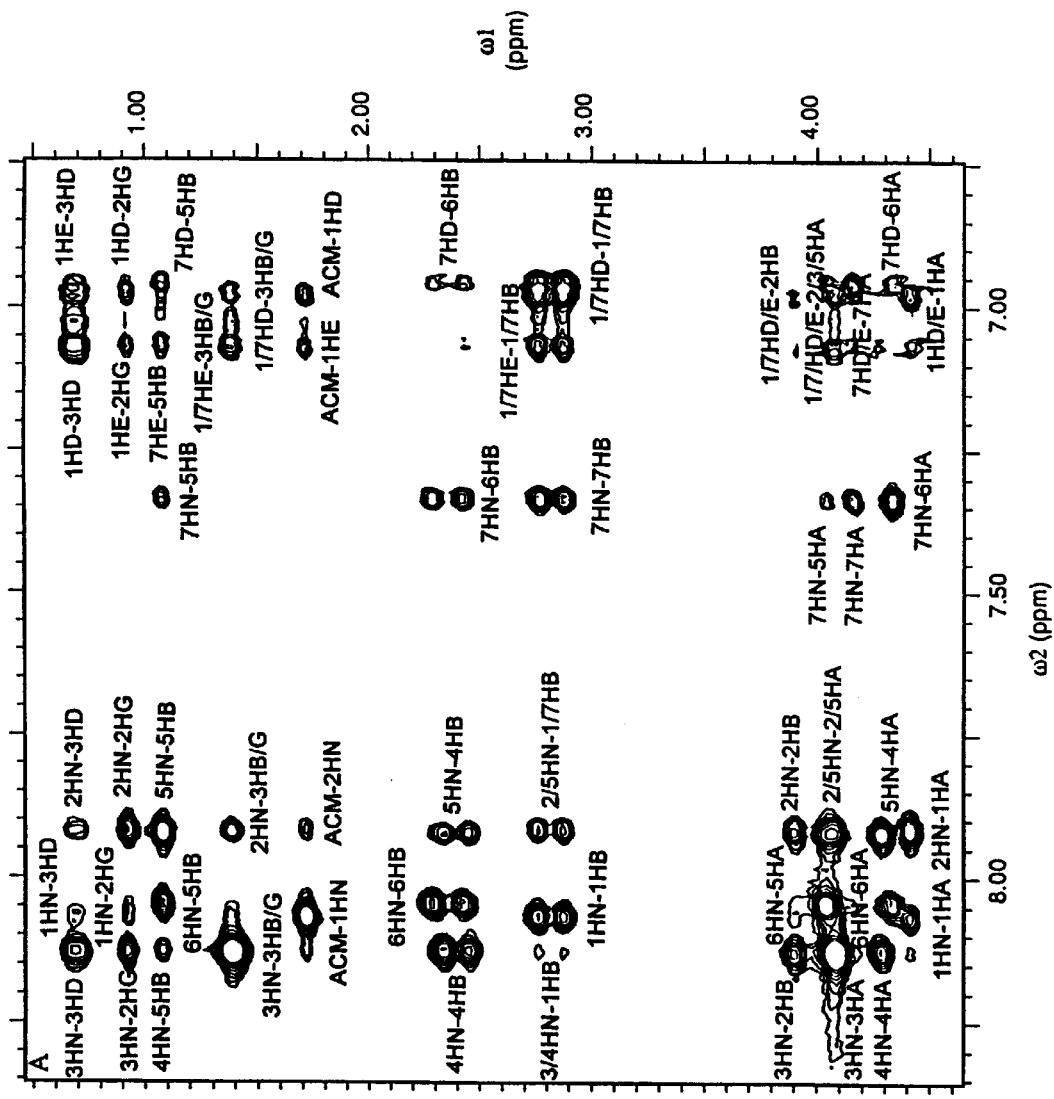
FIG. 9A: NH, aromatic (F2)/$\alpha$, $\beta$, $\gamma$, $\delta$ (F1) region.
Figure 9B:
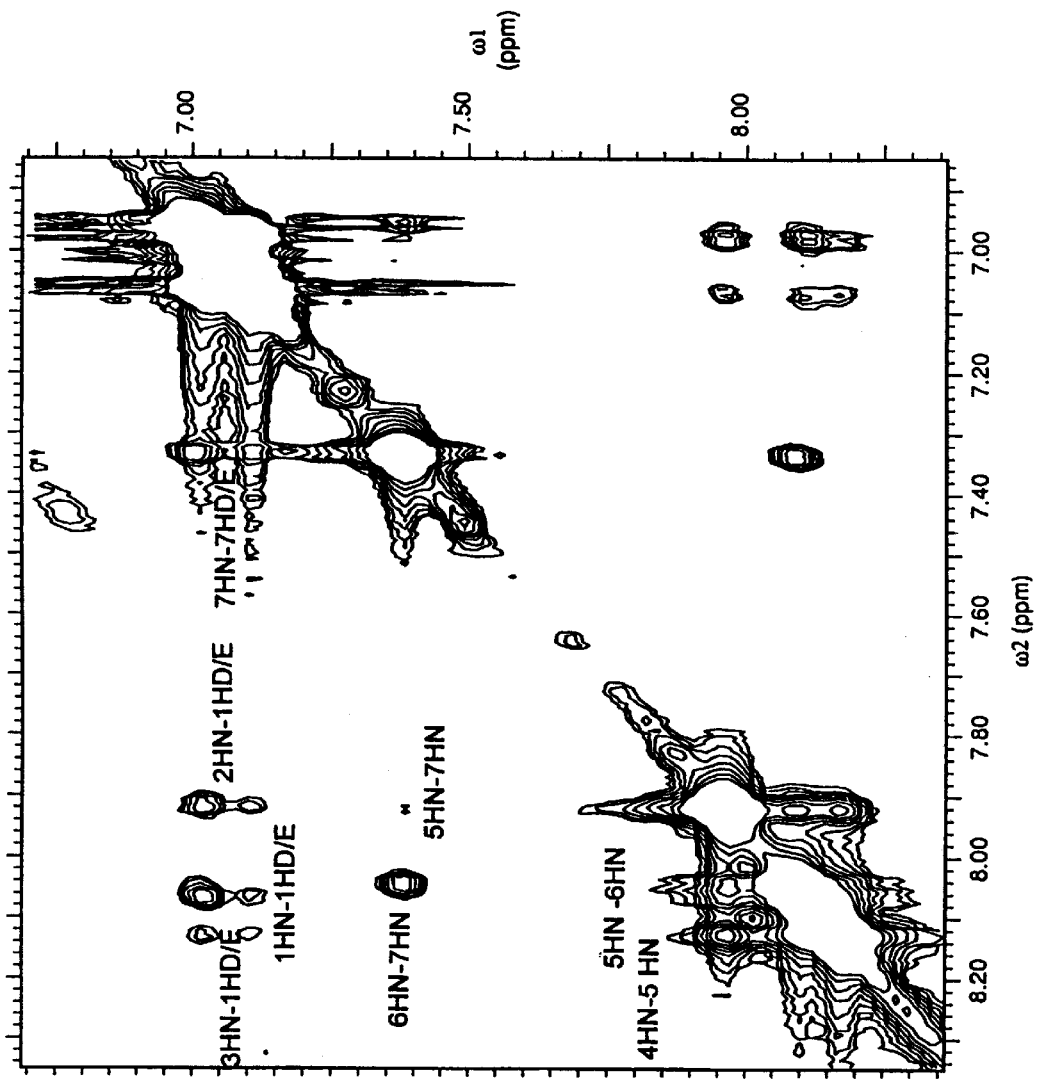
FIG. 9B: NH, aromatic (F2)/NH, aromatic (F1) region.
Figure 9C:
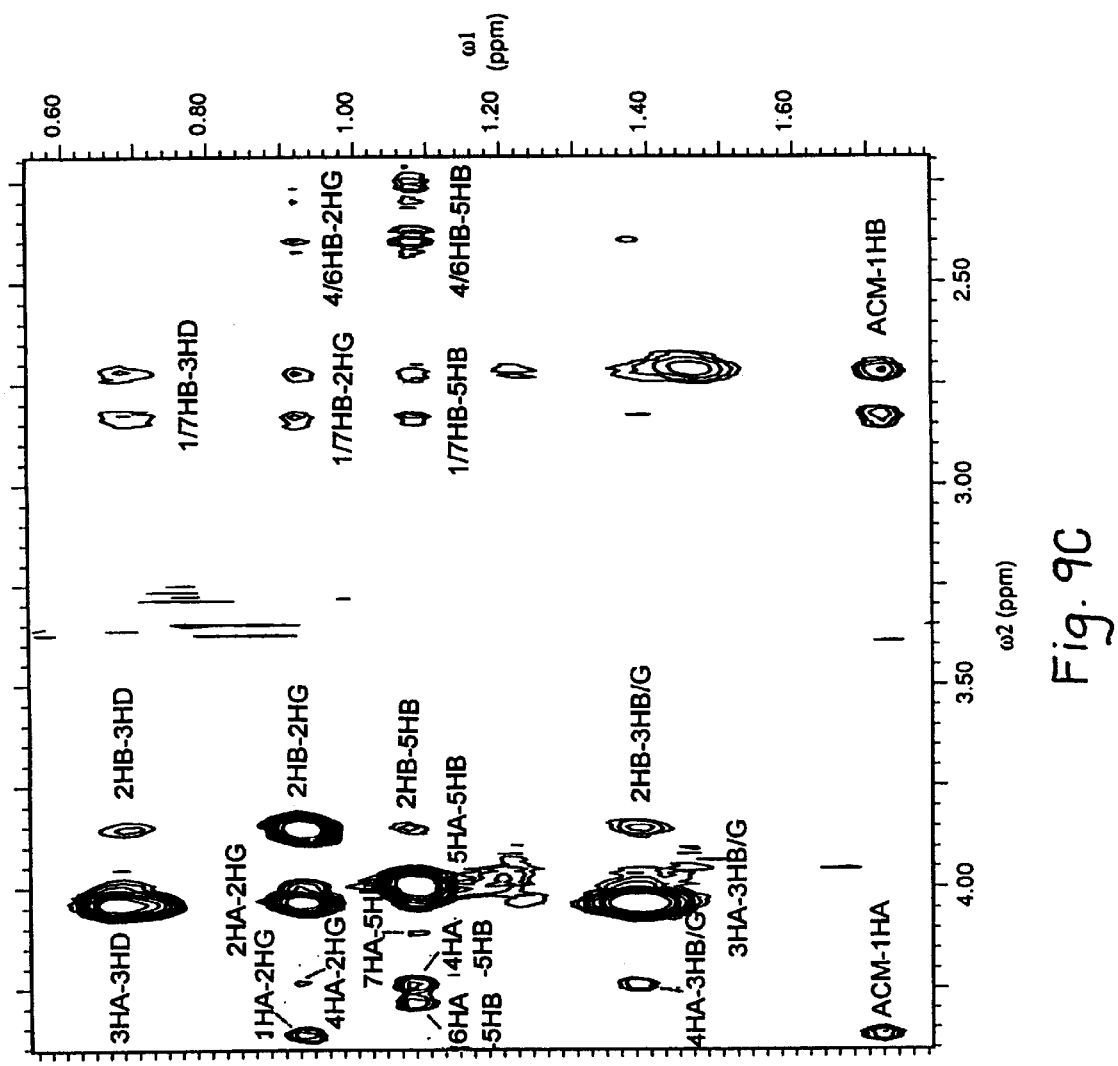
FIG. 9C: $\gamma$, $\delta$ (F2)/$\alpha$,$\beta$ (F1) region.

Addition of mR1 to AcFTLDADF (SEQ ID NO: 16) at a molar ratio of 1:50 induced medium range and backbone (NH—NH i, i+1) NOEs, indicative of formation of a folded structure for the peptide bound to mR1 (FIG. 9). Similar results were obtained with AcYTLDADF (SEQ ID NO: 19) and AcFTLDADL (SEQ ID NO: 18). As expected, chemical shifts of AcFTLDADF (SEQ ID NO: 16) and of the other two peptides did not change on addition of mR1, although line widths were broadened by ~5 to ~40 Hz.

Figure 10:
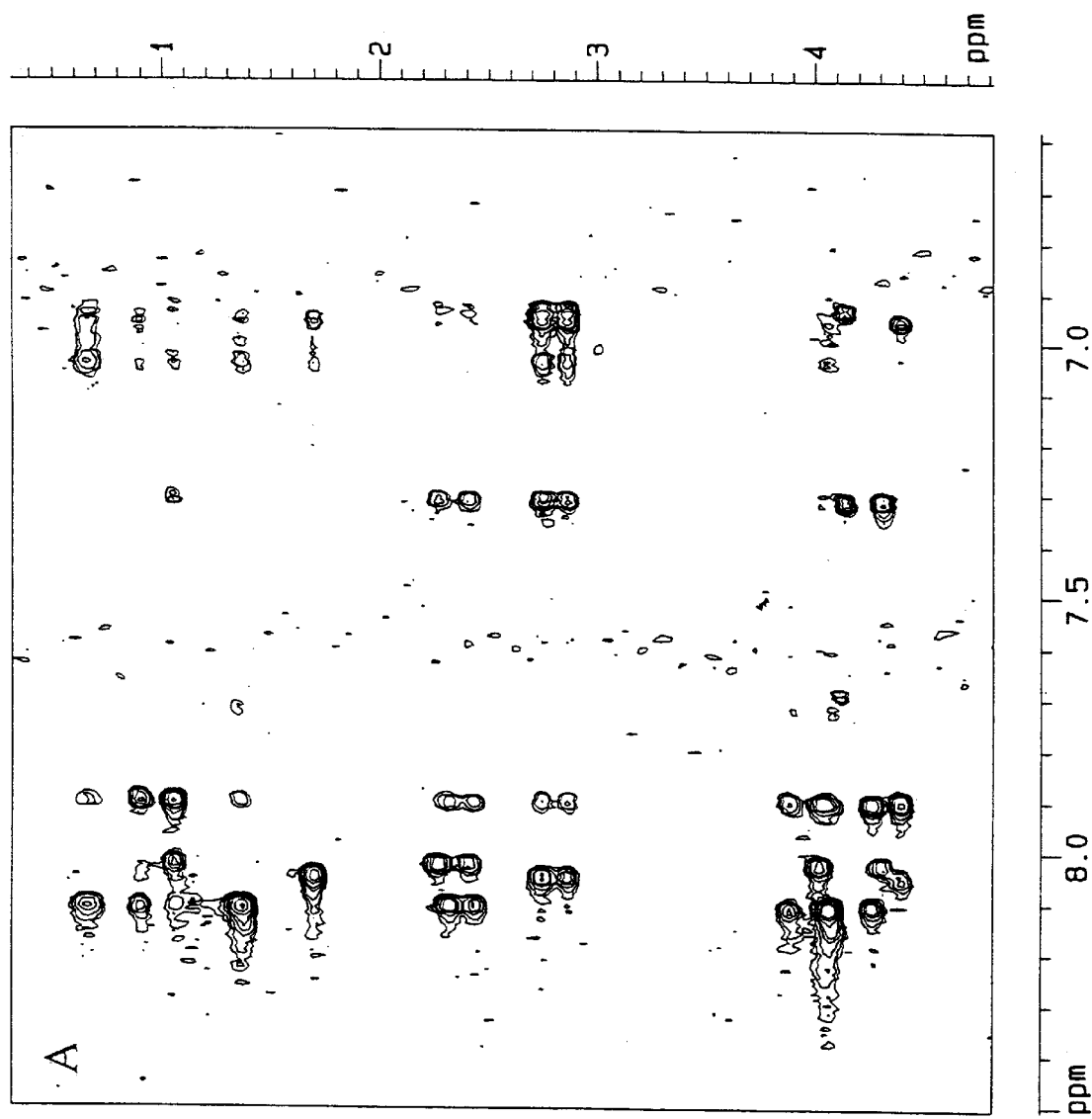
FIG. 10 is a representation of data obtained by 500 mHz $^1$H NOESY of 3 mM AcFTLDADF (SEQ ID NO: 16) plus 60 $\mu$M eR1 collected at 14° C. with mix time of 140-ms. NH, aromatic (F2)/NH, aromatic $\alpha$, $\beta$, $\gamma$, $\delta$ (F1) region.

Interestingly, repeating the same experiment with eR1 in place of mR1 also induced numerous NOEs (FIG. 10).

Virtually all of these NOEs are identical to those seen in FIG. 9, although many were diminished in intensity compared to those induced by mR1, especially sequential and longer range NOEs in the α, β(F2)/β, γ, δ (F1) spectral region. These results indicate that while the peptide binds to eR1 it does so with a less-folded structure than when it binds to mR1, consistent with results showing that AcFTLDADF (SEQ ID NO: 16) binds only very weakly to the *E. coli* R1 protein, with an $IC_{50}$ greater >1 mM (Cosentino et al., 1990, Cell Biol. 69:79–83).

Specificity of mR1-Induced NOESY

Two kinds of control experiments were conducted to determine whether the mR1-induced NOEs arose from specific site binding. First, to assess whether mR1-induced NOEs for AcFTLDADF (SEQ ID NO: 16) might arise nonspecifically from the increased viscosity accompanying the addition of mR1, NOESY spectra were obtained for AcFTLDADF (SEQ ID NO: 16) in the presence of BSA, mR2, or IgG, the latter a protein of equivalent weight to dimeric mR1. In all cases, ID spectra exhibited narrow line widths, in contrast to spectra of AcFTLDADF (SEQ ID NO: 16) with mR1 which exhibited broadened lines. Only intraresidue and sequential NOEs indicative of a random conformation were seen in the presence of R2 or IgG. However, the addition of BSA induced a very weak NOE corresponding to 7HN-5HB, as well as weak NOEs between 4NH–5NH, 5NH–6NH, 6NH–7NH. It is likely that these NOEs arise from nonspecific binding of the peptide to BSA.

Figure 11A:
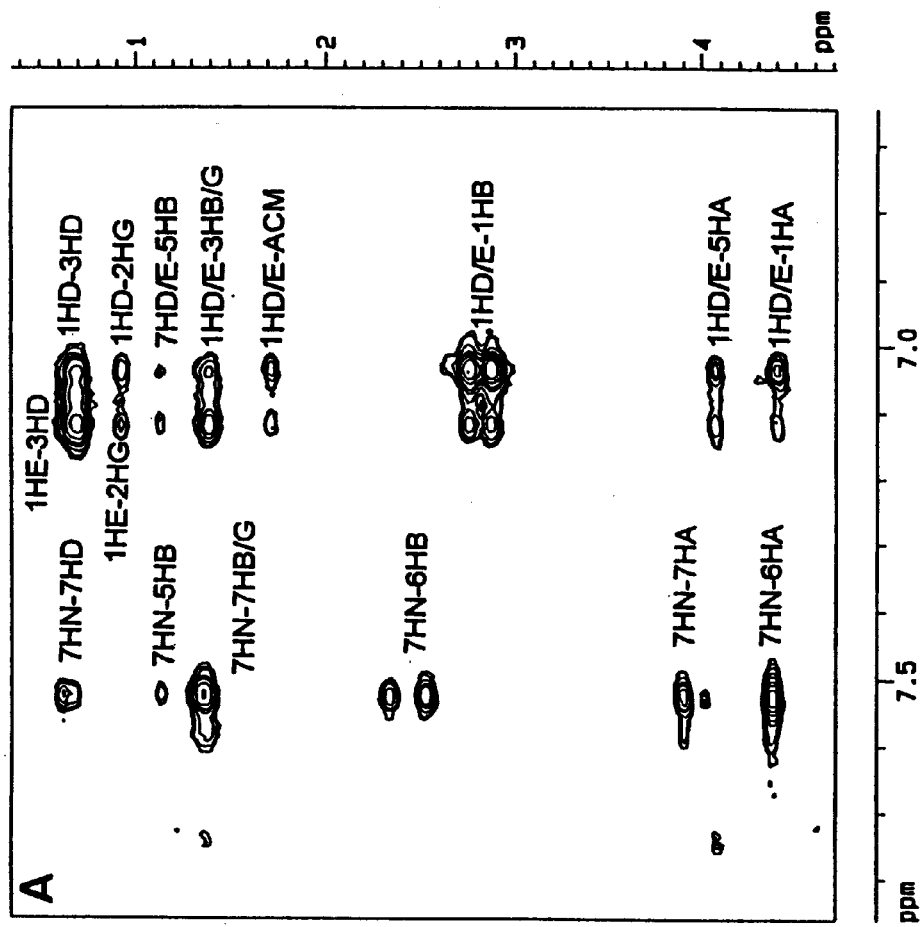
FIG. 11A: NH, aromatic (F2)/$\alpha$, $\beta$, $\gamma$, $\delta$ (F1) region, mix time 100-ms.
Figure 11B:
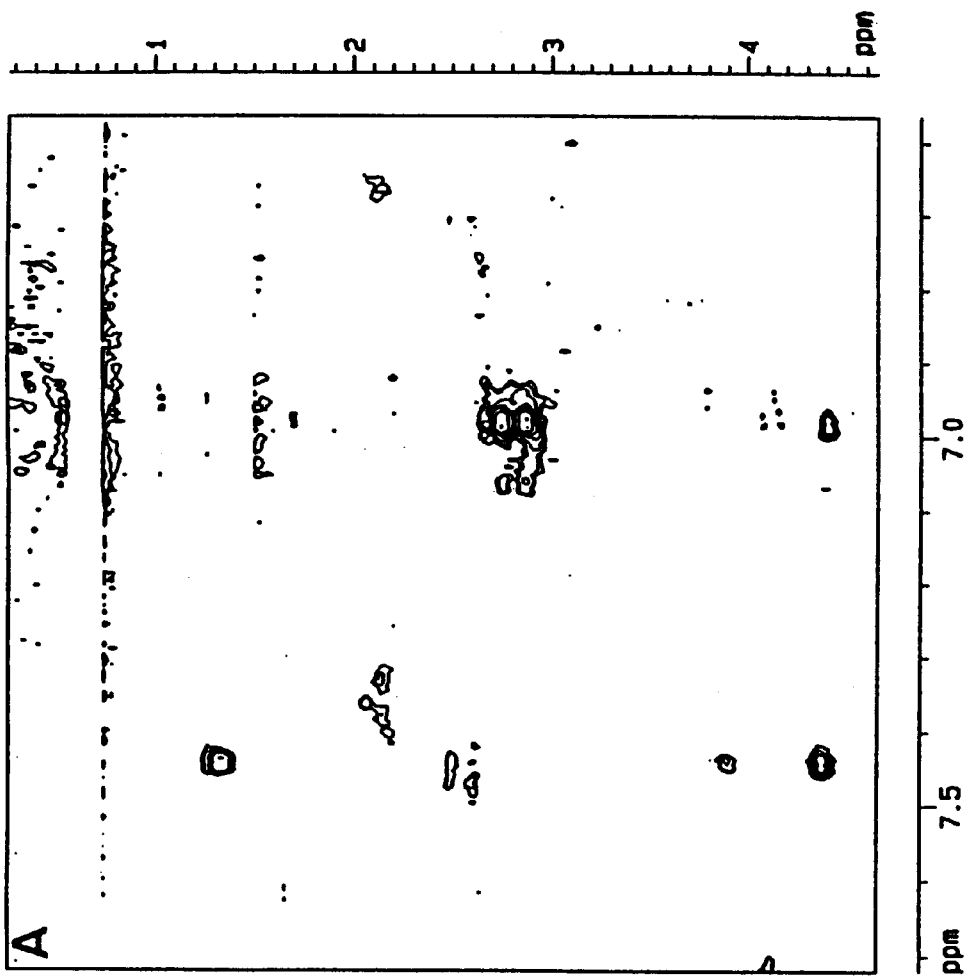
FIG. 11B: same as FIG. 11A with addition of 250 $\mu$M R2 with mix time 140-ms.

Second, competition by mR2 for the binding of peptide to mR1, as measured by effects on trNOE spectra, was used to eliminate nonspecific binding to mR1 as the reason for the mR1-induced NOEs. Dissociation constants reflecting specific site binding, determined by analysis of concentration dependence of mRR activity, are: for R2 dimer binding to R1 dimer, 0.2 μM, for AcFTLDADF (SEQ ID NO: 16) binding to each of two equivalent sites on the R1 dimer, 18 μM (Hamann, 1994, Purification, Characterization and Activity of Chimeric *E. coli*/Mouse and *Plasmodium faciparum* Small Subunits of Type I Ribonucleotide Reductase. Ph.D. Thesis in Chemistry, University of Pennsylvania). The corresponding value for AcFTLDADL (SEQ ID NO: 18) binding is ~400 μM (Fisher et al., 1993, J. Med. Chem. 36:3859–3862). These constants allow the prediction that addition of 250 μM R2 dimer to a solution containing 30 μM R1 dimer and 3 mM of either AcFTLDADF (SEQ ID NO: 16) or AcFTLDADL (SEQ ID NO: 18) will have little effect on the stoichiometry of R1-bound AcFTLDADF (SEQ ID NO: 16) but will strongly decrease the stoichiometry of R1-bound AcFTLDADL (SEQ ID NO: 18). In accord with this prediction, addition of 250 μM R2 dimer had little or no effect on the intensity of the ACFTLDADF (SEQ ID NO: 16) trNOESY peaks as shown in FIG. 9, but strongly decreased the intensity of the mR1-induced AcFTLDADL (SEQ ID NO: 18) trNOESY peaks (FIG. 11).

Summary of mR1-Induced NOESY Cross Peaks for AcFTLDADF

Figure 12:
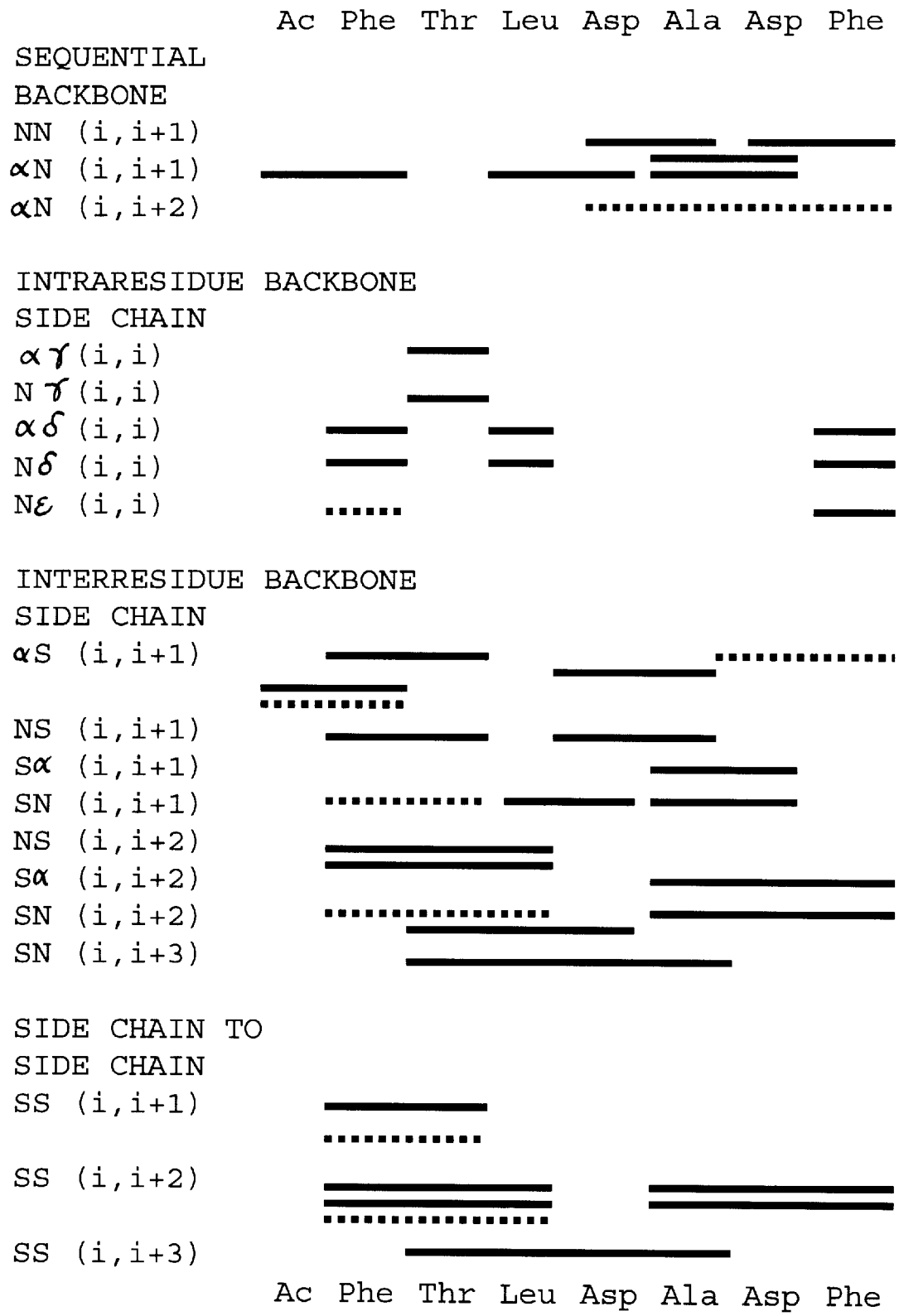
FIG. 12 is a representation of structurally important NOESY cross peaks in AcFTLDADF (SEQ ID NO: 16) bound to R1. Dashed lines denote peaks absent in AcYTLDADF (SEQ ID NO: 19) bound to R1. S, side chain excluding $\beta$ protons, except for Ala 5; N, NH proton.

A schematic representation of the mR1-induced NOESY cross peaks important for determining the structure of bound AcFTLDADF (SEQ ID NO: 16) is presented in FIG. 12. The medium intensity 4HN–5HN, 5HN–6HN and 6HN–7HN cross peaks are consistent with a turn conformation. The six intraresidue NOEs between aromatic protons in each of Phe 1 and Phe 7 and their corresponding α and amide protons suggest that the aromatic rings assume a defined conformation with respect to the backbone. In addition, cross peaks are found between the geminal methyls of Leu 3 and each of the δ, ε, and ζ protons of Phe 1, and between the δ and ε protons of Phe 7 and the methyl group of Ala 5, placing these pairs of side chains in close proximity with one another. Evidence for a turn is also provided by cross peaks between the γ protons of Thr 2 and amide proton of Ala 5 and between the § proton of Thr 2 and the methyl group of Ala 5.

Structure of mR1-Bound AcFTLDADF

With restraints and refinement conditions optimized as described herein, a final set of 299 refined structures were generated, derived from three annealing runs of 50 structures each and one annealing run with 149 structures. Of these, 38 structures meeting the following criteria were selected for further analysis: a) potential energies less than the mean minus one standard deviation; b) no NOE restraint violations >0.25 Å; c) no covalent bond length nor bond angle RMS deviations differing from equilibrium by >0.1 Å or >10°, respectively.

All 38 structures display a reverse turn involving residues Thr 2, Leu 3, Asp 4, and Ala 5. Alignment and visual examination of these structures reveals two distinct groups of structures, Group I, containing 26 structures, and Group II, containing the remaining 12. Although the total PE is identical for each group (36±4 Kcal/mol), they differ in that only Group I structures align well with one another, with mean heavy atom RMSDs of 0.31 Å and 0.81 Å for backbone and all residues, respectively (FIG. 13), for each structure aligned to the average structure of the group. The mean bond length and bond angle RMS deviations from equilibrium are 0.009 Å and 2.91°, respectively, while NOE violations have an RMS value of 0.054 Å. In contrast, Group II structures align poorly, with heavy atom RMSDs of 0.84 Å and 1.38 Å for backbone and all residues, respectively. Another notable difference between the two groups is the distance between the Thr 2 carbonyl oxygen and the Ala 5 nitrogen. With a mean distance of 3.29±0.08 Å, all Group I structures possess a hydrogen bond between this atom pair, whereas it is absent in all Group II structures (4.56±0.58 Å). As a result, in many Group II structures the Thr 2 carbonyl group has an axial orientation with respect to the plane of the reverse turn, although it is not consistently on one side of the plane. Because of the poor definition of Group II structures, the description below focuses on Group I structures only.

From the summary of phi and psi angles presented in Table 5 it is clear that the reverse turn characterizing Group I structures is of a nonstandard type (Rose et al., 1985, Adv. Prot. Chem. 37:1–109): the phi and psi dihedral angles of −89±3° and 41±3° for Leu 3 and −130±2° and −45±3° for Asp 4 differ significantly from the standard values within a four residue type 1 turn of −60° and −30° at residue 2 and −90° and 0° at residue 3. Further, in place of the standard single hydrogen bond between residues i (Thr 2) and i+3 (Ala 5), the carbonyl oxygen of Thr 2 appears to be able to accept three marginal hydrogen bonds donated jointly by the amide groups of Asp 4 (2.88±0.05 Å, 145.1±3.2°) Ala 5 (3.29±0.08 Å, 128.2±3.9°), and Asp 6 (2.75±0.19 Å, 117.5±11.1°). The 2.75 Å distance between the Thr 2 carbonyl and the Asp 6 N suggests that the reverse turn might also be considered to span five residues. The presence of NH (i) to NH (i+1) NOE cross peaks connecting Asp 4 to Ala 5 and Ala 5 to Asp 6 and the absence of such sequential NOEs for Thr 2 and Leu 3 are consistent with the reverse turn, as are the two NOEs connecting the Thr 2 side chain with the methyl and amide groups of Ala 5 (FIG. 9). The close packing of the Phe 1 and Leu 3 side chains and of the Ala 5 and Phe 7 side chains seen in the refined structures is consistent with the several NOE cross peaks connecting these side chains. Other hydrogen bonds present include the Ala 5 NH to the closer of the Asp 4 carboxylate oxygens (3.03±0.57 Å, 127.1±9.9°), and the Thr 2 hydroxyl to the closer of the two C-terminal carboxylate oxygens (3.08±0.10 Å in 19 of 26 structures), as well as to the carbonyl oxygen of Asp 6 (3.37±0.65 Å).

As a second approach, upper bound pseudoatom slack was added simultaneously to several restraints at the C-terminus of AcFTLDADF (SEQ ID NO: 16), including those between the Ala 5 methyl and the backbone and

TABLE 5

Comparison of R1-Bound Structures of AcFTLDADF, AcYTLDADF, and DDLSNFQL

|  |  |  | 1 | 2 | 3 | 4 | 5 | 6 | 7 | all |
|---|---|---|---|---|---|---|---|---|---|---|
| AcFTLDADF | Phi | mean | −127.2 | −115.9 | −89.1 | −130.1 | −104.1 | 117.4 | −114.0 |  |
| (SEQ ID NO: 16) |  | sd | 5.1 | 1.5 | 3.0 | 1.9 | 6.4 | 16.6 | 25.8 |  |
| group I | Psi | mean | −91.4 | 61.0 | 40.7 | −45.3 | −54.9 | −25.3 |  |  |
| N = 26 |  | sd | 3.7 | 6.7 | 2.7 | 2.8 | 4.5 | 22.6 |  |  |
|  | Chi 1 | mean | 51.4 | 56.1 | −63.1 | 35.8 |  | 184.5 | 48.2 |  |
|  |  | sd | 0.8 | 2.0 | 5.6 | 36.4 |  | 23.4 | 38.3 |  |
|  | RMSD | back | 0.25 | 0.22 | 0.20 | 0.12 | 0.19 | 0.32 | 0.47 | 0.31 |
|  |  | resid | 0.85 | 0.34 | 0.38 | 0.76 | 0.18 | 0.75 | 1.21 | 0.81 |
| AcYTLDADF | Phi | mean | −167.8 | −121.4 | −124.3 | −119.3 | −104.7 | −122.6 | −113.1 |  |
| (SEQ ID NO: 19) |  | sd | 8.3 | 37.5 | 3.3 | 2.8 | 2.3 | 3.2 | 5.6 |  |
| N = 20 | Psi | mean | 161.9 | 157.7 | 5.7 | −44.4 | −153.4 | −19.8 |  |  |
|  |  | sd | 46.2 | 2.7 | 4.0 | 2.1 | 78.5 | 22.0 |  |  |
|  | Chi 1 | mean | 54.0 | 55.6 | −41.4 | 52.0 |  | 125.7 | 27.5 |  |
|  |  | sd | 1.5 | 27.4 | 24.5 | 2.1 |  | 84.1 | 36.8 |  |
|  | RMSD | back | 0.20 | 0.16 | 0.13 | 0.09 | 0.09 | 0.34 | 0.70 | 0.31 |
|  |  | resid | 0.83 | 0.21 | 0.53 | 0.57 | 0.09 | 1.02 | 1.34 | 1.08 |
| DDLSNFQL (SEQ ID NO: 36) |  |  | 742 | 743 | 744 | 745 | 746 | 747 | 748 |  |
|  | Phi |  | −93.1 | −59.2 | −65.8 | −94.6 | −58.0 | −93.9 | −71.0 |  |
|  | Psi |  | −31.2 | −34.9 | 1.3 | −21.7 | 126.3 | 110.4 |  |  |
|  | Chi 1 |  | 56.7 | −80.1 | 43.6 | −26.3 | −163.6 | −74.2 | −48.7 |  |

Caption to the Table:
Phi, psi, and chi dihedrals are measured in degrees, with "sd" indicating standard deviation. RMSD values are measured in_and are computed relative to the group's average structure. Residue 1 excludes the N-acetyl group.
X-ray coordinates for DDLSNFQL are available from the Protein Data Bank (1-rlr).

The Phi Dihedral Angle at Asp 6

All 26 group I structures possess a positive phi dihedral angle (117°±17°) at Asp 6, a feature also present in 11 of 12 group II structures. Because positive values of the phi dihedral angle for nonglycine residues are often indicative of strain (Creighton, 1993, Proteins Structures and Molecular Properties. New York: W.H. Freeman and Co. p. 226), the issue of whether this angle measure might be an artifact of refinement was investigated by examining whether it survived the loosening of NOE restraints.

First, the medium intensity NOE restraint between the Ala 5 methyl and the amide proton of Phe 7 was loosened, which examination by molecular graphics suggested was the most clearly implicated in potentially distorting the Asp 6 phi dihedral angle. Because the restraint involves a methyl group, 1 Å could be added to the upper bound limit, this added slack reflecting the effect of three protons contributing to the intensity of the methyl crosspeak. Modeling was then carried out as described using the annealing and refinement protocol as before. Of 189 new structures annealed, 24 met the criteria for further analysis described above, with 19 of these structures retaining the positive Asp 6 phi dihedral angle. Demonstrating the robustness of refinement, the 12 new Group I structures were indistinguishable from the 26 original Group I structures by comparison of overall PE and NOE RMSD, of the phi, psi, and chi 1 dihedral angles, and of the presence and geometry of hydrogen bonds. Each comparison was made using the Mann-Whitney test at the 0.05 significance level to test the null hypothesis that the pair of medians were identical. Furthermore, the difference of median PEs between structures with negative (N=5) or positive (N=19) Asp 6 phi dihedral angle is insignificant for both total PE (P=0.18) and PE after residual NOE energy is subtracted away (P=0.56), suggesting that any strain induced by the Asp 6 phi dihedral angle must be compensated for elsewhere in the molecule.

methylene protons of Asp 6 and Phe 7, the Ala 5 methyl and the aromatic protons of Phe 7, and the Asp 6 amide and its methylene protons. Again, structures with low PE possessed phi and psi dihedral angles similar to those obtained from the unmodified restraint set.

These data establish that the positive phi dihedral angle at Asp 6 is real and well-tolerated, exacting no major energetic penalty.

As discussed herein, there is now abundant evidence that the R2 C-terminal peptide is the main, if not sole, R2 binding determinant linking the R2 and RI subunits in the RR holoenzyme. The results presented herein support two major hypotheses: first, that the conformation of mR2 C-terminus bound to mR1 is likely to be general for the binding of a eukaryotic R2 C-terminus to a eukaryotic R1; second, that important aspects of the R2/R1 interface are conserved between mRR and eRR, despite the limited sequence homology between these enzymes.

Comparing the Structures of AcFTLDADF and AcYTLDADF Bound to mR1

Figure 14A:
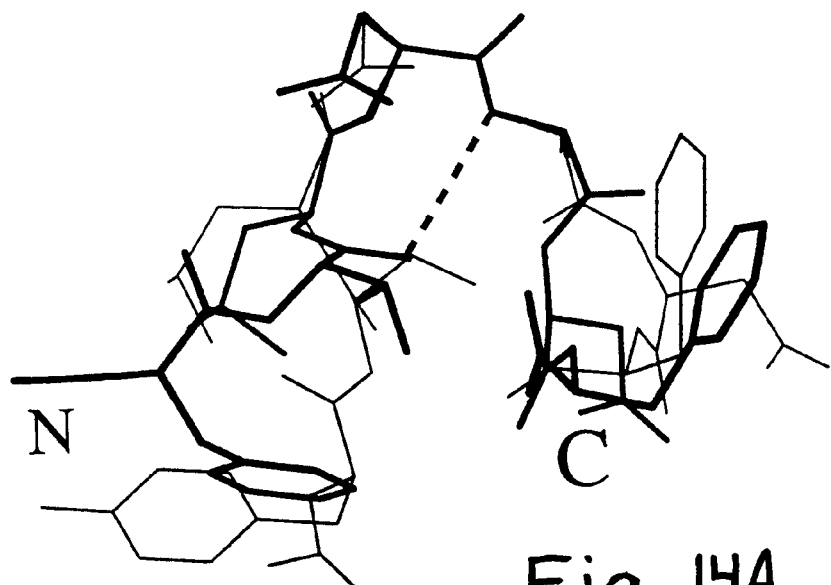
FIG. 14 is an alignment of a representative structure of AcFTLDADF (SEQ ID NO: 16) bound to mR1 with, in FIG. 14A, a representative structure of AcYTLDADF (SEQ ID NO: 19) bound to mR1. Alignment was carried out on the following atoms: all of Leu; Asp, excluding the side-chain carboxylate; all of Ala, except the carbonyl carbon and oxygen. Dotted line is H-bond between Thr carbonyl oxygen and Ala N in AcFTLDADF (SEQ ID NO: 16). Heavy lines, AcFTLDADF (SEQ ID NO: 16), light lines AcYTLDADF (SEQ ID NO: 19).
FIG. 14B is an alignment of a representative structure of the corresponding DDLSNFQL (SEQ ID NO: 36) peptide from the E. coli R2 C-terminus bound to E. coli R1. Alignment was carried out on 11 backbone atoms extending from the Thr carbonyl carbon and oxygen to the Ala NH. Dotted line is H-bond between Leu carbonyl oxygen and Phe N in DDLSNFQL (SEQ ID NO: 36). Heavy lines, DDLSNFQL (SEQ ID NO: 36), light lines AcFTLDADF (SEQ ID NO: 16). N=N-terminus, C=C-terminus; Heavy atoms only are shown.

Of the 97 cross peaks used in modeling AcFTLDADF (SEQ ID NO: 16) and 80 used in modeling AcYTLDADF (SEQ ID NO: 19) (Fisher et al., 1995, Nature Struct. Biol. 2:951–955), 76 were common to both peptides. In this tally, cross peaks to Phe 1 and to Tyr 1 were considered common where the same aromatic protons were involved. The two peptide spectra do differ in some common cross peak intensities; in 24 cases restraint upper bounds differ between the AcFTLDADF (SEQ ID NO: 16) and AcYTLDADF (SEQ ID NO: 19) data sets by one intensity class. Cross peaks important for AcFTLDADF (SEQ ID NO: 16) structure but not found in the trNOE spectrum of AcYTLDADF (SEQ ID NO: 19) are indicated in FIG. 13. As anticipated from the strong overlap in the trNOE peaks, the structures of the two bound peptides display major similarities (FIG. 14A). Both are characterized by a nonstandard type 1 reverse β-turn for residues TLDA, approximately 35% of the type 1 reverse 13-turns found in the protein structure data base are nonstandard (Ball et al., 1990, J. Mol. Recog. 3:55–64; Wilmot et al., 1990, Protein Eng. 3:479–493) and, as a result of similar phi, psi angles at Leu 3 and Asp 4 (Table 5), atoms in the turn region align well between the two peptides. In addition, three types of interactions are conserved in both peptides: 1) the plane of the ring of Phe 7 faces the methyl group of Ala 5; 2) the aromatic ring of position 1 is in close proximity to Leu 3; and 3) the Asp 4 carboxylate forms a hydrogen bond with a backbone NH. The details of the latter two interactions are different in the two bound peptide structures. In AcYTLDADF (SEQ ID NO: 19) the Tyr rings faces outward from the plane of the turn with one edge fitting into the cleft formed by the geminal methyls of Leu, whereas in AcFTLDADF (SEQ ID NO: 16) one edge of the aromatic ring of Phe 1 abuts the turn with the plane of the aromatic ring packing against the protons of the Leu δ-methyls. Also, for Asp 4, the closer of the carboxylate oxygens forms a 3.3 Å hydrogen bond to the amide group of Leu 3 in AcYTLDADF (SEQ ID NO: 19), whereas in AcFTLDADF (SEQ ID NO: 16), it forms a 3.0 Å hydrogen bond to the amide group of Ala 5.

Structure-function studies on the mR2 C-terminal peptide support the notion that the three types of interactions noted above are important for mR2 C-terminal peptide binding to mR1. In particular, the affinity of peptide binding to mR1 exhibits specific side-chain requirements at each of the five positions, 1, 3, 4, 5, and 7, but no such requirements at positions 2 and 6 (Fisher et al., 1993, J. Med. Chem. 36:3859–3862; Fisher et al., 1995, Nature Struct. Biol. 2:951–955). Thus, large decreases in affinity result from the following replacements: of Phe 1 by Tyr, 4-aminophenyl, 4'-azidophenyl, and, most markedly, Leu; of Leu 3 by Ala; of Asp 4 by Ala; of Ala 5 by Gly; and of Phe 7 by Leu. On the other hand, position 3 tolerates replacement by Val or Phe, so that it is preservation of a hydrophobic interaction with Phe in position 1 that matters. Similarly, position 5 tolerates residues with a β-carbon (e.g., Leu), and position 4 tolerates replacement by Asn, which conserves the potential for intraturn hydrogen bonding. The C-terminal peptides of R2 subunits derived from eukaryotes display marked homology (Table 6). Moreover, the substitution patterns derived from comparison of these sequences are consistent with the general importance of the three interactions noted above for eukaryotic R2 C-terminal peptide interaction with eukaryotic R1. Thus, residue 1 is Phe or Leu, and residue 3 is either Leu, Ile, Phe, or Thr, suggesting that the hydrophobic cluster formed by residues 1 and 3 is fully conserved. Similarly, residue 7 is always Phe, and residue 5 is never Gly, allowing conservation of the Phe 7 interaction with a β-carbon at position 5. Finally, residue 4 always is a potential hydrogen bond acceptor, either Asp, Glu or Asn.

TABLE 6

Homologous Eukaryotic R2 C-terminal sequences.
Single-letter amino acid codes are used.

| Organism | Sequence | SEQ ID NO: | Organism | Sequence | SEQ ID NO: |
| --- | --- | --- | --- | --- | --- |
| Clam | FTLDADF | 3 | S. cerevisiae | FTFNEDF | 7 |
| Mouse | FTLDADF | 3 | S. pombe | FTIDEDF | 9 |
| Human | FTLDADF | 3 | P. falciparum | FCLNTEF | 11 |
| Hamster | FTLDADF | 3 | C. elegans | FDLEADF | 44 |
| Tobacco | FKLDEDF | 42 | D. discoidium | LVLDEDF | 45 |

TABLE 6-continued

Homologous Eukaryotic R2 C-terminal sequences.
Single-letter amino acid codes are used.

| Organism | Sequence | SEQ ID NO: | Organism | Sequence | SEQ ID NO: |
| --- | --- | --- | --- | --- | --- |
| A. thaliana | FTTEEDF | 43 | Vaccinia | FSLDVDF | 12 |

The evident evolutionary pressure for conservation of a Phe residue at residue 1 may account for the 15-fold weaker binding of AcYTLDADF vs AcFTLDADF binding to mR1 (Fisher et al., 1995, Nature Struct. Biol. 2:951–955), as well as the significant differences in the structures of the bound peptides that are clear from FIG. 14A and Table 5. Accommodating a Tyr residue in a site that is complementary to a Phe residue apparently requires significant structural rearrangement. With respect to the turn structure, in AcFTLDADF (SEQ ID NO: 16) the carbonyl group of Thr 2 faces into the turn, where it can form hydrogen bonds to three amide groups along the backbone, whereas in AcYTLDADF (SEQ ID NO: 19) the Thr 2 carbonyl group points outward, away from the turn. In addition, the hydroxyl group of Thr 2 forms a hydrogen bond (3.0 Å) across the turn to the carbonyl O of Ala 5 in AcYTLDADF (SEQ ID NO: 19), which is replaced in AcFTLDADF (SEQ ID NO: 16) by a marginal hydrogen bond (3.4 Å) to the carbonyl O of Asp 6. Also worth noting is that the positive-valued Asp 6 phi dihedral found in AcFTLDADF (SEQ ID NO: 16) is absent in AcYTLDADF (SEQ ID NO: 19), where the corresponding phi dihedral angle is −113°.

Comparison of the Conformations of R2 C-terminal Peptides Bound to mR1 and eR1

In contrast to the sequences displayed in Table 2, the R2 C-terminal sequence of E. coli R2, DDLSNFQL (SEQ ID NO: 36), is not homologous to FTLDADF (SEQ ID NO: 3). As a result, while the corresponding E. coli-derived peptide inhibits eRR, it does not inhibit mRR, and, in a parallel manner, AcFTLDADF (SEQ ID NO: 16) is at best a very poor inhibitor of eRR (Cosentino et al., 1990, Biochem. Cell Biol. 69:79–83). Despite these results, we hypothesize that the overall structure of the R2/R1 binding interface is conserved between these two species, such that the R2 C-terminus assumes a conformation having a reverse-turn with a cluster of hydrophobic residues at the C-terminal end of the bound peptide. Here we note that eR1 and mR1 have similar lengths (761 and 802 amino acids, respectively) and are 29% identical. They are thus very likely to be similar in three-dimensional structure (Sander et al., 1991, Proteins: Struct. Funct. Genet. 9:56–68).

The most compelling experimental support for conservation of the overall structure of the R2/R1 binding interface comes from the strong similarities between the structures of AcFTLDADF (SEQ ID NO: 16) bound to mR1 and of the E. coli R2 C-terminal peptide bound to eR1, which are clear despite the evident sequence differences. The E. coli structure is part of the 2.5 Å crystal structure of the complex formed between the eR1 subunit and a 20 residue peptide, corresponding to the C-terminal of the eR2 subunit (Uhlin et al., 1994, Nature. 370, 533–539). In this structure, the ten C-terminal residues, DIDDLSNFQL (SEQ ID NO: 46), are well defined in the electron density (in keeping with the numbering scheme used in the pdb file 1-rlr, DIDDLSNFQL (SEQ ID NO: 46) is numbered from Asp 739 to Leu 748). Superposing by least squares the X-ray coordinates of eR1-bound DDLSNFQL (SEQ ID NO: 36) with the Group I mR1-bound AcFTLDADF (SEQ ID NO: 16) structures, leads to the following alignment, where the residues underlined form a turn in each bound peptide.

E. coli D$^{741}$DLSNFQL$^{748}$ (SEQ ID NO: 36)
mouse AcF$^{1}$TLDADF$^{7}$ (SEQ ID NO: 16)

Figure 14B:
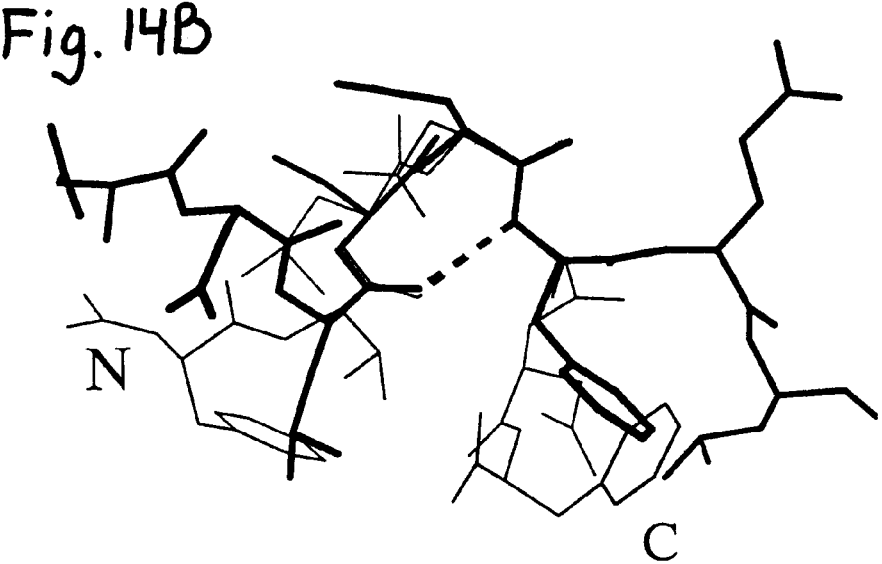

Alignment of each of the 26 selected AcFTLDADF (SEQ ID NO: 16) structures with DDLSNFQL (SEQ ID NO: 36) on the basis of the 12 heavy backbone atoms in the turn, from Cα of Thr 2 (Leu 743) to the NH of Ala 5 (Phe 746) yields a RMSD of 0.35±0.02 Å for these 12 atoms (FIG. 14B). In addition: a) the β carbons of Leu 3 and Ser 744 have similar orientations; b) a comparable region of space is shared between the isosteric Asp 4 and Asn 745 side chains; c) the Phe 7 and Phe 746 aromatic rings, as well as the aromatic group on Phe 1 and hydrophobic side chain of Leu 743, cluster together well; d) the distance between turn residues, Cα 1 (Thr 2 and Leu 743) and Cα 4 (Ala 5 and Phe 746) are 5.4 Å and 5.6 Å, respectively for TLDA (SEQ ID NO: 47) and LSNF (SEQ ID NO: 48) respectively; and e) the distance between the carbonyl oxygen of residue 1 of the turn to the amide proton on residue four of the turn is about 3.3 Å for TLDA (SEQ ID NO: 47) and 2.9 Å for LSNF (SEQ ID NO: 48). Finally, the reverse turns are similar: the mR1-bound TLDA (SEQ ID NO: 47) conformation is a nonstandard type I turn, while the eR1-bound LSNF (SEQ ID NO: 48) conformation is more nearly a standard type I turn, with phi and psi dihedral angles of –66° and ° for Ser 744 and –95° and –22° for Asn 745 (Table 5).

A second argument supporting the conservation of the R2/R1 binding interface comes from consideration of the eR2 C-terminal binding site within eR1. The eight eR2 C-terminal residues bind in a shallow cleft formed by two antiparallel α-helices 13 and I in eR1, corresponding to residues 340–350 and 712–726, respectively. The alignments for the two helices comprising the binding site are shown below. There is very good evidence for the evolutionary conservation of αI as a binding locus for R2 C-terminal peptide. First, it partially overlaps a highly conserved R1 sequence (eR1 residues 725–731), including the functionally important Tyr residues at 730, 731 (Ekberg et al., 1996, J. Biol. Chem. 34: 20655–20659). Second, an azidophenyl derivative of FTLDADF (SEQ ID NO: 3) was found to photoincorporate into the 724–735 peptide of mR1 (Davis et al., 1994, J. Biol. Chem. 269:23171–23176), corresponding to residues 718–728 in E. coli R1. Third, HSV-R1 variants at positions 1090 and 1091, corresponding to eR1 residues 710 and 711, have been isolated from strains of HSV-1 exhibiting weak resistance to an R2 C-terminal peptidomimetic inhibitor (Bonneau et al., 1996, J. Virol. 70:787–793).

```
         <----a13---->        <-----aI------>
         340         350      712      722 726    731
E. coli  NKLMYTRLLKGED        QQLLKDLLTAYKFGVKT.LYY
         (SEQ ID NO:8)          (SEQ ID NO:49)

mouse    PDLFMKRVETNQD        GKLTSMHFYGWKQGLKTGMYY
         (SEQ ID NO:10)         (SEQ ID NO:50)
```

Figure 15:
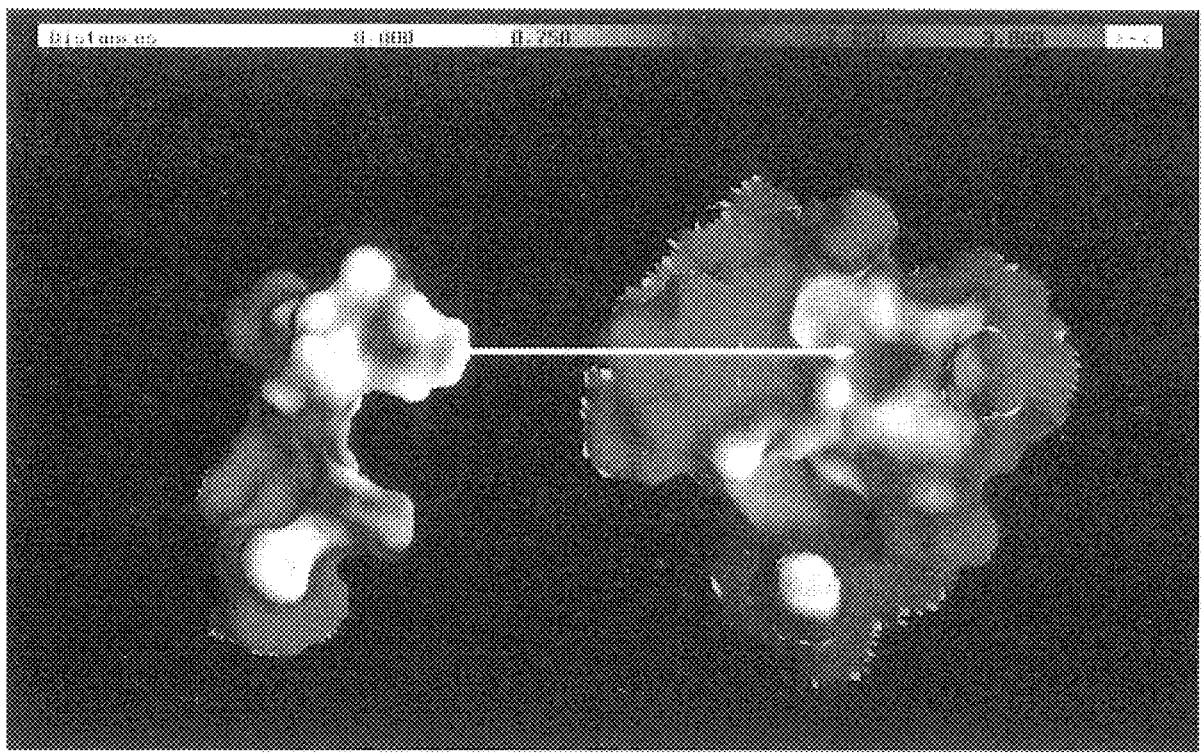
FIG. 15 is a GRASP representation of the surface:surface interaction between the E. coli R2 C-terminal peptide and its binding site in E. coli R1. The distance bar at the top provides a scale for the coloring; white is a close interaction, blue is intermediate, and red is no interaction. The yellow arrow indicates the interaction between R2 C-terminal Leu 748 and its pocket within eR1. For this pocket, Tyr 344 defines the bottom, and Tyr 722 and Leu 348 define the left and right walls, respectively. Leu 748 interactions are also evident with Lys residues 341 and 723. calculated from the 2.5 Å structure of Uhlin et al. (1994, Nature 370:533–539) [pdb: 1RLR].

Additional evidence for the conservation of both α13 and αI as the binding locus for R2 C-terminal peptide comes from the strong interaction, visible in the GRASP analysis of the eR1 structure (FIG. 15), between the hydrophobic side chains of the C-terminal Leu 748 of the peptide and two of the residues forming its binding pocket within eR1, Tyr 344 and Tyr 722 (underlined above), and the evolutionary covariance among these three residues. In the alignments shown above, the mR1 residues predicted to interact strongly with the C-terminal Phe of the bound mammalian peptide are the aligned Met and Trp residues (also underlined). The sequence alignments of R1 and R2 has been examined from 19 organisms available in the SwissProt sequence data base. Without exception, the C-terminal residue of R2 is either a Leu (as in E. coli) or a Phe (as in mouse). Also without exception, for an R2 having a C-terminal Leu, the residues in the corresponding R1 aligned with E. coli R1 344 and 722 are either Phe or Tyr. By contrast, for an R2 having a C-terminal Phe, the residues in the corresponding R1 aligned with E. coli R1 344 and 722 are always Met and Trp, respectively. Residues 344, 722, and 748 thus appear to constitute a conserved hydrophobic cluster of constrained volume (Grantham, 1974, Science 185:862–864) at the R1:R2 interface.

Two additional points support the overall conservation of the R1:R2 interface. First, the similar but lower intensity trNOE peaks induced in AcFTLDADF (SEQ ID NO: 16) by eR1 in comparison with mR1 (FIG. 10) suggest similarities in AcFTLDADF (SEQ ID NO: 16) binding to eR1 and mR1. Second, the GRASP analysis of the E. coli complex presented in FIG. 15 demonstrates several close contacts between eR1 and L743, F746, and L748, with few if any such contacts with either N745 or Q747. This pattern exhibits some correlation with the structure-function studies on the mR2 C-terminal peptide and alignment of the E. coli and mouse peptides presented above. In addition, AcSFTLDADF (SEQ ID NO: 13) and AcNSFTLDADF (SEQ ID NO: 12), the acetylated forms of the mR2 C-terminal octamer and nonamer, have the same affinity for mR1 as AcFTLDADF (SEQ ID NO: 16) (Fisher et al., 1993, J. Med. Chem. 36:3859–3862), which may be consistent with the lack of close contacts between eR1 and D741. However, unlike mR2, the C-terminal region of eR2 probably interacts with eR1 at a position outside of the terminal 7–8 residues, given the 10-fold higher inhibitory potency toward E. coli RR of the eR2 C-terminal 19-mer peptide as compared with the N-acetylated octapeptide (Climent et al., 1991, Biochemistry. 30:5164–5171).

A General Design for RR Inhibitors

Summarizing the results presented herein, the reverse turn in the R2- C-terminal peptide appears to serve as a scaffold that properly positions contacts between the R1 and R2 subunits. Differences in the specific side chain interactions, such as those discussed for the correlated 344, 722, 748 trio, presumably account for differences in binding between species which possess nonhomologous R2 C-terminal sequences. Peptidomimetics incorporating a reverse turn mimicking those found in the bound E. coli and mouse R2 termini (FIG. 14B), and substituted with appropriate substituents, will provide a general design for inhibitors that are specific for RRs from different organisms.

EXAMPLE 11

Other Experiments

Preparation of E. coli RR

Recombinant E. coli R1 and R2 were prepared using expression vectors (Salowe et al., 1986, J. Bacteriol. 165;363–366; Mao et al., 1989, Proc. Natl. Acad. Sci. USA 86:1485–1489).

Preparation of Calf Thymus R1

The older purification procedure, based on the use of a dATP-Sepharose 4B affinity column (Engström et al., 1979, Biochemistry 18:2941–2948; Thelander et al., 1980, J. Biol. Chem. 255:7426–7432; Mattaliono, 1982, Physicochemical Studies on the Catalytic and Regulatory Subunits of Ribonucleotide Reductase from Calf Thymus. Ph.D. thesis, University of New Hampshire) was supplanted with a procedure based on an FTLDADF-Sepharose 4B affinity column (prepared by condensing activated CH-Sepharose 4B with the R2 C-terminal peptide FTLDADF (SEQ ID NO: 3) (Cuatrecasas et al., 1972, Biochemistry 11:2291–2297) that yielded purer R1 devoid of R2 content, a property which is especially useful for the detection of R2-containing fractions during R2 purification. Measured in the presence of excess and near saturating R2 (1.1 $\mu$M), it had a specific activity toward CDP reduction of 70 nmol/min/mg, which compared favorably with the value of 24 nmol/min/mg reported by Engström et al. (Engstrom et al., 1979, Biochemistry 18:2941–2948).

Expression of Mouse Ribonucleotide Reductase

High levels of active mouse R1 have been expressed using a baculovirus expression system. This system has three important advantages over the use of calf thymus enzyme. First, it provides much larger amounts of R1. In the most recent preparations, ~100 mg of pure mouse R1 was obtained per liter of Hi5 cell culture. Expression in Sf9 cells was less efficient, giving yields of the order of 10–20 mg/liter. Second, measured with respect to CDP reduction, recombinant R1 had a specific activity of 200 nmol/min/mg, some three times higher than that observed in the case of calf thymus R1 and some eight times higher than that reported by Engstrom et al. (1979, Biochemistry 18:2941–2948). Similar higher specific activities were also found for ADP and GDP reduction. Third, the availability of an efficient expression system permits site-directed mutagenesis for eventual structure-function studies.

Briefly, the gene encoding mouse R1 (Caras et al., 1985, J. Biol. Chem. 260:7015–7022) was inserted into pBlueBac at the unique Nhe 1 site through the Nhe 1 restriction sites created by the PCR primers at the N- and C-termini of the mouse R1 gene. The site of insertion is downstream from the polyhedrin gene promoter sequences. The recombinant plasmid, denoted pBac-RNR1, was grown and purified from the host bacteria, NM522. Hi5 or Sf9 insect cells were cotransfected with the pBac-RNR1 and wild type baculovirus DNA and high-titer recombinant baculovirus was prepared from the supernatant. The recombinant virus stock was titered on Hi5 or Sf9 cells under agarose overlays and expressed recombinants were identified by visual inspection. The positive clones were plaque-purified and the positives were further characterized by Western blot analysis and DNA sequencing. Recombinant R1 was prepared to homogeneity from Hi5 or Sf9 cultures essentially according to the standard R1 purification protocol described above for the purification of calf thymus R1.

Generation of Recombinant Mouse R2

Recombinant mouse R2 was purified from *E. coli* as described (Mann et al., 1991, Biochemistry 30:1939–1947) from an expression vector. This procedure affords 100–150 mg of pure R2 from 15 liters of culture.

Assays of RR Activity

Standard assays of RR activity used in the studies presented herein involve the conversion of [$^3$H]-ribonucleoside diphosphate (NDP) to [$^3$H]-deoxyribonucleoside diphosphate (dNDP), using dithiothreitol as the external reductant. Three methods were examined: Method 1 (Steeper et al., 1970, Anal. Biochem. 34:123–130), involving the conversion of diphosphates to nucleosides by enzymatic digestion, followed by the separation of deoxynucleoside from nucleoside on Dowex-1-borate columns; Method 2 (Moore et al., 1974, Biochemistry 13:2904–2907), involving the direct separation of dNDP from NDP on aminophenylboronate columns; Method 3 (Sato et al., 1983, Anal. Biochem. 135:431–435) involving the conversion of diphosphates to nucleosides by enzymatic digestion, followed by the separation of deoxynucleoside from nucleoside on polyethyleneimine-cellulose columns.

All three methods yielded acceptable results, with the following limitations. Method 1 is useful for the assay of CDP to dCDP and ADP to dADP conversions, but is not useful for the assay of GDP reduction. It is also sensitive to large changes in the nucleotide composition of the assay medium. Thus, it is quite useful for standard assays (purifications, tests of peptide inhibition), but difficult to apply when concentrations and substrate are widely varied. Method 2 is the easiest to perform on purified enzymes, and can be used with all four NDPs as substrates, but is difficult to use with crude enzyme, largely because contaminating phosphatase activities can skew results. Method 3 is usable with all four NDPs, but is also somewhat sensitive to large changes in the nucleotide composition of the assay medium and requires column separation at 4° C.

Preparation of Peptides.

Peptides are prepared by standard step-wise solid-phase Merrifield techniques using a Milligen/Biosearch Model 9600. Either $N^\alpha$-t-Butyloxycarbonyl (tBoc) protected amino acids or $N^\alpha$-fluorenylmethyloxycarbonyl (Fmoc) protected amino acids were used. For the tBoc procedure, peptides were deprotected and cleaved from resin using HF (Stewart J M; Young J D. Solid Phase Peptide Synthesis, 2nd ed., Pierce Chemical Co., Rockford, Ill. 1984, 84–92). For the Fmoc procedure, Fmoc groups were cleaved in piperidine/toluene/DMF and deprotection of amino acid side chains and cleavage of the peptide from the resin were performed in a mixture of dimethyl sulfide and TFA (Chang et al., 1978, Int. J. Peptide and Protein Res. 2:246–249). Peptides were purified by reverse-phase HPLC, using a $CH_3CN$ gradient in 0.1% trifluoroacetic acid. In general, it was observed that the Fmoc procedure afforded cleaner peptide preparations, thus, this was the method of choice.

$N^\alpha$-acetyl derivatives were obtained by acetylation of peptides with acetic anhydride in methylene chloride prior to release of the peptides from the solid support (Bayer et al., 1970, J. Amer. Chem. Soc. 92:1735–1738). All peptides were of high purity as determined by $^1$H NMR spectra (500 MHZ), high resolution mass spectra (using a VG ZAB E instrument under FAB conditions) and analytical HPLC.

Studies on R1:R2 Subunit Association

Peptide Inhibition of RR Activity.

(Peptide numbering in this section is N-AcF$^7$TLDADF$^1$)

As shown in Table 7, eukaryotic R2s are highly homologous to one another up to seven residues from the C-terminus, at which point the homology is lost. Based on this observation, and by analogy with known inhibition of herpesvirus RR by a nonapeptide corresponding to the C-terminus of viral R2 (Erikson et al., 1989, Allosteric Enzymes 189–215; Stubbe, 1990, Adv. Enzymol. Relat. Areas Mol. Biol. 63:349–419), it was predicted and observed that N-acetyl-FTLDADF (SEQ ID NO: 16), corresponding to the C-terminus of mouse R2 (the acetylation is necessary to neutralize the positive charge on the $\alpha$-amino group, which otherwise interferes with binding), inhibits mammalian RR (Yang et al., 1990, FEBS Lett. 272:61–64).

The above described study was expanded by carrying out a detailed structure-function analysis of peptide inhibition of mammalian and, to a more limited extent, *S. cerevisiae* RRs. These experiments were directed toward determining how the inhibitory potencies of a series of mammalian R2

C-terminal peptide analogues depend on size and sequence and toward exploring whether even the slight differences in the C-terminal sequences of *S. cerevisiae* vs. mammalian R2 could be exploited in developing peptides that show selectivity in the inhibition of the corresponding RR activities.

TABLE 7

Homologous R2 C-terminal sequences

| Organism | Sequence | SEQ ID NO: | Organism | Sequence | SEQ ID NO: |
|---|---|---|---|---|---|
| Clam | FTLDADF | 3 | S. cerevisiae | FTFNEDF | 7 |
| Mouse | FTLDADF | 3 | S. pombe | FTIDEDF | 9 |
| Human | FTLDADF | 3 | P. falciparum | FCLNTEF | 11 |
| Vaccinia | FSLDVDF | 12 | | | |

The results of experiments measuring relative inhibitory potencies (RIs) of mammalian R2 C-terminal peptide analogues are summarized in Table 8.

TABLE 8

Inhibitory potency of mammalian R2 C-terminal peptide analogs toward mammalian ribonucleotide reductase activity.

| | Peptide | $IC_{50}^a$, μM | % $RI^b$ | SEQ. ID NO: |
|---|---|---|---|---|
| 1. | Ac-NSFTLDADF | 9–15 | 100 | 13 |
| 2. | Ac-SFTLDADF | 8–20 | 100 | 14 |
| 3. | SFTLDADF | 80 | 25 | 15 |
| 4. | Ac-FTLDADF | 8–20$^d$ | 100 | 16 |
| 5. | FTLDADF | >400$^d$ | <3 | 3 |
| 6. | Ac-TLDADF | >400 | <3 | 51 |
| 7. | Ac-LDADF | >400 | <3 | 52 |
| 8. | Ac-FTLDADL | 400 | 3 | 18 |
| 8a$^c$ | Ac-YTLDADF | 200 | 7 | 19 |
| 9. | Ac-F(4'-NH$_2$)TLDADF | 100 | 10 | |
| 10. | Ac-F(4'-N$_3$)TLDADF | 100 | 10 | |
| 11. | Ac-FSLDADF | 40–42 | 25 ± 1.1 | 20 |
| 12. | Ac-FALDADF | 35–40 | 24 ± 4.1 | 21 |
| 13. | Ac-FTVDADF | 30 | 35 | 22 |
| 14. | Ac-FTFDADF | 48–58 | 18 ± 4.2 | 23 |
| 15. | Ac-FTADADF | 207 | 4.9 ± 0.60 | 24 |
| 16. | Ac-FTLNADF | 25–29 | 40 ± 2.4 | 25 |
| 17. | Ac-FTLAADF | 286–336 | 2.9 ± 0.4 | 26 |
| 18. | Ac-FTLDGDF | 110–230 | 9 ± 0.6 | 27 |
| 19. | Ac-FTLDLDF | 28 | 35 | 28 |
| 20. | Ac-FTLDAEF | 450–620 | 1.7 ± 0.15 | 29 |
| 21. | Ac-FTLDANF | 32–38 | 23 ± 1.0 | 30 |
| 22. | Ac-FTLDALF | 29–30 | 34 ± 5.0 | 31 |
| 23. | Ac-FTLDAAF | 34–35 | 28 ± 1.3 | 32 |
| 24. | Ac-FTLDADL | >400 | <3 | 33 |
| 25. | Ac-F-LDADF (deletion) | 412 | 2.5 | 53 |
| 26. | Ac-FTLD-DF (deletion) | 322 | 3 | 54 |
| 27. | Ac-FTL--DF (deletion) | 364–460 | 2.5 ± 0.18 | 55 |
| 28. | Ac-FTLDADFAA | 500 | 2.1 | 34 |

$^a$$IC_{50}$ is the concentration of peptide producing 50% inhibition of activity obtained in the absence of peptide. Values are derived from Dixon plots of 4–6 concentration points run in duplicate or triplicate. Range of $IC_{50}$ values are for two independent determinations conducted on different days.
$^b$% relative inhibitory potency, defined as (IC50 AcFTLDADF)/(IC50 peptide analog). Mean values and average deviations based on 2–3 independent determinations. Other values are single determinations.
$^c$Not included in publication #4.

It can be seen that the peptides having significant RR inhibitory activity include those having the general formula $W_1$-$AA_8$-$AA_9$-$AA_{10}$-$AA_{11}$-$AA_{12}$-$AA_{13}$-Phe -$W_2$ wherein:
$W_1$ is selected from the group consisting of acetyl, one amino acid residue, two amino acid residues, one N-acetyl-amino acid residue, and an N-acetyl-amino acid residue linked to a second amino acid residue by a peptide bond;

$AA_8$ is selected from the group consisting of Phe, p-amino-Phe, and p-azido-Phe;

$AA_9$ is selected from the group consisting of Thr, Ser, and Ala;

$AA_{10}$ is selected from the group consisting of Leu, Val, Phe, and Ala;

$AA_{11}$ is selected from the group consisting of Asp, Asn, and Ala;

$AA_{12}$ is selected from the group consisting of Ala, Leu, and Gly;

$AA_{13}$ is selected from the group consisting of Asp, Asn, Leu, Ala, and Glu; and $W_2$ is selected from the group consisting of one amino acid residue and two amino acid residues.

The RIs of the first seven peptides (1–7) confirm the importance of the C-terminal heptapeptide for binding to the R1 subunit. RIs of the N-acetyl octa- and nonapeptides are both one (1,2), showing the lack of importance of positions 8 and 9 (as measured from the C-terminus) for binding to R1, whereas the R's for the N-acetyl hexa- and pentapeptides (6,7) are at least 40 times smaller, implying that Phe in position 7 is important for binding. The low RI of the non-acetylated heptapeptide (5), reproducing an earlier observation (Yang et al., 1990, FEBS Lett. 272:61–64), demonstrates that neutralization of positive charge is essential for high inhibitory potency. Interestingly, the RI of nonacetylated octapeptide (3) demonstrates that the effect of acetylation on inhibitory potency becomes less important as the peptide length is extended beyond a heptamer.

Evidence that the Phe residues in positions 1 and 7 are critical for binding is provided by the over 40-fold decreases in RI observed on substitution of Leu for Phe (8,24). The five to ten-fold decreases in RI on substitution of p-amino-, p-hydroxy- or p-azido-Phe in position 7 (8a,9,10) indicates the strictness of structural requirements at this position. Each of the remaining positions appears to be more tolerant of substitution although some preferences are clear. Position 6 is rather insensitive to substitution by either Ser (11) or Ala (12). In position 5, a bulky aliphatic side-chain appears to be favored based on the effects seen on Val (13), Phe (14), or Ala (15) substitution. Position 4 appears to have a preference for either a polar group or a group of a certain size (or both), since an Asn (16) substitution lowers RI only two-fold, but substitution with Ala (17) leads to over a 30-fold- decrease in RI. In position 3, a minor drop in RI results from a Leu substitution (19), suggesting no specific side chain requirement in this position, although substitution with Gly (18) does lead to a 10-fold decrease in inhibitory potency. The results with position 2 are particularly interesting in that an apparently conservative Glu substitution (20) results in over a 50-fold decrease in RI, whereas other conservative (Asn, 21) or nonconservative (Leu, 22, Ala, 23) substitutions result in much smaller (three to four-fold) decreases in RI.

The results obtained with peptides 8–24 are only partly in accord with simple expectations based on evolutionary conservation (Table 7). As would be expected, positions 1 and 7, which are fully conserved, are quite sensitive to even conservative amino acid substitution, whereas, position 3, which shows the greatest variability, is apparently insensitive to major side chain modifications. In addition, the limited variabilities observed for positions 4 and 5 are consistent with the need for a hydrogen binding and a hydrophobic side chain, respectively, at these positions, in accord with the results in Table 8. On the other hand, considerable variation is tolerated in position 2, in which an acidic side chain is fully conserved. Additionally, the importance of a hydrogen binding side chain in position 6, which could be inferred from Table 7, is not supported by the small decrease in RI on substitution with Ala (12). The low RI values observed with peptides 25–27, in which one or more amino acids have been deleted as compared with N-AcFTLDADF (SEQ ID NO: 16), buttress the conclusion that the acetylated heptapeptide is the minimal length required for effective RR inhibition. In addition, although the low RI that results from adding amino acids to the C-terminus (28) suggests that a free carboxylate at the highly specific position 1 may be important for R1 binding, results with HSV-RR (Liuzzi et al., 1994, Nature, 372:695–698; Moss et al., 1995, J. Med. Chem. 38:3617–3623) establish that the terminal carboxylate can be reduced to an hydroxymethyl group with little effect on inhibitory activity.

TABLE 9

Cross inhibitory potency of S. cerevisiae R2 C-terminal peptide analogs on S. cerevisiae and mammalian ribonucleotide reductase

| Peptide | SEQ. ID NO. | IC50, µM Yeast RR | IC50, µM Mammalian RR29. |
|---|---|---|---|
| AcAGAFTFNEDF | 56 | 25 | — |
| 30.AcFTFNEDF | 57 | 25 | 100 |
| 31.AcTFNEDF | 58 | 600 | 600 |
| 4. AcFTLDADF | 16 | 25 | |

The cross-specificities of mammalian and S. cerevisiae C-terminal R2 peptides, which differ from each other at positions 5–3 from the C-terminus (-FNE- vs -LDA-, Table 7) were examined in Table 9. The N-acetylated C-terminal heptapeptide provides the critical length for inhibition of S. cerevisiae RR, as it does for inhibition of mammalian RR, since N-acetylated peptides corresponding to S. cerevisiae R2 C-terminal deca- and heptapeptides (29,30) have about the same inhibitory potency toward S. cerevisiae RR but the N-acetylated S. cerevisiae hexapeptide (31) is a much weaker inhibitor. Further, whereas mammalian N-acetylated C-terminal heptapeptide (4) has about the same inhibitory potency toward both the S. cerevisiae and mammalian enzymes, the S. cerevisiae enzyme is about 4-fold more sensitive to inhibition by the S. cerevisiae C-terminal peptide (30) than is mammalian RR. The RI of peptide (14) (Table 8) suggests that it is the Phe in position 5 that is principally responsible for this difference.

It has also been established in the present studies that N-AcFCLNTEF (SEQ ID NO: 59), the heptapeptide corresponding to the C-terminus of P. falc. R2, has an inhibitory potency (RI) toward mammalian RR that is 10-fold lower than the mammalian R2 C-terminal peptide. Based on the data presented in Table 8 (especially for peptide 20), this low potency is most likely due primarily to the Glu residue in position 2.

The Structures of N-AcFTLDADF, N-AcYTLDADF, and N-AcFTLDADL Bound to Mammalian R1
(Peptide numbering in this section is N-AcF$^1$TLDADF$^7$)

Transferred nuclear Overhauser effect NMR spectroscopy (TRNOESY) was used to elucidate the structures of N-AcF$^1$TLDADF$^7$ (SEQ ID NO: 16), as well as of two variants N-AcYTLDADF (SEQ ID NO: 19) and N-AcFTLDADL (SEQ ID NO: 18), as they are bound to mouse R1 (mR1). These structures have a remarkable similarity to the structure of the E. coli R2 C-terminal peptide, -DDLSNFQL bound to E. coli R1, determined by X-ray crystallography (Uhlin et al., 1994, Nature 370:533–539), leading to a suggestion for the design of peptide-based inhibitors for type 1 RRs from all species.

Both theoretical and practical aspects of TRNOESY have been extensively considered (Clore et al., 1982, J. Magn. Res. 48:402–417; Bax et al., 1985, J. Magn. Reson. 65:355–360; Bax et al., 1985, J. Magn. Reson. 63,207–213; London et al., 1992, J. Magn. Reson. 97:79–98; Ni, 1992, J. Magn. Reson. 96:651–656; Campbell et al., 1993, Annu. Rev. Biophys. Biomol. Struc.22:99–122), and many examples exist of the use of TRNOESY to determine the conformation and structure of small ligands bound to proteins (Meyer et al., 1988, Biochemistry 27:725–730; Ni et al., 1990, Biochemistry 29:4479–4489; Ni et al., 1992, Biochemistry 31:2545–2554; Dratz et al., 1993, Nature 363:276–280; Srinivasan et al., 1994, Biochemistry 33:13553–13560; Ni et al., 1994, Accts. of Chem. Res. 27, 257–264), including an important study of N-AcDDLSNFQL binding to E. coli R1 indicating that the peptide adopts a turn in the region of the Asn and Phe residues (Bushweller et al., 1991, Biochemistry 30:8144–8151). TRNOESY relies on the transfer of proton cross relaxation effects from the bound to the free state by means of rapid chemical exchange. Under fast exchange, the observed peptide resonances are approximately the same as for free peptide and NOEs between bound peptide protons are manifested as negative TRNOEs on the averaged ligand resonances. The magnitude of a TRNOE peak is proportional both to the mole fraction of bound ligand and to the cross relaxation rate between bound peptide protons. This rate is inversely proportional to the sixth power of the distance between the two nuclei. As a consequence, TRNOE provides a sensitive measure of distance. As determined in the work described in C-3a,c, N-AcFTLDADF binds to mouse R1 with a Kd of approximately 10 µM, and meets the rapid exchange constraint, as do the Tyr1 and Leu7 variants, which bind more weakly (Table 8).

Peak Assignment and Peptide Structure in Solution

For these experiments NMR spectra were taken on one of the following three Bruker spectrometers (AMX-600, AMX-500, DMX-500), each operating in phase sensitive mode. The water resonance was removed by 1.5 s presaturation. The one-dimensional $^1$H NMR spectrum of N-AcFTLDADF in solution (10% D$_2$O or in d$_6$-DMSO) exhibited sharp and well-resolved amide, aromatic side chain, α, β and aliphatic side chain regions and was assigned using standard ROESY (rotating-frame nuclear Overhauser spectroscopy ; 250-ms mix; for Phe and Asp resonances) and TOCSY (total correlated spectroscopy; 65-ms mix; for all other resonances). Based on results obtained with N-AcFTLDADF (SEQ ID NO: 16), assignments for N-AcYTLDADF (SEQ ID NO: 19) and N-AcFTLDADL (SEQ ID NO: 18) were made on the basis of TOCSY alone. For these three peptides, the proton chemical shifts were nearly identical for the TLDAD portion of each molecule.

Addition of R1 to the peptide solutions in amounts typically used in TRNOESY experiments led to peak broadening but no clearly discernible change in proton chemical shifts. NOE experiments and coupling constant measurements on N-AcFTLDADF (SEQ ID NO: 16) and N-AcYTLDADF (SEQ ID NO: 19) in solution demonstrated, as expected, a lack of long range structure.

TRNOESY of Peptide Bound to mR1

Addition of mR1 induced both one-dimensional peak broadening as well as nonsequential and additional sequential TRNOEs. The induced TRNOEs are indicative of a folded structure formed as a result of peptide binding to mR1. Similar results were obtained with N-AcYTLDADF (SEQ ID NO: 19) and N-AcFTLDADL (SEQ ID NO: 18), with the obvious substitution of Phe1 or Phe7 peaks by Tyr1 peaks or Leu7 peaks, respectively. Thus, despite their differences in affinity for mR1, all three peptides appear to bind mR1 with the same conformation (Clore et al., 1982, J. Magn. Res. 48:402–417).

TRNOESY experiments are best carried out under low occupancy conditions. Accordingly, spectra were recorded with a molar ratio of peptide:mR1 subunit of 25–100, with 50 found to be optimal. TRNOESY spectra used for the modeling studies described below were obtained utilizing a mixing time of 75–100 ms. NOEs dropped in intensity at mix times shorter than 75 ms; at longer mix times, intensities begin to equilibrate, in part due to spin diffusion effects. All two-dimensional data were premultiplied by either a 45° or a 90° shifted sine bell in both dimensions. The programs UXNMR (Bruker) and NMR Compass 2.0 (MSI) were run on a Silicon Graphics workstation. A total of 512 FIDs of 2048 complex points were collected with 80–124 scans collected per FID.

Strong evidence that such TRNOE signals reflect a specific binding interaction of these peptides with mR1 is provided by the result that added mR2 strongly reduced the intensity of the TRNOE signals from bound N-AcFTLDADL (SEQ ID NO: 18), as expected based on mR2 competing with N-AcFTLDADL (SEQ ID NO: 18) for binding to mR1 (Fisher et al., 1995, Nature Struct. Biol. 2(11):951–955). N-AcFTLDADL (SEQ ID NO: 18) was selected for this experiment because its comparatively low affinity for R1 allowed its nearly full displacement by mR2 concentrations that were experimentally feasible. In additional controls, no one-dimensional peak broadening or nonsequential TRNOE signals were found when mR1 was replaced by equivalent molar amounts of bovine serum albumin, mR2 or unfractionated IgG, a protein of molecular weight similar to that of mR1.

Modeling the Structure of N-AcYTLDADF Bound to mR1

The TRNOEs observed for N-AcYTLDADF (SEQ ID NO: 19) proved a better choice for initial elucidation of the structure of bound peptide, since the $^1$H NMR spectrum of this peptide contains fewer overlaps than was observed in the case of N-AcFTLDADF (in particular, the D4/L3 and T2/A5 amides and of the F1 and F7 aromatic protons). Proton-proton distances provided by the TRNOEs allowed modeling of the structure of N-AcYTLDADF (SEQ ID NO: 19) bound to mR1 through application of restrained molecular dynamics implementing simulated annealing (Kirkpatrick et al., 1983, Science, 220:671–680; Clore et al., 1989, CRC Crit. Rev. Biochem. Mol. Biol. 24:479–564; Clore et al., 1993, J. Mol. Biol. 231:82–102; Brunger et al., AT. X-PLOR Version 3.1. A system for X-ray crystallography and NMR. 1992, New Haven, Yale University Press). From slightly more than 100 visible cross peaks in the two-dimensional TRNOE spectrum a total of 82 were used as restraints in modeling the structure of N-AcYTLDADF (SEQ ID NO: 19) bound to mR1, with the others unused due to noise, overlap, or ambiguous assignment. Particularly noteworthy for determining the conformation of bound N-AcYTLDADF (SEQ ID NO: 19) were: (1) sequential HN—HN cross peaks for Asp4–Ala5, Ala5–Asp6, and Asp6–Phe7, suggestive of helical or turn-type conformation (Wüthrich, NMR of Proteins and Nucleic Acids. 1986, New York, Wiley); (2) cross peaks from the aromatic δ and ε protons to the backbone for Tyr1 and Phe7, helpful for positioning the aromatic rings; (3) nonsequential cross peaks between side chains (generally the methyls of Thr and Ala) to the backbone, and (4) cross peaks between the side chains of Tyr1 and Leu3, Thr2 and Ala5, and Ala5 and Phe7.

Figure 16:
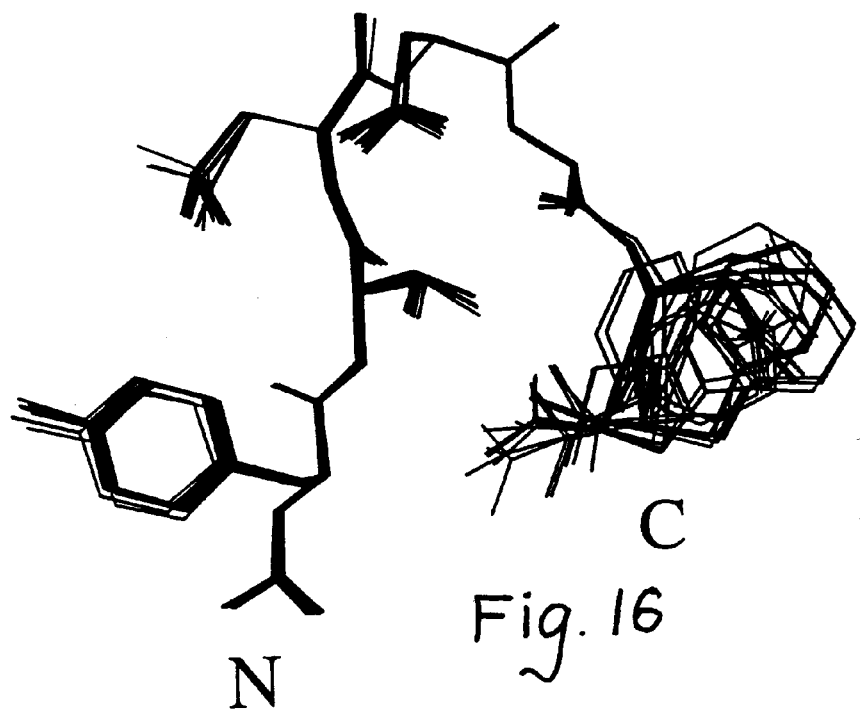
FIG. 16 is a diagram of superposition of 16 of the 20 lowest energy annealed structures (from a total of 150 structures) of AcYTLDADF (SEQ ID NO: 19) aligned on backbone atoms 2–6. N=N-terminus, C=C-terminus; only heavy atoms shown.

The most prominent structural feature (FIG. 16) is the nonideal type 1 reverse turn formed by residues TLDA (mean Φ and Ψ angles of –124° and 7° for Leu 3 and –120° and –45° for Asp4) (Wilmot et al., 1990, Protein Eng. 3:479–493; Rose et al., 1985, Adv. Prot. Chem. 37:1–109). Interestingly, the carbonyl O of Thr2 points outward, eliminating the possibility of a bridging H-bond seen in canonical §-turns. Viewed as a horseshoe, the left and right sides are defined by a clustering of hydrophobic residues: the edge of the Tyr1 ring fits into the groove formed by the methyls of Leu3, and the plane of the Phe7 ring packs against the methyl of Ala5. The side chain of Asp4, though having few distance restraints, has a well-defined coplanar orientation with respect to the reverse turn, held in place by the β-carbon of Thr2 and the methyl of Ala5. Asp4 forms a hydrogen bond with the amide proton of Leu3, at a mean distance of 3.3±0.1 between the nitrogen and the closer carboxylate oxygen. The methyls of Thr2 and Ala5, as well as the carboxylate of Asp4, are positioned above the plane of the turn. Below the plane is a polar grouping, formed by the carbonyl oxygens of residues 2–5, and the carboxylate of Asp6. The open end of the horseshoe is also polar, dominated by the carbonyl oxygen of the acetyl group and the carboxylates of Asp6 and the C-terminal Phe7. Despite the disorder seen for Phe7 (FIG. 16), which may reflect inherent molecular flexibility or insufficient restraints, the packing of the Phe7 ring against the methyl of Ala5 is present in all structures. In contrast, the Asp6 side chain bifurcates into two groups, differing by about a 100° rotation about the χ' dihedral angle.

Modeling the Structure of N-AcFTLDADF Bound to mR1, Comparison with Bound N-AcYTLDADF Given that the structure of bound AcYTLDADF (SEQ ID NO: 19) was determined herein, the more difficult task of determining the structure of bound AcFTLDADF (SEQ ID NO: 16) was next elucidated. The use of a deuterated benzene ring in position Phe1 reduced some ambiguity in assigning resonances. The majority of NOEs found for AcFTLDADF (SEQ ID NO: 16) in the presence of R1 were similar to those seen for AcYTLDADF (SEQ ID NO: 19), except that NOEs to Phe1 replace NOEs to Tyr1. A common set of 76 NOEs were used for modeling of AcFTLDADF (SEQ ID NO: 16) and AcYTLDADF (SEQ ID NO: 19) data sets, with a total of 99 NOEs being used in modeling of AcFTLDADF (SEQ ID NO: 16) vs. the 82 NOEs used for modeling AcYTLDADF (SEQ ID NO: 19). The number of NOEs in common between AcYTLDADF (SEQ ID NO: 19) and AcFTLDADF (SEQ ID NO: 16) spectra indicates that, despite some differences, these peptides take on similar conformations when bound to mR1.

Figure 18:
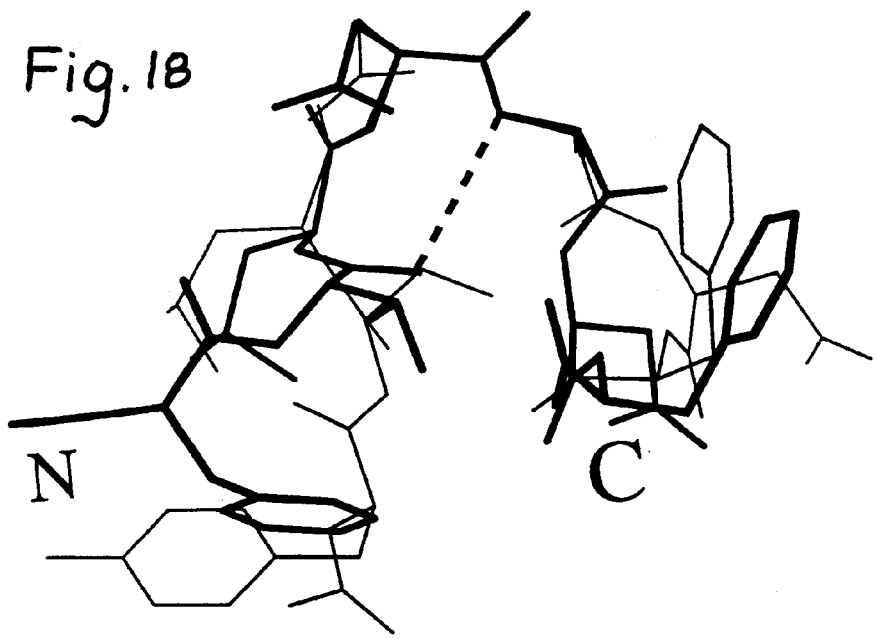
FIG. 18 is a diagram of superposition of representative structures of AcFTLDADF (SEQ ID NO: 16) and AcYTLDADF (SEQ ID NO: 19) aligned on the following atoms: all of Leu; Asp, excluding the side-chain carboxylate; all of Ala, except the carbonyl carbon and oxygen. Heavy lines, AcFTLDADF (SEQ ID NO: 16); light lines, AcYTLDADF (SEQ ID NO: 19).

A major subset (26 in all) and minor subset (9 in all) of clustered, low energy structures were generated for R1-bound AcFTLDADF (SEQ ID NO: 16). As the major subset also self-aligned with a much lower root mean square deviation (RMSD), it is this subset (FIG. 17) that was compared to the single cluster of low energy structures observed for bound AcYTLDADF (SEQ ID NO: 19; FIG. 18).

The major similarities between the structures of the two bound peptides are: 1) both are characterized by a nonstandard type 1 reverse β-turn for residues TLDA (SEQ ID NO: 47). Here it should be emphasized that approximately 35% of the type 1 reverse β-turns found in the protein structure data base are nonstandard (Wilmot et al., 1990, Protein Eng. 3:479–493; Ball et al., 1990, J. Molec. Recog. 3:55–64); 2) atoms in the turn region align well between the two peptides, as a result of similar phi, psi angles at Leu3 and Asp4; 3) the same packing of hydrophobic residues—the N-terminal Phe or Tyr aromatic ring with the Leu geminal methyls and the Ala methyl with the C-terminal Phe aromatic ring—is seen in both; 4) the phi, psi angles for residue 6 and phi angles and for residue 7 are identical.

The major differences between the structures of the two bound peptides, which presumably account for the higher affinity toward R1 of N-AcFTLDADF (SEQ ID NO: 16), are: 1) the reverse-turn in AcFTLDADF (SEQ ID NO: 16) is H-bonded between the Thr2 carbonyl and the Ala5 NH, but the reverse turn in ACYTLDADF (SEQ ID NO: 19) is not; 2) in AcFTLDADF (SEQ ID NO: 16), phi and psi angles for one residue, Asp6, fell into a forbidden region either just outside or on the border of the loop region in the right hand lower quadrant of the Ramachandran plot. There may be some compensating energetic factors associated with the binding event itself that makes these angles allowable. In AcYTLDADF (SEQ ID NO: 19), phi, psi angles at every position fell in allowed regions; 3) at the N-termini, the psi angles for residues 1 and 2 are $-91.4°$ and $61°$ for AcFTLDADF (SEQ ID NO: 16) vs $161.9°$ and $157.7°$ for AcYTLDADF (SEQ ID NO: 19); 4) the positioning of backbone residues 6 and 7, resulting from differences in the rotation of the bond between Ala5 C$\alpha$ and the Ala5 carbonyl carbon; 5) in AcFTLDADF (SEQ ID NO: 16) there is an H-bond between the Thr2 hydroxyl proton and the closer of the Asp4 carboxylate oxygens. In AcYTLDADF (SEQ ID NO: 19), this H-bond is replaced by one between the carboxylate of Asp4 and the Leu3 amide proton.

Peptide Features Important for Binding to mR1

The structures of AcFTLDADF (SEQ ID NO: 16) and AcYTLDADF (SEQ ID NO: 19) bound to R1, taken together with previous structure-activity results (Table 8) and the evolutionary conservation of R2 C-terminal peptides (Table 7), allows some inferences about which features are important for R2 C-terminal peptide binding to R1. One such feature is the hydrophobic surface formed by the packing of Phe1 (Tyr1) into the groove formed by the geminal methyls of Leu3. Thus, replacing Leu3 with relatively large hydrophobic residues (Phe or Val) results in only modest decreases in RI, whereas substitution with Ala results in a large decrease. The weaker binding observed on Tyr1 substitution for Phe1 may be due in part to the introduction of a hydrophilic group onto this surface. Similarly, the importance of Phe7 interaction with a $\beta$-CH$_2$ at position 5 is suggested by the small decreases in RI on substitution of Ala5 with either Val or Glu, whereas a Gly substitution results in a large decrease (Fisher et al., 1993, J. Med. Chem. 36:3859–3862). The hydrogen bond formed by the carboxylate of Asp4, either to the Ala5 amide (in N-AcFTLDADF; SEQ ID NO: 16) or to the Leu3 amide (in N-AcYTLDADF; SEQ ID NO: 19) appears to be another important feature, since Ala substitution for Asp4 results in a large drop in RI, whereas Asn substitution is reasonably well tolerated. The importance of each of these three features is also supported by the evolutionary homologies at positions 1, 3, 4, 5 and 7 evident in Table 7. On the other hand, the importance of hydrogen bond formation from the Thr2 hydroxyl is more ambiguous. A hydrogen bond partner at position 2 is conserved evolutionarily, but substitution with either Ala or O-benzyl-Thr leads to only small decreases in RI (Fisher et al., 1993, J. Med. Chem. 36:3859–3862).

Comparison of the Conformations of R2 C-terminal Peptides Bound to Mouse and E. coli R1

In the X-ray structure of the E. coli R1 subunit complexed with the 20 residue peptide corresponding to the C-terminus of E. coli R2 (Uhlin et al., 1994, Nature 370:533–539), the terminal eight peptide residues, D$^{368}$DLSNFQL$^{375}$ (SEQ ID NO: 36), are well defined in the electron density (B-2). The structures of AcFTLDADF (SEQ ID NO: 16) and AcYTLDADF (SEQ ID NO: 19) bound to mR1 were compared to that DDLSNFQL (SEQ ID NO: 36) bound to E coli R1 by least squares alignment of the carbonyl oxygens and heavy atoms in the backbone, extending from the carbonyl carbon of Thr2 to the amide nitrogen of Ala5 in AcFTLDADF (SEQ ID NO: 16) and AcYTLDADF (SEQ ID NO: 19), with the corresponding atoms from Leu743 to Phe746 in the E. coli peptide. Overall RMSDs of 0.286 Å and 0.33 Å were obtained for AcFTLDADF (SEQ ID NO: 16) and AcYTLDADF (SEQ ID NO: 19), respectively. By the classification criteria of Wilmot and Thornton (Wilmot et al., 1990, Protein Eng. 3:479–493), the bound E. coli R2 C-terminal peptide has an ideal type 1 reverse-turn, whereas both AcFTLDADF (SEQ ID NO: 16) and AcYTLDADF (SEQ ID NO: 19) bind with nonideal type 1 turns.

In addition to the manifest structural similarity of the $\beta$-turns peptides bound to mR1 and to E. coli R1 (FIG. 19), the following comparisons among all three bound peptides should be noted: 1) the $\beta$ carbons of the side chains of Leu3 and Ser744 have similar orientations; 2) a comparable region of space is also shared between the isosteric Asp4 and Asn745 side chains; 3) the Phe7 and Phe746 aromatic rings cluster together well as do the aromatic ring in Phe1 of N-AcFTLDADF (SEQ ID NO: 16) and the hydrophobic side chain of Leu743; 4) the carbonyl oxygen of Leu743 points into the turn, forming a bridging H-bond to the amide nitrogen of Phe746, similar to the H-bond seen between the Thr2 carbonyl and Ala5 amide in N-AcFTLDADF (SEQ ID NO: 16). By contrast, in AcYTLDADF (SEQ ID NO: 19), the carbonyl oxygen of Thr2 points away from the turn; 5) the turn opening is hydrophobic for the E. coli peptide, and polar for the mouse peptides, and the top of the E. coli turn is much less hydrophobic than is the case for the mouse peptides.

Figure 19:
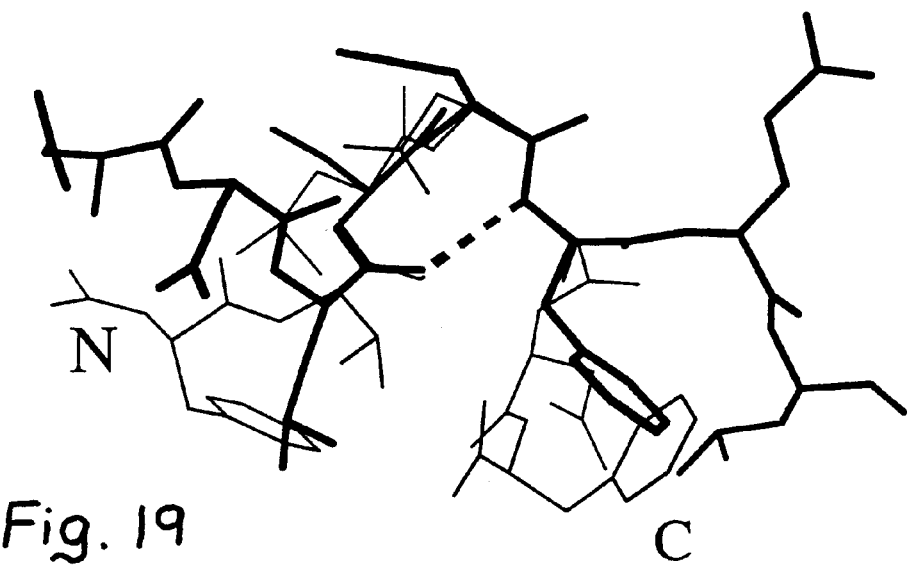
FIG. 19 is a diagram of superposition of AcFTLDADF (SEQ ID NO: 16) with the corresponding DDLSNFQL (SEQ ID NO: 36) peptide from the E. coli R2 C-terminal sequence aligned on 11 backbone atoms extending from the Thr carbonyl carbon and oxygen to the Ala NH in AcFTLDADF (SEQ ID NO: 16) and the corresponding Leu carbonyl carbon and oxygen to the Phe NH in DDLSNFQL (SEQ ID NO: 36). Heavy lines, DDLSNFQL (SEQ ID NO: 36); light lines, AcFTLDADF (SEQ ID NO: 16). Dotted line is H-bond between Leu carbonyl oxygen and Phe N in DDLSNFQL (SEQ ID NO: 36).

These comparisons suggest that there may be evolutionary conservation of the R2/R1 binding interface between divergent species, such that the R2 C-terminus always assumes a conformation having a type 1 reverse-turn with clustering of hydrophobic residues. Such conservation accounts for the observation that addition of E. coli R1 to a solution of AcFTLDADF (SEQ ID NO: 16) induces structural (long range as well as amide to amide backbone) TRNOEs which, though less intense, are similar to those resulting from mR1 addition. TRNOE is a technique capable of detecting weak binding. Although AcFTLDADF (SEQ ID NO: 16) binds very weakly to the E. coli R1 protein, as evidenced by its failure to significantly inhibit E. coli RR up to concentrations of 1 mM (presumably because of differences such as #5 above) (Cosentino et al., 1991, Biochem Cell Biol. 69:79–83), this observation suggests that when it binds it does so with the described conserved conformation. In conclusion, the common turn structure depicted in FIG. 19 provides a basis for the design of high affinity, constrained, peptide or peptidomimetic inhibitors of RR as described herein.

E. coli: Mouse R2 Chimera

The experiments described herein establish the importance of the C-terminus of R2 in the binding of R2 to R1. As a consequence, the failure of E. coli R2 to form an active enzyme with mammalian R1 (Mattaliono, Physicochemical Studies on the Catalytic and Regulatory Subunits of Ribonucleotide Reductase from Calf Thymus. Ph.D. thesis, University of New Hampshire, 1982; ) can be rationalized on the basis of the failure of the two subunits to bind to one another, given the lack of homology in the C-termini of E. coli R2 and mammalian R2 (Table 7).

The question of whether an *E. coli*: mouse R2 chimera, in which the C-terminal residues of *E. coli* R2 are replaced by the C-terminal residues of mouse R2, will form an active enzyme with mammalian R1 is addressed in this section. To accomplish this, a 7-chimera R2, in which the 10 terminal residues of *E. coli* R2 were replaced by the 7 terminal residues of mouse R2, and a 33-chimera R2, in which the 33 terminal residues of *E. coli* R2 were replaced by the 33 terminal residues of mouse R2 were generated and expressed to high yields. Both chimera R2 appeared to fold normally, as evidenced by the identity of their CD spectra with that of wild-type *E. coli* R2 and their migration on native electrophoretic gels as a dimer. Each had an absorption peak at 412 nm and an EPR spectrum (g=2.0045), characteristic of a TyrO radical (Erikson et al., Ribonucleotide Reductase. Allosteric Enzymes. 1989, 189–215; Stubbe et al., 1990, Adv. Enzymol. Relat. Areas Mol. Biol. 63:349–419). The intensity of these spectral features for the chimeric proteins were similar to those obtained with cloned wild-type R2.

Both chimera R2 bind to calf thymus R1 but neither forms an enzymatically active complex with it. The evidence indicates that these subunits bind both directly, using native gel electrophoresis to demonstrate complex formation, and by the fact that chimera R2 is a competitive inhibitor, with respect to wild-type mouse R2, of mammalian RR activity. Detailed analyses of the RR activity as a function of the concentrations of mouse R1, mouse R2, chimera R2, and N-AcFTLDADF (SEQ ID NO: 16), denoted P, permit the following conclusions: 1) $R2_2$ binds to mouse $R1_2$ in a single step to form an $R1_2.R2_2$ complex, with a dissociation constant of 0.24 $\mu$M. This dissociation constant reflects simultaneous binding of both R2 subunits to the two binding sites on $R1_2$; 2) As expected, P binds in two steps, progressively forming the complexes $R1_2.P$ and $R1_2.P_2$. Each of the two binding steps appears to be independent of the other, and each is characterized by a $K_D$ of 18.5 $\mu$M. These results allow calculation of an upper limit for the chelating effect of binding two R2 C-termini simultaneously to $R1_2$, as in the case of $R2_2$, of approximately 70. This upper limit is calculated assuming that, excluding the C-terminus, the remainder of the R2 molecule has no effect on binding to R1. Strong evidence for the validity of this assumption for *E. coli* RR has been presented by Climent et al. (1992, Biochemistry 31:4801–4807); 3) Each chimera binds to $R1_2$ predominantly as dimer to form the $R1_2$.chimera $R2_2$ complex, with dissociation constants of 1.8 $\mu$M and 1.9 $\mu$M for the 7-chimera and 33-chimera, respectively. These constants, which are 7-fold higher than for mouse $R2_2$, indicate a considerably weaker chelating effect for chimera binding to $R1_2$, suggesting that the alignment of R1 and R2 chelating effect for chimera binding to $R1_2$, suggesting that the alignment of R1 and R2 within the $R1_2$.chimera $R2_2$ complex is somewhat altered from what it is in the $R1_2.R2_2$ complex.

The lack of enzymatic activity of either chimera $R2_2.R1_2$ complex may be due to such altered binding. Alternatively, it may reflect a deleterious effect of amino acid substitution at the R2 C-terminus on the rate of electron transfer from the buried tyrosyl free radical in *E. coli* R2 to the R2 surface, a step presumed to be required for RR catalysis of NDP reduction. Here the demonstration by Climent et al. (1992, Biochemistry 31:4801–4807) of the very low or negligible enzymatic activities of the complexes formed with *E. coli* R1 by the *E. coli* R2 variants E350A and Y356A (positions 350 and 356 are at positions 26 and 20 counting from the C-terminus) may be pertinent.

The Catalytic Role of the Stable Tyrosyl Free Radical

The mechanism of action of RR is thought to involve a long-range electron transfer between a stable tyrosyl radical (Y177 in mouse, Y122 in *E. coli*) in the R2 subunit and the substrate bound to R1. Evidence for the central role of Y 122 in the *E. coli* enzyme was provided by the low activity observed for the *E. coli* Y1 22F-R2 variant (1–2% of wild-type) (Larsson et al.,1986, EMBO J. 5:2037–2040). However, it was unclear from this experiment whether this small amount of activity reflected the presence of a small amount of chromosomally encoded wild-type R2 contaminating the Y122F-R2 preparation, or whether it was due to an intrinsic activity of the Y122F-R2 variant. In order to more definitively analyze the central role of the tyrosyl residue in catalysis, the mouse Y177F-R2 variant was generated in an *E. coli* expression system (Mann et al., 1991, Biochemistry 30:1939–1947). The structural integrity of the mutant was confirmed by the similarity of its CD spectrum and stoichiometry of iron binding. It was discovered that combining mouse Y177F-R2 with saturating amounts of recombinant mouse R1 (Salem et al., 1993, FEBS Lett. 323:93–95) generates an enzyme having 0.5% the RR activity of the wild-type enzyme. Inhibition of this low level of activity displays properties characteristic of RRs in general and of mammalian RR in particular. Thus, inhibition is observed at low concentrations of the negative allosteric effector, dATP ($IC_{50}$, 20 mM) in the presence of relatively high concentrations of the positive effector, ATP (Thelander et al., 1980, J. Biol. Chem. 255:7426–7432) and in the presence of hydroxyurea, a potent inactivator of iron-containing RRs ($IC_{50}$, 210 mM) (Sahlin et al., 1989, Biochemistry 28:2618–2625; Nyholm et al., 1993, Biochemistry 32:11569–11574). Most importantly, Y177F-R2-dependent activity is strongly inhibited by N-AcFTLDADF (SEQ ID NO: 16), corresponding to the C-terminus of mouse R2, but only weakly inhibited by the similar peptide N-AcFTLDADL (SEQ ID NO: 18), and so displays the same specificity toward peptide inhibition as does wild-type enzyme.

Two further results demonstrate that the mammalian RR activity measured for Y177F-R2 is not due to a small amount of contaminating wild-type RR. First, no tyrosyl radical was detected in a 270 $\mu$M solution of Y177F-R2, using EPR conditions capable of detecting as little as 0.5 $\mu$M wild-type R2 tyrosyl radical. Approximately 1.5 $\mu$M wild type R2 would have been required to account for the observed activity. Second, PCR analysis of DNA extracted from *E. coli* expressing Y177F-R2, using wild-type primers, failed to detect a PCR product, indicating the absence of a gene encoding wild-type R2. The limit of detection for this analysis was determined to be 1 part in 1000, well beyond the 1 part in 200 that would be needed to account for the observed RR activity.

It is likely that other tyrosine and tryptophan radicals, as have been observed for the Y122F-R2 protein from *E. coli*. (Bollinger et al., 1991, Science 253:292–298; Sahlin et al., 1994, J. Biol. Chem. 269:11699–11702; Bollinger et al., 1994, J. Am. Chem. Soc. 116:8024–8032) may substitute for Y177 in catalyzing substrate reduction. The much lower activity measured for Y177F-R2 may reflect a less favorable electron transfer pathway from the residue substituting for Y177 and/or the lower stability of the substituted radical. Efforts are underway to characterize more fully the mechanism of the Y177F-R2-dependent activity, and to more fully describe the electron transfer pathway in wild-type enzyme, but are not part of this application.

EXAMPLE 12

Inhibition of Tumor Cell Proliferation and Virus Replication in Tissue Culture Entry of RR Inhibitory Peptides or Peptide Mimetics into Cells Liuzzi et al. (1994, Nature, 372, 695–698) have demonstrated that the molecule BI-LD-1263, an analogue of the VVNDL (SEQ ID NO: 37) peptide that corresponds to the R2 C-terminus of HSV-RR, inhibits the replication of HSV types 1 and 2 in cell culture ($EC_{50}$ 3 and 4 μM, respectively), most likely due to suppression of HSV-induced dNTP pools in infected cells, and that such inhibition displays a synergistic effect when added to cell culture together with acyclovir. Furthermore, BI-LD-1263 reduces the severity of HSV-1-induced keratitis in a murine ocular model. It is possible that the potent RR inhibitors described herein will be able to directly inhibit tumor cell proliferation or virus replication. However, the $IC_{50}$ value for VVNDL (SEQ ID NO: 37) toward virus growth in cell culture was $10^4$-fold higher than dissociation constant measured in vitro for binding to HSV-R1 (0.3 nM), and the parent nonapeptide, YAGAVVNDL (SEQ ID NO: 38), having a much higher $IC_{50}$ value toward HSV-RR of 25 μM, did not inhibit viral growth in cell culture. This disparity between effects in vitro and effects in cell culture is almost certainly due to the poor uptake of peptides into cells. Thus, approaches which facilitate entry of RR inhibitors into cells are now described, wherein the inhibitors remain effective as inhibitors of virus replication and tumor cell proliferation.

Via Folate

Leamon et al. (1991, Proc. Natl. Acad. Sci. USA 88:5572–5576; Leamon et al., 1993, Biochem. J. 291:855–860; Leamon et al., 1993, J. Biol. Chem. 268 (33):24847–24854) have demonstrated that proteins covalently attached to folic acid are taken up into cells by folate binding protein (FBP) mediated endocytosis, and have used this approach to introduce toxic proteins such as momordin, a ribosome-inactivating protein into cells, thereby killing them. Because FBP is vastly overexpressed on certain malignant cell surfaces, including those of Hela and Caco-2 cells (Leamon et al., 1994, J. Drug Target 2:101–112; Weitman et al., 1992, Cancer Res. 52:3396–3401), this approach can in some cases permit selective destruction of malignant cells. More recently, Low and colleagues have extended this approach by demonstrating that liposomes (66 nm) conjugated to folate via a polyethylene glycol (PEG) spacer ($M_r$ ~3250) can be used to deliver materials contained within the liposome, such as antisense oligonucleotides and doxorubicin, into cancer cells (Lee et al., 1994, J. Biol. Chem. 269:3198–3204; Lee et al., 1995, Biochim. Biophys. Acta 1233, 134–144; Wang et al., 1995, Proc. Natl. Acad. Sci. USA 92:3318–3322).

Figure 20:
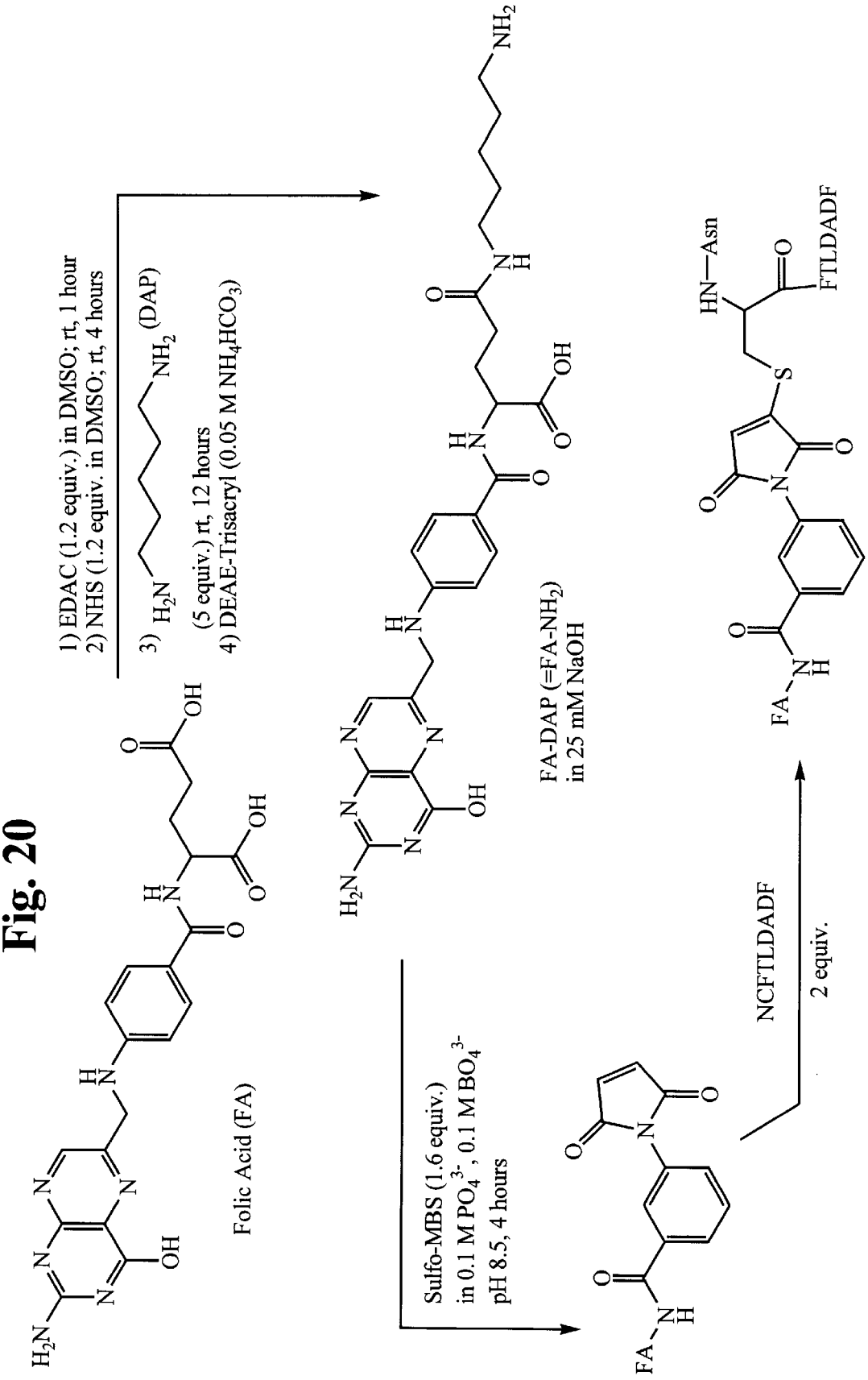
FIG. 20 is a scheme depicting peptide coupling to folate via sulfo-MBS.

Folate is likely an effective vehicle for uptake of peptides or peptide mimetic inhibitors of R1 as well. An attractive approach is to first condense folate with 1,5-diaminopentane, using EDAC (1-ethyl-3-[3-dimethylaminopropyl carbodiimide]) and NHS (N-hydroxysuccinimide) as described (Leamon et al., 1993, J. Biol. Chem. 268 (33):24847–24854), and then couple the resulting free amino group with the peptide or peptide mimetic. This approach permits separation of the γ-1,5-diaminopentane condensate, which is active in uptake, from the α-1,5-diaminopentane condensate, which is not (Wang et al., 1996, Bioconjugate Chem. 7:56–62), prior to coupling with peptide. This approach was used to couple the γ-1,5-diaminopentane folate condensate with the free thiol of the peptide NCFTLDADF (SEQ ID NO: 60), using the standard amine-thiol coupling reagent, sulfo-MBS (m-maleimidobenzoyl-N-hydroxysulfosuccinimide ester, available from Pierce) (FIG. 20). The folate-peptide conjugate FA-DAP-C(N)FTLDADF has been purified to homogeneity by RP-HPLC. Mass, UV, and $^1$H NMR spectra are in accord with the expected structure.

As expected based on the results in Table 8 showing that extensions at the N-terminus do not affect affinity for mR1, both NCFTLDADF (SEQ ID NO: 60) and FA-DAP-C(N) FTLDADF were comparable to AcFTLDADF (SEQ ID NO: 16) as RR inhibitors. FA-DAβ-C(N)FTLDADF may be tested for its effects on Hela cell proliferation (D-4b), using the standard MTT(3-(4,5-dimethylthiazol-2-yl)-2,5-diphenyltetrazlium bromide) assay (Alley et al., 1988, Cancer Research 48:589–601; Hansen et al., 1989, J. Immunol. Methods 119:203–210) in which conversion of the tetrazolium salt to a purple formazan, monitored at 570 nm, provides a direct measure of live cells.

Figure 21:
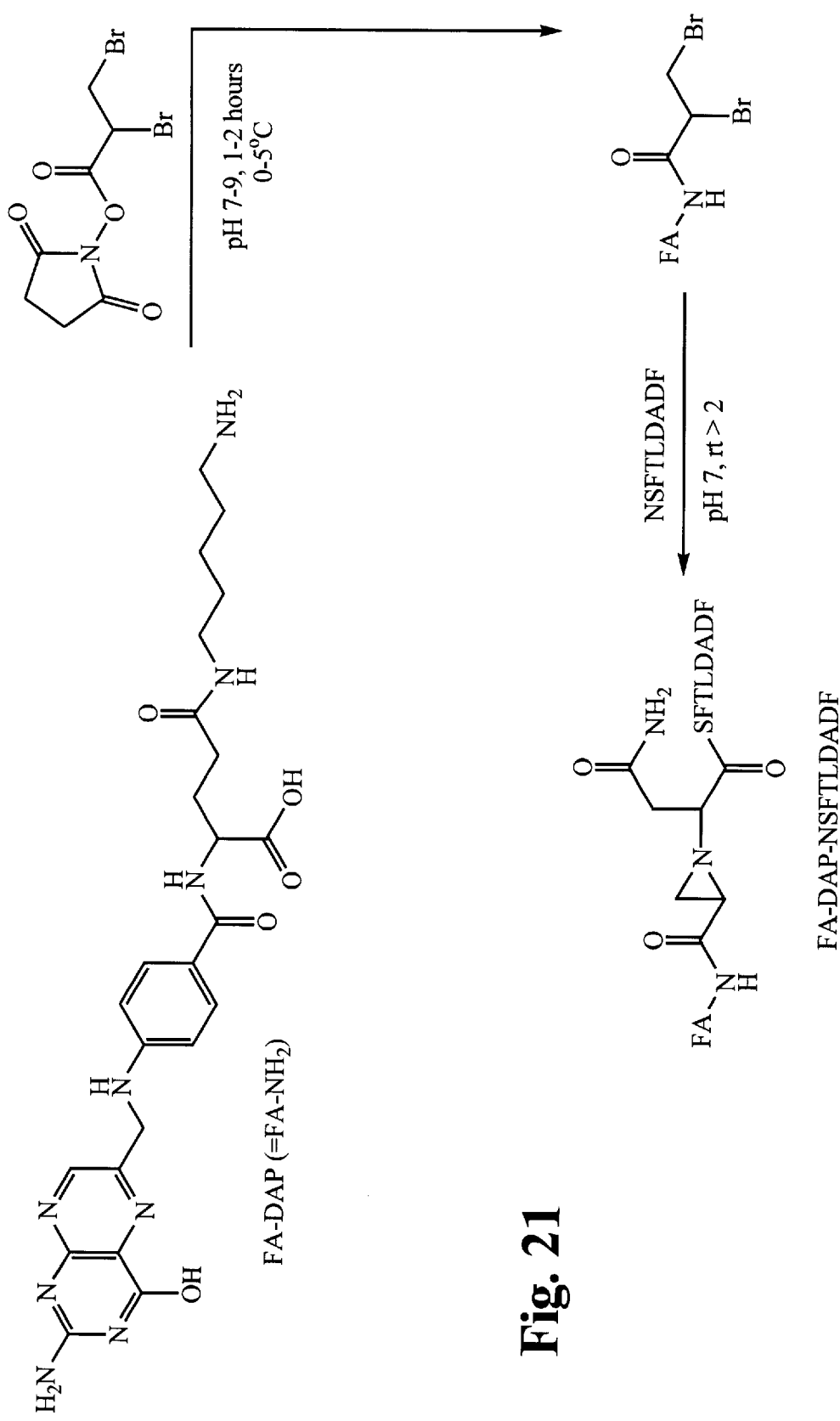
FIG. 21 is a scheme depicting amine-amine coupling of peptide to folate.

The carbodiimide, NHS activation procedure may also be used to directly couple the free amino group of the peptide or nonpeptide peptidomimetic to folic acid, thus eliminating the need for the second coupling step. For example, NSFTLDADF may be coupled to folate, where the nonapeptide is used to insure that all of the critical heptapeptide region (C-3a.) is available for binding to R1. The foreseeable problem with this approach is the potential difficulty in separating the α- and γ-adducts prior to use in cell assay. However, since the γ-1,5-diaminopentane adduct is formed preferentially over the α-1,5-diaminopentane adduct by about 4:1, and Wang et al. (1996, Bioconjugate Chem. 7, 56–62) obtain similar results on direct condensation of deferoxamine with folate, this approach should be useful for generating preliminary results on mixtures, prior to isolating the pure γ-adduct. An additional possibility, if needed, is to couple peptides to the γ-1,5-diaminopentane folate condensate with the amine-amine coupling reagent N-hydroxysuccinimidyl-2,3-dibromopropionate, (FIG. 21) thus eliminating the need for Cys-containing peptides.

In addition, the liposome-PEG-folate conjugate may be prepared and tested as a vehicle for delivery of peptides to Hela and Caco-2 cells, and its effectiveness may be compared to what is observed in the case of the direct folate-peptide conjugates. If it is comparable or better, this could well be the method of choice, since it would obviate the need to synthesize each peptide-folate conjugate separately.

Via Enterotoxin B

Marcello et al. (1994, Proc. Natl. Acad. Sci. USA 91:8994–8998) have demonstrated the nontoxic B subunit of *E. coli* heat-labile enterotoxin (EntB) can be used as a recombinant carrier, in the form of a fusion protein EntB-YAGAVVNDL, for receptor mediated delivery of YAGAVVNDL (SEQ ID NO: 38) into HSV-infected Vero cells. The fusion protein inhibits viral replication with an $IC_{50}$ of 200 nM and is synergistic with acyclovir. The approach is based on the ability of EntB to enter cells by GM1-ganglioside receptor binding and vesicular trafficking. Unclear at present is whether inhibition within the cell is due to EntB-YAGAVVNDL itself, or rather to the free peptide that is released by proteolysis following entry of EntB-YAGAVVNDL into the cell.

To use this approach, an EntB fusion protein is first made with the nonapeptide NSFTLDADF (SEQ ID NO: 61). Generation of the fusion protein is as described by Marcello et al. (1994, Proc. Natl. Acad. Sci. USA 91:8994–8998), by ligating the EcoRI-HindIII fragment from pMMB138 (Sandkvist et al., 1987, J. Bacteriol. 169:4570–4576) to the appropriate synthetic oligonucleotide coding for NSFTLDADF (SEQ ID NO: 61) and to any higher affinity natural peptides resulting from the search of linear peptide libraries described herein.

Extension of the EntB strategy to constrained peptides and peptide mimetics resulting from the work described herein is possible by chemically coupling a free amino group on the inhibitory molecule to either carboxylates or amines on EntB, using chemistries similar to those described herein.

For example, this may be accomplished via activation of protein carboxylates by reaction with EDAC and, following removal of excess reagent, coupling to the peptide or non-peptide peptidomimetic. Alternatively, peptide or nonpeptide peptidomimetic may first be reacted with excess amine-amine coupling reagent, and EntB added after excess reagent is removed.

A possible problem with chemical coupling is that the free peptide (or mimetic) might be required for intracellular inhibition of viral growth, and that the chemically-coupled inhibitor might be resistant to proteolytic release. Variation of the linker dipeptide sequence, -Asn-Ser-, to conform to the specificities of intracellular proteases provides an approach to the solution of this potential problem.

Testing of EntB- and Folate-Coupled Peptides and Peptide Mimetics

The coupled materials described herein may be tested for their efficacies in inhibiting Hela and Caco-2 tumor cell proliferation, and in inhibiting HIV-1 replication, in the presence and absence of nucleoside inhibitors. Based on the results and information provided herein, it is predicted that as inhibitors, the folate-coupled material will be superior toward tumor cell proliferation, whereas the EntB-coupled material will be superior toward HIV-1 replication.

EXAMPLE 13

Synthesis of Peptide 8

Figure 27A:
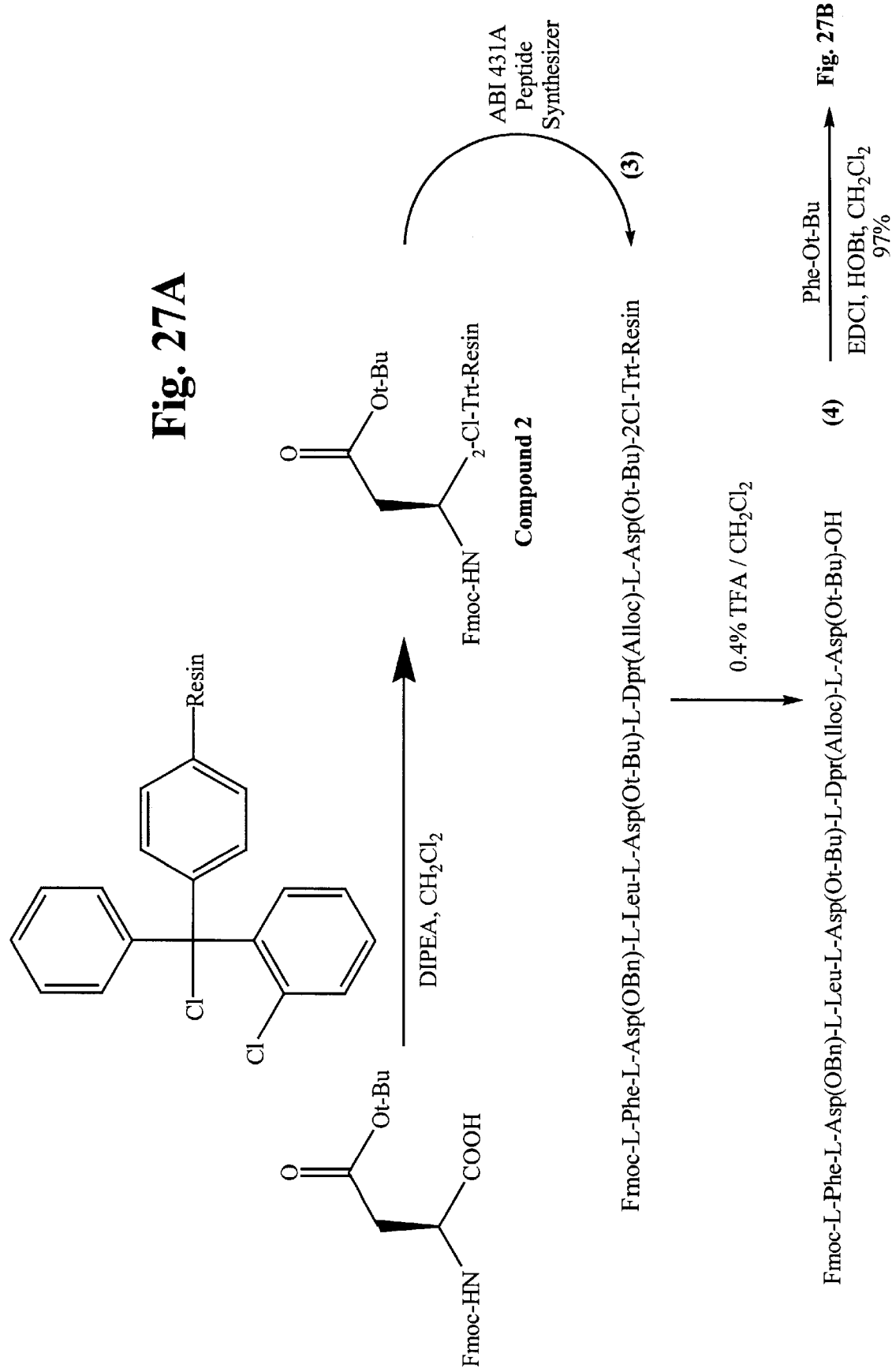
FIG. 27 depicts a chemical synthetic scheme described herein for making Peptide 8.
Figure 27B:
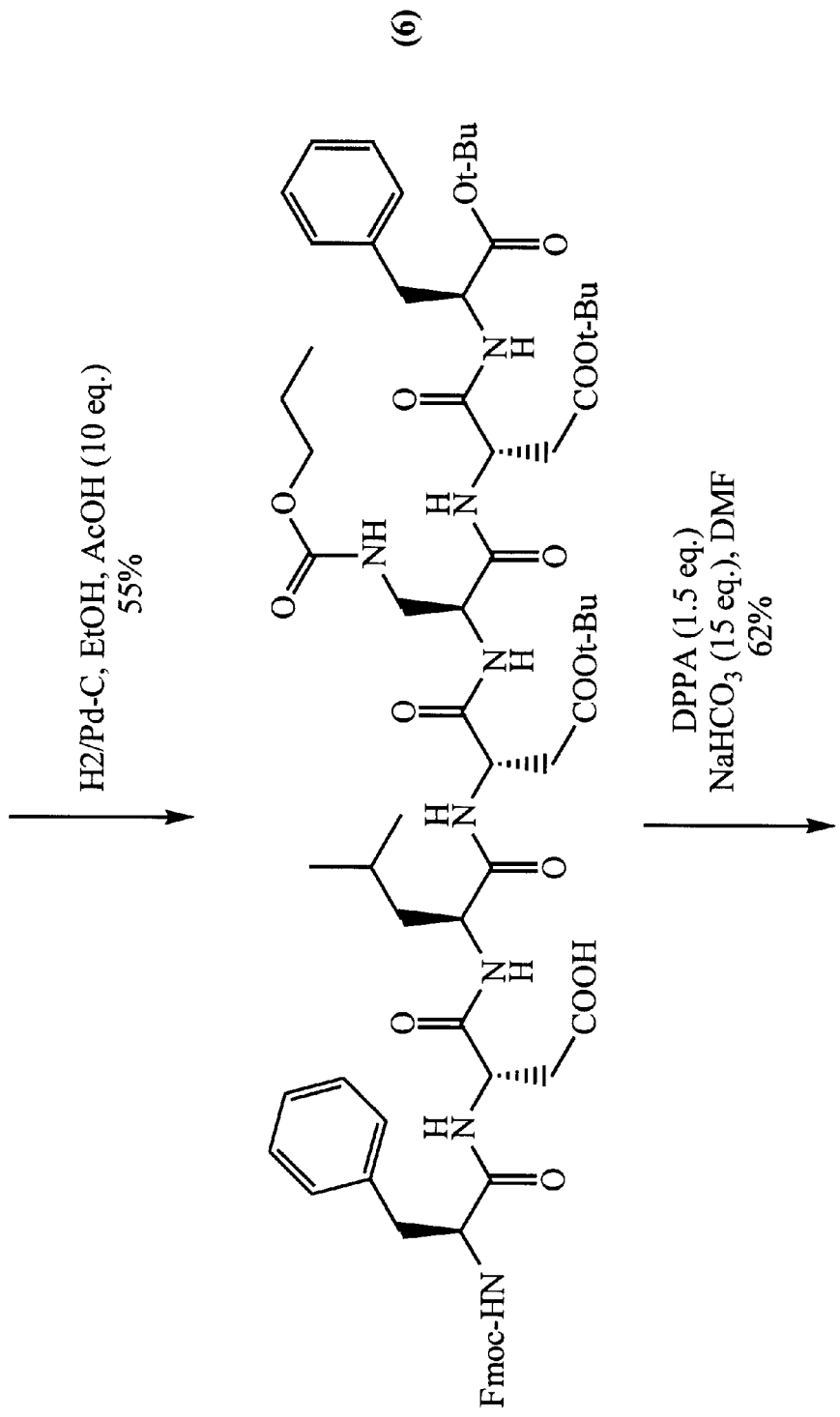
Figure 27C:
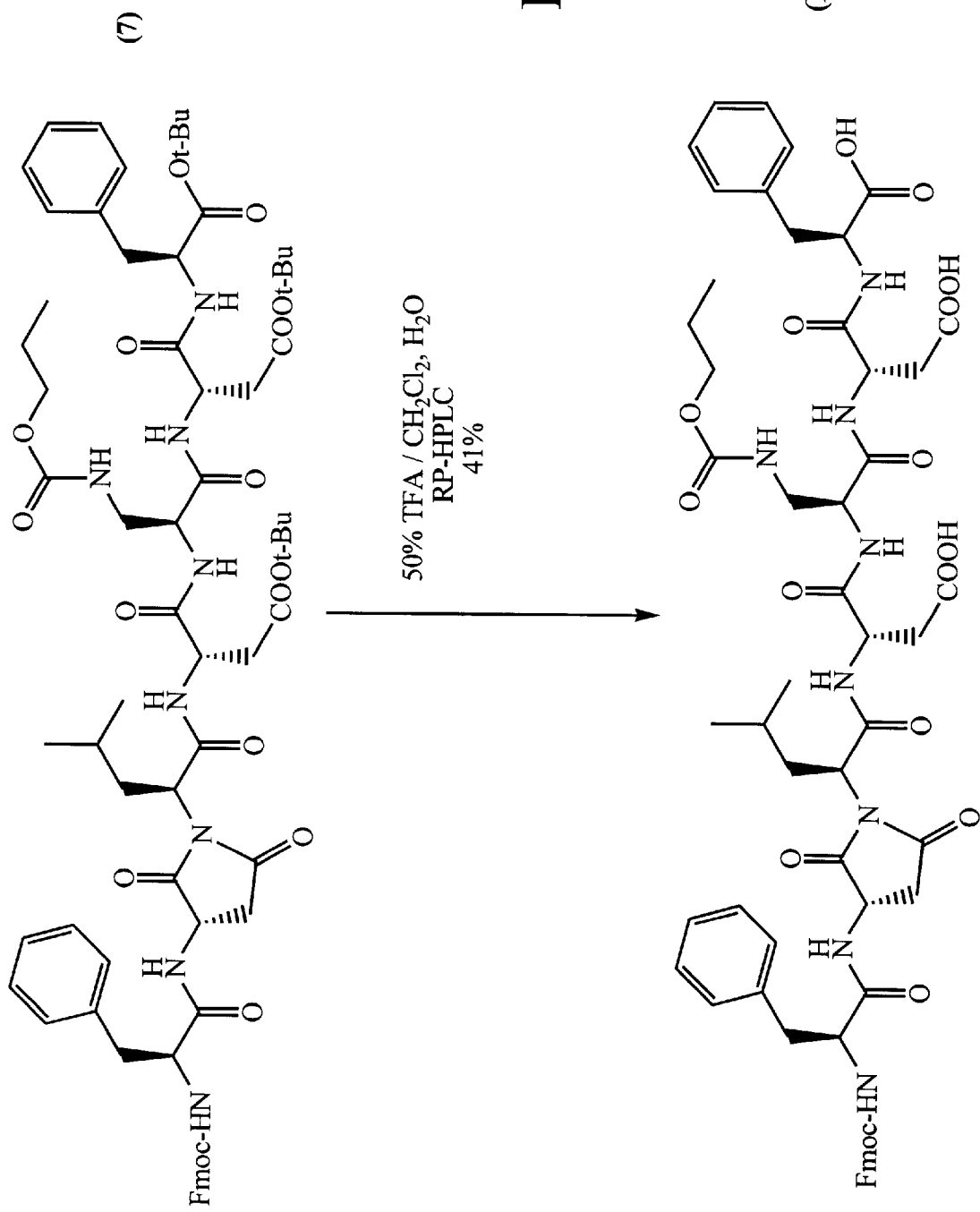

The synthesis of Peptide 8 is depicted in FIG. 27 and described herein. All reactions were carried out under inert atmosphere unless otherwise noted. Anhydrous solvents were purchased from Aldrich and were used as such or were dried over 4 Å molecular sieves. Unless otherwise indicated, all reagents were obtained from commercial sources and were used without further purification. All reactions were monitored by Thin Layer Chromatography (TLC) on Anal tech plates (Silica gel GF, 250μ). Flash column chromatography was performed on silica gel (230–400 mesh, 60 Å). Analytical reverse-phased HPLC was performed on a Perkin-Elmer system fitted with a series 410 BIO LC pump and a LC-235 Diode Array detector. The HPLC columns which were used were either Synchropak RP-P or RP-8 (250×4.6 mm) for analytical runs and (250×10 mm) for semi-preparative runs. Mobile solvents were buffer A ($CH_3CN$, 0.1%TFA) and buffer B ($H_2O$, 0.1%TFA). $^1$H-NMR and $^{13}$C-NMR spectra were recorded on a Bruker AMX-500 spectrophotometer. The chemical shifts are reported in (δ) ppm relative to TMS. FAB-mass spectra were obtained using a VG-ZAB-E spectrometer.

Synthesis of Fmoc-Asp(O-t-Bu)-2-Cl-Trt-resin (Compound (2)).

2-Chlorotrityl resin (1.3 mmol/g, Novabiochem) and Fmoc-Asp(O-t-Bu)-OH (Compound (1)) were dried under vacuum over KOH for 12 h. 2-Chlorotrityl resin (0.50 g, 0.65 mmol) was taken in a dry 100 mL rb flask along with DCM (4 mL) and gently stirred at room temperature to swell the resin. Fmoc-Asp(O-t-Bu)-OH (0.79 g, 1.91 mmol) was dissolved in DCM:DMF (8 mL, 1:1) and added to the flask with continuous stirring along with a total amount of DIPEA (1.33 mL, 7.65 mmol). The reaction was vigorously stirred for 1.5 h, after which time the reaction was quenched by addition of 20 mL MeOH:DIPEA (9:1) and stirring for another 10 min. The reaction mixture was filtered under vacuum and the resin was successively washed with DMF (20 mL×3), iPr-OH (20 mL×2), DMF (20 mL×4), iPr-OH (15 mL×2), MeOH (20 mL×1) and EtOH (20 mL×3). The resin was further dried in a vacuum desiccator over KOH till it appeared as free flowing pale yellow beads (0.637 g).

The substitution level, by weight, of the resin was determined to be approximately 0.573 mmol/g of resin. The substitution level of the resin was also determined by measuring the absorbance of N-(9-fluorenylmethyl) piperidine at 301 nm (ε=7800). In a test tube, 5.1 mg of the Fmoc-Asp(O-t-Bu)-resin was weighed out. 0.5 mL of 20% piperidine in DMF was added. 0.5 mL 20% piperidine in DMF in an empty test tube was used as a blank. Over the next 1 h, the test tube containing the Fmoc-AA-resin was swirled several times to ensure that all the resin came in contact with the piperidine solution. DMF was added to both tubes to bring the volume to 50 mL in a volumetric flask. The spectrophotometer was zeroed at 301 nm with the blank, and the absorbance of the Fmoc-Asp(O-t-Bu)-resin solution was read. The process was repeated twice. The average absorbance at 301 nm was 0.466, corresponding to a substitution level of approximately 0.58 mmol/g.

Synthesis of the Fmoc-L-Phe-L-Asp(OBn)-L-Leu-L-Asp (O-t-Bu)-L-Dpr(Alloc)-L-Asp(O-t-Bu)-2-Cl-Trt-resin (Compound (3)).

Assembly of the peptide on the solid support was carried out using an Applied Biosystems, Inc. Model 431 automated peptide synthesizer. Fmoc amino acids from Bachem (Torrance, Calif.) and SNPE (Princeton, N.J.) with appropriately protected side-chains were employed throughout. Starting with 0.25 mmol of Fmoc-L-Asp(O-t-Bu)-2-chlorotrityl resin (0.44 g, 0.57 mmol/g), Fmoc-L-Phe-L-Asp (OBn)-L-Leu-L-Asp(O-t-Bu)-L-Dpr(Alloc)-L-Asp(O-t-Bu)-2-Cl-Trt-resin was assembled according to the standard procedure, with some modification as described herein. Fmoc removal using 20% piperidine in DMF, 1.0 mmol individual amino acids, and HBTU as the coupling agent were used in each of the coupling steps. The coupling reaction was carried out at room temperature for 2 h. The following amino acids were incorporated in the order: Fmoc-L-Dpr(Alloc)-OH, Fmoc-L-Asp(O-t-Bu)-OH, Fmoc-L-Leu-OH, Fmoc-L-Asp(OBn)-OH, and Fmoc-L-Phe-OH. After each coupling, a Kaiser test was performed to monitor completion of the coupling reaction. If necessary, a second coupling reaction was performed. After the completion of the solid-phase synthesis, the resin was dried under vacuum to yield 0.676 g of the peptide resin (Compound (3)).

Synthesis of the Fmoc-L-Phe-L-Asp(OBn)-L-Leu-L-Asp (O-t-Bu)-L-Dpr(Alloc)-L-Asp(O-t-Bu)-OH (Compound (4)).

Fmoc-L-Phe-L-Asp(OBn)-L-Leu-L-Asp(O-t-Bu)-L-Dpr (Alloc)-L-Asp(O-t-Bu)-2-Cl-Trt-resin (Compound (3); 0.65 g) was treated with $TFA/CH_2Cl_2$ (0.40% v/v, 15 mL) at room temperature. After 45 min, the orange colored slurry was filtered and washed several times with a solution comprising 0.40% v/v $TFA/CH_2Cl_2$. The filtrate was concentrated to half its original volume, and was flushed with benzene. The resulting solid was triturated using ice-cold dry ether to obtain 0.40 g of a white crystalline solid (Compound 4). This material was reasonably pure and was taken for the next step without any purification.

Compound 4 had the following properties. TLC: $CH_2Cl_2$/MeOH/AcOH=9/1/0.01, $R_f$=0.36. RP-HPLC (analytical): gradient 30% buffer A-2'; 30-20'-70% A; 70-45'-100% A; 100% A-5'; 0.7 mL/min monitored at 215 nm, fraction eluting at 28.6 min. $^1$H-NMR (500 MHZ, $CDCl_3$): δ 0.80–0.90 (dd, 6H), 1.35–1.45 (s, 18H), 1.60–1.75 (m, 3H), 2.80–3.20 (m, 6H), 3.20–3.80 (m, 4H), 4.20 (t, Fmoc-CH, 1H), 4.30 (d, J=6.99 Hz, 2H), 4.40 (d, J=5.08 Hz, 2H, Fmoc-$CH_2$), 5.1 (s, 2H), 5.2 (d, J=1.18 Hz, 1H), 5.3 (d, J=1.24 Hz, 1H), 5.8–6.0 (m, 1H), 4.30–4.90 (m, 6H), 7.20–7.30 (m, 12H), 7.40–7.50 (m, 2H), 7.50–7.65 (m, 2H), 7.70–7.85 (d, 2H). $^{13}$C-NMR (125 MHZ, CDCl$_3$): 28.39, 34.87, 125.41, 127.52, 128.28, 128.60, 129.04, 141.68. FAB-Mass spectrum: Calculated for C$_{64}$H$_{79}$N$_7$O$_{17}$ (1217.55). Found 1240.50 (M+Na$^+$).

Synthesis of the Fmoc-L-Phe-L-Asp(OBn)-L-Leu-L-Asp (O-t-Bu)-L-Dpr(Alloc)-L-Asp(O-t-Bu)-L-Phe-O-t-Bu (Compound (5).

Fmoc-L-Phe-L-Asp(OBn)-L-Leu-L-Asp(O-t-Bu)-L-Dpr (Alloc)-L-Asp(O-t-Bu)-OH (Compound (4); 31.0 mg, 0.025 mmol) was dissolved in 3 mL of dry CH$_2$Cl$_2$ and stirred at 0° C. HOBt (6.00 mg, 0.038 mmol) and EDC (7.20 mg, 0.038 mmol) was added to this solution. Phe-O-t-Bu (HCl salt; 7.00 mg, 0.028 mmol) was separately dissolved in 3 mL CH$_2$Cl$_2$ along with 1 equivalent of TEA (4.0 μL). The clear solution that was obtained was added to the original flask along with 1.2 equivalent of TEA (4.1 μL, total of 0.055 mmol). The reaction was stirred overnight and allowed to warm to room temperature. After completion of the reaction (TLC), the solvent was removed in vacuo and the residual oil was taken up in 60 mL of EtOAc. The organic layer was washed with 1 N HCl (30 mL×2), saturated NaHCO$_3$ (30 mL×2), brine (30 mL), dried over Na$_2$SO$_4$ and filtered. The filtrate was evaporated in vacuo to yield Compound 5 in the form of a white solid (0.035 g, 96.7%) which was used without further purification.

Compound 5 had the following properties. TLC: CH$_2$Cl$_2$/MeOH/AcOH=9.5/0.5/0.01, R$_f$=0.70. RP-HPLC (analytical): gradient 50% buffer A-2'; 50-50'-100% A; 0.7 mL/min monitored at 215 nm, fraction eluting at 44.3 min. $^1$H-NMR (500 MHZ, CDCl$_3$): δ 0.80–0.95 (m, 6H), 1.10–1.30 (bs, 27H), 1.65–1.85 (m, 3H), 2.70–2.80 (m, 2H), 2.80–2.90 (m, 2H), 2.95–3.15 (m, 4H), 3.20–3.70 (m, 4H), 4.2 (d, J=7 Hz, 2H), 4.30–4.40 (d, 3H, Fmoc-CH$_2$ & CH), 5.10 (s, 2H), 5.20 (d, J=1.18 Hz, 1H), 5.30 (d, J=1.20 Hz, 1H), 5.80–5.90 (m, 1H), 7.10–7.50 (bm, 17H), 7.50–7.60 (m, 4H), 7.70–7.85 (m, 4H). $^{13}$C-NMR (125 MHZ, CDCl$_3$): 11.37, 14.46, 14.53, 21.76, 23.33, 23.39, 24.17, 25.28, 28.28, 28.42, 28.43, 29.34, 29.77, 30.11, 30.78, 36.94, 37.71, 38.21, 39.93, 42.41, 47.33, 50.24, 51.26, 54.30, 54.71, 66.22, 67.63, 68.16, 68.57, 81.66, 82.24, 118.03, 120.48, 125.48, 127.52, 128.64, 128.71, 128.96, 129.04, 129.22, 129.44, 129.54, 129.83, 129.90, 131.29, 135.31, 143.82, 144.05, 157.33, 170.34, 170.70, 170.90, 171.64, 172.02. FAB-Mass spectrum: Calculated for C$_{77}$H$_{96}$N$_8$O$_{18}$ (1420.68). Found 1444 (M+Na$^+$)

Synthesis of Compound (6) in FIG. 27.

Fmoc-L-Phe-L-Asp(OBn)-L-Leu-L-Asp(O-t-Bu)-L-Dpr (Alloc)-L-Asp(O-t-Bu)-L-Phe-O-t-Bu (Compound (5); 0.20 gram, 0.14 millimole) was dissolved in 20 mL of ethanol and 80 μL (1.4 millimole) AcOH and shaken for two days under a 55 psi H$_2$ atmosphere in a Parr shaker in the presence of 30 milligrams of palladium catalyst (Pd—C; 10% w/w). The concentration was about 7–8 millimolar. This shaking procedure effected complete removal of the benzyl group from the Asp residue and reduction of the alloc group on the Dpr, as evidenced by NMR. The catalyst was filtered over celite and washed several times with ethanol. The filtrate was evaporated in vacuo to yield a colorless oil. The oil was chromatographed on a silica gel flash column using a 9:1 mixture of CH$_2$Cl$_2$:methanol. Next, preparative thin layer chromatography was performed using a 250 millimeter by 250 millimeter plate having a 500 micrometer layer of silica gel deposited thereon. The solvent used was an 8:2:0.01 mixture of CH$_2$Cl$_2$:methanol:AcOH. This treatment yielded Compound (6) in FIG. 27 as a pure white solid (0.103 gram, 55.1%).

Compound (6) had the following properties. TLC: CH$_2$Cl$_2$:methanol:AcOH (9.5:0.5:0.01), R$_f$=0.27 RP-HPLC (analytical): gradient 50% buffer A-2'; 50-50'-100% A; 0.7 mL/minute monitored at 215 nanometers, fraction eluting at 38.1 minute. $^1$H-NMR (500 MHz, CDCl$_3$): δ 0.90–1.0 (m, 9H), 1.30–1.50 (bs, 27H), 1.60–1.80 (m, 3H), 2.0–2.4 (m, 2H), 2.70–2.90 (bm, 4H), 3.0–3.2 (m, 4H), 3.5–3.6 (m, 2H), 4.0–4.1 (m, 2H), 4.1–4.3 (m, 2H), 4.3–4.5 (m, 3H), 4.6–4.7 (m, 3H), 4.80–4.95 (m, 4H), 7.10–7.40 (m, 12H), 7.40–7.50 (m, 4H), 7.50–7.65 (m, 4H), 7.70–7.80 (d, 2H). FAB-Mass spectrum: Calculated for C$_{70}$H$_{92}$N$_8$O$_{18}$ (1333.55). Found 1355 (M+Na$^+$).

Synthesis of Compound (7) in FIG. 27.

10 μL (0.048 millimole) of DPPA was added dropwise to a suspension of 40.0 mg (0.030 millimole) of compound (6) and 40.0 mg (0.48 millimole) of NaHCO$_3$ in 22 mL dry DMF. The reaction mixture was stirred at 4° C. until the reaction reached completion, as monitored by analytical RP-HPLC. After stirring at 4° C. for 36 hours, the reaction mixture was filtered and washed with DMF. The combined filtrates were concentrated in vacuo. The resulting crude material was further purified by semi-preparative RP-HPLC (Synchropak: RP-P, 250×10 mm, gradient 60% buffer A-1'; 60-5'-70% A; 70-20'-90% A at 2 mL/minute monitored at 215 and 255 nanometers. The fraction eluting at 18.6 minutes was collected and lyophilized to yield compound (7) in FIG. 27 as a white amorphous solid (0.024 g, 61.5%).

Compound (7) had the following properties. TLC: CH$_2$Cl$_2$:methanol:AcOH (9.5:0.5:0.01), R$_f$=0.45.

$^1$H-NMR (500 MHz, CD$_3$OD): δ 0.90–1.0 (m, 9H), 1.30–1.50 (bs, 27H), 1.60–1.75 (m, 3H), 1.90–2.20 (m, 2H), 2.50–2.70 (m, 2H), 2.70–2.85 (m, 2H), 2.90–3.10 (m, 4H), 3.10–3.25 (m, 2H), 3.40–3.60 (m, 2H), 4.0–4.1 (m, 2H), 4.15–4.30 (m, 2H), 4.30–4.50 (m, 3H), 4.50–4.60 (m, 1H), 4.60–4.70 (m, 1H), 4.70–4.85 (m, 1H), 4.85–4.95 (m, 2H, obscured), 7.10–7.40 (bs, 12H), 7.40–7.60 (m, 4H), 7.75–7.85 (d, 2H). FAB-Mass spectrum: Calculated for C$_{70}$H$_{90}$N$_8$O$_{17}$ (1315.53). Found 1337 (M+Na$^+$).

Synthesis of Peptide 8.

20.0 mg (0.015 millimole) of compound (7) was dissolved in 2 mL CH$_2$Cl$_2$ and 0.1 mL H$_2$O. 2 mL of TFA was added dropwise to this mixture at room temperature. The resulting mixture was stirred for 90 minutes. After completion, the reaction mixture was concentrated to half its original volume and flushed with dry ether. The resulting solid was further triturated with ice-cold ether and evaporated to dryness. The crude solid obtained was purified on a semi-preparative RP-HPLC (Synchropak: RP-P, 250×10 mm, gradient 40% buffer A-1'; 40-40'-80% A; at 1.5 mL per minute, monitored at 215 and 255 nanometers). The fraction eluting at 25.4 minutes was collected and lyophilized to yield Peptide 8 as a white fluffy solid (0.007 gram, 41.2%).

Peptide 8 had the following properties: $^1$H-NMR (500 MHz, CD$_3$OD): δ 0.90–1.0 (m, 9H), 1.60–1.80 (m, 3H), 1.90–2.20 (m, 2H), 2.50–2.70 (m, 2H), 2.80–3.10 (m, 6H), 3.20–3.35 (m, 2H), 3.40–3.55 (m, 2H), 3.95–4.05 (d, 2H), 4.10–4.30 (m, 2H), 4.30–4.55 (dd, 4H), 4.60–4.75 (m, 2H), 4.80–4.90 (m, 2H, obscured), 7.10–7.30 (m, 12H), 7.35–7.45 (m, 2H), 7.50–7.60 (m, 2H), 7.80–7.95 (m, 2H). $^{13}$C-NMR (124 MHz, CD$_3$OD): δ 20.67, 22.41, 22.77, 24.74, 36.18, 47.34, 47.49, 47.66, 47.83, 48.00, 48.17, 48.34, 48.51, 49.63, 52.43, 56.30, 66.98, 67.13, 119.90, 125.22, 125.31, 126.78, 126.83, 127.19, 127.79, 128.50, 128.54, 129.43, 129.52, 141.56. FAB-Mass spectrum: Calculated for C$_{58}$H$_{66}$N$_8$O$_{17}$ (1147.21). Found 1169 (M+Na$^+$).

As described in Table 10, Peptide 8 is a RR inhibitor.

TABLE 10

Biological Evaluation of Compound (8)

| Compound (μM) | SEQ ID NO. | RR Activity |
|---|---|---|
| Ac-FTLDADF-OH (10) | SEQ ID NO: 16 | 0.39 ± 0.07 |
| Ac-FTLDADF-OH (66) | SEQ ID NO: 16 | 0.12 |
| Peptide 8 (10) | | 0.68 ± 0.31 |
| Peptide 8 (66) | | 0.19 ± 0.03 |

The disclosures of each and every patent, patent application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising an inhibitor of ribonucleotide reductase, wherein the inhibitor has the structure $Y_2$-$Y_3$-Phe-$Y_5$-Asp-$Y_6$-$Y_4$-OH, wherein $Y_2$ is H or a blocking group;

$Y_3$ is from zero to twenty amino acids;

$Y_4$ is from zero to five amino acids;

$Y_5$ has a structure selected from the group consisting of formula II, wherein $R_1$ and $R_2$ are independently selected from the group consisting of amino acid side chain moieties and Z is selected from the group consisting of amide and disulfide bonds, and formula II is

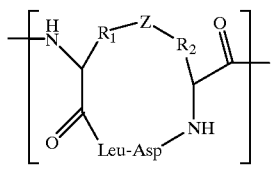

and formula III, wherein formula III is

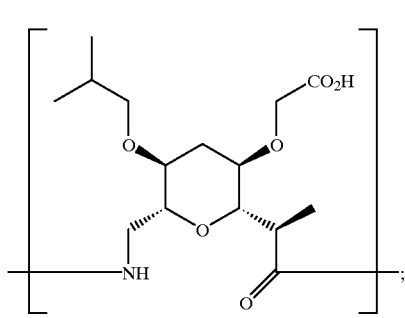

and $Y_6$ is selected from the group consisting of Phe, Tyr, Trp, N-methyl-Phe, D-Phe, o-methyl Phe, m-methyl Phe, o,o-dimethyl Phe, o,m-dimethyl Phe, o-hydroxyl Phe, m-hydroxyl Phe, p-hydroxyl Phe, m-chloro Phe, o-pyridyl Phe, and p-pyridyl Phe.

2. The composition of claim 1, wherein $Y_3$ is from zero to ten amino acids, $Y_4$ is from zero to five amino acids, and $Y_6$ is Phe.

3. The composition of claim 1, wherein $Y_3$ is from zero to five amino acids, $Y_4$ is from zero to one amino acid, and $Y_6$ is Phe.

4. The composition of claim 1, wherein $Y_3$ and $Y_4$ are each zero amino acids and $Y_6$ is Phe.

5. The composition of claim 1, wherein $Y_2$ is acyl, $Y_3$ is Asn-Ser, $Y_4$ is zero amino acids, $Y_6$ is Phe, and $Y_5$ has the structure formula II, wherein formula II is

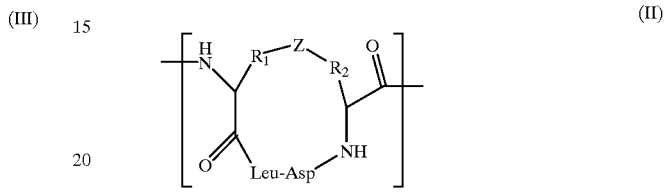

wherein the structures of $-R_1-Z-R_2$ is selected from the group consisting of formulas IV, V, and VI, wherein formula IV is $-CH_2-CO-NHCH_2-$;
formula V is $-CH_2S-SCH_2-$; and
formula VI is $-C(CH_3)_2S-SC(CH_3)_2-$.

6. The composition of claim 1, wherein said inhibitor has a structure selected from the group consisting of (i) formula 1a–h, wherein n is an integer selected from the group consisting of 1 and 2, m is an integer selected from the group consisting of 1–4, and formula 1a–h is

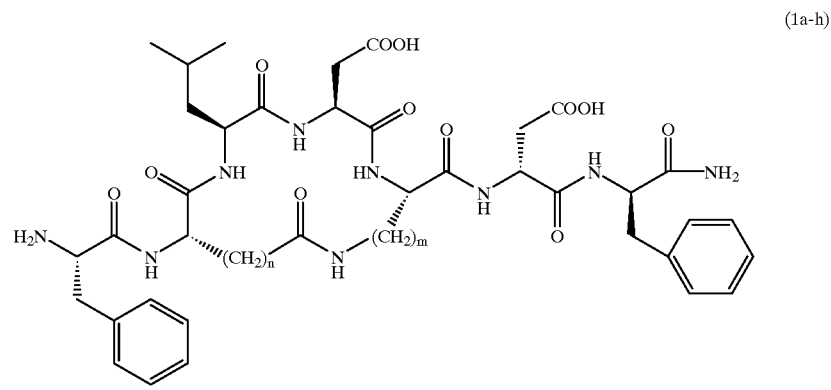

(ii) formula 2a–h, wherein n is an integer selected from the group consisting of 1 and 2, m is an integer selected from the group consisting of 1–4, and formula 2a–h is

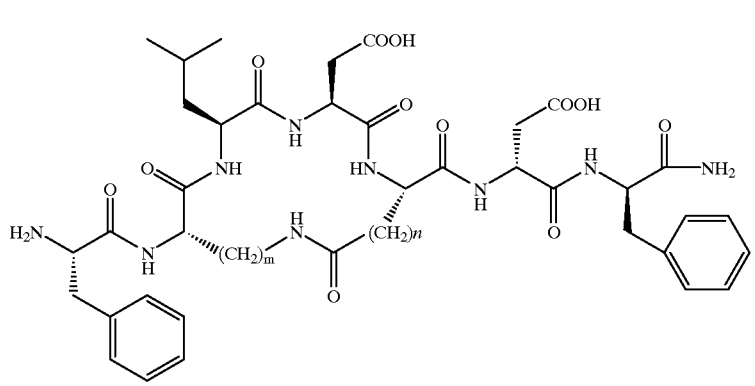

(2a-h)

(iii) formula 3a–i, wherein X and Y are independently selected from —CH$_2$—, —(CH$_2$)$_2$—, and —CMe$_2$—, and formula 3a–i is

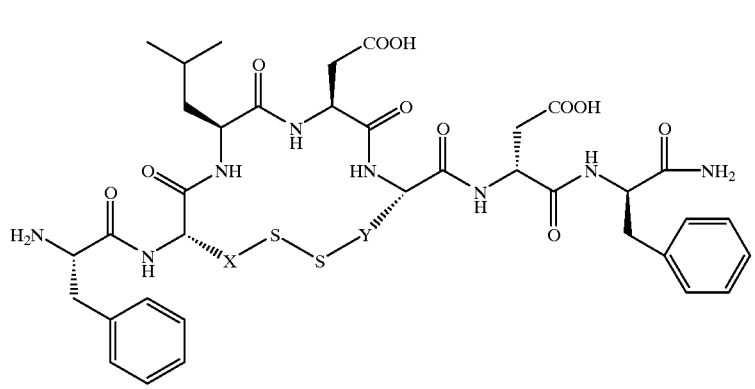

(3a-i)

(iv) formula 4a–d, wherein X and Y are independently selected from —CH$_2$— and —(CH$_2$)$_2$—, and formula 4a–d is

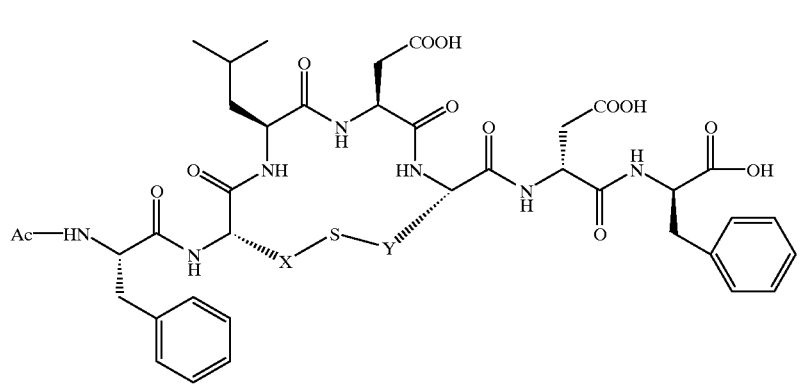

(4a-d)

and (v) formula 5a–i, wherein n is an integer selected from the group consisting of 1 and 2, X and Y are independently selected from —CH$_2$—, —(CH$_2$)$_2$—, and —CMe$_2$—, and formula 5a–i is

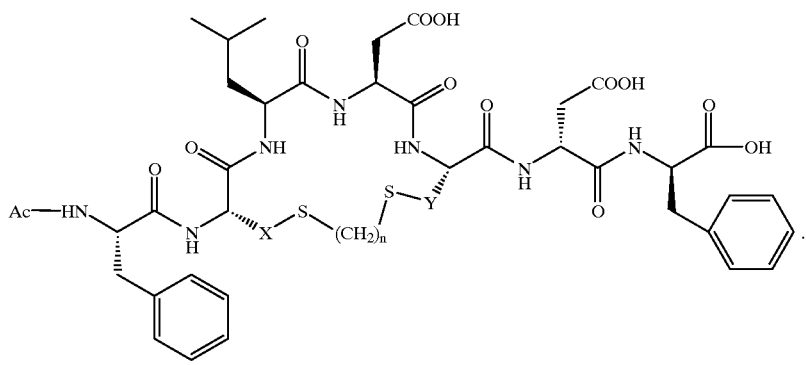
(5a-i)
7. The composition of claim 1, wherein said inhibitor has a structure of formula CVIII, wherein formula CVIII is
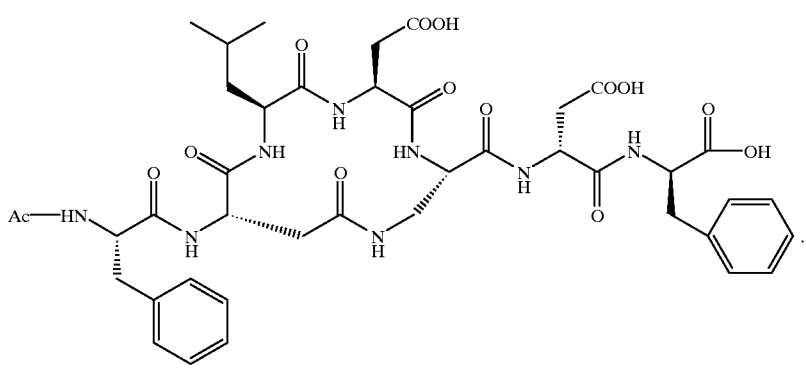
(CVIII)
* * * * *

```
                        SEQUENCE LISTING

<160> NUMBER OF SEQ ID NOS: 61

<210> SEQ ID NO 1
<211> LENGTH: 9
<212> TYPE: PRT
<213> ORGANISM: herpes simplex virus
<220> FEATURE:
<223> OTHER INFORMATION: HSV R2 C-terminal sequence

<400> SEQUENCE: 1

Tyr Ala Gly Ala Val Val Asn Asp Leu
  1               5

<210> SEQ ID NO 2
<211> LENGTH: 9
<212> TYPE: PRT
<213> ORGANISM: Homo sapiens
<220> FEATURE:
<223> OTHER INFORMATION: Mammalian R2 C-terminal sequence

<400> SEQUENCE: 2

Asn Ser Phe Thr Leu Asp Ala Asp Phe
  1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence:  R1-binding
      peptide

<400> SEQUENCE: 3

Phe Thr Leu Asp Ala Asp Phe
  1               5

<210> SEQ ID NO 4
<211> LENGTH: 24
<212> TYPE: PRT
<213> ORGANISM: Mus musculus
<220> FEATURE:
<223> OTHER INFORMATION: Murine R1 residues 715-738

<400> SEQUENCE: 4

Pro Asn Tyr Gly Lys Leu Thr Ser Met His Phe Tyr Gly Trp Lys Gln
  1               5                  10                  15

Gly Leu Lys Thr Gly Met Tyr Tyr
              20
```

```
<210> SEQ ID NO 5
<211> LENGTH: 24
<212> TYPE: PRT
<213> ORGANISM: herpes simplex virus
<220> FEATURE:
<223> OTHER INFORMATION: HIV-1 R1 residues 1089-1112

<400> SEQUENCE: 5

Ile Pro Ala Ser Thr Leu Val Arg Leu Leu Val His Ala Tyr Lys Arg
 1               5                   10                  15

Gly Leu Lys Thr Gly Met Tyr Tyr
            20

<210> SEQ ID NO 6
<211> LENGTH: 23
<212> TYPE: PRT
<213> ORGANISM: Escherichia coli
<220> FEATURE:
<223> OTHER INFORMATION: E. coli R1 residues 709-731

<400> SEQUENCE: 6

Val Pro Met Gln Gln Leu Leu Lys Asp Leu Leu Thr Ala Tyr Lys Phe
 1               5                   10                  15

Gly Val Lys Thr Leu Tyr Tyr
            20

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 7

Phe Thr Phe Asn Glu Asp Phe
 1               5

<210> SEQ ID NO 8
<211> LENGTH: 13
<212> TYPE: PRT
<213> ORGANISM: Escherichia coli
<220> FEATURE:
<223> OTHER INFORMATION: alpha 13 helix region of E. coli R1

<400> SEQUENCE: 8

Asn Lys Leu Met Tyr Thr Arg Leu Leu Lys Gly Glu Asp
 1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide

<400> SEQUENCE: 9

Phe Thr Ile Asp Glu Asp Phe
 1               5

<210> SEQ ID NO 10
<211> LENGTH: 13
```

```
<212> TYPE: PRT
<213> ORGANISM: Mus musculus
<220> FEATURE:
<223> OTHER INFORMATION: alpha13 helix-like region of murine R1

<400> SEQUENCE: 10

Pro Asp Leu Phe Met Lys Arg Val Glu Thr Asn Gln Asp
 1               5                  10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide

<400> SEQUENCE: 11

Phe Cys Leu Asn Thr Glu Phe
 1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide

<400> SEQUENCE: 12

Phe Ser Leu Asp Val Asp Phe
 1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 13

Asn Ser Phe Thr Leu Asp Ala Asp Phe
 1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 14

Ser Phe Thr Leu Asp Ala Asp Phe
 1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
```

-continued

<400> SEQUENCE: 15

Ser Phe Thr Leu Asp Ala Asp Phe
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 16

Phe Thr Leu Asp Ala Asp Phe
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide

<400> SEQUENCE: 17

Phe Thr Leu Asp Ala Asp Phe
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 18

Phe Thr Leu Asp Ala Asp Leu
 1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES ACETYLATION

<400> SEQUENCE: 19

Tyr Thr Leu Asp Ala Asp Phe
 1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 20

Phe Ser Leu Asp Ala Asp Phe
 1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 21

Phe Ala Leu Asp Ala Asp Phe
 1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 22

Phe Thr Val Asp Ala Asp Phe
 1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 23

Phe Thr Phe Asp Ala Asp Phe
 1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 24

Phe Thr Ala Asp Ala Asp Phe
 1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION -continued

```
<400> SEQUENCE: 25

Phe Thr Leu Asn Ala Asp Phe
  1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 26

Phe Thr Leu Ala Ala Asp Phe
  1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 27

Phe Thr Leu Asp Gly Asp Phe
  1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 28

Phe Thr Leu Asp Leu Asp Phe
  1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 29

Phe Thr Leu Asp Ala Glu Phe
  1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION
```

```
<400> SEQUENCE: 30

Phe Thr Leu Asp Ala Asn Phe
 1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 31

Phe Thr Leu Asp Ala Leu Phe
 1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 32

Phe Thr Leu Asp Ala Ala Phe
 1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 33

Phe Thr Leu Asp Ala Asp Leu
 1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 34

Phe Thr Leu Asp Ala Asp Phe Ala Ala
 1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence:
      Acetylated E. coli R2 C-terminal peptide
<220> FEATURE:
```

<223> OTHER INFORMATION: residue 1: MOD_RES:  ACETYLATION

<400> SEQUENCE: 35

Asp Asp Leu Ser Asn Phe Gln Leu
 1               5

<210> SEQ ID NO 36
<211> LENGTH: 8
<212> TYPE: PRT
<213> ORGANISM: Escherichia coli
<220> FEATURE:
<223> OTHER INFORMATION: E. coli R2 C-terminal peptide

<400> SEQUENCE: 36

Asp Asp Leu Ser Asn Phe Gln Leu
 1               5

<210> SEQ ID NO 37
<211> LENGTH: 5
<212> TYPE: PRT
<213> ORGANISM: herpes simplex virus
<220> FEATURE:
<223> OTHER INFORMATION: HSV R2 C-terminal sequence

<400> SEQUENCE: 37

Val Val Asn Asp Leu
 1               5

<210> SEQ ID NO 38
<211> LENGTH: 9
<212> TYPE: PRT
<213> ORGANISM: herpes simplex virus
<220> FEATURE:
<223> OTHER INFORMATION: HSV R2 C-terminal sequence

<400> SEQUENCE: 38

Tyr Ala Gly Ala Val Val Asn Asp Leu
 1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence:  Mammalian
      ribonucleotide reductase inhibitor peptide
<220> FEATURE:
<223> OTHER INFORMATION: residue 1: MOD_RES:  ACETYLATION

<400> SEQUENCE: 39

Phe Thr Leu Asp Ala Asp Gln
 1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence:  Portion of
      murine ribonucleotide reductase sequence

<400> SEQUENCE: 40

Thr Leu Asp Ala Asp
 1               5

<210> SEQ ID NO 41
<211> LENGTH:

<212> TYPE:
<213> ORGANISM:

<400> SEQUENCE: 41

This Sequence is intentionally skipped

<210> SEQ ID NO 42
<211> LENGTH: 7
<212> TYPE: PRT
<213> ORGANISM: Nicotiana angustifolia
<220> FEATURE:
<223> OTHER INFORMATION: Tobacco R2 C2-terminal sequence

<400> SEQUENCE: 42

Phe Lys Leu Asp Glu Asp Phe
  1               5

<210> SEQ ID NO 43
<211> LENGTH: 7
<212> TYPE: PRT
<213> ORGANISM: Arabidopsis thaliana
<220> FEATURE:
<223> OTHER INFORMATION: R2 C-terminal sequence

<400> SEQUENCE: 43

Phe Thr Thr Glu Glu Asp Phe
  1               5

<210> SEQ ID NO 44
<211> LENGTH: 7
<212> TYPE: PRT
<213> ORGANISM: Caenorhabditis elegans
<220> FEATURE:
<223> OTHER INFORMATION: R2 C-terminal sequence

<400> SEQUENCE: 44

Phe Asp Leu Glu Ala Asp Phe
  1               5

<210> SEQ ID NO 45
<211> LENGTH: 7
<212> TYPE: PRT
<213> ORGANISM: Dictyostelium discoideum
<220> FEATURE:
<223> OTHER INFORMATION: R2 C-terminal sequence

<400> SEQUENCE: 45

Leu Val Leu Asp Glu Asp Phe
  1               5

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence:  E. coli R2
      C-terminal sequence

<400> SEQUENCE: 46

Asp Ile Asp Asp Leu Ser Asn Phe Gln Leu
  1               5                  10

<210> SEQ ID NO 47
<211> LENGTH: 4
<212> TYPE: PRT
<213> ORGANISM: Escherichia coli
<220> FEATURE:

```
<223> OTHER INFORMATION: Portion of E. coli R1 sequence

<400> SEQUENCE: 47

Thr Leu Asp Ala
  1

<210> SEQ ID NO 48
<211> LENGTH: 4
<212> TYPE: PRT
<213> ORGANISM: Escherichia coli
<220> FEATURE:
<223> OTHER INFORMATION: Portion of E. coli R2 sequence

<400> SEQUENCE: 48

Leu Ser Asn Phe
  1

<210> SEQ ID NO 49
<211> LENGTH: 20
<212> TYPE: PRT
<213> ORGANISM: Escherichia coli
<220> FEATURE:
<223> OTHER INFORMATION: alphaI helix region of E. coli R1

<400> SEQUENCE: 49

Gln Gln Leu Leu Lys Asp Leu Leu Thr Ala Tyr Lys Phe Gly Val Lys
  1               5                  10                  15

Thr Leu Tyr Tyr
            20

<210> SEQ ID NO 50
<211> LENGTH: 21
<212> TYPE: PRT
<213> ORGANISM: Mus musculus
<220> FEATURE:
<223> OTHER INFORMATION: alphaI helix-like region of murine R1

<400> SEQUENCE: 50

Gly Lys Leu Thr Ser Met His Phe Tyr Gly Trp Lys Gln Gly Leu Lys
  1               5                  10                  15

Thr Gly Met Tyr Tyr
            20

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 51

Thr Leu Asp Ala Asp Phe
  1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION
```

```
<400> SEQUENCE: 52

Leu Asp Ala Asp Phe
 1               5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 53

Phe Leu Asp Ala Asp Phe
 1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 54

Phe Thr Leu Asp Asp Phe
 1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence:
      Ribonucleotide reductase inhibitor peptide
<220> FEATURE:
<223> OTHER INFORMATION: residue 1:  MOD_RES:  ACETYLATION

<400> SEQUENCE: 55

Phe Thr Leu Asp Phe
 1               5

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence:
      Saccharomyces cerevisiae R2 C-terminus peptide analog
<220> FEATURE:
<223> OTHER INFORMATION: residue 1:  MOD_RES:  ACETYLATION

<400> SEQUENCE: 56

Ala Gly Ala Phe Thr Phe Asn Glu Asp Phe
 1               5                  10

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence:
      Saccharomyces cerevisiae R2 C-terminus peptide analog
<220> FEATURE:
<223> OTHER INFORMATION: residue 1:  MOD_RES:  ACETYLATION
```

```
<400> SEQUENCE: 57

Phe Thr Phe Asn Glu Asp Phe
 1               5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence:
      Saccharomyces cerevisiae R2 C-terminus peptide analog
<220> FEATURE:
<223> OTHER INFORMATION: residue 1:  MOD_RES:   ACETYLATION

<400> SEQUENCE: 58

Thr Phe Asn Glu Asp Phe
 1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence:  Plasmodium
      falciparum R2 C-terminus peptide analog
<220> FEATURE:
<223> OTHER INFORMATION: residue 1:  MOD_RES:   ACETYLATION

<400> SEQUENCE: 59

Phe Cys Leu Asn Thr Glu Phe
 1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence:
      Ribonucleotide reductase inhibitor peptide

<400> SEQUENCE: 60

Asn Cys Phe Thr Leu Asp Ala Asp Phe
 1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence:
      Ribonucleotide reductase inhibitor peptide

<400> SEQUENCE: 61

Asn Ser Phe Thr Leu Asp Ala Asp Phe
 1               5
```